United States Patent
Andres et al.

(10) Patent No.: US 10,647,765 B2
(45) Date of Patent: *May 12, 2020

(54) AMINO ACID SEQUENCE PRESENTING FUSION POLYPEPTIDE AND ITS USE

(71) Applicant: HOFFMANN-LA ROCHE INC., Little Falls, NJ (US)

(72) Inventors: Herbert Andres, Penzberg (DE); David Casagolda Vallribera, Penzberg (DE); Hartmut Duefel, Schlehdorf (DE); Michael Gerg, Munich (DE); Christian Scholz, Penzberg (DE); Michael Schraeml, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 40 days.

This patent is subject to a terminal disclaimer.

(21) Appl. No.: 15/924,110

(22) Filed: Mar. 16, 2018

(65) Prior Publication Data

US 2019/0367601 A1 Dec. 5, 2019

Related U.S. Application Data

(60) Division of application No. 14/877,475, filed on Oct. 7, 2015, now Pat. No. 9,938,340, which is a division of application No. 14/112,108, filed on Oct. 16, 2013, now Pat. No. 9,266,962, which is a continuation-in-part of application No. PCT/EP2012/058207, filed on May 4, 2012.

(30) Foreign Application Priority Data

May 5, 2011 (EP) .................................. 11164957
Feb. 16, 2012 (EP) .................................. 12155742

(51) Int. Cl.
| | | |
|---|---|---|
| A61K 39/00 | (2006.01) |
| C07K 16/22 | (2006.01) |
| C07K 16/12 | (2006.01) |
| C12N 9/90 | (2006.01) |
| G01N 33/74 | (2006.01) |
| C07K 16/40 | (2006.01) |
| G01N 33/573 | (2006.01) |
| C07K 14/475 | (2006.01) |
| C07K 14/65 | (2006.01) |

(52) U.S. Cl.
CPC ............ *C07K 16/22* (2013.01); *C07K 14/475* (2013.01); *C07K 14/65* (2013.01); *C07K 16/1203* (2013.01); *C07K 16/40* (2013.01); *C12N 9/90* (2013.01); *G01N 33/573* (2013.01); *G01N 33/74* (2013.01); *C07K 2317/34* (2013.01); *C07K 2317/565* (2013.01); *C07K 2317/92* (2013.01); *C07K 2319/00* (2013.01); *C07K 2319/21* (2013.01); *C07K 2319/22* (2013.01); *C07K 2319/23* (2013.01); *C07K 2319/24* (2013.01); *C07K 2319/35* (2013.01); *C07K 2319/41* (2013.01); *C07K 2319/43* (2013.01); *C12Y 502/01008* (2013.01); *G01N 2333/99* (2013.01)

(58) Field of Classification Search
CPC ....................................................... C07K 16/22
See application file for complete search history.

(56) References Cited

U.S. PATENT DOCUMENTS

| | | | |
|---|---|---|---|
| 9,266,962 B2 | 2/2016 | Andres et al. | |
| 9,938,340 B2 * | 4/2018 | Andres | C07K 16/22 |
| 2006/0246521 A1 | 11/2006 | Xuan et al. | |
| 2009/0028893 A1 | 1/2009 | Scholz et al. | |

FOREIGN PATENT DOCUMENTS

| | | |
|---|---|---|
| EP | 1354959 A1 | 10/2003 |
| EP | 1516928 A1 | 3/2005 |
| EP | 1621555 A1 | 2/2006 |
| EP | 1780282 A1 | 5/2007 |
| RU | 2186770 C2 | 8/2002 |
| WO | WO 2003000878 A2 | 1/2003 |
| WO | WO 2004056855 A1 | 7/2004 |
| WO | WO 2007077008 A1 | 7/2007 |
| WO | 2007118214 A2 | 10/2007 |

OTHER PUBLICATIONS

The European Communication, dated Dec. 10, 2018, in the related European Appl. No. 12720476.6.
Database UniProt, Jul. 28, 2009, retrieved from EBI accession No. UNIPROT:C5A384.
Zivanovic Y. et al., "Genome analysis and genome-wide proteomics of Thermococcus gammatolerans, the most radioresistant organism known amongst the Archaea,"Genome Biology vol. 10, No. 6, Jun. 26, 2009, p. R70.
Christie-Oleza et al., "In-depth analysis of exoproteomes from marine bacteria by shotgun liquid chromatography-tandem mass spectrometry: the Ruegeria pomeroyi DSS-3 case-study", Mar Drugs, 8(8):2223-2239 (2010).
Database UniProt [Online] Jul. 5, 2004, "Peptidyl-prolyl cis-trans isomerase; EC=5.2.1.8 from Thermus thermophilus (strain HB27 / ATCC BAA-163 / DSM 7039)", retreived from EBI accession No. UNIPROT:Q72H58.

(Continued)

*Primary Examiner* — Albert M Navarro

(57) ABSTRACT

Herein is reported a fusion polypeptide according to formula I

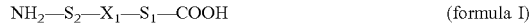

$$NH_2-S_2-X_1-S_1-COOH \quad \text{(formula I)}$$

wherein
$X_1$ comprises either a random amino acid sequence or an amino acid sequence derived from a first polypeptide,
S2 and S1 are non-overlapping amino acid sequences derived from a second polypeptide, and
— denotes a peptide bond,
wherein the second polypeptide is a polypeptide with peptidyl-prolyl cis/trans-isomerase activity (PPIase activity) or is derived from the FKBP-fold domain family, wherein $X_1$ is inserted in place of the insert-in-flap-domain of the second polypeptide.

4 Claims, 42 Drawing Sheets

Specification includes a Sequence Listing.

(56) References Cited

OTHER PUBLICATIONS

Henne et al., "The genome sequence of the extreme thermophile Thermus thermophilus", Nat Biotechnol., 22(5):547-553 (2004).

Ideno et al., "Expression of foreign proteins in *Escherichia coli* by fusing with an archaeal FK506 binding protein", Appl Microbiol Biotechnol., 64(1):99-105 (2004).

Ideno et al., "FK506-binding protein of the hyperthermophilic archaeum, Thermococcus sp. KS-1, a cold-shock-inducible peptidyl-prolyl cis-trans isomerase with activities to trap and refold denatured proteins", Biochem J., 357(Pt 2):465-71 (2001).

Knappe et al., "Insertion of a chaperone domain converts FKBP12 into a powerful catalyst of protein folding", J. Mol. Biol., 368:1458-1468 (2007).

Low et al., "Crystal structure determination and functional characterization of the metallochaperone SlyD from Thermus thermophilus", J. Mol. Biol., 398(3):375-390 (2010).

Rebuzzini, "Study of the hepatitis C virus NS3 helicase domain for application in a chemiluminescent immunoassay", PhD. Thesis, Universitá degli Studi di Milano-Bicocca, Italy, XP55408751 (2009). Retrieved from the Internet on Sep. 21, 2017: https://boa.unimib.it/retrieve/handle/10281/7477/8823/phd_unimib_033809.pdf.

Scholz et al., "Chaperone-aided in vitro renaturation of an engineered E1 envelope protein for detection of anti-Rubella virus IgG antibodies", Biochemistry, 47(14):4276-4287 (2008).

The International Search Report and Written Opinion, dated Sep. 14, 2012, in the corresponding PCT Patent Application No. PCT/EP2012/058207.

Zivanovie et al., "FKBP-type peptidyl-prolyl cis-trans isomerase (slyD) [Thermococcus gammatolerans EJ3]", (Online) Accession No. ACS32696, Nov. 29, 2010, retrieved from the Internet: http://www.ncbi.nlm.nih.gov/protein/239909805?sal=14&silkey=10484338.

Zoldak et al., "Consequences of domain insertion on the stability and folding mechanism of a protein", J. Mol. Biol., 386(4):1138-1152 (2009).

The Argentinian search report, dated Feb. 10, 2020, in the related Argentinian Patent Appl. No. 20120101552 (1 page).

* cited by examiner

| Antibody | Analyte | Binding Late (RU) | Stability Late (RU) | kd (1/s) | t1/2 (min) |
|---|---|---|---|---|---|
| 5.001.015 | SlyD/FKBP12-ERCC1 | 48 | 49 | < 1E-05 | > 1155 |
| | SlyD/FKBP12-crtl | 0 | 0 | - | - |
| 5.001.017 | SlyD/FKBP12-ERCC1 | 68 | 69 | 5.86E-05 | 197 |
| | SlyD/FKBP12-crtl | 0 | -1 | - | - |
| 5.001.019 | SlyD/FKBP12-ERCC1 | 68 | 68 | 1.17E-04 | 99 |
| | SlyD/FKBP12-crtl | -1 | -1 | - | - |
| 5.001.025 | SlyD/FKBP12-ERCC1 | 58 | 59 | 9.42E-05 | 123 |
| | SlyD/FKBP12-crtl | 0 | 0 | - | - |
| 5.001.035 | SlyD/FKBP12-ERCC1 | 138.2 | 138.8 | 5.66E-05 | 204 |
| | SlyD/FKBP12-crtl | -0.2 | -0.1 | - | - |
| 5.001.041 | SlyD/FKBP12-crtl | 0 | -1 | - | - |
| | SlyD/FKBP12-ERCC1 | 0 | 0 | - | - |
| 5.001.060 | SlyD/FKBP12-ERCC1 | 51 | 52 | 8.19E-05 | 141 |
| | SlyD/FKBP12-crtl | 0 | 0 | - | - |
| 5.001.062 | SlyD/FKBP12-ERCC1 | 70 | 71 | 6.98E-05 | 165 |
| | SlyD/FKBP12-crtl | 0 | 1 | - | - |
| 5.002.015 | SlyD/FKBP12-ERCC1 | 64 | 65 | 3.90E-05 | 296 |
| | SlyD/FKBP12-crtl | 0 | 0 | - | - |
| 5.002.017 | SlyD/FKBP12-ERCC1 | 69 | 70 | 6.43E-05 | 180 |
| | SlyD/FKBP12-crtl | 0 | 0 | - | - |
| 5.002.019 | SlyD/FKBP12-ERCC1 | 67 | 68 | 7.02E-05 | 165 |
| | SlyD/FKBP12-crtl | 0 | 0 | - | - |
| 5.002.025 | SlyD/FKBP12-ERCC1 | 51 | 52 | 1.22E-04 | 95 |
| | SlyD/FKBP12-crtl | -1 | -1 | - | - |
| 5.002.035 | SlyD/FKBP12-ERCC1 | 159 | 160 | 5.66E-05 | 204 |
| | SlyD/FKBP12-crtl | -1 | 0 | - | - |
| 5.002.041 | SlyD/FKBP12-crtl | 0 | 1 | - | - |
| | SlyD/FKBP12-ERCC1 | 1 | 1 | - | - |
| 5.002.060 | SlyD/FKBP12-ERCC1 | 51 | 52 | 4.98E-05 | 232 |
| | SlyD/FKBP12-crtl | 0 | 0 | - | - |
| 5.002.062 | SlyD/FKBP12-ERCC1 | 61 | 62 | 9.11E-05 | 127 |
| | SlyD/FKBP12-crtl | -1 | -1 | - | - |
| 5.005.015 | SlyD/FKBP12-ERCC1 | 61 | 61 | 8.52E-05 | 136 |
| | SlyD/FKBP12-crtl | -1 | 0 | - | - |
| 5.005.017 | SlyD/FKBP12-ERCC1 | 60 | 61 | 1.19E-04 | 97 |
| | SlyD/FKBP12-crtl | -1 | 0 | - | - |
| 5.005.019 | SlyD/FKBP12-ERCC1 | 86 | 87 | 7.11E-05 | 163 |
| | SlyD/FKBP12-crtl | 0 | 0 | - | - |
| 5.005.025 | SlyD/FKBP12-ERCC1 | 53 | 54 | 1.23E-04 | 94 |
| | SlyD/FKBP12-crtl | 0 | 0 | - | - |
| 5.005.035 | SlyD/FKBP12-ERCC1 | 141 | 142 | 5.66E-05 | 204 |
| | SlyD/FKBP12-crtl | -1 | 0 | - | - |
| 5.005.041 | SlyD/FKBP12-crtl | 0 | 0 | - | - |
| | SlyD/FKBP12-ERCC1 | 4 | 4 | - | - |
| 5.005.062 | SlyD/FKBP12-ERCC1 | 55 | 55 | 1.20E-04 | 96 |
| | SlyD/FKBP12-crtl | 0 | 0 | - | - |

FIG. 12

| Antibody | Analyte | Binding Late (RU) | Stability Late (RU) | kd (1/s) | t1/2 (min) |
|---|---|---|---|---|---|
| 5.003.015 | SlyD/FKBP12-ERCC1 | 74 | 75 | 6.70E-05 | 172 |
| | SlyD/FKBP12-crtl | 1 | 2 | - | - |
| 5.003.017 | SlyD/FKBP12-ERCC1 | 76 | 76 | 1.01E-04 | 115 |
| | SlyD/FKBP12-crtl | 0 | 0 | - | - |
| 5.003.019 | SlyD/FKBP12-ERCC1 | 77 | 79 | 2.93E-05 | 394 |
| | SlyD/FKBP12-crtl | 0 | 0 | - | - |
| 5.003.025 | SlyD/FKBP12-ERCC1 | 52 | 52 | 1.01E-04 | 114 |
| | SlyD/FKBP12-crtl | 0 | -1 | - | - |
| 5.003.035 | SlyD/FKBP12-ERCC1 | 167 | 167 | 5.66E-05 | 204 |
| | SlyD/FKBP12-crtl | 0 | -1 | - | - |
| 5.003.041 | SlyD/FKBP12-crtl | -1 | -1 | - | - |
| | SlyD/FKBP12-ERCC1 | 3 | 3 | - | - |
| 5.003.060 | SlyD/FKBP12-ERCC1 | 55 | 56 | 8.52E-05 | 136 |
| | SlyD/FKBP12-crtl | 0 | 0 | - | - |
| 5.003.062 | SlyD/FKBP12-ERCC1 | 60 | 61 | 1.04E-04 | 111 |
| | SlyD/FKBP12-crtl | -1 | -1 | - | - |
| 5.004.015 | SlyD/FKBP12-ERCC1 | 60 | 61 | 6.07E-05 | 190 |
| | SlyD/FKBP12-crtl | 0 | 0 | - | - |
| 5.004.017 | SlyD/FKBP12-ERCC1 | 69 | 70 | 7.52E-05 | 154 |
| | SlyD/FKBP12-crtl | 0 | 0 | - | - |
| 5.004.019 | SlyD/FKBP12-ERCC1 | 69 | 70 | 2.23E-05 | 517 |
| | SlyD/FKBP12-crtl | 0 | -1 | - | - |
| 5.004.025 | SlyD/FKBP12-ERCC1 | 53 | 54 | 1.52E-04 | 76 |
| | SlyD/FKBP12-crtl | -1 | -1 | - | - |
| 5.004.035 | SlyD/FKBP12-ERCC1 | 159.7 | 160.6 | 5.66E-05 | 204 |
| | SlyD/FKBP12-crtl | -0.8 | 0 | - | - |
| 5.004.041 | SlyD/FKBP12-crtl | 1 | 1 | - | - |
| | SlyD/FKBP12-ERCC1 | 5 | 5 | - | - |
| 5.004.060 | SlyD/FKBP12-ERCC1 | 52 | 52 | 7.89E-05 | 146 |
| | SlyD/FKBP12-crtl | 0 | 0 | - | - |
| 5.004.062 | SlyD/FKBP12-ERCC1 | 61 | 62 | 1.03E-04 | 112 |
| | SlyD/FKBP12-crtl | -1 | -1 | - | - |
| 5.006.015 | SlyD/FKBP12-ERCC1 | 65 | 65 | 8.99E-05 | 128 |
| | SlyD/FKBP12-crtl | -1 | 0 | - | - |
| 5.006.017 | SlyD/FKBP12-ERCC1 | 55 | 57 | 8.14E-05 | 142 |
| | SlyD/FKBP12-crtl | -1 | 0 | - | - |
| 5.006.035 | SlyD/FKBP12-ERCC1 | 125 | 126 | 5.66E-05 | 204 |
| | SlyD/FKBP12-crtl | 0 | 0 | - | - |
| 5.006.041 | SlyD/FKBP12-crtl | 1 | 2 | - | - |
| | SlyD/FKBP12-ERCC1 | 4 | 5 | - | - |
| 5.006.060 | SlyD/FKBP12-ERCC1 | 63 | 64 | 2.02E-05 | 573 |
| | SlyD/FKBP12-crtl | 0 | -1 | - | - |
| 5.006.062 | SlyD/FKBP12-ERCC1 | 64 | 65 | 1.14E-04 | 101 |
| | SlyD/FKBP12-crtl | 0 | 0 | - | - |

*FIG. 12 (continued)*

| mice no. | mice IC50 serum titer IC50 [mE] | |
|---|---|---|
| | IGF-1 | SlyD/FKBP12-IGF-1 (74-90) |
| K1575M1 | 189 | 2911 |
| K1575M2 | 395 | 1470 |
| K1575M3 | 465 | 4126 |
| K1575M4 | 564 | 2426 |
| K1576M1 | 2143 | 8302 |
| K1576M2 | - | 2960 |
| K1576M3 | - | 2978 |
| K1576M4 | - | 6957 |
| K1576M5 | - | 11221 |

FIG. 19

| mice no. | mice IC50 serum titer IC50 [mE] ||
| --- | --- | --- |
| | IGF-1 | *T.thermophilus* SlyD-IGF-1(74-90) |
| K1643M1 | 800 | 10000 |
| K1643M2 | 1000 | 15000 |
| K1643M3 | 4700 | 50000 |
| K1643M4 | 500 | 7000 |
| K1643M5 | 2500 | 26000 |
| K1644M1 | 2800 | 32000 |
| K1644M2 | 280 | - |
| K1644M3 | 250 | 300 |
| K1644M4 | 150 | 800 |
| K1644M5 | 150 | - |

*FIG. 20*

| primary culture no. | reactivity [mE] | | |
|---|---|---|---|
| | IGF-1 | T.thermophilus SlyD-IGF-1(74-90) | T.thermophilus SlyD |
| 10.0.1 | 1013 | 957 | 347 |
| 10.0.2 | 217 | 127 | 45 |
| 10.0.3 | 941 | 1061 | 50 |
| 10.0.4 | 993 | 1023 | 900 |
| 10.0.5 | 998 | 1084 | 1023 |
| 10.0.6 | 32 | 56 | 55 |
| 10.0.7 | 988 | 1032 | 64 |
| 10.0.8 | 973 | 992 | 46 |
| 10.0.9 | 818 | 943 | 35 |
| 10.0.10 | 819 | 734 | 35 |
| 10.0.11 | 809 | 848 | 160 |
| 10.0.12 | 729 | 848 | 42 |
| 10.0.13 | 140 | 961 | 741 |
| 11.0.14 | 30 | 32 | 33 |
| 11.0.15 | 1087 | 1156 | 30 |
| 11.0.16 | 982 | 977 | 33 |
| 11.0.17 | 922 | 1021 | 28 |

FIG. 21

FIG. 23 reactivity [mE]

| clone culture | IGF-1 | T.thermophilus Sly D-IGF-1(74-90) | T.thermophilus SlyD |
|---|---|---|---|
| 10.1.3 | 2748 | 2116 | 37 |
| 10.2.3 | 2768 | 2112 | 40 |
| 10.3.7 | 2712 | 2091 | 32 |
| 10.4.7 | 2700 | 2109 | 35 |
| 10.5.8 | 2501 | 1993 | 35 |
| 10.6.8 | 2410 | 1955 | 36 |
| 10.7.9 | 2111 | 1899 | 36 |
| 10.8.9 | 2145 | 1911 | 38 |
| 11.9.15 | 2578 | 2389 | 32 |
| 11.10.15 | 2585 | 2396 | 33 |
| 11.11.17 | 2427 | 2154 | 32 |
| 11.12.17 | 2372 | 2142 | 32 |

| mAb | RU | Antigen | kDa | °C | $k_a$ 1/Ms | $k_d$ 1/s | $t_{1/2}$-diss min | $K_D$ nM | $R_{max}$ RU | MR | $Chi^2$ RU² |
|---|---|---|---|---|---|---|---|---|---|---|---|
| M-11.11.17 | 457 | IGF-I (native) | 8 | | 2,0E+06 | 2,1E-05 | 560 | 0,01 | 46 | 2,0 | 0,0 |
| | 439 | IGF-II (native) | 8 | | n.d. | n.d. | n.d. | n.d. | n.d. | n.d. | n.d. |
| | 432 | TtSlyD-IGF-1(74-90) | 14 | 25 | 7,1E+05 | 1,0E-05 | 1113 | 0,01 | 83 | 2,0 | 0,0 |
| | 427 | TgSlyD-IGF-2(53-65) | 14 | | n.d. | n.d. | n.d. | n.d. | n.d. | n.d. | n.d. |
| | 421 | TtSlyD-wt | 18 | | n.d. | n.d. | n.d. | n.d. | n.d. | n.d. | n.d. |
| | 419 | TgSlyD-wt | 18 | | n.d. | n.d. | n.d. | n.d. | n.d. | n.d. | n.d. |
| | 418 | TgSlyD-dIF-wt | 15 | | n.d. | n.d. | n.d. | n.d. | n.d. | n.d. | n.d. |
| M-10.7.9 | 512 | hIGF-I (native) | 8 | | 9,2E+05 | 1,5E-03 | 8 | 1,6 | 44 | 1,7 | 0,0 |
| | 494 | hIGF-II (native) | 8 | | n.d. | n.d. | n.d. | n.d. | n.d. | n.d. | n.d. |
| | 485 | TtSlyD-IGF-1(74-90) | 14 | 25 | 2,9E+05 | 6,9E-04 | 17 | 2,4 | 84 | 1,8 | 0,0 |
| | 479 | TgSlyD-IGF-2(53-65) | 14 | | n.d. | n.d. | n.d. | n.d. | n.d. | n.d. | n.d. |
| | 470 | TtSlyD-wt | 18 | | n.d. | n.d. | n.d. | n.d. | n.d. | n.d. | n.d. |
| | 468 | TgSlyD-wt | 18 | | n.d. | n.d. | n.d. | n.d. | n.d. | n.d. | n.d. |
| | 465 | TgSlyD-dIF-wt | 15 | | n.d. | n.d. | n.d. | n.d. | n.d. | n.d. | n.d. |
| M-2.28.44 | 731 | hIGF-I (native) | 8 | | 3,9E+06 | 1,3E-04 | 92 | 0,03 | 68 | 1,8 | 0,0 |
| | 717 | hIGF-II (native) | 8 | | 4,9E+06 | 2,4E-03 | 5 | 0,5 | 67 | 1,8 | 0,3 |
| | 704 | TtSlyD-IGF-1(74-90) | 14 | 25 | n.d. | n.d. | n.d. | n.d. | n.d. | n.d. | n.d. |
| | 693 | TgSlyD-IGF-2(53-65) | 14 | | n.d. | n.d. | n.d. | n.d. | n.d. | n.d. | n.d. |
| | 672 | TtSlyD-wt | 18 | | n.d. | n.d. | n.d. | n.d. | n.d. | n.d. | n.d. |
| | 664 | TgSlyD-wt | 18 | | n.d. | n.d. | n.d. | n.d. | n.d. | n.d. | n.d. |
| | 655 | TgSlyD-dIF-wt | 15 | | n.d. | n.d. | n.d. | n.d. | n.d. | n.d. | n.d. |

FIG. 25

| Ligand | Analyte | BL [RU] | SL [RU] | kd [1/s] | t/2 diss [min] |
|---|---|---|---|---|---|
| 10.0.15 | IGF1 | 22 | 22 | 4.08E-05 | 283 |
| 10.0.15 | thermoSlyD-IGF-1 | 43 | 43 | 3.66E-05 | 315 |
| 10.0.15 | thermoSlyD (wildtyp) | 1 | -1 | n.d. | n.d. |
| 10.0.15 | IGF2 | 2 | 0 | n.d. | n.d. |
| 10.0.17 | IGF1 | 9 | 8 | 1.33E-04 | 87 |
| 10.0.17 | thermoSlyD-IGF-1 | 18 | 17 | 1.25E-04 | 92 |
| 10.0.17 | thermoSlyD (wildtyp) | 2 | -1 | n.d. | n.d. |
| 10.0.17 | IGF2 | 2 | 0 | n.d. | n.d. |
| 10.0.01 | IGF1 | 4 | 2 | 1.43E-03 | 8 |
| 10.0.01 | thermoSlyD-IGF-1 | 18 | 16 | 4.21E-04 | 27 |
| 10.0.01 | thermoSlyD (wildtyp) | 13 | 12 | 1.39E-04 | 83 |
| 10.0.01 | IGF2 | 1 | 0 | n.d. | n.d. |
| 10.0.03 | IGF1 | 16 | 12 | 7.43E-04 | 16 |
| 10.0.03 | thermoSlyD-IGF-1 | 35 | 31 | 3.86E-04 | 30 |
| 10.0.03 | thermoSlyD (wildtyp) | 3 | 1 | n.d. | n.d. |
| 10.0.03 | IGF2 | 3 | 1 | n.d. | n.d. |
| 10.0.04 | IGF1 | 6 | 5 | 2.93E-04 | 39 |
| 10.0.04 | thermoSlyD-IGF-1 | 23 | 16 | 6.58E-04 | 18 |
| 10.0.04 | thermoSlyD (wildtyp) | 16 | 4 | 2.40E-03 | 5 |
| 10.0.04 | IGF2 | 2 | 0 | n.d. | n.d. |
| 10.0.05 | IGF1 | 7 | 6 | 8.04E-04 | 14 |
| 10.0.05 | thermoSlyD-IGF-1 | 38 | 35 | 3.02E-04 | 38 |
| 10.0.05 | thermoSlyD (wildtyp) | 31 | 28 | 1.96E-04 | 59 |
| 10.0.05 | IGF2 | 2 | 0 | n.d. | n.d. |
| 10.0.07 | IGF1 | 18 | 13 | 9.26E-04 | 12 |
| 10.0.07 | thermoSlyD-IGF-1 | 37 | 31 | 5.08E-04 | 23 |
| 10.0.07 | thermoSlyD (wildtyp) | 0 | -2 | n.d. | n.d. |
| 10.0.07 | IGF2 | 1 | -1 | n.d. | n.d. |
| 10.0.08 | IGF1 | 17 | 11 | 1.31E-03 | 9 |
| 10.0.08 | thermoSlyD-IGF-1 | 35 | 29 | 6.40E-04 | 18 |
| 10.0.08 | thermoSlyD (wildtyp) | 2 | 1 | n.d. | n.d. |
| 10.0.08 | IGF2 | 2 | 1 | n.d. | n.d. |

*FIG. 32A*

| 3 | 2 | 1 | M* | °C | kd [1/s] | t/2 diss [min] |
|---|---|---|---|---|---|---|
| | | 10.1.3 | IGF1 | 37 | 3.25E-04 | 36 |
| | | 10.1.3 | IGF2 | 37 | | |
| | | 10.1.3 | tSlyD-GF1 | 37 | 1.00E-05 | 1155 |
| | | 10.1.3 | tS1/d-wt | 37 | | |
| | | 10.2.3 | IGF1 | 37 | 8.80E-04 | 13 |
| | | 10.2.3 | IGF2 | 37 | | |
| | | 10.2.3 | tSlyD-GF1 | 37 | 1.00E-05 | 1155 |
| | | 10.2.3 | tS1/d-wt | 37 | | |
| | | 10.3.7 | IGF1 | 37 | 1.18E-03 | 10 |
| | | 10.3.7 | IGF2 | 37 | | |
| | | 10.3.7 | tSlyD-GF1 | 37 | 1.00E-05 | 1155 |
| | | 10.3.7 | tS1/d-wt | 37 | | |
| | | 10.4.7 | IGF1 | 37 | 1.00E-05 | 1155 |
| | | 10.4.7 | IGF2 | 37 | | |
| | | 10.4.7 | tSlyD-GF1 | 37 | 1.00E-05 | 1155 |
| | | 10.4.7 | tS1/d-wt | 37 | | |
| | | 10.5.8 | IGF1 | 37 | 1.00E-05 | 1155 |
| | | 10.5.8 | IGF2 | 37 | | |
| | | 10.5.8 | tSlyD-GF1 | 37 | 1.00E-05 | 1155 |
| | | 10.5.8 | tS1/d-wt | 37 | | |
| | | 10.6.8 | IGF1 | 37 | 1.25E-04 | 92 |
| | | 10.6.8 | IGF2 | 37 | | |
| | | 10.6.8 | tSlyD-GF1 | 37 | 1.00E-05 | 1155 |
| | | 10.6.8 | tS1/d-wt | 37 | | |
| | | 10.7.9 | IGF1 | 37 | 1.00E-05 | 1155 |
| | | 10.7.9 | IGF2 | 37 | | |
| | | 10.7.9 | tSlyD-GF1 | 37 | 1.00E-05 | 1155 |
| | | 10.7.9 | tS1/d-wt | 37 | | |
| | | 10.8.9 | IGF1 | 37 | 1.00E-05 | 1155 |
| | | 10.8.9 | IGF2 | 37 | | |
| | | 10.8.9 | tSlyD-GF1 | 37 | 1.00E-05 | 1155 |
| | | 10.8.9 | tS1/d-wt | 37 | | |
| | | 11.9.15 | IGF1 | 37 | 1.00E-05 | 1155 |
| | | 11.9.15 | IGF2 | 37 | | |
| | | 11.9.15 | tSlyD-GF1 | 37 | 1.00E-05 | 1155 |
| | | 11.9.15 | tS1/d-wt | 37 | | |
| | | 11.10.15 | IGF1 | 37 | 1.00E-05 | 1155 |
| | | 11.10.15 | IGF2 | 37 | | |
| | | 11.10.15 | tSlyD-GF1 | 37 | 1.00E-05 | 1155 |
| | | 11.10.15 | tS1/d-wt | 37 | | |
| | | 11.11.17 | IGF1 | 37 | 1.00E-05 | 1155 |
| | | 11.11.17 | IGF2 | 37 | | |
| | | 11.11.17 | tSlyD-GF1 | 37 | 1.00E-05 | 1155 |
| | | 11.11.17 | tS1/d-wt | 37 | | |
| | | 11.12.17 | IGF1 | 37 | 1.00E-05 | 1155 |
| | | 11.12.17 | IGF2 | 37 | | |
| | | 11.12.17 | tSlyD-GF1 | 37 | 1.00E-05 | 1155 |
| | | 11.12.17 | tS1/d-wt | 37 | | |

FIG. 32B

| pAb | Ag | °C | ka 1/Ms | kd 1/s | t/2-diss min | KA l/mol | KD M | KD nM |
|---|---|---|---|---|---|---|---|---|
| 10.1.3 | IGF1 | 37 | 1.8E+06 | 6.0E-03 | 2 | 3.1E+08 | 3.3E-09 | 3.3 |
| 10.2.3 | IGF1 | 37 | 1.2E+06 | 5.9E-03 | 2 | 2.0E+08 | 5.1E-09 | 5.1 |
| 10.3.7 | IGF1 | 37 | 1.6E+06 | 6.0E-03 | 2 | 2.6E+08 | 3.8E-09 | 3.8 |
| 10.4.7 | IGF1 | 37 | 1.5E+06 | 6.2E-03 | 2 | 2.3E+08 | 4.3E-09 | 4.3 |
| 10.5.8 | IGF1 | 37 | 1.7E+06 | 6.7E-03 | 2 | 2.6E+08 | 3.9E-09 | 3.9 |
| 10.6.8 | IGF1 | 37 | 1.5E+06 | 6.2E-03 | 2 | 2.4E+08 | 4.2E-09 | 4.2 |
| 10.7.9 | IGF1 | 37 | 1.3E+06 | 6.0E-03 | 2 | 2.2E+08 | 4.5E-09 | 4.5 |
| 10.8.9 | IGF1 | 37 | 1.7E+06 | 6.8E-03 | 2 | 2.4E+08 | 4.1E-09 | 4.1 |
| 11.9.15 | IGF1 | 37 | 3.0E+06 | 2.8E-04 | 41 | 1.1E+10 | 9.4E-11 | 0.1 |
| 11.10.15 | IGF1 | 37 | 2.2E+06 | 1.7E-04 | 68 | 1.3E+10 | 7.7E-11 | 0.1 |
| 11.11.17 | IGF1 | 37 | 3.1E+06 | 1.4E-04 | 81 | 2.2E+10 | 4.6E-11 | 0.0 |
| 11.12.17 | IGF1 | 37 | 2.9E+06 | 1.8E-04 | 64 | 1.6E+10 | 6.2E-11 | 0.1 |

FIG. 33

SEQUENCE LISTING

```
<160> NUMBER OF SEQ ID NOS: 143

<210> SEQ ID NO 1
<211> LENGTH: 129
<212> TYPE: PRT
<213> ORGANISM: Arabidopsis thaliana

<400> SEQUENCE: 1

Glu Thr Thr Ser Cys Glu Phe Ser Val Ser Pro Ser Gly Leu Ala Phe
1               5                   10                  15

Cys Asp Lys Val Val Gly Tyr Gly Pro Glu Ala Val Lys Gly Gln Leu
            20                  25                  30

Ile Lys Ala His Tyr Val Gly Lys Leu Glu Asn Gly Lys Val Phe Asp
        35                  40                  45

Ser Ser Tyr Asn Arg Gly Lys Pro Leu Thr Phe Arg Ile Gly Val Gly
    50                  55                  60

Glu Val Ile Lys Gly Trp Asp Gln Gly Ile Leu Gly Ser Asp Gly Ile
65                  70                  75                  80

Pro Pro Met Leu Thr Gly Gly Lys Arg Thr Leu Arg Ile Pro Pro Glu
                85                  90                  95

Leu Ala Tyr Gly Asp Arg Gly Ala Gly Cys Lys Gly Gly Ser Cys Leu
            100                 105                 110

Ile Pro Pro Ala Ser Val Leu Leu Phe Asp Ile Glu Tyr Ile Gly Lys
        115                 120                 125

Ala

<210> SEQ ID NO 2
<211> LENGTH: 6
<212> TYPE: PRT
<213> ORGANISM: Arabidopsis thaliana

<400> SEQUENCE: 2

Asp Arg Gly Ala Gly Cys
1               5

<210> SEQ ID NO 3
<211> LENGTH: 8
<212> TYPE: PRT
<213> ORGANISM: Arabidopsis thaliana

<400> SEQUENCE: 3

Cys Leu Ile Pro Pro Ala Ser Val
1               5

<210> SEQ ID NO 4
<211> LENGTH: 106
<212> TYPE: PRT
```

<213> ORGANISM: Arabidopsis thaliana

<400> SEQUENCE: 4

Glu Thr Thr Ser Cys Glu Phe Ser Val Ser Pro Gly Leu Ala Phe
1               5                   10                  15

Cys Asp Lys Val Val Gly Tyr Gly Pro Glu Ala Val Lys Gly Gln Leu
            20                  25                  30

Ile Lys Ala His Tyr Val Gly Lys Leu Glu Asn Gly Lys Val Phe Asp
        35                  40                  45

Ser Ser Tyr Asn Arg Gly Lys Pro Leu Thr Phe Arg Ile Gly Val Gly
    50                  55                  60

Glu Val Ile Lys Gly Trp Asp Gln Gly Ile Leu Gly Ser Asp Gly Ile
65                  70                  75                  80

Pro Pro Met Leu Thr Gly Gly Lys Arg Thr Leu Arg Ile Pro Pro Glu
                85                  90                  95

Leu Ala Tyr Gly Asp Arg Gly Ala Gly Cys
            100                 105

<210> SEQ ID NO 5
<211> LENGTH: 19
<212> TYPE: PRT
<213> ORGANISM: Arabidopsis thaliana

<400> SEQUENCE: 5

Cys Leu Ile Pro Pro Ala Ser Val Leu Leu Phe Asp Ile Glu Tyr Ile
1               5                   10                  15

Gly Lys Ala

<210> SEQ ID NO 6
<211> LENGTH: 108
<212> TYPE: PRT
<213> ORGANISM: Homo sapiens

<400> SEQUENCE: 6

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 7
<211> LENGTH: 83
<212> TYPE: PRT
<213> ORGANISM: Homo sapiens

<400> SEQUENCE: 7

Gly Val Gln Val Glu Thr Ile Ser Pro Gly Asp Gly Arg Thr Phe Pro
1               5                   10                  15

Lys Arg Gly Gln Thr Ala Val Val His Tyr Thr Gly Met Leu Glu Asp

```
                 20                  25                  30
Gly Lys Lys Phe Asp Ser Ser Arg Asp Arg Asn Lys Pro Phe Lys Phe
             35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly

<210> SEQ ID NO 8
<211> LENGTH: 11
<212> TYPE: PRT
<213> ORGANISM: Homo sapiens

<400> SEQUENCE: 8

Leu Val Phe Asp Val Glu Leu Leu Lys Leu Glu
  1               5                  10

<210> SEQ ID NO 9
<211> LENGTH: 149
<212> TYPE: PRT
<213> ORGANISM: Thermus thermophilus

<400> SEQUENCE: 9

Met Lys Val Gly Gln Asp Lys Val Val Thr Ile Arg Tyr Thr Leu Gln
  1               5                  10                  15

Val Glu Gly Glu Val Leu Asp Gln Gly Glu Leu Ser Tyr Leu His Gly
             20                  25                  30

His Arg Asn Leu Ile Pro Gly Leu Glu Glu Ala Leu Glu Gly Arg Glu
         35                  40                  45

Glu Gly Glu Ala Phe Gln Ala His Val Pro Ala Glu Lys Ala Tyr Gly
 50                  55                  60

Pro His Asp Pro Glu Gly Val Gln Val Val Pro Leu Ser Ala Phe Pro
 65                  70                  75                  80

Glu Asp Ala Glu Val Val Pro Gly Ala Gln Phe Tyr Ala Gln Asp Met
                 85                  90                  95

Glu Gly Asn Pro Met Pro Leu Thr Val Val Ala Val Glu Gly Glu Glu
            100                 105                 110

Val Thr Val Asp Phe Asn His Pro Leu Ala Gly Lys Asp Leu Asp Phe
        115                 120                 125

Gln Val Glu Val Val Lys Val Arg Glu Ala Thr Pro Glu Glu Leu Leu
    130                 135                 140

His Gly His Ala His
145

<210> SEQ ID NO 10
<211> LENGTH: 63
<212> TYPE: PRT
<213> ORGANISM: Thermus thermophilus

<400> SEQUENCE: 10

Lys Val Gly Gln Asp Lys Val Val Thr Ile Arg Tyr Thr Leu Gln Val
  1               5                  10                  15

Glu Gly Glu Val Leu Asp Gln Gly Glu Leu Ser Tyr Leu His Gly His
             20                  25                  30

Arg Asn Leu Ile Pro Gly Leu Glu Glu Ala Leu Glu Gly Arg Glu Glu
         35                  40                  45
```

```
Gly Glu Ala Phe Gln Ala His Val Pro Ala Glu Lys Ala Tyr Gly
    50                  55                  60
```

<210> SEQ ID NO 11
<211> LENGTH: 27
<212> TYPE: PRT
<213> ORGANISM: Thermus thermophilus

<400> SEQUENCE: 11

```
Gly Lys Asp Leu Asp Phe Gln Val Glu Val Lys Val Arg Glu Ala
1               5                   10                  15

Thr Pro Glu Glu Leu Leu His Gly His Ala His
            20                  25
```

<210> SEQ ID NO 12
<211> LENGTH: 165
<212> TYPE: PRT
<213> ORGANISM: Escherichia coli

<400> SEQUENCE: 12

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp
                165
```

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      X2 linker peptide

<400> SEQUENCE: 13

```
Gly Gly Gly Ser Gly Gly Gly Ser Gly Gly Gly Ser
1               5                   10
```

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic X2 linker peptide

<400> SEQUENCE: 14

Gly Gly Gly Ser Gly Gly Gly Ser Gly Gly Gly Ser Gly Gly Gly Ser
1               5                   10                  15

Gly Gly Gly Ser Gly Gly Gly
            20

<210> SEQ ID NO 15
<211> LENGTH: 100
<212> TYPE: PRT
<213> ORGANISM: Artificial Sequence
<220> FEATURE:
<223> OTHER INFORMATION: Description of Artificial Sequence: Synthetic
      X1 linker peptide
<220> FEATURE:
<221> NAME/KEY: MOD_RES
<222> LOCATION: (9)..(93)
<223> OTHER INFORMATION: Any amino acid and this region may encompass 9
      to 85 residues

<400> SEQUENCE: 15

Gly Gly Gly Ser Gly Gly Asn Pro Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Gly Pro Thr
                85                  90                  95

Gly Gly Gly Ser
            100

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      purification tag peptide

<400> SEQUENCE: 16

Gly Ser Arg Lys His His His His His His His His
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptidic linker sequence

<400> SEQUENCE: 17

Gly Gly Gly Gly Ser
1               5

<210> SEQ ID NO 18
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptidic linker sequence

<400> SEQUENCE: 18

Gln Gln Gln Gln Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptidic linker sequence

<400> SEQUENCE: 19

Ser Ser Ser Ser Gly
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptidic linker sequence

<400> SEQUENCE: 20

Gly Ser Ser Ser Ser Ser Ser Ser Ser Ser Ser Ser Ser Ser Ser
1               5                   10                  15

Gly

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptidic linker sequence

<400> SEQUENCE: 21

Gly Gln Gln Gln Gln Gly Gln Gln Gln Gln Gly Gln Gln Gln Gln Gly
1               5                   10                  15

Asn Asn

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptidic linker sequence

<400> SEQUENCE: 22

Gly Gly Gly Ser Gly Gly Gly Gly Ser Gly Gly Gly Gly Ser Gly
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptidic linker sequence
```

```
<400> SEQUENCE: 23

Gly Gly Gly Ser Gly Gly Gly Ser Gly Gly Gly Ser Gly Gly
1               5                   10                  15

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptidic linker sequence

<400> SEQUENCE: 24

Gly Gly Gly Ser Gly Gly Gly Ser Gly Gly Gly Ser Gly Gly Gly Ser
1               5                   10                  15

Gly Gly Gly Ser Gly Gly Gly
            20

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 25

Gly Gln Gln Gln Gln Gly Gln Gln Gln Gln Gly Gln Gln Gln Gln
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 26

Gly Gln Gln Gln Gln Gly Gln Gln Gln Gln Gly Gln Gln Gln Gln Gly
1               5                   10                  15

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 27

Gly Gln Gln Gln Gln Gly Gln Gln Gln Gln Gly Gln Gln Gln Gln Gly
1               5                   10                  15

Asn Asn

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 28

Gly Gly Ser Gly Gly Ser Gly Gly Ser
1               5
```

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 29

Gly Gly Ser Gly Gly Ser Gly Gly Ser Gly Gly Ser
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 30

Gly Gly Ser Gly Gly Ser Gly Gly Ser Gly Gly Ser Gly Gly Ser
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 31

Gly Gly Gly Ser Gly Gly Gly Ser Gly Gly Gly Ser
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 32

Gly Gly Gly Ser Gly Gly Gly Ser Gly Gly Gly Ser Gly Gly Gly Ser
1               5                   10                  15

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 33

Gly Gly Gly Ser Gly Gly Gly Ser Gly Gly Gly Ser Gly Gly Gly Ser
1               5                   10                  15

Gly Gly Gly Ser
            20

<210> SEQ ID NO 34
<211> LENGTH: 23
<212> TYPE: PRT
<213> ORGANISM: Artificial Sequence

```
<220> FEATURE:
<223> OTHER INFORMATION: Description of Artificial Sequence: Synthetic
      connector peptide

<400> SEQUENCE: 34

Gly Gly Gly Ser Gly Gly Gly Ser Gly Gly Gly Ser Gly Gly Gly Ser
1               5                   10                  15

Gly Gly Gly Ser Gly Gly Gly
            20

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 35

Gly Gly Gly Gly Ser Gly Gly Gly Gly Ser
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 36

Gly Gly Gly Gly Ser Gly Gly Gly Gly Ser Gly
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 37

Gly Gly Gly Gly Ser Gly Gly Gly Gly Ser Gly Gly
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 38

Gly Gly Gly Gly Ser Gly Gly Gly Gly Ser Gly Gly Gly
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 39
```

Gly Gly Gly Gly Ser Gly Gly Gly Gly Ser Gly Asn
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 40

Gly Gly Gly Gly Ser Gly Gly Gly Gly Ser Gly Gly Gly Gly Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 41

Gly Gly Gly Gly Ser Gly Gly Gly Gly Ser Gly Gly Gly Gly Ser Gly
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 42

Gly Gly Gly Gly Ser Gly Gly Gly Gly Ser Gly Gly Gly Gly Ser Thr
1               5                   10                  15

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 43

Gly Gly Gly Gly Ser Gly Gly Gly Gly Ser Gly Gly Gly Gly Ser Gly
1               5                   10                  15

Gly

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 44

Gly Gly Gly Gly Ser Gly Gly Gly Gly Ser Gly Gly Gly Gly Ser Gly
1               5                   10                  15

Gly Thr

<210> SEQ ID NO 45

```
<211> LENGTH: 18
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 45

Gly Gly Gly Gly Ser Gly Gly Gly Ser Gly Gly Gly Gly Ser Gly
1               5                   10                  15

Gly Asn

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 46

Gly Gly Gly Gly Ser Gly Gly Gly Ser Gly Gly Gly Gly Ser Gly
1               5                   10                  15

Ala Ser

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 47

Gly Gly Gly Gly Ser Gly Gly Gly Gly Ser Gly Gly Gly Ser Gly
1               5                   10                  15

Gly Gly Gly Ser
            20

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 48

Gly Gly Gly Gly Ser Gly Gly Gly Gly Ser Gly Gly Gly Ser Gly
1               5                   10                  15

Gly Gly Ser Gly Gly Gly Gly Ser
            20                  25

<210> SEQ ID NO 49
<211> LENGTH: 26
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 49

Gly Gly Gly Gly Ser Gly Gly Gly Ser Gly Gly Gly Gly Ser Gly
1               5                   10                  15

Gly Gly Ser Gly Gly Gly Gly Ser Gly
```

20 25

<210> SEQ ID NO 50
<211> LENGTH: 27
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 50

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 51

Gly Gly Gly Gly Ser Gly Gly Gly Ser Gly Gly Gly Gly Ser Gly
1               5                   10                  15

Gly Gly Gly Ser Gly Gly Gly Gly Ser Gly Ala Ser
            20                  25

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 52

Gly Ser Ser Ser Ser Ser Ser Ser Ser Ser Ser Ser Ser Ser Ser
1               5                   10                  15

Gly

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      connector peptide

<400> SEQUENCE: 53

Gly Ser Ser Ser Ser Ser Ser Ser Ser Ser Ser Ser Ser Ser Ser
1               5                   10                  15

Gly Ala Ser

<210> SEQ ID NO 54
<211> LENGTH: 116
<212> TYPE: PRT
<213> ORGANISM: Artificial Sequence
<220> FEATURE:
<223> OTHER INFORMATION: Description of Artificial Sequence: Synthetic
      FKBP12/13 polypeptide
<220> FEATURE:
<221> NAME/KEY: misc_feature
<222> LOCATION: (94)..(95)

<223> OTHER INFORMATION: Residues at these positions are separated by an
     undefined amino acid sequence of a linker, or a peptide, or an
     antigen, or a secondary or tertiary structure to be presented by
     the FKBP12/13 fusion polypeptide
<220> FEATURE:
<223> OTHER INFORMATION: See specification as filed for detailed
     description of substitutions and preferred embodiments

<400> SEQUENCE: 54

Met Arg Ser Gly Val Gln Val Glu Thr Ile Ser Pro Gly Asp Gly Arg
1               5                   10                  15

Thr Phe Pro Lys Arg Gly Gln Thr Ala Val Val His Tyr Thr Gly Met
            20                  25                  30

Leu Glu Asp Gly Lys Lys Phe Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Asp Arg Gly Ala Gly Cys Gly Ser Gly Ser
                85                  90                  95

Ser Cys Leu Ile Pro Pro Ala Ser Val Leu Val Phe Asp Val Glu Leu
            100                 105                 110

Leu Lys Leu Glu
        115

<210> SEQ ID NO 55
<211> LENGTH: 278
<212> TYPE: PRT
<213> ORGANISM: Artificial Sequence
<220> FEATURE:
<223> OTHER INFORMATION: Description of Artificial Sequence: Synthetic
     SlyD-SKBP12/13 fusion polypeptide
<220> FEATURE:
<221> NAME/KEY: misc_feature
<222> LOCATION: (165)..(166)
<223> OTHER INFORMATION: Residues at these positions are separated by an
     undefined amino acid linker
<220> FEATURE:
<221> NAME/KEY: misc_feature
<222> LOCATION: (256)..(257)
<223> OTHER INFORMATION: Residues at these positions are separated by an
     undefined amino acid sequence of a linker, or a peptide, or an
     antigen, or a secondary or tertiary structure to be presented by
     the SlyD-FKBP12/13 fusion polypeptide
<220> FEATURE:
<223> OTHER INFORMATION: See specification as filed for detailed
     description of substitutions and preferred embodiments

<400> SEQUENCE: 55

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val

```
                    100                 105                 110
Glu Asp Asp His Val Val Asp Gly Asn His Met Leu Ala Gly Gln
            115                 120                 125

Asn Leu Lys Phe Asn Val Glu Val Ala Ile Arg Glu Ala Thr Glu
        130                 135                 140

Glu Glu Leu Ala His Gly His Val His Gly Ala His Asp His His
145                 150                 155                 160

Asp His Asp His Asp Gly Val Gln Val Glu Thr Ile Ser Pro Gly Asp
                165                 170                 175

Gly Arg Thr Phe Pro Lys Arg Gly Gln Thr Ala Val Val His Tyr Thr
                180                 185                 190

Gly Met Leu Glu Asp Gly Lys Lys Phe Asp Ser Ser Arg Asp Arg Asn
        195                 200                 205

Lys Pro Phe Lys Phe Met Leu Gly Lys Gln Glu Val Ile Arg Gly Trp
210                 215                 220

Glu Glu Gly Val Ala Gln Met Ser Val Gly Gln Arg Ala Lys Leu Thr
225                 230                 235                 240

Ile Ser Pro Asp Tyr Ala Tyr Gly Asp Arg Gly Ala Gly Cys Gly Ser
                245                 250                 255

Gly Ser Ser Cys Leu Ile Pro Pro Ala Ser Val Leu Val Phe Asp Val
                260                 265                 270

Glu Leu Leu Lys Leu Glu
            275

<210> SEQ ID NO 56
<211> LENGTH: 92
<212> TYPE: PRT
<213> ORGANISM: Artificial Sequence
<220> FEATURE:
<223> OTHER INFORMATION: Description of Artificial Sequence: Synthetic
      ttslyD fusion polypeptide
<220> FEATURE:
<221> NAME/KEY: misc_feature
<222> LOCATION: (65)..(66)
<223> OTHER INFORMATION: Residues at these positions are separated by an
      undefined amino acid sequence of a linker, or a peptide, or an
      antigen, or a secondary or tertiary structure to be presented by
      the Thermus thermophilus SlyD fusion polypeptide
<220> FEATURE:
<223> OTHER INFORMATION: See specification as filed for detailed
      description of substitutions and preferred embodiments

<400> SEQUENCE: 56

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Lys Asp Leu Asp Phe Gln Val Glu Val Val Lys Val Arg Glu
65                  70                  75                  80

Ala Thr Pro Glu Glu Leu Leu His Gly His Ala His
            85                  90

<210> SEQ ID NO 57
<211> LENGTH: 254
<212> TYPE: PRT
<213> ORGANISM: Artificial Sequence
```

-continued

```
<220> FEATURE:
<223> OTHER INFORMATION: Description of Artificial Sequence: Synthetic
      ttslyD-ecslyD fusion polypeptide
<220> FEATURE:
<221> NAME/KEY: misc_feature
<222> LOCATION: (165)..(166)
<223> OTHER INFORMATION: Residues at these positions are separated by an
      undefined amino acid linker
<220> FEATURE:
<221> NAME/KEY: misc_feature
<222> LOCATION: (227)..(228)
<223> OTHER INFORMATION: Residues at these positions are separated by an
      undefined amino acid sequence of a linker, or a peptide, or an
      antigen, or a secondary or tertiary structure to be presented by
      the SlyD-Thermus thermophilus SlyD fusion polypeptide
<220> FEATURE:
<223> OTHER INFORMATION: See specification as filed for detailed
      description of substitutions and preferred embodiments

<400> SEQUENCE: 57

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Lys Val Gly Gln Asp Lys Val Val Thr Ile Arg
                165                 170                 175

Tyr Thr Leu Gln Val Glu Gly Glu Val Leu Asp Gln Gly Glu Leu Ser
            180                 185                 190

Tyr Leu His Gly His Arg Asn Leu Ile Pro Gly Leu Glu Glu Ala Leu
        195                 200                 205

Glu Gly Arg Glu Glu Gly Glu Ala Phe Gln Ala His Val Pro Ala Glu
    210                 215                 220

Lys Ala Tyr Gly Lys Asp Leu Asp Phe Gln Val Glu Val Val Lys Val
225                 230                 235                 240

Arg Glu Ala Thr Pro Glu Glu Leu Leu His Gly His Ala His
                245                 250

<210> SEQ ID NO 58
<211> LENGTH: 109
<212> TYPE: PRT
<213> ORGANISM: Artificial Sequence
<220> FEATURE:
<223> OTHER INFORMATION: Description of Artificial Sequence: Synthetic
      T.thermophilus SlyD-FKBP13 fusion polypeptide
<220> FEATURE:
<221> NAME/KEY: misc_feature
```

```
<222> LOCATION: (74)..(75)
<223> OTHER INFORMATION: Residues at these positions are separated by an
      undefined amino acid sequence of a linker, or a peptide, or an
      antigen, or a secondary or tertiary structure to be presented by
      the Thermus thermophilus SlyD-FKBP13 fusion polypeptide
<220> FEATURE:
<223> OTHER INFORMATION: See specification as filed for detailed
      description of substitutions and preferred embodiments

<400> SEQUENCE: 58

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Gly Glu Ala Phe Gln Ala His Val Pro Ala Glu Lys Ala
50                  55                  60

Tyr Gly Asp Arg Gly Ala Gly Cys Gly Ser Gly Ser Ser Cys Leu Ile
65                  70                  75                  80

Pro Pro Ala Ser Val Leu Asp Phe Gln Val Glu Val Val Lys Val Arg
            85                  90                  95

Glu Ala Thr Pro Glu Glu Leu Leu His Gly His Ala His
            100                 105

<210> SEQ ID NO 59
<211> LENGTH: 271
<212> TYPE: PRT
<213> ORGANISM: Artificial Sequence
<220> FEATURE:
<223> OTHER INFORMATION: Description of Artificial Sequence: Synthetic
      SlyD-T.thermophilus SlyD-FKBP13 fusion polypeptide
<220> FEATURE:
<221> NAME/KEY: misc_feature
<222> LOCATION: (165)..(166)
<223> OTHER INFORMATION: Residues at these positions are separated by an
      undefined amino acid linker
<220> FEATURE:
<221> NAME/KEY: misc_feature
<222> LOCATION: (236)..(237)
<223> OTHER INFORMATION: Residues at these positions are separated by an
      undefined amino acid sequence of a linker, or a peptide, or an
      antigen, or a secondary or tertiary structure to be presented by
      the SlyD-Thermus thermophilus SlyD-FKBP13 fusion polypeptide
<220> FEATURE:
<223> OTHER INFORMATION: See specification as filed for detailed
      description of substitutions and preferred embodiments

<400> SEQUENCE: 59

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110
```

Glu Asp Asp His Val Val Asp Gly Asn His Met Leu Ala Gly Gln
            115                 120                 125

Asn Leu Lys Phe Asn Val Glu Val Ala Ile Arg Glu Ala Thr Glu
            130                 135                 140

Glu Glu Leu Ala His Gly His Val His Gly Ala His Asp His His
145                 150                 155                 160

Asp His Asp His Asp Lys Val Gly Gln Asp Lys Val Val Thr Ile Arg
                165                 170                 175

Tyr Thr Leu Gln Val Glu Gly Glu Val Leu Asp Gln Gly Glu Leu Ser
            180                 185                 190

Tyr Leu His Gly His Arg Asn Leu Ile Pro Gly Leu Glu Glu Ala Leu
            195                 200                 205

Glu Gly Arg Glu Glu Gly Glu Ala Phe Gln Ala His Val Pro Ala Glu
            210                 215                 220

Lys Ala Tyr Gly Asp Arg Gly Ala Gly Cys Gly Ser Gly Ser Ser Cys
225                 230                 235                 240

Leu Ile Pro Pro Ala Ser Val Leu Asp Phe Gln Val Glu Val Val Lys
            245                 250                 255

Val Arg Glu Ala Thr Pro Glu Glu Leu Leu His Gly His Ala His
            260                 265                 270

<210> SEQ ID NO 60
<211> LENGTH: 130
<212> TYPE: PRT
<213> ORGANISM: Artificial Sequence
<220> FEATURE:
<223> OTHER INFORMATION: Description of Artificial Sequence: Synthetic
      A.thaliana FKBP13 fusion polypeptide
<220> FEATURE:
<221> NAME/KEY: misc_feature
<222> LOCATION: (108)..(109)
<223> OTHER INFORMATION: Residues at these positions are separated by an
      undefined amino acid sequence of a linker, or a peptide, or an
      antigen, or a secondary or tertiary structure to be presented by
      the Arabidopsis thaliana FKBP13 fusion polypeptide
<220> FEATURE:
<223> OTHER INFORMATION: See specification as filed for detailed
      description of substitutions and preferred embodiments

<400> SEQUENCE: 60

Glu Thr Thr Ser Cys Glu Phe Ser Val Ser Pro Ser Gly Leu Ala Phe
1               5                   10                  15

Cys Asp Lys Val Val Gly Tyr Gly Pro Glu Ala Val Lys Gly Gln Leu
            20                  25                  30

Ile Lys Ala His Tyr Val Gly Lys Leu Glu Asn Gly Lys Val Phe Asp
            35                  40                  45

Ser Ser Tyr Asn Arg Gly Lys Pro Leu Thr Phe Arg Ile Gly Val Gly
50                  55                  60

Glu Val Ile Lys Gly Trp Asp Gln Gly Ile Leu Gly Ser Asp Gly Ile
65                  70                  75                  80

Pro Pro Met Leu Thr Gly Gly Lys Arg Thr Leu Arg Ile Pro Pro Glu
            85                  90                  95

Leu Ala Tyr Gly Asp Arg Gly Ala Gly Cys Gly Ser Gly Ser Ser Cys
            100                 105                 110

Leu Ile Pro Pro Ala Ser Val Leu Leu Phe Asp Ile Glu Tyr Ile Gly
            115                 120                 125

Lys Ala
    130

```
<210> SEQ ID NO 61
<211> LENGTH: 295
<212> TYPE: PRT
<213> ORGANISM: Artificial Sequence
<220> FEATURE:
<223> OTHER INFORMATION: Description of Artificial Sequence: Synthetic
      SlyD-A.thaliana FKBP13 fusion polypeptide
<220> FEATURE:
<221> NAME/KEY: misc_feature
<222> LOCATION: (165)..(166)
<223> OTHER INFORMATION: Residues at these positions are separated by an
      undefined amino acid linker
<220> FEATURE:
<221> NAME/KEY: misc_feature
<222> LOCATION: (273)..(274)
<223> OTHER INFORMATION: Residues at these positions are separated by an
      undefined amino acid sequence of a linker, or a peptide, or an
      antigen, or a secondary or tertiary structure to be presented by
      the SlyD-Arabidopsis thaliana FKBP13 fusion polypeptide
<220> FEATURE:
<223> OTHER INFORMATION: See specification as filed for detailed
      description of substitutions and preferred embodiments

<400> SEQUENCE: 61

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Glu Thr Thr Ser Cys Glu Phe Ser Val Ser Pro
                165                 170                 175

Ser Gly Leu Ala Phe Cys Asp Lys Val Val Gly Tyr Gly Pro Glu Ala
            180                 185                 190

Val Lys Gly Gln Leu Ile Lys Ala His Tyr Val Gly Lys Leu Glu Asn
        195                 200                 205

Gly Lys Val Phe Asp Ser Ser Tyr Asn Arg Gly Lys Pro Leu Thr Phe
    210                 215                 220

Arg Ile Gly Val Gly Glu Val Ile Lys Gly Trp Asp Gln Gly Ile Leu
225                 230                 235                 240

Gly Ser Asp Gly Ile Pro Pro Met Leu Thr Gly Gly Lys Arg Thr Leu
                245                 250                 255

Arg Ile Pro Pro Glu Leu Ala Tyr Gly Asp Arg Gly Ala Gly Cys Gly
            260                 265                 270

Ser Gly Ser Ser Cys Leu Ile Pro Pro Ala Ser Val Leu Leu Phe Asp
        275                 280                 285
```

Ile Glu Tyr Ile Gly Lys Ala
    290             295

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 62

Arg Arg Arg Arg Arg
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 63

Arg Arg Arg Arg Arg Arg
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 64

His His His His His His
1               5

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 65

Lys Asp His Leu Ile His Asn Val His Lys Glu Phe His Ala His Ala
1               5                   10                  15

His Asn Lys

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 66

Asp Tyr Lys Asp Asp Asp Asp Lys
1               5

<210> SEQ ID NO 67
<211> LENGTH: 22
<212> TYPE: PRT

```
<213> ORGANISM: Artificial Sequence
<220> FEATURE:
<223> OTHER INFORMATION: Description of Artificial Sequence: Synthetic
      amino acid tag peptide

<400> SEQUENCE: 67

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 68

Ala Trp Arg His Pro Gln Phe Gly Gly
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 69

Trp Ser His Pro Gln Phe Glu Lys
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 70

Met Asp Val Glu Ala Trp Leu Gly Ala Arg
1               5                   10

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 71

Met Asp Val Glu Ala Trp Leu Gly Ala Arg Val Pro Leu Val Glu Thr
1               5                   10                  15

<210> SEQ ID NO 72
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 72
```

```
Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 73

Glu Gln Lys Leu Ile Ser Glu Glu Asp Leu
1               5                   10

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 74

Lys Glu Thr Ala Ala Ala Lys Phe Glu Arg Gln His Met Asp Ser
1               5                   10                  15

<210> SEQ ID NO 75
<211> LENGTH: 26
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 75

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 76
<211> LENGTH: 47
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 76

Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
                35                  40                  45

<210> SEQ ID NO 77
<211> LENGTH: 32
<212> TYPE: PRT
```

<213> ORGANISM: Butyrivibrio fibrisolvens

<400> SEQUENCE: 77

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30

<210> SEQ ID NO 78
<211> LENGTH: 51
<212> TYPE: PRT
<213> ORGANISM: Artificial Sequence
<220> FEATURE:
<223> OTHER INFORMATION: Description of Artificial Sequence: Synthetic
      amino acid tag peptide

<400> SEQUENCE: 78

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50

<210> SEQ ID NO 79
<211> LENGTH: 209
<212> TYPE: PRT
<213> ORGANISM: Chondrus crispus

<400> SEQUENCE: 79

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
            20                  25                  30

Arg Val Val Phe Asp His Trp Lys Glu Ala Lys Pro Lys Thr Pro Tyr
        35                  40                  45

Ala Ala Leu Pro Met Leu Thr Val Asp Gly Met Gln Val Ala Gln Ser
    50                  55                  60

Asp Ala Ile Leu Arg Tyr Cys Gly Lys Leu Ala Gly Leu Tyr Pro Ser
65                  70                  75                  80

Asp Pro Leu Glu Ala Ala Lys Val Asp Glu Val Gly Val Ile Asp
            85                  90                  95

Asp Val Thr His Ala Met Tyr Arg Tyr Arg Gly Asp Asp Lys Asp Lys
            100                 105                 110

Leu Arg Glu Glu Arg Asp Lys Phe Ser Lys Val Asp Val Pro Arg Tyr
        115                 120                 125

Val Gly Ala Leu Glu Lys Arg Leu Glu Ala Phe Gly Asp Gly Pro Trp
    130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Lys Asp Leu
            165                 170                 175

Leu Glu Gly Tyr Val Arg Ile Val Lys Ser Tyr Ser Ala Val Met Glu
        180                 185                 190

His Pro Lys Val Thr Glu Trp Tyr Glu Lys Lys Pro Val Lys Met Phe
    195                 200                 205

Ser

<210> SEQ ID NO 80
<211> LENGTH: 396
<212> TYPE: PRT
<213> ORGANISM: Escherichia coli

<400> SEQUENCE: 80

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365
```

```
Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys
385                 390                 395

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 81

Gly Gly Gly Ser
1

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 82

Gly Gly Gly Ser Gly Gly Asn Pro
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 83

Gly Pro Thr Gly Gly Gly Ser
1               5

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      FKBP12-antigen fusion polypeptide
<220> FEATURE:
<221> NAME/KEY: misc_feature
<222> LOCATION: (87)..(88)
<223> OTHER INFORMATION: Residues at these positions are separated by an
      undefined amino acid sequence of a linker, or a peptide, or an
      antigen, or a secondary or tertiary structure to be presented by
      the FKBP12-antigen fusion polypeptide
<220> FEATURE:
<223> OTHER INFORMATION: See specification as filed for detailed
      description of substitutions and preferred embodiments

<400> SEQUENCE: 84

Met Gly Val Gln Val Glu Thr Ile Ser Pro Gly Asp Gly Arg Thr Phe
1               5                   10                  15

Pro Lys Arg Gly Gln Thr Ala Trp His Tyr Thr Gly Met Leu Glu Asp
                20                  25                  30

Gly Lys Lys Phe Asp Ser Ser Arg Asp Arg Asn Lys Pro Phe Lys Phe
            35                  40                  45
```

```
Met Leu Gly Lys Gln Glu Val Ile Arg Gly Trp Glu Gly Val Ala
        50                  55                  60

Gln Met Ser Val Gly Gln Arg Ala Lys Leu Thr Ile Ser Pro Asp Tyr
 65                  70                  75                  80

Ala Tyr Gly Gly Gly Gly Ser Gly Gly Gly Ser Thr Leu Val Phe Asp
                    85                  90                  95

Val Glu Leu Leu Lys Leu Glu Gly Gly Gly Ser Arg Lys His His His
                100                 105                 110

His His His His His
            115

<210> SEQ ID NO 85
<211> LENGTH: 305
<212> TYPE: PRT
<213> ORGANISM: Artificial Sequence
<220> FEATURE:
<223> OTHER INFORMATION: Description of Artificial Sequence: Synthetic
      SlyD/FKBP12-antigen fusion polypeptide
<220> FEATURE:
<221> NAME/KEY: misc_feature
<222> LOCATION: (275)..(276)
<223> OTHER INFORMATION: Residues at these positions are separated by an
      undefined amino acid sequence of a linker, or a peptide, or an
      antigen, or a secondary or tertiary structure to be presented by
      the SlyD/FKBP12-antigen fusion polypeptide
<220> FEATURE:
<223> OTHER INFORMATION: See specification as filed for detailed
      description of substitutions and preferred embodiments

<400> SEQUENCE: 85

Met Lys Val Ala Lys Asp Leu Val Val Ser Leu Ala Tyr Gln Val Arg
 1               5                  10                  15

Thr Glu Asp Gly Val Leu Val Asp Glu Ser Pro Val Ser Ala Pro Leu
                20                  25                  30

Asp Tyr Leu His Gly His Gly Ser Leu Ile Ser Gly Leu Glu Thr Ala
                35                  40                  45

Leu Glu Gly His Glu Val Gly Asp Lys Phe Asp Val Ala Val Gly Ala
        50                  55                  60

Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
                100                 105                 110

Glu Asp Asp His Val Val Val Asp Gly Asn His Met Leu Ala Gly Gln
                115                 120                 125

Asn Leu Lys Phe Asn Val Glu Val Val Ala Ile Arg Glu Ala Thr Glu
130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Val Gln Val
                180                 185                 190

Glu Thr Ile Ser Pro Gly Asp Gly Arg Thr Phe Pro Lys Arg Gly Gln
                195                 200                 205

Thr Ala Val Val His Tyr Thr Gly Met Leu Glu Asp Gly Lys Lys Phe
                210                 215                 220

Asp Ser Ser Arg Asp Arg Asn Lys Pro Phe Lys Phe Met Leu Gly Lys
```

```
225                 230                 235                 240

Gln Glu Val Ile Arg Gly Trp Glu Glu Gly Val Ala Gln Met Ser Val
                245                 250                 255

Gly Gln Arg Ala Lys Leu Thr Ile Ser Pro Asp Tyr Ala Tyr Gly Gly
                260                 265                 270

Gly Gly Ser Gly Gly Gly Ser Thr Leu Val Phe Asp Val Glu Leu Leu
                275                 280                 285

Lys Leu Glu Gly Gly Ser Arg Lys His His His His His His
290                 295                 300

His
305

<210> SEQ ID NO 86
<211> LENGTH: 312
<212> TYPE: PRT
<213> ORGANISM: Artificial Sequence
<220> FEATURE:
<223> OTHER INFORMATION: Description of Artificial Sequence: Synthetic
      SlyD/FKBP12-control polypeptide

<400> SEQUENCE: 86

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
                20                  25                  30

Asp Tyr Leu His Gly His Gly Ser Leu Ile Ser Gly Leu Glu Thr Ala
                35                  40                  45

Leu Glu Gly His Glu Val Gly Asp Lys Phe Asp Val Ala Val Gly Ala
50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
                100                 105                 110

Glu Asp Asp His Val Val Asp Gly Asn His Met Leu Ala Gly Gln
                115                 120                 125

Asn Leu Lys Phe Asn Val Glu Val Val Ala Ile Arg Glu Ala Thr Glu
                130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Val Gln Val
                180                 185                 190

Glu Thr Ile Ser Pro Gly Asp Gly Arg Thr Phe Pro Lys Arg Gly Gln
                195                 200                 205

Thr Ala Val Val His Tyr Thr Gly Met Leu Glu Asp Gly Lys Lys Phe
                210                 215                 220

Asp Ser Ser Arg Asp Arg Asn Lys Pro Phe Lys Phe Met Leu Gly Lys
225                 230                 235                 240

Gln Glu Val Ile Arg Gly Trp Glu Glu Gly Val Ala Gln Met Ser Val
                245                 250                 255

Gly Gln Arg Ala Lys Leu Thr Ile Ser Pro Asp Tyr Ala Tyr Gly Gly
                260                 265                 270
```

```
Gly Gly Ser Gly Gly Asn Pro Gly Pro Thr Gly Gly Ser Thr Leu
        275                 280                 285

Val Phe Asp Val Glu Leu Leu Lys Leu Glu Gly Gly Ser Arg Lys
    290                 295                 300

His His His His His His His His
305                 310

<210> SEQ ID NO 87
<211> LENGTH: 113
<212> TYPE: PRT
<213> ORGANISM: Artificial Sequence
<220> FEATURE:
<223> OTHER INFORMATION: Description of Artificial Sequence: Synthetic
      Thermus Thermophilus-SlyD-antigen fusion polypeptide
<220> FEATURE:
<221> NAME/KEY: misc_feature
<222> LOCATION: (70)..(71)
<223> OTHER INFORMATION: Residues at these positions are separated by an
      undefined amino acid sequence of a linker, or a peptide, or an
      antigen, or a secondary or tertiary structure to be presented by
      the Thermus Thermophilus-SlyD-antigen fusion polypeptide
<220> FEATURE:
<223> OTHER INFORMATION: See specification as filed for detailed
      description of substitutions and preferred embodiments

<400> SEQUENCE: 87

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
                20                  25                  30

Leu His Gly His Arg Asn Leu Ile Pro Gly Leu Glu Glu Ala Leu Glu
            35                  40                  45

Gly Arg Glu Glu Gly Glu Ala Phe Gln Ala His Val Pro Ala Glu Lys
        50                  55                  60

Ala Tyr Gly Pro His Gly Gly Ala Gly Lys Asp Leu Asp Phe Gln Val
65                  70                  75                  80

Glu Val Val Lys Val Arg Glu Ala Thr Pro Glu Glu Leu Leu His Gly
                85                  90                  95

His Ala His Gly Gly Gly Ser Arg Lys His His His His His His
            100                 105                 110

His

<210> SEQ ID NO 88
<211> LENGTH: 113
<212> TYPE: PRT
<213> ORGANISM: Artificial Sequence
<220> FEATURE:
<223> OTHER INFORMATION: Description of Artificial Sequence: Synthetic
      disulfide stabilized Thermus Thermophilus-SlyD-antigen
      fusion polypeptide
<220> FEATURE:
<221> NAME/KEY: misc_feature
<222> LOCATION: (70)..(71)
<223> OTHER INFORMATION: Residues at these positions are separated by an
      undefined amino acid sequence of a linker, or a peptide, or an
      antigen, or secondary or tertiary structure to be presented by the
      disulfide stabilized Thermus Thermophilus-SlyD-antigen fusion
      polypeptide
<220> FEATURE:
<223> OTHER INFORMATION: See specification as filed for detailed
      description of substitutions and preferred embodiments

<400> SEQUENCE: 88

Met Arg Gly Ser Lys Val Gly Gln Asp Lys Val Val Thr Ile Arg Tyr
1               5                   10                  15
```

Thr Leu Gln Val Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro Cys Gly Cys Gly Lys Asp Leu Asp Phe Gln Val
65              70                  75                  80

Glu Val Val Lys Val Arg Glu Ala Thr Pro Glu Glu Leu Leu His Gly
                85                  90                  95

His Ala His Gly Gly Gly Ser Arg Lys His His His His His His
            100                 105                 110

His

<210> SEQ ID NO 89
<211> LENGTH: 24
<212> TYPE: PRT
<213> ORGANISM: Homo sapiens

<400> SEQUENCE: 89

Ile Ala Ala Ser Arg Glu Asp Leu Ala Leu Ser Pro Gly Leu Gly Pro
1               5                   10                  15

Gln Lys Ala Arg Arg Leu Phe Asp
            20

<210> SEQ ID NO 90
<211> LENGTH: 149
<212> TYPE: PRT
<213> ORGANISM: Artificial Sequence
<220> FEATURE:
<223> OTHER INFORMATION: Description of Artificial Sequence: Synthetic
      FKBP12-ERCC1 fusion polypeptide

<400> SEQUENCE: 90

Met Gly Val Gln Val Glu Thr Ile Ser Pro Gly Asp Gly Arg Thr Phe
1               5                   10                  15

Pro Lys Arg Gly Gln Thr Ala Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65              70                  75                  80

Tyr Ala Tyr Gly Gly Gly Gly Ser Gly Gly Asn Pro Ile Ala Ala Ser
                85                  90                  95

Arg Glu Asp Leu Ala Leu Ser Pro Gly Leu Gly Pro Gln Lys Ala Arg
            100                 105                 110

Arg Leu Phe Asp Gly Pro Thr Gly Gly Ser Thr Leu Val Phe Asp
        115                 120                 125

Val Glu Leu Leu Lys Leu Glu Gly Gly Ser Arg Lys His His His
    130                 135                 140

His His His His His
145

<210> SEQ ID NO 91
<211> LENGTH: 322
<212> TYPE: PRT

<213> ORGANISM: Artificial Sequence
<220> FEATURE:
<223> OTHER INFORMATION: Description of Artificial Sequence: Synthetic
      SlyD/FKBP12-ERCC1 polypeptide

<400> SEQUENCE: 91

Met Lys Val Ala Lys Asp Leu Trp Ser Leu Ala Tyr Val Arg Thr Glu
1               5                   10                  15

Asp Gly Val Leu Val Asp Glu Ser Pro Val Ser Ala Pro Leu Asp Tyr
            20                  25                  30

Leu His Gly His Gly Ser Leu Ile Ser Gly Leu Glu Thr Ala Leu Glu
        35                  40                  45

Gly His Glu Val Gly Asp Lys Phe Asp Val Ala Val Gly Ala Asn Asp
    50                  55                  60

Ala Tyr Gly Tyr Asp Glu Asn Leu Val Arg Val Pro Lys Asp Val Phe
65                  70                  75                  80

Met Gly Val Asp Glu Leu Val Gly Met Arg Phe Leu Ala Glu Thr Asp
                85                  90                  95

Gly Pro Val Pro Val Glu Ile Thr Ala Val Glu Asp Asp His Val Trp
            100                 105                 110

Asp Gly Asn His Met Leu Ala Gly Asn Leu Lys Phe Asn Val Glu Trp
        115                 120                 125

Ala Ile Arg Glu Ala Thr Glu Glu Leu Ala His Gly His Val His
    130                 135                 140

Gly Ala His Asp His His Asp His Asp Gly Gly Ser
145                 150                 155                 160

Gly Gly Gly Ser Gly Gly Gly Ser Gly Gly Ser Gly Gly Gly Ser
                165                 170                 175

Gly Gly Gly Gly Val Val Glu Thr Ile Ser Pro Gly Asp Gly Arg Thr
            180                 185                 190

Phe Pro Lys Arg Gly Thr Ala Trp His Tyr Thr Gly Met Leu Glu Asp
            195                 200                 205

Gly Lys Lys Phe Asp Ser Ser Arg Asp Arg Asn Lys Pro Phe Lys Phe
            210                 215                 220

Met Leu Gly Lys Glu Val Ile Arg Gly Trp Glu Glu Gly Val Ala Gln
225                 230                 235                 240

Met Ser Val Gly Arg Ala Lys Leu Thr Ile Ser Pro Asp Tyr Ala Tyr
                245                 250                 255

Gly Gly Gly Gly Ser Gly Gly Asn Pro Ile Ala Ala Ser Arg Glu Asp
            260                 265                 270

Leu Ala Leu Ser Pro Gly Leu Gly Pro Gln Lys Ala Arg Arg Leu Phe
            275                 280                 285

Asp Gly Pro Thr Gly Gly Ser Thr Leu Val Phe Asp Val Glu Leu
            290                 295                 300

Leu Lys Leu Glu Gly Gly Gly Ser Arg Lys His His His His His
305                 310                 315                 320

His His

<210> SEQ ID NO 92
<211> LENGTH: 17
<212> TYPE: PRT
<213> ORGANISM: Homo sapiens

<400> SEQUENCE: 92

Asn Lys Pro Thr Gly Tyr Gly Ser Ser Ser Arg Arg Ala Pro Gln Thr
1               5                   10                  15

Gly

<210> SEQ ID NO 93
<211> LENGTH: 134
<212> TYPE: PRT
<213> ORGANISM: Artificial Sequence
<220> FEATURE:
<223> OTHER INFORMATION: Description of Artificial Sequence: Synthetic
      FKBP12-IGF-1 fusion polypeptide

<400> SEQUENCE: 93

```
Met Gly Val Gln Val Glu Thr Ile Ser Pro Gly Asp Gly Arg Thr Phe
1               5                   10                  15

Pro Lys Arg Gly Gln Thr Ala Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Gly Gly Ser Asn Lys Pro Thr Gly Tyr Gly Ser
                85                  90                  95

Ser Ser Arg Arg Ala Pro Gln Thr Gly Gly Ser Thr Leu Val Phe
            100                 105                 110

Asp Val Glu Leu Leu Lys Leu Glu Gly Gly Ser Arg Lys His His
        115                 120                 125

His His His His His His
        130
```

<210> SEQ ID NO 94
<211> LENGTH: 322
<212> TYPE: PRT
<213> ORGANISM: Artificial Sequence
<220> FEATURE:
<223> OTHER INFORMATION: Description of Artificial Sequence: Synthetic
      SlyD/FKBP12-IGF-1 fusion polypeptide

<400> SEQUENCE: 94

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140
```

```
Glu Glu Leu Ala His Gly His Val His Gly Ala His Asp His His
145                 150                 155                 160

Asp His Asp His Asp Gly Gly Ser Gly Gly Gly Ser Gly Gly
                165                 170                 175

Ser Gly Gly Gly Ser Gly Gly Ser Gly Gly Gly Val Gln Val
            180                 185                 190

Glu Thr Ile Ser Pro Gly Asp Gly Arg Thr Phe Pro Lys Arg Gly Gln
            195                 200                 205

Thr Ala Val Val His Tyr Thr Gly Met Leu Glu Asp Gly Lys Lys Phe
        210                 215                 220

Asp Ser Ser Arg Asp Arg Asn Lys Pro Phe Lys Phe Met Leu Gly Lys
225                 230                 235                 240

Gln Glu Val Ile Arg Gly Trp Glu Glu Gly Val Ala Gln Met Ser Val
                245                 250                 255

Gly Gln Arg Ala Lys Leu Thr Ile Ser Pro Asp Tyr Ala Tyr Gly Gly
                260                 265                 270

Gly Gly Ser Asn Lys Pro Thr Gly Tyr Gly Ser Ser Ser Arg Arg Ala
            275                 280                 285

Pro Gln Thr Gly Gly Gly Ser Thr Leu Val Phe Asp Val Glu Leu
            290                 295                 300

Leu Lys Leu Glu Gly Gly Gly Ser Arg Lys His His His His His
305                 310                 315                 320

His His
```

<210> SEQ ID NO 95
<211> LENGTH: 130
<212> TYPE: PRT
<213> ORGANISM: Artificial Sequence
<220> FEATURE:
<223> OTHER INFORMATION: Description of Artificial Sequence: Synthetic
      Thermus Thermophilus-SlyD-IGF-1 fusion polypeptide

<400> SEQUENCE: 95

```
Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro His Gly Asn Lys Pro Thr Gly Tyr Gly Ser Ser Ser
65                  70                  75                  80

Arg Arg Ala Pro Gln Thr Gly Gly Ala Gly Lys Asp Leu Asp Phe Gln
                85                  90                  95

Val Glu Val Val Lys Val Arg Glu Ala Thr Pro Glu Glu Leu Leu His
            100                 105                 110

Gly His Ala His Gly Gly Gly Ser Arg Lys His His His His His His
        115                 120                 125

His His
    130
```

<210> SEQ ID NO 96
<211> LENGTH: 122
<212> TYPE: PRT
<213> ORGANISM: Artificial Sequence
<220> FEATURE:

<223> OTHER INFORMATION: Description of Artificial Sequence: Synthetic
      Thermus Thermophilus-SlyD-IGF-1 fusion polypeptide

<400> SEQUENCE: 96

Met Lys Val Gly Gln Asp Lys Val Val Thr Ile Arg Tyr Thr Leu Gln
1               5                   10                  15

Val Glu Gly Glu Val Leu Asp Gln Gly Glu Leu Ser Tyr Leu His Gly
            20                  25                  30

His Arg Asn Leu Ile Pro Gly Leu Glu Glu Ala Leu Glu Gly Arg Glu
        35                  40                  45

Glu Gly Glu Ala Phe Gln Ala His Val Pro Ala Glu Lys Ala Tyr Gly
    50                  55                  60

Pro His Gly Asn Lys Pro Thr Gly Tyr Gly Ser Ser Arg Arg Ala
65                  70                  75                  80

Pro Gln Thr Gly Gly Ala Gly Lys Asp Leu Asp Phe Gln Val Glu Val
                85                  90                  95

Val Lys Val Arg Glu Ala Thr Pro Glu Glu Leu Leu His Gly His Ala
            100                 105                 110

His Pro Ser Gly His His His His His His
        115                 120

<210> SEQ ID NO 97
<211> LENGTH: 166
<212> TYPE: PRT
<213> ORGANISM: Artificial Sequence
<220> FEATURE:
<223> OTHER INFORMATION: Description of Artificial Sequence: Synthetic
      Thermus thermophilus-SlyD wild type polypeptide

<400> SEQUENCE: 97

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro His Asp Pro Glu Gly Val Gln Val Val Pro Leu Ser
65                  70                  75                  80

Ala Phe Pro Glu Asp Ala Glu Val Val Pro Gly Ala Gln Phe Tyr Ala
                85                  90                  95

Gln Asp Met Glu Gly Asn Pro Met Pro Leu Thr Val Val Ala Val Glu
            100                 105                 110

Gly Glu Glu Val Thr Val Asp Phe Asn His Pro Leu Ala Gly Lys Asp
        115                 120                 125

Leu Asp Phe Gln Val Glu Val Val Lys Val Arg Glu Ala Thr Pro Glu
    130                 135                 140

Glu Leu Leu His Gly His Ala His Gly Gly Gly Ser Arg Lys His His
145                 150                 155                 160

His His His His His
            165

<210> SEQ ID NO 98
<211> LENGTH: 17
<212> TYPE: PRT
<213> ORGANISM: Homo sapiens

```
<400> SEQUENCE: 98

Asp Trp Ser Glu Tyr Pro Ser Glu Val Glu His Met Phe Ser Pro Ser
1               5                   10                  15

Ser

<210> SEQ ID NO 99
<211> LENGTH: 134
<212> TYPE: PRT
<213> ORGANISM: Artificial Sequence
<220> FEATURE:
<223> OTHER INFORMATION: Description of Artificial Sequence: Synthetic
      FKBP12-PLGF fusion polypeptide

<400> SEQUENCE: 99

Met Gly Val Gln Val Glu Thr Ile Ser Pro Gly Asp Gly Arg Thr Phe
1               5                   10                  15

Pro Lys Arg Gly Gln Thr Ala Trp His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Gly Gly Ser Asp Trp Ser Glu Tyr Pro Ser Glu Val
                85                  90                  95

Glu His Met Phe Ser Pro Ser Ser Gly Gly Gly Ser Thr Leu Val Phe
                100                 105                 110

Asp Val Glu Leu Leu Lys Leu Glu Gly Gly Gly Ser Arg Lys His His
            115                 120                 125

His His His His His
        130

<210> SEQ ID NO 100
<211> LENGTH: 323
<212> TYPE: PRT
<213> ORGANISM: Artificial Sequence
<220> FEATURE:
<223> OTHER INFORMATION: Description of Artificial Sequence: Synthetic
      SlyD/FKBP12-PLGF fusion polypeptide

<400> SEQUENCE: 100

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
                20                  25                  30

Asp Tyr Leu His Gly His Gly Ser Leu Ile Ser Gly Leu Glu Thr Ala
            35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
                100                 105                 110

Glu Asp Asp His Val Val Val Asp Gly Asn His Met Leu Ala Gly Gln
            115                 120                 125
```

Asn Leu Lys Phe Asn Val Glu Val Val Ala Ile Arg Glu Ala Thr Glu
            130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Val Gln Val
            180                 185                 190

Glu Thr Ile Ser Pro Gly Asp Gly Arg Thr Phe Pro Lys Arg Gly Gln
            195                 200                 205

Thr Ala Val Val His Tyr Thr Gly Met Leu Glu Asp Gly Lys Lys Phe
            210                 215                 220

Asp Ser Ser Arg Asp Arg Asn Lys Pro Phe Lys Phe Met Leu Gly Lys
225                 230                 235                 240

Gln Glu Val Ile Arg Gly Trp Glu Glu Gly Val Ala Gln Met Ser Val
                245                 250                 255

Gly Gln Arg Ala Lys Leu Thr Ile Ser Pro Asp Tyr Ala Tyr Gly Gly
            260                 265                 270

Gly Gly Ser Asp Val Val Ser Glu Tyr Pro Ser Glu Val Glu His Met
            275                 280                 285

Phe Ser Pro Ser Ser Gly Gly Gly Ser Thr Leu Val Phe Asp Val Glu
            290                 295                 300

Leu Leu Lys Leu Glu Gly Gly Ser Arg Lys His His His His His
305                 310                 315                 320

His His His

<210> SEQ ID NO 101
<211> LENGTH: 130
<212> TYPE: PRT
<213> ORGANISM: Artificial Sequence
<220> FEATURE:
<223> OTHER INFORMATION: Description of Artificial Sequence: Synthetic
      FKBP12-IGF-1-fusion polypeptide

<400> SEQUENCE: 101

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
50                  55                  60

Ala Tyr Gly Pro His Gly Asn Lys Pro Thr Gly Tyr Gly Ser Ser Ser
65                  70                  75                  80

Arg Arg Ala Pro Gln Thr Gly Gly Ala Gly Lys Asp Leu Asp Phe Gln
                85                  90                  95

Val Glu Val Val Lys Val Arg Glu Ala Thr Pro Glu Glu Leu Leu His
            100                 105                 110

Gly His Ala His Gly Gly Gly Ser Arg Lys His His His His His His
        115                 120                 125

His His
    130

<210> SEQ ID NO 102

<211> LENGTH: 130
<212> TYPE: PRT
<213> ORGANISM: Artificial Sequence
<220> FEATURE:
<223> OTHER INFORMATION: Description of Artificial Sequence: Synthetic
      FKBP12-IGF-1 fusion polypeptide

<400> SEQUENCE: 102

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro Cys Gly Asn Lys Pro Thr Gly Tyr Gly Ser Ser Ser
65                  70                  75                  80

Arg Arg Ala Pro Gln Thr Gly Gly Cys Gly Lys Asp Leu Asp Phe Gln
                85                  90                  95

Val Glu Val Val Lys Val Arg Glu Ala Thr Pro Glu Glu Leu Leu His
            100                 105                 110

Gly His Ala His Gly Gly Gly Ser Arg Lys His His His His His His
        115                 120                 125

His His
    130

<210> SEQ ID NO 103
<211> LENGTH: 437
<212> TYPE: DNA
<213> ORGANISM: Artificial Sequence
<220> FEATURE:
<223> OTHER INFORMATION: Description of Artificial Sequence: Synthetic
      FKBP12-IGF-1 fusion polypeptide encoding nucleic acid

<400> SEQUENCE: 103
atgcgaattc attaaagagg agaaattaac tatgagagga tcgaaggttg gacaggacaa       60
ggttgtgacc atccgctaca ccctccaggt ggagggtgag gttctggacc aggggagct      120 ttcctacctc cacggccacc gtaacctcat cccgggcctc gaggaggccc tggagggccg     180
ggaggagggg gaggctttcc aggcccacgt ccccgccgag aaggcctacg gcccccacgg     240
caataaaccg accggttatg gcagcagttc tcgccgtgct ccacaaactg gtggtgcggg     300
caaggacctg gacttccagg tggaggtggt gaaggtccgc gaggccaccc ccgaggaact     360
cctgcacggc cacgcccacg gtggcggttc tcgtaaacac catcaccatc accatcacca     420
ttaatgaaag cttatgc                                                    437

<210> SEQ ID NO 104
<211> LENGTH: 166
<212> TYPE: PRT
<213> ORGANISM: Artificial Sequence
<220> FEATURE:
<223> OTHER INFORMATION: Description of Artificial Sequence: Synthetic
      slyD control fusion polypeptide

<400> SEQUENCE: 104

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

```
Leu His Gly His Arg Asn Leu Ile Pro Gly Leu Glu Glu Ala Leu Glu
            35                  40                  45

Gly Arg Glu Glu Gly Glu Ala Phe Gln Ala His Val Pro Ala Glu Lys
 50                  55                  60

Ala Tyr Gly Pro His Asp Pro Glu Gly Val Gln Val Val Pro Leu Ser
 65                  70                  75                  80

Ala Phe Pro Glu Asp Ala Glu Val Val Pro Gly Ala Gln Phe Tyr Ala
                85                  90                  95

Gln Asp Met Glu Gly Asn Pro Met Pro Leu Thr Val Val Ala Val Glu
            100                 105                 110

Gly Glu Glu Val Thr Val Asp Phe Asn His Pro Leu Ala Gly Lys Asp
        115                 120                 125

Leu Asp Phe Gln Val Glu Val Val Lys Val Arg Glu Ala Thr Pro Glu
130                 135                 140

Glu Leu Leu His Gly His Ala His Gly Gly Gly Ser Arg Lys His His
145                 150                 155                 160

His His His His His
                165

<210> SEQ ID NO 105
<211> LENGTH: 545
<212> TYPE: DNA
<213> ORGANISM: Artificial Sequence
<220> FEATURE:
<223> OTHER INFORMATION: Description of Artificial Sequence: Synthetic
      slyD control fusion polypeptide encoding nucleic acid

<400> SEQUENCE: 105
atgcgaattc attaaagagg agaaattaac tatgagagga tcgaaggttg gacaggacaa      60
ggttgtgacc atccgctaca ccctccaggt ggagggtgag gttctggacc aggggagct     120 ttcctacctc cacggccacc gtaacctcat cccgggcctc gaggaggccc tggagggccg     180
ggaggagggg gaggctttcc aggcccacgt ccccgccgag aaggcctacg ccccccacga     240
ccccgagggg gtccaggtgg tgcccctctc cgccttcccc gaggacgccg aggtggttcc     300
cggggcccag ttctacgccc aggacatgga ggggaacccc atgcccctca ccgtggtggc     360
ggtggaaggg gaggaggtga ccgtggactt caaccacccc ctggcgggca aggacctgga     420
cttccaggtg gaggtggtga aggtccgcga ggccaccccc gaggaactcc tgcacggcca     480
cgcccacggt ggcggttctc gtaaacacca tcaccatcac catcaccatt aatgaaagct     540
tatgc                                                                545

<210> SEQ ID NO 106
<211> LENGTH: 156
<212> TYPE: PRT
<213> ORGANISM: Artificial Sequence
<220> FEATURE:
<223> OTHER INFORMATION: Description of Artificial Sequence: Synthetic
      Thermococcus gammatolerans SlyD

<400> SEQUENCE: 106

Met Lys Val Glu Arg Gly Asp Phe Val Leu Phe Asn Tyr Val Gly Arg
 1               5                  10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45
```

```
Thr Val Gly Ala Gly Glu Ile Ile Pro Gly Ile Glu Glu Ala Leu Leu
    50                  55                  60

Gly Met Glu Leu Gly Glu Lys Lys Glu Val Val Pro Pro Glu Lys
65                  70                  75                  80

Gly Tyr Gly Met Pro Arg Glu Asp Leu Ile Val Pro Val Pro Ile Glu
                85                  90                  95

Gln Phe Thr Ser Ala Gly Leu Glu Pro Val Glu Gly Met Tyr Val Met
                100                 105                 110

Thr Asp Ala Gly Ile Ala Lys Ile Leu Lys Val Glu Lys Thr Val
                115                 120                 125

Arg Leu Asp Phe Asn His Pro Leu Ala Gly Lys Thr Ala Ile Phe Glu
    130                 135                 140

Ile Glu Val Val Glu Ile Lys Lys Ala Gly Glu Ala
145                 150                 155

<210> SEQ ID NO 107
<211> LENGTH: 84
<212> TYPE: PRT
<213> ORGANISM: Artificial Sequence
<220> FEATURE:
<223> OTHER INFORMATION: Description of Artificial Sequence: Synthetic
      Thermococcus gammatolerans SlyD N-terminal fragment

<400> SEQUENCE: 107

Lys Val Glu Arg Gly Asp Phe Val Leu Phe Asn Tyr Val Gly Arg Tyr
1               5                   10                  15

Glu Asn Gly Glu Val Phe Asp Thr Ser Tyr Glu Ser Val Ala Arg Glu
                20                  25                  30

Gln Gly Ile Phe Val Glu Glu Arg Glu Tyr Ser Pro Ile Gly Val Thr
            35                  40                  45

Val Gly Ala Gly Glu Ile Ile Pro Gly Ile Glu Glu Ala Leu Leu Gly
    50                  55                  60

Met Glu Leu Gly Glu Lys Lys Glu Val Val Pro Pro Glu Lys Gly
65                  70                  75                  80

Tyr Gly Met Pro

<210> SEQ ID NO 108
<211> LENGTH: 20
<212> TYPE: PRT
<213> ORGANISM: Artificial Sequence
<220> FEATURE:
<223> OTHER INFORMATION: Description of Artificial Sequence: Synthetic
      Thermococcus gammatolerans C-terminal fragment

<400> SEQUENCE: 108

Ala Gly Lys Thr Ala Ile Phe Glu Ile Glu Val Val Glu Ile Lys Lys
1               5                   10                  15

Ala Gly Glu Ala
                20

<210> SEQ ID NO 109
<211> LENGTH: 98
<212> TYPE: PRT
<213> ORGANISM: Artificial Sequence
<220> FEATURE:
<223> OTHER INFORMATION: Description of Artificial Sequence: Synthetic
      FKBP12 fusion polypeptide
<220> FEATURE:
<221> NAME/KEY: misc_feature
<222> LOCATION: (86)..(87)
<223> OTHER INFORMATION: Residues at these positions are separated by an
      undefined amino acid sequence of a linker, or a peptide, or an
```

-continued antigen, or a secondary or tertiary structure to be presented by
the FKBP12 fusion polypeptide
<220> FEATURE:
<223> OTHER INFORMATION: See specification as filed for detailed
    description of substitutions and preferred embodiments

<400> SEQUENCE: 109

Met Arg Ser Gly Val Gln Val Glu Thr Ile Ser Pro Gly Asp Gly Arg
1               5                   10                  15

Thr Phe Pro Lys Arg Gly Gln Thr Ala Val Val His Tyr Thr Gly Met
            20                  25                  30

Leu Glu Asp Gly Lys Lys Phe Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Thr Leu Val Phe Asp Val Glu Leu Leu Lys
                85                  90                  95

Leu Glu

<210> SEQ ID NO 110
<211> LENGTH: 262
<212> TYPE: PRT
<213> ORGANISM: Artificial Sequence
<220> FEATURE:
<223> OTHER INFORMATION: Description of Artificial Sequence: Synthetic
    SlyD-FKBP12 fusion polypeptide
<220> FEATURE:
<221> NAME/KEY: misc_feature
<222> LOCATION: (165)..(166)
<223> OTHER INFORMATION: Residues at these positions are separated by an
    undefined amino acid linker
<220> FEATURE:
<221> NAME/KEY: misc_feature
<222> LOCATION: (250)..(251)
<223> OTHER INFORMATION: Residues at these positions are separated by an
    undefined amino acid sequence of a linker, or a peptide, or an
    antigen, or a secondary or tertiary structure to be presented by
    the SlyD-FKBP12 fusion polypeptide
<220> FEATURE:
<223> OTHER INFORMATION: See specification as filed for detailed
    description of substitutions and preferred embodiments

<400> SEQUENCE: 110

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
                100                 105                 110

Glu Asp Asp His Val Val Asp Gly Asn His Met Leu Ala Gly Gln
            115                 120                 125

Asn Leu Lys Phe Asn Val Glu Val Val Ala Ile Arg Glu Ala Thr Glu

```
                      130                 135                 140

Glu Glu Leu Ala His Gly His Val His Gly Ala His Asp His His
145                 150                 155                 160

Asp His Asp His Asp Arg Ser Gly Val Gln Val Glu Thr Ile Ser Pro
                    165                 170                 175

Gly Asp Gly Arg Thr Phe Pro Lys Arg Gly Gln Thr Ala Val Val His
                180                 185                 190

Tyr Thr Gly Met Leu Glu Asp Gly Lys Lys Phe Asp Ser Ser Arg Asp
            195                 200                 205

Arg Asn Lys Pro Phe Lys Phe Met Leu Gly Lys Gln Glu Val Ile Arg
        210                 215                 220

Gly Trp Glu Glu Gly Val Ala Gln Met Ser Val Gly Gln Arg Ala Lys
225                 230                 235                 240

Leu Thr Ile Ser Pro Asp Tyr Ala Tyr Gly Thr Leu Val Phe Asp Val
                245                 250                 255

Glu Leu Leu Lys Leu Glu
            260

<210> SEQ ID NO 111
<211> LENGTH: 105
<212> TYPE: PRT
<213> ORGANISM: Artificial Sequence
<220> FEATURE:
<223> OTHER INFORMATION: Description of Artificial Sequence: Synthetic
      T.gammatolerans SlyD fusion polypeptide
<220> FEATURE:
<221> NAME/KEY: misc_feature
<222> LOCATION: (85)..(86)
<223> OTHER INFORMATION: Residues at these positions are separated by an
      undefined amino acid sequence of a linker, or a peptide, or an
      antigen, or a secondary or tertiary structure to be presented by
      the Thermococcus gammatolerans SlyD fusion polypeptide
<220> FEATURE:
<223> OTHER INFORMATION: See specification as filed for detailed
      description of substitutions and preferred embodiments

<400> SEQUENCE: 111

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Glu Lys Lys Glu Val Val Val Pro Pro Glu Lys
65                  70                  75                  80

Gly Tyr Gly Met Pro Ala Gly Lys Thr Ala Ile Phe Glu Ile Glu Val
                85                  90                  95

Val Glu Ile Lys Lys Ala Gly Glu Ala
            100                 105

<210> SEQ ID NO 112
<211> LENGTH: 269
<212> TYPE: PRT
<213> ORGANISM: Artificial Sequence
<220> FEATURE:
<223> OTHER INFORMATION: Description of Artificial Sequence: Synthetic
      SlyD-T.gammatolerans SlyD fusion polypeptide
<220> FEATURE:
<221> NAME/KEY: misc_feature
<222> LOCATION: (165)..(166)
```

<223> OTHER INFORMATION: Residues at these positions are separated by an undefined amino acid linker
<220> FEATURE:
<221> NAME/KEY: misc_feature
<222> LOCATION: (249)..(250)
<223> OTHER INFORMATION: Residues at these positions are separated by an undefined amino acid sequence of a linker, or a peptide, or an antigen, or a secondary or tertiary structure to be presented by the Thermococcus gammatolerans SlyD fusion polypeptide
<220> FEATURE:
<223> OTHER INFORMATION: See specification as filed for detailed description of substitutions and preferred embodiments

<400> SEQUENCE: 112

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Val Ala Ile Arg Glu Ala Thr Glu
130                 135                 140

Glu Glu Leu Ala His Gly His Val His Gly Ala His Asp His His His
145                 150                 155                 160

Asp His Asp His Asp Lys Val Glu Arg Gly Asp Phe Val Leu Phe Asn
                165                 170                 175

Tyr Val Gly Arg Tyr Glu Asn Gly Glu Val Phe Asp Thr Ser Tyr Glu
            180                 185                 190

Ser Val Ala Arg Glu Gln Gly Ile Phe Val Glu Glu Arg Glu Tyr Ser
        195                 200                 205

Pro Ile Gly Val Thr Val Gly Ala Gly Glu Ile Ile Pro Gly Ile Glu
210                 215                 220

Glu Ala Leu Leu Gly Met Glu Leu Gly Glu Lys Lys Glu Val Val Val
225                 230                 235                 240

Pro Pro Glu Lys Gly Tyr Gly Met Pro Ala Gly Lys Thr Ala Ile Phe
                245                 250                 255

Glu Ile Glu Val Val Glu Ile Lys Lys Ala Gly Glu Ala
            260                 265
```

<210> SEQ ID NO 113
<211> LENGTH: 237
<212> TYPE: PRT
<213> ORGANISM: Artificial Sequence
<220> FEATURE:
<223> OTHER INFORMATION: Description of Artificial Sequence: Synthetic SlyD-FKBP12/13 fusion polypeptide
<220> FEATURE:
<221> NAME/KEY: misc_feature
<222> LOCATION: (115)..(116)
<223> OTHER INFORMATION: Residues at these positions are separated by an undefined amino acid linker
<220> FEATURE:
<221> NAME/KEY: misc_feature
<222> LOCATION: (204)..(205)
<223> OTHER INFORMATION: Residues at these positions are separated by an
      undefined amino acid sequence of a linker, or a peptide, or an
      antigen, or a secondary or tertiary structure to be presented by
      the SlyD-FKBP12/13 fusion polypeptide
<220> FEATURE:
<223> OTHER INFORMATION: See specification as filed for detailed
      description of substitutions and preferred embodiments

<400> SEQUENCE: 113

Gly His Glu Val Gly Asp Lys Phe Asp Val Ala Val Gly Ala Asn Asp
1               5                   10                  15

Ala Tyr Gly Gln Tyr Asp Glu Asn Leu Val Gln Arg Val Pro Lys Asp
            20                  25                  30

Val Phe Met Gly Val Asp Glu Leu Gln Val Gly Met Arg Phe Leu Ala
        35                  40                  45

Glu Thr Asp Gln Gly Pro Val Pro Val Glu Ile Thr Ala Val Glu Asp
    50                  55                  60

Asp His Val Val Val Asp Gly Asn His Met Leu Ala Gly Gln Asn Leu
65              70                  75                  80

Lys Phe Asn Val Glu Val Val Ala Ile Arg Glu Ala Thr Glu Glu Glu
                85                  90                  95

Leu Ala His Gly His Val His Gly Ala His Asp His His His Asp His
            100                 105                 110

Asp His Asp Gly Val Gln Val Glu Thr Ile Ser Pro Gly Asp Gly Arg
        115                 120                 125

Thr Phe Pro Lys Arg Gly Gln Thr Ala Val Val His Tyr Thr Gly Met
    130                 135                 140

Leu Glu Asp Gly Lys Lys Phe Asp Ser Ser Arg Asp Arg Asn Lys Pro
145                 150                 155                 160

Phe Lys Phe Met Leu Gly Lys Gln Glu Val Ile Arg Gly Trp Glu Glu
                165                 170                 175

Gly Val Ala Gln Met Ser Val Gly Gln Arg Ala Lys Leu Thr Ile Ser
            180                 185                 190

Pro Asp Tyr Ala Tyr Gly Asp Arg Gly Ala Gly Cys Cys Leu Ile Pro
        195                 200                 205

Pro Ala Ser Val Leu Val Phe Asp Val Glu Leu Leu Lys Leu Glu Gly
    210                 215                 220

Gly Gly Ser Arg Pro Leu Leu Pro Pro Leu Pro Gly Gly
225                 230                 235

<210> SEQ ID NO 114
<211> LENGTH: 119
<212> TYPE: PRT
<213> ORGANISM: Artificial Sequence
<220> FEATURE:
<223> OTHER INFORMATION: Description of Artificial Sequence: Synthetic
      Thermococcus gammatolerans-SlyD-antigen fusion polypeptide
<220> FEATURE:
<221> NAME/KEY: misc_feature
<222> LOCATION: (85)..(86)
<223> OTHER INFORMATION: Residues at these positions are separated by an
      undefined amino acid sequence of a linker, or a peptide, or an
      antigen, or a secondary or tertiary structure to be presented by
      the Thermococcus gammatolerans-SlyD-antigen fusion polypeptide
<220> FEATURE:
<223> OTHER INFORMATION: See specification as filed for detailed
      description of substitutions and preferred embodiments

<400> SEQUENCE: 114

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Glu Lys Lys Glu Val Val Pro Pro Glu Lys
65                  70                  75                  80

Gly Tyr Gly Met Pro Ala Gly Lys Thr Ala Ile Phe Glu Ile Glu Val
            85                  90                  95

Val Glu Ile Lys Lys Ala Gly Glu Ala Gly Gly Ser Arg Lys His
            100                 105                 110

His His His His His His
        115

<210> SEQ ID NO 115
<211> LENGTH: 123
<212> TYPE: PRT
<213> ORGANISM: Artificial Sequence
<220> FEATURE:
<223> OTHER INFORMATION: Description of Artificial Sequence: Synthetic
      disulfide stabilized Thermococcus gammadurans-SlyD-antigen
      fusion polypeptide
<220> FEATURE:
<221> NAME/KEY: misc_feature
<222> LOCATION: (87)..(88)
<223> OTHER INFORMATION: Residues at these positions are separated by an
      undefined amino acid sequence of a linker, or a peptide, or an
      antigen, or a secondary or tertiary structure to be presented by
      the Thermococcus gammatolerans-SlyD-antigen fusion polypeptide
<220> FEATURE:
<223> OTHER INFORMATION: See specification as filed for detailed
      description of substitutions and preferred embodiments

<400> SEQUENCE: 115

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Glu Lys Lys Glu Val Val Pro Pro Glu Lys
65                  70                  75                  80

Gly Tyr Gly Met Pro Cys Gly Gly Cys Ala Gly Lys Thr Ala Ile Phe
            85                  90                  95

Glu Ile Glu Val Val Glu Ile Lys Lys Ala Gly Glu Ala Gly Gly Gly
            100                 105                 110

Ser Arg Lys His His His His His His His
        115                 120

<210> SEQ ID NO 116
<211> LENGTH: 119
<212> TYPE: PRT
<213> ORGANISM: Artificial Sequence
<220> FEATURE:
<223> OTHER INFORMATION: Description of Artificial Sequence: Synthetic
      Thermus thermophilus SlyD-IF fusion polypeptide

<400> SEQUENCE: 116

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
                20                  25                  30

Leu His Gly His Arg Asn Leu Ile Pro Gly Leu Glu Glu Ala Leu Glu
            35                  40                  45

Gly Arg Glu Glu Gly Glu Ala Phe Gln Ala His Val Pro Ala Glu Lys
50                  55                  60

Ala Tyr Gly Pro His Gly Ala Gly Ser Gly Ser Gly Ala Gly Lys
65                  70                  75                  80

Asp Leu Asp Phe Gln Val Glu Val Val Lys Val Arg Glu Ala Thr Pro
                85                  90                  95

Glu Glu Leu Leu His Gly His Ala His Gly Gly Ser Arg Lys His
            100                 105                 110

His His His His His His
        115

<210> SEQ ID NO 117
<211> LENGTH: 130
<212> TYPE: PRT
<213> ORGANISM: Artificial Sequence
<220> FEATURE:
<223> OTHER INFORMATION: Description of Artificial Sequence: Synthetic
      Thermococcus gammadurans SlyD-IGF-2(53-65) fusion polypeptide

<400> SEQUENCE: 117

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
                20                  25                  30

Glu Gln Gly Ile Phe Val Glu Glu Arg Glu Tyr Ser Pro Ile Gly Val
            35                  40                  45

Thr Val Gly Ala Gly Glu Ile Ile Pro Gly Ile Glu Glu Ala Leu Leu
50                  55                  60

Gly Met Glu Leu Gly Glu Lys Lys Glu Val Val Pro Pro Glu Lys
65                  70                  75                  80

Gly Tyr Gly Met Pro Gly Ser Arg Val Ser Arg Arg Ser Arg Gly Gly
                85                  90                  95

Ala Gly Lys Thr Ala Ile Phe Glu Ile Glu Val Val Glu Ile Lys Lys
            100                 105                 110

Ala Gly Glu Ala Gly Gly Ser Arg Lys His His His His His His
            115                 120                 125

His His
    130

<210> SEQ ID NO 118
<211> LENGTH: 130
<212> TYPE: PRT
<213> ORGANISM: Artificial Sequence
<220> FEATURE:
<223> OTHER INFORMATION: Description of Artificial Sequence: Synthetic
      FKBP12/13 fusion polypeptide

<400> SEQUENCE: 118

Met Arg Ser Gly Val Gln Val Glu Thr Ile Ser Pro Gly Asp Gly Arg
1               5                   10                  15

Thr Phe Pro Lys Arg Gly Gln Thr Ala Val Val His Tyr Thr Gly Met

```
                      20                  25                  30

Leu Glu Asp Gly Lys Lys Phe Asp Ser Ser Arg Asp Arg Asn Lys Pro
        35                  40                  45

Phe Lys Phe Met Leu Gly Lys Gln Glu Val Ile Arg Gly Trp Glu Glu
 50                  55                  60

Gly Val Ala Gln Met Ser Val Gly Gln Arg Ala Lys Leu Thr Ile Ser
 65                  70                  75                  80

Pro Asp Tyr Ala Tyr Gly Asp Arg Gly Ala Gly Cys Gly Ser Gly Ser
                    85                  90                  95

Ser Cys Leu Ile Pro Pro Ala Ser Val Leu Val Phe Asp Val Glu Leu
                100                 105                 110

Leu Lys Leu Glu Gly Gly Gly Ser Arg Lys His His His His His His
            115                 120                 125

His His
    130

<210> SEQ ID NO 119
<211> LENGTH: 369
<212> TYPE: PRT
<213> ORGANISM: Artificial Sequence
<220> FEATURE:
<223> OTHER INFORMATION: Description of Artificial Sequence: Synthetic
      SlyD-FKBP12/13-CSF1R fusion polypeptide

<400> SEQUENCE: 119

Met Lys Val Ala Lys Asp Leu Val Val Ser Leu Ala Tyr Gln Val Arg
 1               5                  10                  15

Thr Glu Asp Gly Val Leu Val Asp Glu Ser Pro Val Ser Ala Pro Leu
                    20                  25                  30

Asp Tyr Leu His Gly His Gly Ser Leu Ile Ser Gly Leu Glu Thr Ala
            35                  40                  45

Leu Glu Gly His Glu Val Gly Asp Lys Phe Asp Val Ala Val Gly Ala
 50                  55                  60

Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                    85                  90                  95

Leu Ala Glu Thr Asp Gln Gly Pro Val Pro Val Glu Ile Thr Ala Val
                100                 105                 110

Glu Asp Asp His Val Val Val Asp Gly Asn His Met Leu Ala Gly Gln
            115                 120                 125

Asn Leu Lys Phe Asn Val Glu Val Val Ala Ile Arg Glu Ala Thr Glu
130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Val Gln Val Glu Thr Ile Ser Pro Gly Asp Gly Arg Thr Phe
            180                 185                 190

Pro Lys Arg Gly Gln Thr Ala Val Val His Tyr Thr Gly Met Leu Glu
        195                 200                 205

Asp Gly Lys Lys Phe Asp Ser Ser Arg Asp Arg Asn Lys Pro Phe Lys
    210                 215                 220

Phe Met Leu Gly Lys Gln Glu Val Ile Arg Gly Trp Glu Glu Gly Val
225                 230                 235                 240
```

```
Ala Gln Met Ser Val Gly Gln Arg Ala Lys Leu Thr Ile Ser Pro Asp
                245                 250                 255

Tyr Ala Tyr Gly Asp Arg Gly Ala Gly Cys Gly Ser Gly Gly Val Asp
            260                 265                 270

Tyr Lys Asn Ile His Leu Glu Lys Lys Tyr Val Arg Arg Asp Ser Gly
        275                 280                 285

Phe Ser Ser Gln Gly Val Asp Thr Tyr Val Glu Met Arg Pro Val Ser
    290                 295                 300

Thr Ser Ser Asn Asp Ser Phe Ser Glu Gln Asp Leu Asp Lys Glu Asp
305                 310                 315                 320

Gly Gly Ser Ser Cys Leu Ile Pro Pro Ala Ser Val Leu Val Phe Asp
                325                 330                 335

Val Glu Leu Leu Lys Leu Glu Gly Gly Ser Arg Pro Leu Leu Pro
            340                 345                 350

Pro Leu Pro Gly Gly Gly Ser Arg Lys His His His His His His
        355                 360                 365

His

<210> SEQ ID NO 120
<211> LENGTH: 119
<212> TYPE: PRT
<213> ORGANISM: Artificial Sequence
<220> FEATURE:
<223> OTHER INFORMATION: Description of Artificial Sequence: Synthetic
      Thermus thermophilus SlyD-deltaIF fusion polypeptide

<400> SEQUENCE: 120

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro His Gly Ala Gly Ser Gly Ser Ser Gly Ala Gly Lys
65                  70                  75                  80

Asp Leu Asp Phe Gln Val Glu Val Val Lys Val Arg Glu Ala Thr Pro
                85                  90                  95

Glu Glu Leu Leu His Gly His Ala His Gly Gly Gly Ser Arg Lys His
            100                 105                 110

His His His His His His
        115

<210> SEQ ID NO 121
<211> LENGTH: 168
<212> TYPE: PRT
<213> ORGANISM: Artificial Sequence
<220> FEATURE:
<223> OTHER INFORMATION: Description of Artificial Sequence: Synthetic
      native SlyD from Thermococcus gammatolerans comprising
      a C-terminal amino acid sequence tag of SEQ ID NO: 16

<400> SEQUENCE: 121

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30
```

```
Glu Gln Gly Ile Phe Val Glu Glu Arg Glu Tyr Ser Pro Ile Gly Val
            35                  40                  45

Thr Val Gly Ala Gly Glu Ile Ile Pro Gly Ile Glu Glu Ala Leu Leu
 50                  55                  60

Gly Met Glu Leu Gly Glu Lys Lys Glu Val Val Pro Pro Glu Lys
 65                  70                  75                  80

Gly Tyr Gly Met Pro Arg Glu Asp Leu Ile Val Pro Val Pro Ile Glu
                    85                  90                  95

Gln Phe Thr Ser Ala Gly Leu Glu Pro Val Gly Met Tyr Val Met
                100                 105                 110

Thr Asp Ala Gly Ile Ala Lys Ile Leu Lys Val Glu Glu Lys Thr Val
                115                 120                 125

Arg Leu Asp Phe Asn His Pro Leu Ala Gly Lys Thr Ala Ile Phe Glu
130                 135                 140

Ile Glu Val Val Glu Ile Lys Lys Ala Gly Glu Ala Gly Gly Gly Ser
145                 150                 155                 160

Arg Lys His His His His His His
                165

<210> SEQ ID NO 122
<211> LENGTH: 128
<212> TYPE: PRT
<213> ORGANISM: Artificial Sequence
<220> FEATURE:
<223> OTHER INFORMATION: Description of Artificial Sequence: Synthetic
      Thermococcus gammatolerans SlyD-IGF-2(53-65) fusion polypeptide

<400> SEQUENCE: 122

Met Lys Val Glu Arg Gly Asp Phe Val Leu Phe Asn Tyr Val Gly Arg
 1               5                  10                  15

Tyr Glu Asn Gly Glu Val Phe Asp Thr Ser Tyr Glu Ser Val Ala Arg
                20                  25                  30

Glu Gln Gly Ile Phe Val Glu Glu Arg Glu Tyr Ser Pro Ile Gly Val
            35                  40                  45

Thr Val Gly Ala Gly Glu Ile Ile Pro Gly Ile Glu Glu Ala Leu Leu
 50                  55                  60

Gly Met Glu Leu Gly Glu Lys Lys Glu Val Val Pro Pro Glu Lys
 65                  70                  75                  80

Gly Tyr Gly Met Pro Gly Ser Arg Val Ser Arg Arg Ser Arg Gly Gly
                    85                  90                  95

Ala Gly Lys Thr Ala Ile Phe Glu Ile Glu Val Val Glu Ile Lys Lys
                100                 105                 110

Ala Gly Glu Ala Gly Gly Gly Ser Arg Lys His His His His His His
            115                 120                 125

<210> SEQ ID NO 123
<211> LENGTH: 130
<212> TYPE: PRT
<213> ORGANISM: Artificial Sequence
<220> FEATURE:
<223> OTHER INFORMATION: Description of Artificial Sequence: Synthetic
      FKBP12/13 fusion polypeptide

<400> SEQUENCE: 123

Met Arg Ser Gly Val Gln Val Glu Thr Ile Ser Pro Gly Asp Gly Arg
 1               5                  10                  15

Thr Phe Pro Lys Arg Gly Gln Thr Ala Val Val His Tyr Thr Gly Met
                20                  25                  30
```

```
Leu Glu Asp Gly Lys Lys Phe Asp Ser Ser Arg Asp Arg Asn Lys Pro
            35                  40                  45
Phe Lys Phe Met Leu Gly Lys Gln Glu Val Ile Arg Gly Trp Glu Glu
 50                  55                  60
Gly Val Ala Gln Met Ser Val Gly Gln Arg Ala Lys Leu Thr Ile Ser
 65                  70                  75                  80
Pro Asp Tyr Ala Tyr Gly Asp Arg Gly Ala Gly Cys Gly Ser Gly Ser
                85                  90                  95
Ser Cys Leu Ile Pro Pro Ala Ser Val Leu Val Phe Asp Val Glu Leu
            100                 105                 110
Leu Lys Leu Glu Gly Gly Gly Ser Arg Lys His His His His His His
            115                 120                 125
His His
    130

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      IGF-1 epitope sequence

<400> SEQUENCE: 124

Thr Gly Tyr Gly Ser Ser Ser Arg
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      IGF-1 epitope sequence

<400> SEQUENCE: 125

Pro Thr Gly Tyr Gly Ser Ser Ser Arg
1               5

<210> SEQ ID NO 126
<211> LENGTH: 340
<212> TYPE: PRT
<213> ORGANISM: Artificial Sequence
<220> FEATURE:
<223> OTHER INFORMATION: Description of Artificial Sequence: Synthetic
      SlyD-FKBP12-CD81 fusion polypeptide

<400> SEQUENCE: 126

Met Lys Val Ala Lys Asp Leu Val Val Ser Leu Ala Tyr Gln Val Arg
1               5                   10                  15
Thr Glu Asp Gly Val Leu Val Asp Glu Ser Pro Val Ser Ala Pro Leu
            20                  25                  30
Asp Tyr Leu His Gly His Gly Ser Leu Ile Ser Gly Leu Glu Thr Ala
            35                  40                  45
Leu Glu Gly His Glu Val Gly Asp Lys Phe Asp Val Ala Val Gly Ala
 50                  55                  60
Asn Asp Ala Tyr Gly Gln Tyr Asp Glu Asn Leu Val Gln Arg Val Pro
 65                  70                  75                  80
Lys Asp Val Phe Met Gly Val Asp Glu Leu Gln Val Gly Met Arg Phe
                85                  90                  95
Leu Ala Glu Thr Asp Gln Gly Pro Val Pro Val Glu Ile Thr Ala Val
```

```
                100              105               110
Glu Asp Asp His Val Val Asp Gly Asn His Met Leu Ala Gly Gln
            115                 120             125
Asn Leu Lys Phe Asn Val Glu Val Val Ala Ile Arg Glu Ala Thr Glu
130                 135             140
Glu Glu Leu Ala His Gly His Val His Gly Ala His Asp His His
145             150              155                 160
Asp His Asp His Asp Gly Gly Ser Gly Gly Gly Ser Gly Gly Gly
                165             170              175
Ser Gly Gly Gly Ser Gly Gly Gly Ser Gly Gly Gly Val Gln Val
            180             185              190
Glu Thr Ile Ser Pro Gly Asp Gly Arg Thr Phe Pro Lys Arg Gly Gln
            195             200             205
Thr Ala Val Val His Tyr Thr Gly Met Leu Glu Asp Gly Lys Lys Phe
            210             215             220
Asp Ser Ser Arg Asp Arg Asn Lys Pro Phe Lys Phe Met Leu Gly Lys
225             230             235             240
Gln Glu Val Ile Arg Gly Trp Glu Glu Gly Val Ala Gln Met Ser Val
                245             250             255
Gly Gln Arg Ala Lys Leu Thr Ile Ser Pro Asp Tyr Ala Tyr Gly Gly
            260             265             270
Gly Gly Ser Cys Cys Gly Ser Ser Thr Leu Thr Ala Leu Thr Thr Ser
            275             280             285
Val Leu Lys Asn Asn Leu Cys Pro Ser Gly Ser Asn Ile Ile Ser Asn
290             295             300
Leu Phe Lys Glu Asp Cys Gly Gly Ser Thr Leu Val Phe Asp Val
305             310             315             320
Glu Leu Leu Lys Leu Glu Gly Gly Ser Arg Lys His His His His
                325             330             335
His His His His
            340

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(3)
<223> OTHER INFORMATION: Residues at these positions are separated by an
      undefined random amino acid sequence or an amino acid sequence
      derived from a first polypeptide
<220> FEATURE:
<223> OTHER INFORMATION: See specification as filed for detailed
      description of substitutions and preferred embodiments

<400> SEQUENCE: 127

Gly Ser Gly Ser Ser
1               5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: misc_feature
<222> LOCATION: (3)..(4)
<223> OTHER INFORMATION: Residues at these positions are separated by an
      undefined random amino acid sequence or an amino acid sequence
      derived from a first polypeptide
<220> FEATURE:
<223> OTHER INFORMATION: See specification as filed for detailed
      description of substitutions and preferred embodiments

<400> SEQUENCE: 128

Ala Gly Ser Gly Ser Ser
1               5

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(3)
<223> OTHER INFORMATION: Residues at these positions are separated by an
      undefined random amino acid sequence or an amino acid sequence
      derived from a first polypeptide
<220> FEATURE:
<223> OTHER INFORMATION: See specification as filed for detailed
      description of substitutions and preferred embodiments

<400> SEQUENCE: 129

Cys Gly Gly Cys
1

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Residues at these positions are separated by an
      undefined random amino acid sequence or an amino acid sequence
      derived from a first polypeptide
<220> FEATURE:
<223> OTHER INFORMATION: See specification as filed for detailed
      description of substitutions and preferred embodiments

<400> SEQUENCE: 130

Ser Gly Ser Ser
1

<210> SEQ ID NO 131
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(3)
<223> OTHER INFORMATION: Residues at these positions are separated by an
      undefined random amino acid sequence or an amino acid sequence
      derived from a first polypeptide
<220> FEATURE:
<223> OTHER INFORMATION: See specification as filed for detailed
      description of substitutions and preferred embodiments

<400> SEQUENCE: 131
```

```
Gly Gly Gly Gly
1

<210> SEQ ID NO 132
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Residues at these positions are separated by an
      undefined random amino acid sequence or an amino acid sequence
      derived from a first polypeptide
<220> FEATURE:
<223> OTHER INFORMATION: See specification as filed for detailed
      description of substitutions and preferred embodiments

<400> SEQUENCE: 132

Gly Thr Gly Gly
1

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(5)
<223> OTHER INFORMATION: Residues at these positions are separated by an
      undefined random amino acid sequence or an amino acid sequence
      derived from a first polypeptide
<220> FEATURE:
<223> OTHER INFORMATION: See specification as filed for detailed
      description of substitutions and preferred embodiments

<400> SEQUENCE: 133

Gly Gly Gly Ser Gly Gly Gly Ser
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(5)
<223> OTHER INFORMATION: Residues at these positions are separated by an
      undefined random amino acid sequence or an amino acid sequence
      derived from a first polypeptide
<220> FEATURE:
<223> OTHER INFORMATION: See specification as filed for detailed
      description of substitutions and preferred embodiments

<400> SEQUENCE: 134

Gly Gly Asn Pro Gly Pro Thr
1               5

<210> SEQ ID NO 135
<211> LENGTH: 5
<212> TYPE: PRT
<213> ORGANISM: Artificial Sequence
<220> FEATURE:
```

```
<223>  OTHER INFORMATION: Description of Artificial Sequence: Synthetic
       peptide
<220>  FEATURE:
<221>  NAME/KEY: MOD_RES
<222>  LOCATION: (1)..(1)
<223>  OTHER INFORMATION: May or may not be present
<220>  FEATURE:
<221>  NAME/KEY: misc_feature
<222>  LOCATION: (3)..(4)
<223>  OTHER INFORMATION: Residues at these positions are separated by an
       undefined random amino acid sequence or an amino acid sequence
       derived from a first polypeptide
<220>  FEATURE:
<223>  OTHER INFORMATION: See specification as filed for detailed
       description of substitutions and preferred embodiments

<400>  SEQUENCE: 135

Pro Cys Gly Gly Cys
1               5

<210>  SEQ ID NO 136
<211>  LENGTH: 100
<212>  TYPE: PRT
<213>  ORGANISM: Artificial Sequence
<220>  FEATURE:
<223>  OTHER INFORMATION: Description of Artificial Sequence: Synthetic
       polypeptide
<220>  FEATURE:
<221>  NAME/KEY: MOD_RES
<222>  LOCATION: (9)..(93)
<223>  OTHER INFORMATION: Any amino acid and this region may encompass 4
       to 85 residues
<220>  FEATURE:
<223>  OTHER INFORMATION: See specification as filed for detailed
       description of substitutions and preferred embodiments

<400>  SEQUENCE: 136

Gly Gly Gly Ser Gly Gly Asn Pro Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Gly Pro Thr
                85                  90                  95

Gly Gly Gly Ser
            100

<210>  SEQ ID NO 137
<211>  LENGTH: 8
<212>  TYPE: PRT
<213>  ORGANISM: Artificial Sequence
<220>  FEATURE:
<223>  OTHER INFORMATION: Description of Artificial Sequence: Synthetic
       peptide

<400>  SEQUENCE: 137

His His His His His His His His
1               5

<210>  SEQ ID NO 138
<211>  LENGTH: 9
<212>  TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 138

Gly Gly Gly Gly Ser Gly Gly Asn Pro
1               5

<210> SEQ ID NO 139
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Lys Val Gly Gln Asp Lys Val Val Thr Ile Arg Tyr Thr Leu Gln
1               5                   10                  15

Val Glu Gly Glu Val Leu Asp Gln Gly Glu Leu Ser Tyr Leu His Gly
            20                  25                  30

His Arg Asn Leu Ile Pro Gly Leu Glu Glu Ala Leu Glu Gly Arg Glu
        35                  40                  45

Glu Gly Glu Ala Phe Gln Ala His Val Pro Ala Glu Lys Ala Tyr Gly
    50                  55                  60

Pro His Asp Pro Glu Gly Val Gln Val Val Pro Leu Ser Ala Phe Pro
65                  70                  75                  80

Glu Asp Ala Glu Val Val Pro Gly Ala Gln Phe Tyr Ala Gln Asp Met
                85                  90                  95

Glu Gly Asn Pro Met Pro Leu Thr Val Ala Val Glu Gly Glu Glu
            100                 105                 110

Val Thr Val Asp Phe Asn His Pro Leu Ala Gly Lys Asp Leu Asp Phe
        115                 120                 125

Gln Val Glu Val Val Lys Val Arg Glu Ala Thr Pro Glu Glu Leu Leu
    130                 135                 140

His Gly His Ala His Gly Gly Ser Arg Lys His His His His
145                 150                 155                 160

His

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Gly Ser Gly Ser Ser
1               5

<210> SEQ ID NO 141
<211> LENGTH: 67
<212> TYPE: PRT
<213> ORGANISM: Homo sapiens

<400> SEQUENCE: 141

Glu Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
```

```
                    20                  25                  30

Ser Arg Arg Ala Pro Gln Thr Gly Ile Val Asp Glu Cys Cys Phe Arg
                35                  40                  45

Ser Cys Asp Leu Arg Arg Leu Glu Met Tyr Cys Ala Pro Leu Lys Pro
            50                  55                  60

Ala Lys Ser
65

<210> SEQ ID NO 142
<211> LENGTH: 61
<212> TYPE: PRT
<213> ORGANISM: Homo sapiens

<400> SEQUENCE: 142

Glu Thr Leu Cys Gly Gly Glu Leu Val Asp Thr Leu Gln Phe Val Cys
1               5                   10                  15

Gly Asp Arg Gly Phe Tyr Phe Ser Arg Pro Ala Ser Arg Val Ser Arg
                20                  25                  30

Arg Ser Arg Gly Ile Val Glu Cys Cys Phe Arg Ser Cys Asp Leu
            35                  40                  45

Ala Leu Leu Glu Thr Tyr Cys Ala Thr Pro Ala Lys Ser
        50                  55                  60

<210> SEQ ID NO 143
<211> LENGTH: 287
<212> TYPE: PRT
<213> ORGANISM: Artificial Sequence
<220> FEATURE:
<223> OTHER INFORMATION: Description of Artificial Sequence: Synthetic
      SlyD-FKBP12/13 fusion polypeptide
<220> FEATURE:
<221> NAME/KEY: misc_feature
<222> LOCATION: (165)..(166)
<223> OTHER INFORMATION: Residues at these positions are separated by an
      undefined amino acid linker
<220> FEATURE:
<221> NAME/KEY: misc_feature
<222> LOCATION: (254)..(255)
<223> OTHER INFORMATION: Residues at these positions are separated by an
      undefined amino acid sequence of a linker, or a peptide, or an
      antigen, or a secondary or tertiary structure to be presented by
      the SlyD-FKBP12/13 fusion polypeptide
<220> FEATURE:
<223> OTHER INFORMATION: See specification as filed for detailed
      description of substitutions and preferred embodiments

<400> SEQUENCE: 143

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
                20                  25                  30

Asp Tyr Leu His Gly His Gly Ser Leu Ile Ser Gly Leu Glu Thr Ala
            35                  40                  45

Leu Glu Gly His Glu Val Gly Asp Lys Phe Asp Val Ala Val Gly Ala
        50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
```

```
                115                 120                 125
Asn Leu Lys Phe Asn Val Glu Val Val Ala Ile Arg Glu Ala Thr Glu
        130                 135                 140
Glu Glu Leu Ala His Gly His Val His Gly Ala His Asp His His His
145                 150                 155                 160
Asp His Asp His Asp Gly Val Gln Val Glu Thr Ile Ser Pro Gly Asp
                165                 170                 175
Gly Arg Thr Phe Pro Lys Arg Gly Gln Thr Ala Val Val His Tyr Thr
                180                 185                 190
Gly Met Leu Glu Asp Gly Lys Lys Phe Asp Ser Ser Arg Asp Arg Asn
        195                 200                 205
Lys Pro Phe Lys Phe Met Leu Gly Lys Gln Glu Val Ile Arg Gly Trp
        210                 215                 220
Glu Glu Gly Val Ala Gln Met Ser Val Gly Gln Arg Ala Lys Leu Thr
225                 230                 235                 240
Ile Ser Pro Asp Tyr Ala Tyr Gly Asp Arg Gly Ala Gly Cys Cys Leu
                245                 250                 255
Ile Pro Pro Ala Ser Val Leu Val Phe Asp Val Glu Leu Leu Lys Leu
                260                 265                 270
Glu Gly Gly Gly Ser Arg Pro Leu Leu Pro Pro Leu Pro Gly Gly
                275                 280                 285
```

AMINO ACID SEQUENCE PRESENTING FUSION POLYPEPTIDE AND ITS USE

This application is a divisional of U.S. patent application Ser. No. 14/877,475, filed Oct. 7, 2015, now U.S. Pat. No. 9,938,340, issued on Apr. 10, 2018, which is a divisional of U.S. patent application Ser. No. 14/112,108, filed Oct. 16, 2013, now U.S. Pat. No. 9,266,962, issued on Feb. 23, 2016, which is a continuation-in-part of International Patent Application No. PCT/EP012/058207, filed May 4, 2012, which claims the benefit of priority to European Patent Application Nos. 12155742.5, filed Feb. 16, 2012, and 11164957.0, filed May 5, 2011, which all are hereby incorporated by reference in their entireties.

SEQUENCE LISTING

This application incorporates by reference the Computer Readable Form (CRF) of a Substitute Sequence Listing in ASCII text format submitted via a compact disk. The Substitute Sequence Listing text file submitted via a compact disk, entitled 12279-788-999_SUB_SEQ_LISTING.txt, was created on Aug. 14, 2018, and is 132,993 bytes in size.

Herein is reported a fusion polypeptide comprising one or more fragments of one or more peptidyl-prolyl cis/trans isomerase or FKBP family members and its use in methods for antibody screening/selection, for epitope mapping as well as its use as immunogen for the production of antibodies specifically binding an immunogenic peptide or secondary structure presented by the fusion polypeptide.

BACKGROUND OF THE INVENTION

In recent years the production of therapeutic antibodies has steadily increased and it is likely that therapeutic antibodies will become the biggest group of therapeutics available for the treatment of various diseases in the near future. The impact of therapeutic antibodies emerges from their specificity, such as the specific target recognition and binding function.

Antibodies can be obtained from an experimental animal that has been immunized with an immunogen. The immunogen is in most cases a polypeptide or a fragment of a polypeptide. To provide the immunogen in sufficient quantity and purity a recombinantly produced immunogen can be employed.

Generally prokaryotic and eukaryotic cells can be used for the recombinant production of polypeptides. The recombinant polypeptides can be obtained either in soluble form or as precipitate (inclusion body). Prior to chromatographic purification the insoluble polypeptide contained in the inclusion bodies has to be solubilized.

Generally the immunogen is a synthetic or a peptidic or a recombinantly produced or a fusion or a chimeric or a support conjugated polypeptide. For immunization the immunogen can be administered either alone or in combination with an adjuvant, such as Freud's adjuvant.

Knappe, T. A., et al. (J. Mol. Biol. 368 (2007) 1458-1468) reported that the Flap-region of FKBP12 can be replaced by the IF domain of the structurally related E. coli chaperone SlyD. The chimeric FKBP12-SlyD fusion polypeptide has a 200-times increase peptidyl-prolyl-cis/trans isomerase activity compared to the isolated polypeptide.

The E. coli SlyD and FKBP12 (wild type and mutants C23A and C23S) can be recombinantly produced in E. coli in high yield in soluble form (Standaert, R. F., et al., Nature 346 (1990) 671-674).

FKBP derived from thermophilic organisms and E. coli SlyD can be used as chaperons in the recombinant expression of fusion polypeptides in E. coli (Ideno, A., et al., Appl. Microbiol. Biotechnol. 64 (2004) 99-105). The E. coli SlyD and FKBP12 polypeptides are reversibly folding polypeptides (Scholz, C., et al., J. Biol. Chem. 271 (1996) 12703-12707).

The amino acid sequence of the FKBP12 polypeptide comprises a single tryptophan residue at position 60. Thus, FKBP12 mutants can be analyzed for structural integrity simply by analyzing the tryptophan fluorescence (DeCenzo, M. T., et al., Protein Eng. 9 (1996) 173-180). A test for remaining catalytic activity of the FKBP12 mutant can be performed by determining the remaining rotamase activity (Brecht, S., et al., Neuroscience 120 (2003) 1037-1048; Schories, B., et al., J. Pept. Sci. 13 (2007) 475-480; Timerman, A. P., et al., J. Biol. Chem. 270 (1995) 2451-2459). It is also possible to determine the structural integrity of FKBP12 mutants by determining the FK506- or Rapamycin binding (DeCenzo, M. T., et al., Protein Eng. 9 (1996) 173-180).

McNamara, A., et al. (J. Org. Chem. 66 (2001) 4585-4594) report peptides constrained by an aliphatic linkage between two C(alpha) sites: design, synthesis, and unexpected conformational properties of an i,(i+4)-linked peptide.

Suzuki, et al. (Suzuki, R., et al., J. Mol. Biol. 328 (2003) 1149-1160) report the three-dimensional solution structure of an archaic FKBP with a dual function of peptidyl-prolyl-cis-trans isomerase and chaperone-like activities. Expression vector, host, fused polypeptide, process for producing fused polypeptide and process for producing protein are reported in EP 1 516 928. Knappe, T. A., et al., reports that the insertion of a chaperone domain converts FKBP12 into a powerful catalyst of protein folding (J. Mol. Biol. 368 (2007) 1458-1468). A chimeric fusion polypeptide with superior chaperone and folding activities is reported in WO 2007/077008. In WO 03/000878 the use of FKBP chaperones as expression tool is reported. In EP 1 621 555 an immunogen, composition for immunological use, and method of producing antibody using the same are reported. Rebuzzini, G. (PhD work at the University of Milano-Bicocca (Italy) (2009)) reports a study of the hepatitis C virus NS3 helicase domain for application in a chemiluminescent immunoassay.

In WO 2007/077008 chimeric fusion proteins with superior chaperone and folding activities are reported. The conversion of FKBP12 into a powerful catalyst of protein folding by insertion of a chaperone domain is reported by Knappe et al. (Knappe, T. A., et al., J. Mol. Biol. 368 (2007) 1458-1468).

SUMMARY OF THE INVENTION

The fusion polypeptides as reported herein are fusion polypeptides comprising i) one or more parts derived from one, i.e. the same, or different polypeptides with PPIase activity or belonging to the FKBP family, and ii) an immunogenic polypeptide inserted therein in between.

The fusion polypeptides as reported herein can be used for the immunization of an animal for the generation of antibodies specifically binding to the immunogenic polypeptide inserted into the one or more parts derived from the one or more polypeptides with PPIase activity or belonging to the FKBP family.

One aspect as reported herein is a fusion polypeptide according to formula I $$NH_2—S_2—X_1—S_1—COOH \quad \text{(formula I)}$$

wherein
$X_1$ comprises either a random amino acid sequence or an amino acid sequence derived from a first polypeptide,
$S_2$ and $S_1$ are non-overlapping amino acid sequences derived from a second polypeptide, and
— denotes a peptide bond,
wherein the second polypeptide is a polypeptide with peptidyl-prolyl cis/trans-isomerase activity (PPIase activity) or is derived from the FKBP domain family.

It has been found that with the fusion polypeptides as reported herein antibodies, which specifically bind to internal (so called hidden or buried) epitopes of a (naturally occurring) amino acid sequence, can be obtained. Internal epitopes are not accessible in classical immunization protocols as these are e.g. only accessible upon activation and concomitant conformational changes of the antigenic polypeptide (such as a receptor). Furthermore, antibodies can be obtained that specifically bind to immunogenic polypeptides, which are derived from structures otherwise difficult to be provided in sufficient amount or quality.

The fusion polypeptides as reported herein are chimeric, recombinant polypeptides that can be used for peptide, secondary and tertiary structure display e.g. in methods for antibody screening/selection or for epitope mapping as well as immunogen for the production of antibodies specifically binding the presented antigenic amino acid sequence or secondary structure. The polypeptides as reported herein can be recombinantly produced, are thermodynamically stable, monomeric and soluble in aqueous solutions.

One aspect as reported herein is a fusion polypeptide according to formula II $$NH_2—S_4—X_2—S_3—S_2—X_1—S_1—S_0—COOH \quad \text{(formula II)}$$

wherein
$X_1$ comprises either a random amino acid sequence or an amino acid sequence derived from a first polypeptide,
$S_2$ and $S_1$ are non-overlapping amino acid sequences derived from a second polypeptide,
$S_3$ and $S_0$ are either absent or non-overlapping amino acid sequences derived from a third polypeptide,
$S_4$ is either absent or an amino acid sequence derived from a fourth polypeptide,
$X_2$ is either absent or a peptidic linker sequence, and
— denotes a peptide bond,
wherein the second polypeptide and the third polypeptide and the fourth polypeptide are different from each other and are polypeptides with peptidyl-prolyl cis/trans-isomerase activity (PPIase activity) or which are derived from the FKBP domain family.

In one embodiment of all aspects as reported herein the second polypeptide with peptidyl-prolyl cis/trans-isomerase activity or derived from the FKBP domain family is SlyD.

In one embodiment of all aspects as reported herein the second polypeptide is a polypeptide from a thermophile.

In one embodiment the thermophile is a thermophile bacterium. In one embodiment the thermophile bacterium is from the family of Thermaceae. In one embodiment the thermophile is *Thermus thermophilus*.

In one embodiment the thermophile is a thermophile Archaea. In one embodiment the thermophile Archaea is a hyperthermophilic Archaea. In one embodiment the thermophile is from the class of Thermococci. In one embodiment the thermophile is *Thermococcus gammatolerans*

In one embodiment the thermophile has an optimal growth temperature of at least 60° C.

In one embodiment of all aspects as reported herein the immunogenic sequence is comprised in the $X_1$ amino acid sequence. In one embodiment the $X_1$ amino acid sequences comprises the immunogenic sequence and one or more parts derived from a further polypeptide with peptidyl-prolyl cis/trans-isomerase activity (PPIase activity) or derived from a further polypeptide from the FKBP-fold domain family, whereby the further polypeptide is different from the second polypeptide.

The amino acid sequence of $X_1$ is inserted in place of the insert-in-flap-domain (IF-domain) of the second polypeptide. Thus, if $X_1$ is identical to the IF-domain, i.e. has the amino acid sequence of the IF-domain, the fusion polypeptide $S_2—X_1—S_1$ is identical to the corresponding part of the naturally occurring second polypeptide.

In one embodiment of all aspects as reported herein the $S_2$ and $S_1$ amino acid sequences derived from a second polypeptide are connected (directly) to each other by the IF-domain in the wild-type (naturally occurring) second polypeptide.

In one embodiment of all aspects as reported herein $X_1$ is inserted in place of the insert-in-flap-domain (IF-domain) of the second polypeptide.

One aspect as reported herein is a polypeptide that has at least 70% amino acid sequence identity to the polypeptide of formula I when determined excluding $X_1$, or formula II when determined excluding $X_1$, $X_2$ and the absent sequences. In one embodiment the polypeptide has at least 80% amino acid sequence identity. In one embodiment the polypeptide has at least 90% amino acid sequence identity. In one embodiment the polypeptide has at least 95% amino acid sequence identity. In one embodiment the polypeptide has at least 98% amino acid sequence identity.

In one embodiment of all aspects as reported herein $X_1$ comprises an amino acid sequence that corresponds to a hidden epitope.

In one embodiment of all aspects as reported herein $X_1$ has an amino acid sequence length from 4 to about 500 amino acid residues. In one embodiment $X_1$ has an amino acid sequence length from 5 to about 100 amino acid residues. In one embodiment $X_1$ has an amino acid sequence length of about 7 to about 60 amino acid residues.

In one embodiment of all aspects as reported herein at least one amino acid residue of $X_1$ comprises a post-translational modification. In one embodiment one, or two, or three, or four, or five, or six, or seven, or eight, or nine, or ten amino acid residues of $X_1$ comprise a post-translational modification.

In one embodiment the fusion polypeptide is according to the following formula $$NH_2—S_3—S_2—X_1—S_1—S_0—COOH$$

wherein $X_1$ comprises either a random amino acid sequence or an amino acid sequence derived from a first polypeptide, $S_2$ and $S_1$ are non-overlapping amino acid sequences derived from a second polypeptide, $S_3$ and $S_0$ are either absent or non-overlapping amino acid sequences derived from a third polypeptide, and — denotes a peptide bond, wherein the second polypeptide and the third polypeptide are different from each other and are polypeptides with peptidyl-prolyl cis/trans-isomerase activity (PPIase activity) or which are derived from the FKBP domain family.

In one embodiment of all aspects as reported herein the second polypeptide and the third polypeptide and the fourth polypeptide are from different species.

In one embodiment of all aspects as reported herein the second polypeptide is a human polypeptide, or a plant polypeptide, or a bacterial polypeptide, or an archaic polypeptide.

In one embodiment of all aspects as reported herein the third polypeptide is a human polypeptide, or a bacterial polypeptide, or an archaic polypeptide.

In one embodiment of all aspects as reported herein the fourth polypeptide is a bacterial polypeptide, or an archaic polypeptide.

In one embodiment of all aspects as reported herein the fourth polypeptide is a bacterial polypeptide. In one embodiment the bacterial polypeptide is a polypeptide from a thermophilic bacterium. In one embodiment the thermophile is from the family of Thermaceae. In one embodiment the thermophile is *Thermus thermophilus*.

In one embodiment of all aspects as reported herein the fourth polypeptide is an archaic polypeptide. In one embodiment the archaic polypeptide is a polypeptide from a hyperthermophilic Archaea. In one embodiment the thermophile is from the class of Thermococci. In one embodiment the archaic organism is *Thermococcus gammatolerans*.

In one embodiment of all aspects as reported herein the thermophile has an optimal growth temperature of at least 60° C.

In one embodiment of all aspects as reported herein the first polypeptide is a human polypeptide.

In one embodiment of all aspects as reported herein $X_1$ is either a random amino acid sequence or an amino acid sequence derived from a first polypeptide wherein the dipeptide GS is added at the N-terminus and the tripeptide GSS is added at the C-terminus.

In one embodiment of all aspects as reported herein $X_1$ is a polypeptide of formula III $$X_a X_b X_c X_d - X_0 - X_e - X_f - X_g X_h \quad \text{(formula III)}$$

wherein $X_0$ is either a random amino acid sequence or an amino acid sequence of a first polypeptide, and
wherein each of $X_a$ to $X_h$ denotes an (naturally occurring) amino acid residue and any of $X_{a-h}$ may be individually present or absent.

In one embodiment of all aspects as reported herein $X_1$ is a polypeptide selected from the group of formula IV to formula XIII, with

| | |
|---|---|
| GS-$X_0$-GSS (SEQ ID NO: 127) | (formula IV), |
| AGS-$X_0$-GSS (SEQ ID NO: 128) | (formula V), |
| CG-$X_0$-GC (SEQ ID NO: 129) | (formula VI), |
| C-$X_0$-GC | (formula VII), |
| G-$X_0$-G | (formula VIII), |
| S-$X_0$-GSS (SEQ ID NO: 130) | (formula IX), |
| GG-$X_0$-GG (SEQ ID NO: 131) | (formula X), |
| G-$X_0$-TGG (SEQ ID NO: 132) | (formula XI), |
| GGGS-$X_0$-GGGS (SEQ ID NO: 133) | (formula XII), |
| GGNP-$X_0$-GPT (SEQ ID NO: 134) | (formula XIII), | wherein $X_0$ is either a random amino acid sequence or an amino acid sequence derived from a first polypeptide.

In one embodiment $X_0$ is flanked at its N- and C-terminus by individual (single) cysteine residues.

In one embodiment $X_1$ comprises a cysteine residue within the N-terminal amino acid residues and a cysteine residue within the C-terminal amino acid residues. In one embodiment the N- or C-terminal amino acid residues are the eight terminal residues. In one embodiment $X_1$ comprises one cysteine residue at its N-terminus and one cysteine residue at its C-terminus.

In one embodiment $X_1$ is a circularly constrained polypeptide.

In one embodiment $X_1$ is a circular polypeptide.

In one embodiment the cysteine residues of $X_1$ have an alpha carbon atom distance of 4.3 Angstroms to 6.5 Angstroms. In one embodiment the cysteine residues of $X_1$ have an alpha carbon distance of 4.5 Angstroms. In one embodiment the cysteine residues of $X_1$ have a mean alpha carbon atoms distance of 5.6 Angstroms.

In one embodiment of all aspects as reported herein $X_1$ or $X_0$ has a length from 4 to about 500 amino acid residues.

In one embodiment of all aspects as reported herein $X_2$ is a linker amino acid sequence of from about 10 to about 30 amino acid residues.

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, and $S_4$, $X_2$, $S_3$, and $S_0$ are absent. In one embodiment $S_2$ has the amino acid sequence SEQ ID NO: 02 (DRGAGC), and $S_1$ has the amino acid sequence SEQ ID NO: 03 (CLIPPASV), and $S_4$, $X_2$, $S_3$, and $S_0$ are absent. In one embodiment $S_2$ has the amino acid sequence SEQ ID NO: 04, and $S_1$ has the amino acid sequence SEQ ID NO: 05, $S_4$, $X_2$, $S_3$, and $S_0$ are absent, and $X_1$ is a polypeptide of formula IV (GS-$X_0$-GSS) (SEQ ID NO: 127).

In one embodiment of all aspects as reported herein the second polypeptide is human FKBP12 (SEQ ID NO: 06), or a polypeptide with at least 70%, or at least 80%, or at least 90%, or at least 95%, or at least 98% amino acid sequence identity, and $S_4$, $X_2$, $S_3$, and $S_0$ are absent. In one embodiment $S_2$ has the amino acid sequence SEQ ID NO: 07, and $S_1$ has the amino acid sequence SEQ ID NO: 08 (LVFD-VELLKLE), and $S_4$, $X_2$, $S_3$, and $S_0$ are absent, and $X_1$ is a polypeptide of formula III (GS-$X_0$-GSS) (SEQ ID NO: 127) or formula VI ((P)CG-$X_0$-GC) (SEQ ID NO: 135).

In one embodiment of all aspects as reported herein the second polypeptide is *Thermus thermophilus* SlyD (SEQ ID NO: 09), or a polypeptide with at least 70%, or at least 80%, or at least 90%, or at least 95%, or at least 98% amino acid sequence identity, and $S_4$, $X_2$, $S_3$, and $S_0$ are absent. In one embodiment $S_2$ has the amino acid sequence SEQ ID NO: 10, and $S_1$ has the amino acid sequence SEQ ID NO: 11, and $S_4$, $X_2$, $S_3$, and $S_0$ are absent, and $X_1$ is a polypeptide of formula V (AGS-$X_0$-GSS) (SEQ ID NO: 128) or formula VI ((P)CG-$X_0$-GC) (SEQ ID NO: 135).

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, and the third polypeptide is human FKBP12 (SEQ ID NO: 06), or a polypeptide with at least 70%, or at least 80%, or at least 90%, or at least 95%, or at least 98% amino acid sequence identity, and $S_4$ and $X_2$ are absent. In one embodiment $S_3$ has the amino acid sequence of SEQ ID NO: 07, $S_2$ has the amino acid sequence SEQ ID NO: 02 (DRGAGC), $S_1$ has the amino acid sequence SEQ ID NO: 03 (CLIPPASV), $S_0$ has the amino acid sequence SEQ ID NO: 08 (LVFDVELLKLE), $S_4$ and $X_2$ are absent, and $X_1$ is a polypeptide of formula IV (GS-$X_0$-GSS) (SEQ ID NO: 127) or formula VI ((P)CG-$X_0$-GC) (SEQ ID NO: 135).

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, and the third polypeptide is *Thermus thermophilus* SlyD (SEQ ID NO: 09), or a polypeptide with at least 70%, or at least 80%, or at least 90%, or at least 95%, or at least 98% amino acid sequence identity, and $S_4$ and $X_2$ are absent. In one embodiment $S_3$ has the amino acid sequence of SEQ ID NO: 10, $S_2$ has the amino acid sequence SEQ ID NO: 02 (DRGAGC), $S_1$ has the amino acid sequence SEQ ID NO: 03 (CLIPPASV), $S_0$ has the amino acid sequence SEQ ID NO: 11 (LVFDVELLKLE), $S_4$ and $X_2$ are absent, and $X_1$ is a polypeptide of formula IV (GS-$X_0$-GSS) (SEQ ID NO: 127) or formula VI ((P)CG-$X_0$-GC) (SEQ ID NO: 135).

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, and the third polypeptide is human FKBP12 (SEQ ID NO: 06), or a polypeptide with at least 70%, or at least 80%, or at least 90%, or at least 95%, or at least 98% amino acid sequence identity, and $S_4$ and $X_2$ are absent. In one embodiment $S_3$ has the amino acid sequence of SEQ ID NO: 07, $S_2$ has the amino acid sequence SEQ ID NO: 02 (DRGAGC), $S_1$ has the amino acid sequence SEQ ID NO: 03 (CLIPPASV), $S_0$ has the amino acid sequence SEQ ID NO: 08 (LVFDVELLKLE), $S_4$ and $X_2$ are absent, and $X_1$ is a polypeptide of formula IV (GS-$X_0$-GSS) (SEQ ID NO: 127) or formula VI ((P)CG-$X_0$-GC) (SEQ ID NO: 135).

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, the third polypeptide is human FKBP12 (SEQ ID NO: 06), or a polypeptide with at least 70%, or at least 80%, or at least 90%, or at least 95%, or at least 98% amino acid sequence identity, and the fourth polypeptide is *E. coli* SlyD (SEQ ID NO: 12), or a polypeptide with at least 70%, or at least 80%, or at least 90%, or at least 95%, or at least 98% amino acid sequence identity. In one embodiment $S_4$ has the amino acid sequence SEQ ID NO:12, $X_2$ has the amino acid sequence SEQ ID NO: 13, $S_3$ has the amino acid sequence of SEQ ID NO: 07, $S_2$ has the amino acid sequence SEQ ID NO: 02 (DRGAGC), $S_1$ has the amino acid sequence SEQ ID NO: 03 (CLIPPASV), $S_0$ has the amino acid sequence SEQ ID NO: 08 (LVFDVELLKLE), and $X_1$ is a polypeptide of formula IV (GS-$X_0$-GSS) (SEQ ID NO: 127) or formula VI ((P)CG-$X_0$-GC) (SEQ ID NO:135

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, the third polypeptide is *Thermus thermophilus* SlyD (SEQ ID NO: 09), or a polypeptide with at least 70%, or at least 80%, or at least 90%, or at least 95%, or at least 98% amino acid sequence identity, and the fourth polypeptide is *E. coli* SlyD (SEQ ID NO: 12), or a polypeptide with at least 70%, or at least 80%, or at least 90%, or at least 95%, or at least 98% amino acid sequence identity. In one embodiment $S_4$ has the amino acid sequence SEQ ID NO:12, $X_2$ has the amino acid sequence SEQ ID NO: 13, $S_3$ has the amino acid sequence of SEQ ID NO: 10, $S_2$ has the amino acid sequence SEQ ID NO: 02 (DRGAGC), $S_1$ has the amino acid sequence SEQ ID NO: 03 (CLIPPASV), $S_0$ has the amino acid sequence SEQ ID NO: 11 (LVFDVELLKLE), and $X_1$ is a polypeptide of formula IV (GS-$X_0$-GSS) (SEQ ID NO: 127) or formula VI ((P)CG-$X_0$-GC) (SEQ ID NO: 135).

In one embodiment of all aspects as reported herein the second polypeptide is *Thermus thermophilus* SlyD (SEQ ID NO: 09), or a polypeptide with at least 70%, or at least 80%, or at least 90%, or at least 95%, or at least 98% amino acid sequence identity, and the fourth polypeptide is *E. coli* SlyD (SEQ ID NO: 12), or a polypeptide with at least 70%, or at least 80%, or at least 90%, or at least 95%, or at least 98% amino acid sequence identity, and $S_3$ and $S_0$ are absent. In one embodiment $S_4$ has the amino acid sequence SEQ ID NO: 12, $X_2$ has the amino acid sequence SEQ ID NO: 13, $S_2$ has the amino acid sequence SEQ ID NO: 10, $S_1$ has the amino acid sequence SEQ ID NO: 11, $S_3$ and $S_0$ are absent, and $X_1$ is a polypeptide of formula V (AGS-$X_0$-GSS) (SEQ ID NO: 128) or formula VI ((P)CG-$X_0$-GC) (SEQ ID NO: 135).

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, and the fourth polypeptide is *E. coli* SlyD (SEQ ID NO: 12), or a polypeptide with at least 70%, or at least 80%, or at least 90%, or at least 95%, or at least 98% amino acid sequence identity, and $S_3$ and $S_0$ are absent. In one embodiment $S_4$ has the amino acid sequence SEQ ID NO: 12, $X_2$ has the amino acid sequence SEQ ID NO: 13, $S_2$ has the amino acid sequence SEQ ID NO: 04, $S_1$ has the amino acid sequence SEQ ID NO: 05, $S_3$ and $S_0$ are absent, and $X_1$ is a polypeptide of formula IV (GS-$X_0$-GSS) (SEQ ID NO: 127) or formula VI ((P)CG-$X_0$-GC) (SEQ ID NO: 135).

In one embodiment of all aspects as reported herein the second polypeptide is *Thermococcus gammatolerans* SlyD (SEQ ID NO: 106), or a polypeptide with at least 70%, or at least 80%, or at least 90%, or at least 95%, or at least 98% amino acid sequence identity, and $S_4$, $X_2$, $S_3$, and $S_0$ are absent. In one embodiment $S_2$ has the amino acid sequence SEQ ID NO: 107, $S_1$ has the amino acid sequence SEQ ID NO: 108, $S_4$, $X_2$, $S_3$, and $S_0$ are absent, and $X_1$ is a polypeptide selected from formula IV to formula XIII.

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, and the third polypeptide is *Thermococcus gammatolerans* SlyD (SEQ ID NO: 106), or a polypeptide with at least 70%, or at least 80%, or at least 90%, or at least 95%, or at least 98% amino acid sequence identity, and $S_4$ and $X_2$ are absent. In one embodiment $S_3$ has the amino acid sequence of SEQ ID NO: 107, $S_2$ has the amino acid sequence SEQ ID NO: 02 (DRGAGC), $S_1$ has the amino acid sequence SEQ ID NO: 03 (CLIPPASV), $S_0$ has the amino acid sequence SEQ ID NO: 108, $S_4$ and $X_2$ are absent, and $X_1$ is a polypeptide selected from formula IV to formula XIII.

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, the third polypeptide is human FKBP12 (SEQ ID NO: 06), or a polypeptide with at least 70%, or at least 80%, or at least 90%, or at least 95%, or at least 98% amino acid sequence identity, and the fourth polypeptide is *Thermococcus gammatolerans* SlyD (SEQ ID NO: 106), or a polypeptide with at least 70%, or at least 80%, or at least 90%, or at least 95%, or at least 98% amino acid sequence identity. In one embodiment $S_4$ has the amino acid sequence SEQ ID NO: 106, $X_2$ has the amino acid sequence SEQ ID NO: 13, $S_3$ has the amino acid sequence of SEQ ID NO: 07, $S_2$ has the amino acid sequence SEQ ID NO: 02 (DRGAGC), $S_1$ has the amino acid sequence SEQ ID NO: 03 (CLIPPASV), $S_0$ has the amino acid sequence SEQ ID NO: 08 (LVFDVELLKLE), and $X_1$ is a polypeptide selected from formula IV to formula XIII.

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, the third polypeptide is *Thermococcus gammatolerans* SlyD (SEQ ID NO: 106), or a polypeptide with at least 70%, or at least 80%, or at least 90%, or at least 95%, or at least 98% amino acid sequence identity, and the fourth polypeptide is *E. coli* SlyD (SEQ ID NO: 12), or a polypeptide with at least 70%, or at least 80%, or at least 90%, or at least 95%, or at least 98% amino acid sequence identity. In a specific embodiment $S_4$ has the amino acid sequence SEQ ID NO: 12, $X_2$ has the amino acid sequence SEQ ID NO: 13, $S_3$ has the amino acid sequence of SEQ ID NO: 107, $S_2$ has the amino acid sequence SEQ ID NO: 02 (DRGAGC), $S_1$ has the amino acid sequence SEQ ID NO: 03 (CLIPPASV), $S_0$ has the amino acid sequence SEQ ID NO: 108, and $X_1$ is a polypeptide selected from formula IV to formula XIII.

In one embodiment of all aspects as reported herein the second polypeptide is *Thermococcus gammatolerans* SlyD (SEQ ID NO: 106), or a polypeptide with at least 70%, or at least 80%, or at least 90%, or at least 95%, or at least 98% amino acid sequence identity, and the fourth polypeptide is *E. coli* SlyD (SEQ ID NO: 12), or a polypeptide with at least 70%, or at least 80%, or at least 90%, or at least 95%, or at least 98% amino acid sequence identity, and $S_3$ and $S_0$ are absent. In one embodiment $S_4$ has the amino acid sequence SEQ ID NO: 12, $X_2$ has the amino acid sequence SEQ ID NO: 13, $S_2$ has the amino acid sequence SEQ ID NO: 107, $S_1$ has the amino acid sequence SEQ ID NO: 108, $S_3$ and $S_0$ are absent, and $X_1$ is a polypeptide selected from formula IV to formula XIII.

In one embodiment of all aspects as reported herein the second polypeptide is *Arabidopsis thaliana* FKBP13 (SEQ ID NO: 01), or a polypeptide with at least 70%, or at least 80%, or at least 90%, or at least 95%, or at least 98% amino acid sequence identity, and the fourth polypeptide is *Thermococcus gammatolerans* SlyD (SEQ ID NO: 106), or a polypeptide with at least 70%, or at least 80%, or at least 90%, or at least 95%, or at least 98% amino acid sequence identity, and $S_3$ and $S_0$ are absent. In one embodiment $S_4$ has the amino acid sequence SEQ ID NO: 107, $X_2$ has the amino acid sequence SEQ ID NO: 13, $S_2$ has the amino acid sequence SEQ ID NO: 04, $S_1$ has the amino acid sequence SEQ ID NO: 05, $S_3$ and $S_0$ are absent, and $X_1$ is a polypeptide selected from formula IV to formula XIII.

The fusion polypeptides of the aspects as reported herein have many applications because they can be produced recombinantly in good yields e.g. in *E. coli*. For example the fusion polypeptides can be used for presenting amino acid sequence for immunization, antibody generation, antibody screening, antibody epitope mapping, or immunohistochemistry screening.

In one embodiment of all aspects as reported herein $X_2$ has the amino acid sequence GGGSGGGSGGGSGGGSGGGSGGG (SEQ ID NO: 14).

In one embodiment of all aspects as reported herein $X_1$ has the amino acid sequence GGGSGGNPX$_0$GPTGGGS (SEQ ID NO: 136), wherein $X_0$ is an amino acid sequence from 4 to 85 amino acid residues.

In one embodiment a fusion polypeptide comprising *E. coli* SlyD and human FKBP12 amino acid sequences is used for the presentation of non-stable conformational polypeptides.

In one embodiment a fusion polypeptide comprising human FKBP12 and *Arabidopsis thaliana* FKBP13, or solely *Thermus thermophilus* SlyD, or *Thermus thermophilus* SlyD and *Arabidopsis thaliana* FKBP13, or solely *Thermococcus gammatolerans* SlyD, or *Thermococcus gammatolerans* SlyD and *Arabidopsis thaliana* FKBP13 amino acid sequences is used for the presentation of stable secondary structures.

One aspect as reported herein is the use of a fusion polypeptide as reported herein for eliciting an immune response against $X_1$ or $X_0$ in an animal.

One aspect as reported herein is a method for eliciting an immune response in an animal against a polypeptide comprising the step of administering to the animal a fusion polypeptide as reported herein for at least one time, whereby $X_0$ is the immunogenic amino acid sequence.

One aspect as reported herein is a method for obtaining a nucleic acid encoding an antibody specifically binding to a target antigen comprising the following steps:
a) administering to an animal a fusion polypeptide as reported herein for at least one time, whereby the amino acid sequence of $X_1$ comprises the amino acid sequence of the target antigen,
b) recovering from the animal three to ten days after the last administration of the polypeptide B-cells that produce the antibody specifically binding to the target antigen, and
c) obtaining from the B-cells the nucleic acid encoding an antibody specifically binding to a target antigen.

One aspect as reported herein is a method for the production of an antibody specifically binding to a target antigen comprising the following steps:
a) administering to an animal a fusion polypeptide as reported herein for at least one time, whereby the amino acid sequence of $X_1$ comprises the amino acid sequence of the target antigen,
b) recovering from the animal three to ten days after the last administration of the polypeptide B-cells that produce the antibody specifically binding to the target antigen,
c) optionally obtaining from the B-cells the nucleic acid encoding the antibody specifically binding to the target antigen, and
d) cultivating a cell comprising a nucleic acid encoding the antibody specifically binding to the target antigen and recovering the antibody from the cell or the cultivation medium and thereby producing an antibody specifically binding to a target antigen.

One aspect as reported herein is a method for the production of an antibody specifically binding to a target antigen comprising the following steps:
a) recovering from an experimental animal after the administration of a fusion polypeptide as reported herein B-cells that produce the antibody specifically binding to the target antigen that has the amino acid sequence of $X_0$, and b) cultivating a cell comprising a nucleic acid encoding the antibody specifically binding to the amino acid sequence of $X_0$ and recovering the antibody from the cell or the cultivation medium and thereby producing an antibody specifically binding to a target antigen.

One aspect as reported herein is the use of a fusion polypeptide as reported herein for epitope mapping, whereby the amino acid sequence of $X_1$ comprises the epitope.

One aspect as reported herein is a method for selecting an antibody specifically binding to a target antigen comprising the following steps:

a) determining the binding affinity of a plurality of antibodies to a target antigen, whereby the amino acid sequence of $X_1$ of a fusion polypeptide as reported herein comprises the target antigen amino acid sequence, b) selecting the antibody having an apparent complex stability above a pre-defined threshold level.

One aspect as reported herein is a method for selecting an antibody suitable for immunohistochemical analysis of a target polypeptide comprising the following steps:

a) determining the binding kinetics of a plurality of antibodies, c) selecting the antibody having an apparent complex stability above a pre-defined threshold level.

One aspect as reported herein is a method for mapping a binding site of an antibody to a target amino acid sequence comprising the following steps:

a) contacting a solid support to which a fusion polypeptide as reported herein is immobilized, whereby the amino acid sequence of $X_1$ comprises the target amino acid sequence, with an antibody, b) determining the kinetic properties of the antibody with the fusion polypeptide as reported herein, c) selecting the antibody having an apparent complex stability above a pre-defined threshold level.

One aspect as reported herein is the use of a fusion polypeptide as reported herein for determining structure-function-relationships, whereby the amino acid sequence of $X_1$ comprises the polypeptide for which the structure-function-relationship shall be determined.

One aspect as reported herein is the use of a fusion polypeptide as reported herein for presenting a polypeptide with its correct secondary and/or tertiary structure, whereby the amino acid sequence of $X_1$ comprises the polypeptide.

One aspect as reported herein is the use of a fusion polypeptide as reported herein in a screening method.

In one embodiment the screening method is a screening method for identifying or selecting molecules that specifically bind to $X_1$. In one embodiment the molecule is a small molecule or a polypeptide. In one embodiment the polypeptide is an antibody, or antibody-fragment, or antibody-fusion polypeptide.

One aspect as reported herein is the use of a fusion polypeptide as reported herein in ribosome display.

One aspect as reported herein is the use of a fusion polypeptide as reported herein in phage display.

One aspect as reported herein is the use of a polypeptide as reported herein in cell surface display. In one embodiment the cell is a prokaryotic cell. In one embodiment the prokaryotic cell is a bacterial cell. In one embodiment the cell is a eukaryotic cell. In one embodiment the eukaryotic cell is a CHO cell, or a HEK cell, or a BHK cell, or a Sp2/0 cell, or a NS0 cell, or a yeast cell.

One aspect as reported herein is the antibody produced by a method as reported herein.

One aspect as reported herein is a pharmaceutical formulation comprising the fusion polypeptide as reported herein and a pharmaceutically acceptable carrier.

One aspect as reported herein is a diagnostic formulation comprising the fusion polypeptide as reported herein conjugated to a detectable label.

One aspect as reported herein is the use of a fusion polypeptide as reported herein for the manufacture of a medicament.

One aspect as reported herein is the use of a fusion polypeptide as reported herein for the treatment of a disease.

One aspect as reported herein is a method of treating an individual comprising administering to the individual an effective amount of the fusion polypeptide as reported herein.

DETAILED DESCRIPTION OF THE INVENTION

In general, the antigen or antigenic or immunogenic amino acid sequence, e.g. comprised in the amino acid sequence of $X_1$ is inserted in place of the insert-in-flap-domain (IF-domain) of the SlyD part of the second polypeptide in the fusion polypeptide as reported herein.

In one embodiment of all aspects as reported herein $X_0$ is selected from a fragment of a naturally occurring polypeptide or is a randomized amino acid sequence. In one embodiment the naturally occurring polypeptide is a human polypeptide.

The fusion polypeptide comprising the $X_1$ amino acid sequence can be used on the one hand for the immunization of animals to generate antibodies and on the other hand for the screening of antibody libraries obtained by randomization or after immunization. Specific binders can also be identified using any screening and display methodology, such as ribosome display, phage display, cell surface display, viral display and a fusion polypeptide based display as reported herein.

*Thermus thermophilus* SlyD as well as *Thermococcus gammadurans* SlyD are highly stable proteins with the ability to reversibly fold even when their Flap domain is being replaced by a foreign amino acid insertion X1. These molecules can be used in ribosome display, basically according to the method of Mattheakis, L. C., et al. Proc. Natl. Acad. Sci USA 91 (1994) 9022-9026) to display a polypeptide sequence X1 in the frames of *Thermus thermophilus* SlyD or *Thermococcus gammadurans* SlyD. The so called ternary complex consists of (1) the ribosomal subunits attached to the (2) mRNA encoding the genetic information of the (3) ribosomally presented fusion polypeptide.

The ternary complexes can be used in panning procedures versus antibodies or antibody fragments, which specifically recognize the X1 amino acid sequence.

The fusion polypeptide as reported herein can be used for the screening/selection of antibodies obtained by the immunization of animals using the fusion polypeptide as reported herein, wherein the fusion polypeptide used for the immunization of the animal and the fusion polypeptide used for the screening of the obtained antibodies have the identical $X_1$ amino acid sequence and the remaining amino acid sequence is different. This allows deselecting antibodies that specifically bind to the scaffold and not to the immunogenic peptide $X_1$.

In one embodiment has the fusion polypeptide used for the immunization and the fusion polypeptide used for the screening a sequence identity of less than 20%. In one embodiment the sequence identity is less than 10%.

Herein is reported as one aspect a fusion polypeptide comprising at its N-terminus an N-terminal fragment of the *Thermus thermophilus* SlyD polypeptide (SEQ ID NO: 10), i.e. residues 2 to 64 of the *Thermus thermophilus* SlyD polypeptide (numbering starts with M as residue 1 of SEQ ID NO: 09). Thereafter the immunogenic sequence comprised in $X_1$ is inserted. The C-terminus of the fusion polypeptide is formed by amino acid residues 123 to 149 of the *Thermus thermophilus* SlyD polypeptide (SEQ ID NO: 11) and an optional purification tag with the amino acid sequence GSRKHHHHHHHH (SEQ ID NO: 16).

Herein is reported as one aspect a fusion polypeptide comprising at its N-terminus an N-terminal fragment of the *Thermococcus gammatolerans* SlyD polypeptide (SEQ ID NO: 106), i.e. residues 2 to 85 of the *Thermococcus gammatolerans* SlyD polypeptide (numbering starts with M as residue 1 of SEQ ID NO: 107). Thereafter the immunogenic sequence comprised in $X_1$ is inserted. The C-terminus of the fusion polypeptide is formed by amino acid residues 137 to 156 of the *Thermococcus gammatolerans* SlyD polypeptide (SEQ ID NO: 108) and an optional purification tag with the amino acid sequence GSRKHHHHHHHH (SEQ ID NO: 16).

Herein is reported as one aspect a polypeptide comprising at its N-terminus an N-terminal fragment of the *E. coli* SlyD polypeptide, i.e. residues 1 to 165 of the *E. coli* SlyD polypeptide (numbering starts with M as residue 1). Thereafter a linker is inserted which connects the C-terminus of the *E. coli* SlyD fragment with a fragment of the N-terminus of the human FKBP12 polypeptide, i.e. residues 2 to 84 of the human FKBP12 polypeptide (numbering starts with M as residue 1). Thereafter an amino acid sequence from 5 to 500 amino acid residues can be inserted. The C-terminus of the polypeptide is formed by amino acid residues 97 to 108 of the human FKBP12 polypeptide and a purification tag with the amino acid sequence GSRKHHHHHHHH (SEQ ID NO: 16).

One aspect as reported herein is a variant of the fusion polypeptide as reported herein that has at least 70% amino acid sequence identity with respect to the parent polypeptide, and that has a melting point that is increased compared to the parent polypeptide. In one embodiment the melting point is at least 55° C. In one embodiment the melting point is at least 60° C. In one embodiment the melting point is at least 65° C.

The term "derived from a polypeptide" denotes that a fragment of the full length amino acid sequence of the respective polypeptide is present, whereby the fragment has at least 70% amino acid sequence identity to the respective sequence in the full length polypeptide.

The $X_1$ and $X_0$ amino acid sequence, respectively, can freely be chosen as long it is at least 5 amino acid residues in length. For example the inserted sequence can be derived from, i.e. can comprise a fragment of, the leukocyte markers, CD2, CD3, CD4, CD S, CD6, CD7, CD8, CD11a,b,c, CD13, CD14, CD18, CD19, CD20, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, CDw52 (Campath antigen), CD56, CD58, CD69, CD72, CTLA-4, LFA-1 and TCR; the histocompatibility antigens, MHC class I or II, the Lewis Y antigens, SLex, SLey, SLea, and SLeb; the integrins, VLA-1, VLA-2, VLA-3, VLA-4, VLA-5, VLA-6, αVβ3, and LFA-1, Mac-1, and p150,95, αVβ1, gpIIbIIIa, αR β3, α6β4, αVβ5, αVβ6, and αV 62 7; the selectins, L-selectin, P-selectin, and E-selectin and their counter receptors VCAM-1, ICAM-1, ICAM-2, and LFA-3; the interleukins, IL-1, IL-2, IL-3, IL-4, IL-5, IL-6, IL-7, IL-8, IL-9, IL-10, IL-11, IL-12, IL-13, IL-14, and IL-15; the interleukin receptor is selected from the group consisting of IL-1R, IL-2R, IL-3R, IL-4R, IL-5R, IL-6R, IL-7R, IL-8R, IL-9R, IL-10R, IL-11R, IL-12R, IL-13R, IL-14R, and IL-15R; the chemokine is selected from the group consisting of PF4, RANTES, MIP1α, MCP1, NAP-2, Groα, Groβ, and IL-8; the growth factor is selected from the group consisting of TNFalpha, TGFbeta, TSH, VEGF/VPF, VEGFA, VEGFB, VEGF111, VEGF121, VEGF165, VEGF189, VEGF206, PTHrP, EGF family, FGF, PDGF family, endothelin, Fibrosin (FSF-1), human Laminin, and gastrin releasing peptide (GRP), PLGF, HGH, HGHR; the growth factor receptor is selected from the group consisting of TNFalphaR, RGFbetaR, TSHR, VEGFR/VPFR, FGFR, EGFR, PTHrPR, PDGFR family, EPO-R, GCSF-R and other hematopoietic receptors; the interferon receptor is selected from the group consisting of IFNCαR, IFNβR, and IFNλR; the Ig and its receptor is selected from the group consisting of IgE, FcγRI, and FcγRII; the tumor antigen is selected from the group consisting of her2-neu, mucin, CEA and endosialin; the allergen is selected from the group consisting of house dust mite antigen, lol p1 (grass) antigens, and urushiol; the viral polypeptide is selected from the group consisting of CMV glycoproteins B, H, and gCIII, HIV-1 envelope glycoproteins, RSV envelope glycoproteins, HSV envelope glycoproteins, HPV envelope glycoproteins, Hepatitis family surface antigens; the toxin is selected from the group consisting of *pseudomonas* endotoxin and osteopontin/uropontin, snake venom, spider venom, and bee venom conotoxin; the blood factor is selected from the group consisting of complement C3b, complement C4a, complement C4b-9, Rh factor, fibrinogen, fibrin, and myelin associated growth inhibitor; and the enzyme is selected from the group consisting of cholesterol ester transfer polypeptide, membrane bound matrix metalloproteases, and glutamic acid decarboxylase (GAD).

The term "peptidic linker sequence" denotes peptide linkers of natural and/or synthetic origin. They consist of a linear amino acid chain wherein the 20 naturally occurring amino acids are the monomeric building blocks. The chain has a length of from 10 to 50 amino acids, particularly of from 10 to 30 amino acids. The linker may contain repetitive amino acid sequences or sequences of naturally occurring polypeptides, such as polypeptides with a hinge-function. In one embodiment the peptidic linker amino acid sequence is a "synthetic linker amino acid sequence" that is designated to be rich in glycine, glutamine, and/or serine residues. These residues are arranged e.g. in small repetitive units of up to five amino acids, such as GGGGS, QQQQG, or SSSSG (SEQ ID NO: 17, 18, or 19). This small repetitive unit may be repeated for two to six times to form a multimeric unit. At the amino- and/or carboxy-terminal ends of the multimeric unit up to six additional arbitrary, naturally occurring amino acids may be added. Other synthetic peptidic linkers are composed of a single amino acid, that is repeated between 10 to 20 times and may comprise at the amino- and/or carboxy-terminal end up to six additional arbitrary, naturally occurring amino acids, such as e.g. serine in the linker GSSSSSSSSSSSSSSSG (SEQ ID NO: 20). Particular linker amino acid sequences are shown in the following Table. In one embodiment the linker amino acid sequence is selected from $[GQ_4]_3GNN$ (SEQ ID NO: 21), G$_3$[SG$_4$]$_2$SG (SEQ ID NO: 22), G$_3$[SG$_4$]$_2$SG$_2$ (SEQ ID NO: 23), (G$_3$S)$_5$GGG (SEQ ID NO: 24). All peptidic linkers can be encoded by a nucleic acid molecule and therefore can be recombinantly expressed.

TABLE

| linker amino acid sequence | SEQ ID NO: |
|---|---|
| (GQ$_4$)$_3$ | 25 |
| (GQ$_4$)$_3$G | 26 |
| (GQ$_4$)$_3$GNN | 27 |
| (G$_2$S)$_3$ | 28 |
| (G$_2$S)$_4$ | 29 |
| (G$_2$S)$_5$ | 30 |
| (G$_3$S)$_3$ | 31 |
| (G$_3$S)$_4$ | 32 |
| (G$_3$S)$_5$ | 33 |
| (G$_3$S)$_5$GGG | 34 |
| (G$_4$S)$_2$ | 35 |
| (G$_4$S)$_2$G | 36 |
| (G$_4$S)$_2$GG | 37 |
| (G$_4$S)$_2$GGG | 38 |
| (G$_4$S)$_2$GN | 39 |
| (G$_4$S)$_3$ | 40 |
| (G$_4$S)$_3$G | 41 |
| (G$_4$S)$_3$T | 42 |
| (G$_4$S)$_3$GG | 43 |
| (G$_4$S)$_3$GGT | 44 |
| (G$_4$S)$_3$GGN | 45 |
| (G$_4$S)$_3$GAS | 46 |
| (G$_4$S)$_4$ | 47 |
| (G$_4$S)$_5$ | 48 |
| (G$_4$S)$_5$G | 49 |
| (G$_4$S)$_5$GG | 50 |
| (G$_4$S)$_5$GAS | 51 |
| G(S)$_{15}$G | 52 |
| G(S)$_{15}$GAS | 53 |

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "animal" denotes an animal selected from the group of mouse, rat, rabbit, sheep, cat, dog, hamster, cynomolgus, and chimpanzee. Particularly, the animal is a mouse or a rabbit or a hamster or a rat. In one embodiment the animal is a non-human animal.

In one embodiment the term "recovering" comprises a) (i) immortalizing B-cells from the animal immunized with the target antigen, and (ii) screening the resulting immortalized cells for the secretion of the antibody specifically binding to the target antigen, or b) (i) co-cultivating single deposited B-cells in the presence of feeder cells, and (ii) screening the cultivation supernatant for the presence of antibodies specifically binding to the target antigen.

The term "specifically binding to a target antigen" denotes that an antibody is binding to the target antigen with a dissociation constant (=K$_{Diss.}$) of at least $10^{-8}$ mol/l, particularly with a K$_{Diss.}$ of at least $10^{-10}$ mol/l. At the same time the property of not specifically binding to a target antigen is insured by a K$_{Diss.}$ of $10^{-7}$ mol/l or worse, e.g. of $10^{-5}$ mol/l.

The term "pharmaceutical formulation" denotes a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "E. coli SlyD" denotes a polypeptide that has the following amino acid sequence:

(SEQ ID NO: 12)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFLAET

DQGPVPVEITAVEDDHVVVDGNHMLAGQNLKFNVEVVAIREATEEELAHG

HVHGAHDHHHDHDHD.

The term "denotes a polypeptide that has the following amino acid sequence" denotes a polypeptide of the given amino acid sequence and also includes variants thereof that have the same properties as the polypeptide with respect to X$_1$. In one embodiment the term denotes a polypeptide with at least 70% amino acid sequence identity. In one embodiment the term denotes a polypeptide with at least 80% amino acid sequence identity. In one embodiment the term denotes a polypeptide with at least 90% amino acid sequence identity. In one embodiment the term denotes a polypeptide with at least 95% amino acid sequence identity. In one embodiment the term denotes a polypeptide with at least 98% amino acid sequence identity.

If a polypeptide is produced in or derived from *E. coli* the amino-terminal methionine residue is usually not efficiently cleaved off by proteases, thus the amino-terminal methionine residue is partially present in the produced polypeptide. In order to account for this all sequence are given with the starting methionine residue.

The term "*Thermus thermophilus* SlyD" denotes a polypeptide that has the following amino acid sequence:

(SEQ ID NO: 09)
MKVGQDKVVTIRYTLQVEGEVLDQGELSYLHGHRNLIPGLEEALEGREEG

EAFQAHVPAEKAYGPHDPEGVQVVPLSAFPEDAEVVPGAQFYAQDMEGNP

MPLTVVAVEGEEVTVDFNHPLAGKDLDFQVEVVKVREATPEELLHGHAH.

The term "*Thermococcus gammatolerans* SlyD" denotes a polypeptide that has the following amino acid sequence:

(SEQ ID NO: 106)
MKVERGDFVLFNYVGRYENGEVFDTSYESVAREQGIFVEEREYSPIGVT

VGAGEIIPGIEEALLGMELGEKKEVVVPPEKGYGMPREDLIVPVPIEQF

TSAGLEPVEGMYVMTDAGIAKILKVEEKTVRLDFNHPLAGKTAIFEIEV

VEIKKAGEA.

The term "human FKBP12" denotes a polypeptide that has the following amino acid sequence:

(SEQ ID NO: 06)
MGVQVETISPGDGRTFPKRGQTCVVHYTGMLEDGKKFDSSRDRNKPFKF

MLGKQEVIRGWEEGVAQMSVGQRAKLTISPDYAYGATGHPGIIPPHATL

VFDVELLKLE.

The term "*Arabidopsis thaliana* FKBP13" denotes a polypeptide that has the following amino acid sequence:

(SEQ ID NO: 01)
ETTSCEFSVSPSGLAFCDKVVGYGPEAVKGQLIKAHYVGKLENGKVFDS

SYNRGKPLTFRIGVGEVIKGWDQGILGSDGIPPMLTGGKRTLRIPPELA

YGDRGAGCKGGSCLIPPASVLLFDIEYIGKA.

The term "FKBP12 fusion polypeptide" denotes a polypeptide that has the following amino acid sequence:

(SEQ ID NO: 109)
MRSGVQVETISPGDGRTFPKRGQTAVVHYTGMLEDGKKFDSSRDRNKPF

KFMLGKQEVIRGWEEGVAQMSVGQRAKLTISPDYAYG-$X_1$-TLVFDVEL

LKLE, wherein $X_1$ is the amino acid sequence of a linker, or a peptide, or an antigen, or a secondary or tertiary structure to be presented by the FKBP12 fusion polypeptide.

This amino acid sequence and variants thereof are individual aspects as reported herein.

The term "SlyD-FKBP12 fusion polypeptide" denotes a polypeptide that has the following amino acid sequence:

(SEQ ID NO: 110)
MKVAKDLVVSLAYQVRTEDGVLVDESPVSAPLDYLHGHGSLISGLETAL

EGHEVGDKFDVAVGANDAYGQYDENLVQRVPKDVFMGVDELQVGMRFL

AETDQGPVPVEITAVEDDHVVVDGNHMLAGQNLKFNVEVVAIREATEEE

LAHGHVHGAHDHHHDHDHD-$X_2$-RSGVQVETISPGDGRTFPKRGQTAVV

HYTGMLEDGKKFDSSRDRNKPFKFMLGKQEVIRGWEEGVAQMSVGQRAK

LTISPDYAYG-$X_1$-TLVFDVELLKLE, wherein $X_1$ is the amino acid sequence of a linker, or a peptide, or an antigen, or a secondary or tertiary structure to be presented by the SlyD-FKBP12 fusion polypeptide, and wherein $X_2$ is the amino acid sequence of a linker.

This amino acid sequence and variants thereof are individual aspects as reported herein.

The term "FKBP12/13 fusion polypeptide" denotes a polypeptide that has the following amino acid sequence:

(SEQ ID NO: 54)
MRSGVQVETISPGDGRTFPKRGQTAVVHYTGMLEDGKKFDSSRDRNKPF

KFMLGKQEVIRGWEEGVAQMSVGQRAKLTISPDYAYGDRGAGCGS-$X_1$-

GSSCLIPPASVLVFDVELLKLE, wherein $X_1$ is the amino acid sequence of a linker, or a peptide, or an antigen, or a secondary or tertiary structure to be presented by the FKBP12/13 fusion polypeptide.

This amino acid sequence and variants thereof are individual aspects as reported herein.

The term "SlyD-FKBP12/13 fusion polypeptide" denotes a polypeptide that has the following amino acid sequence:

(SEQ ID NO: 55)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHD-$X_2$-GVQVETISPGDGRTFPKRGQTAVVHYTG

MLEDGKKFDSSRDRNKPFKFMGKQEVIRGWEEGVAQMLSVGQRAKLTISP

DYAYGDRGAGCGS-$X_1$-GSSCLIPPASVLVFDVELLKLE, wherein $X_1$ is the amino acid sequence of a linker, or a peptide, or an antigen, or a secondary or tertiary structure to be presented by the SlyD-FKBP12/13 fusion polypeptide, and wherein $X_2$ is the amino acid sequence of a linker.

This amino acid sequence and variants thereof are individual aspects as reported herein.

The term "*Thermus thermophilus* SlyD fusion polypeptide" denotes a polypeptide that has the following amino acid sequence:

(SEQ ID NO: 56)
MRSKVGQDKVVTIRYTLQVEGEVLDQGELSYLHGHRNLIPGLEEALEGRE

EGEAFQAHVPAEKAY-$X_1$-GKDLDFQVEVVKVREATPEELLHGHAH, wherein $X_1$ is the amino acid sequence of a linker, or a peptide, or an antigen, or a secondary or tertiary structure to be presented by the *Thermus thermophilus* SlyD fusion polypeptide.

This amino acid sequence and variants thereof are individual aspects as reported herein.

The term "SlyD-*Thermus thermophilus* SlyD fusion polypeptide" denotes a polypeptide that has the following amino acid sequence:

(SEQ ID NO: 57)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHD-X$_2$-KVGQDKVVTIRYTLQVEGEVLDQGELS

YLHGHRNLIPGLEEALEGREEGEAFQAHVPAEKAY-X$_1$-GKDLDFQVEV

VKVREATPEELLHGHAH, wherein X$_1$ is the amino acid sequence of a linker, or a peptide, or an antigen, or a secondary or tertiary structure to be presented by the SlyD-*Thermus thermophilus* SlyD fusion polypeptide, and wherein X$_2$ is the amino acid sequence of a linker.

This amino acid sequence and variants thereof are individual aspects as reported herein.

The term "*Thermococcus gammatolerans* SlyD fusion polypeptide" denotes a polypeptide that has the following amino acid sequence:

(SEQ ID NO: 111)
MKVERGDFVLFNYVGRYENGEVFDTSYESVAREQGIFVEEREYSPIGVT

VGAGEIIPGIEEALLGMELGEKKEVVVPPEKGYGMP-X$_1$-AGKTAIFEIE

VVEIKKAGEA wherein X$_1$ is the amino acid sequence of a linker, or a peptide, or an antigen, or a secondary or tertiary structure to be presented by the *Thermococcus gammatolerans* SlyD fusion polypeptide.

This amino acid sequence and variants thereof are individual aspects as reported herein.

The term "SlyD-*Thermococcus gammatolerans* SlyD fusion polypeptide" denotes a polypeptide that has the following amino acid sequence:

(SEQ ID NO: 112)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHD-X$_2$-KVERGDFVLFNYVGRYENGEVFDTSYES

VAREQGIFVEEREYSPIGVTVGAGEIIPGIEEALLGMELGEKKEVVVPP

EKGYGMP-X$_1$-AGKTAIFEIEVVEIKKAGEA wherein X$_1$ is the amino acid sequence of a linker, or a peptide, or an antigen, or a secondary or tertiary structure to be presented by the *Thermococcus gammatolerans* SlyD fusion polypeptide, and wherein X$_2$ is the amino acid sequence of a linker.

This amino acid sequence and variants thereof are individual aspects as reported herein. The term "*Thermus thermophilus* SlyD-FKBP13 fusion polypeptide" denotes a polypeptide that has the following amino acid sequence:

GDRGAGCGS-X$_1$-GSSCLIPPASVLDFQVEVVKVREATPEELLHGHAH
(residues 66-109 of SEQ ID NO: 58), wherein X$_1$ is the amino acid sequence of a linker, or a peptide, or an antigen, or a secondary or tertiary structure to be presented by the *Thermus thermophilus* SlyD-FKBP13 fusion polypeptide.

This amino acid sequence and variants thereof are individual aspects as reported herein.

The term "SlyD-*Thermus thermophilus* SlyD-FKBP13 fusion polypeptide" denotes a polypeptide that has the following amino acid sequence:

(SEQ ID NO: 59)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHD-X$_2$-KVGQDKVVTIRYTLQVEGEVLDQGELS

YLHGHRNLIPGLEEALEGREEGEAFQAHVPAEKAYGDRGAGCGS-X$_1$-

GSSCLIPPASVLDFQVEVVKVREATPEELLHGHAH, wherein X$_1$ is the amino acid sequence of a linker, or a peptide, or an antigen, or a secondary or tertiary structure to be presented by the SlyD-*Thermus thermophilus* SlyD-FKBP13 fusion polypeptide, and wherein X$_2$ is the amino acid sequence of a linker.

This amino acid sequence and variants thereof are individual aspects as reported herein.

The term "*Arabidopsis thaliana* FKBP13 fusion polypeptide" denotes a polypeptide that has the following amino acid sequence:

(SEQ ID NO: 60)
ETTSCEFSVSPSGLAFCDKVVGYGPEAVKGQLIKAHYVGKLENGKVFDS

SYNRGKPLTFRIGVGEVIKGWDQGILGSDGIPPMLTGGKRTLRIPPELAY

GDRGAGCGS-X$_1$-GSSCLIPPASVLLFDIEYIGKA, wherein X$_1$ is the amino acid sequence of a linker, or a peptide, or an antigen, or a secondary or tertiary structure to be presented by the *Arabidopsis thaliana* FKBP13 fusion polypeptide.

This amino acid sequence and variants thereof are individual aspects as reported herein.

The term "SlyD-*Arabidopsis thaliana* FKBP13 fusion polypeptide" denotes a polypeptide that has the following amino acid sequence:

(SEQ ID NO: 61)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHD-X$_2$-ETTSCEFSVSPSGLAFCDKVVGYGPEA

VKGQLIKAHYVGKLENGKVFDSSYNRGKPLTFRIGVGEVIKGWDQGILGS

DGIPPMLTGGKRTLRIPPELAYGDRGAGCGS-X$_1$-GSSCLIPPASVLLFD

IEYIGKA, wherein X$_1$ is the amino acid sequence of a linker, or a peptide, or an antigen, or a secondary or tertiary structure to be presented by the SlyD-*Arabidopsis thaliana* FKBP13 fusion polypeptide, and wherein X₂ is the amino acid sequence of a linker.

This amino acid sequence and variants thereof are individual aspects as reported herein.

The term "SlyD-FKBP12/13 fusion polypeptide" denotes a polypeptide that has the following amino acid sequence:

(SEQ ID NO: 143)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHD-X₂-

GVQVETISPGDGRTFPKRGQTAVVHYTGMLEDGKKFDSSRDRNKPFKFML

GKQEVIRGWEEGVAQMSVGQRAKLTISPDYAYGDRGAGC-X₁-

CLIPPASVLVFDVELLKLEGGGSRPLLPPLPGG, wherein $X_1$ is the amino acid sequence of a linker, or a peptide, or an antigen, or a secondary or tertiary structure to be presented by the SlyD-FKBP12/13 fusion polypeptide, and wherein $X_2$ is the amino acid sequence of a linker.

In one embodiment of the above aspects $X_2$ has the amino acid sequence GGGSGGGSGGGS (SEQ ID NO: 13).

For direct detection the detectable label can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of detectable labels are luminescent metal complexes, such as ruthenium or europium complexes, enzymes, e.g. as used for ELISA or for CEDIA (Cloned Enzyme Donor Immunoassay), and radioisotopes. Metal chelates which can be detected by electrochemiluminescense are also in one embodiment signal-emitting groups used as detectable labels, with particular preference being given to ruthenium chelates. In one embodiment the labeling group is a ruthenium (bispyridyl)$_3^{2+}$ chelate.

Indirect detection systems comprise, for example, that the detection reagent, e.g. the detection antibody, is labeled with a first partner of a binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. In one embodiment the first binding pair member is selected from hapten, antigen and hormone. In one embodiment the hapten is selected from digoxin and biotin and analogues thereof. The second partner of such binding pair, e.g. an antibody, streptavidin, etc., usually is labeled to allow for direct detection, e.g. by the labels as mentioned above.

The fusion polypeptides as reported herein are based on polypeptides from the FKBP domain protein family (i.e. proteins with PPIase activity), such as human FKBP12 (Handschumacher, R. E., et al., Science 226 (1984) 544-547), or *Arabidopsis thaliana* FKBP13, or *E. coli* SlyD, or *Thermos thermophilus* SlyD, or *Thermococcus gammatolerans* SlyD. The fusion polypeptides as reported herein are a scaffold for the presentation of polypeptides comprised in the amino acid sequence of $X_1$.

The amino acid sequence of $X_1$ can replace the Flap domain (amino acid residues A85 to A96) and the beta-bulge (amino acid residues $S_{39}$ to P46) in the FKBP12 part and/or the IF domain (amino acid residues G69 to D120) in SlyD part. Therewith it is possible to omit the time consuming recombinant preparation and purification of full length proteinaceous immunogens.

The defined presentation of the inserted amino acid sequences and/or structural motifs related thereto of polypeptides $X_1$ or $X_0$, respectively, in the fusion polypeptide as reported herein allows an efficient and cost effective production of the immunogenic amino acid sequence contained in $X_1$ and $X_0$, respectively, in sufficient amount, quality and with correct three dimensional structure.

Any amino acid sequence can be inserted, such as helices, helix-turn-helix motifs, coiled coil structures, helix bundles, turn-loop motifs, beta-hairpin structures, beta sheets, sheet-helix motifs, sheet-turn-sheet motifs etc. It is also possible to present defined native tertiary structures, individual domains of a multi-domain polypeptide or subdomains, binding domains, antibody fragments, enzymes etc.

The immunogenic polypeptide can be improved compared to the full length polypeptide from which the amino acid sequence of $X_1$ or $X_0$, respectively, is derived, e.g. with respect to solubility and/or reversible folding (naturation/denaturation). The fusion polypeptide as reported herein provides the scaffold into which the amino acid sequence of $X_1$ that is derived from a polypeptide, to which an antibody shall be obtained, is inserted and it stabilizes the structure of the amino acid sequence of $X_1$ and $X_0$, respectively, as the conformational entropy is reduced.

If present, an N-terminal SlyD mediates chaperone functionality and keeps the complete fusion polypeptide as a monomeric, soluble and stable polypeptide. Furthermore, it increases the molecular weight of the fusion polypeptide, which is beneficial for its usage in mass sensitive analyses, like SPR measurements.

The SlyD derived polypeptide portion(s) of the fusion polypeptide, independently of the presence of FKBP12 with its flap-region, folds into the correct (native) three-dimensional conformation. The chimeric FKBP12 domain of the fusion polypeptide seems to be not correctly folded. In contrast to the wild-type FKBP12 polypeptide, which shows an intrinsic Trp fluorescence emission peak at 320 nm, fluorescence spectroscopic analyses of SlyD-FKBP12 fusion polypeptide showed no peak at 320 nm but a typical extrinsic Trp emission shift at 350 nm. The 350 nm peak is broadened. The single Trp moiety in the SlyD-FKBP12 fusion polypeptide is solvent exposed. This indicates that the FKBP domain within in the SlyD-FKBP12 fusion polypeptide is partly or completely unfolded.

Also a BIAcore binding assay of a SlyD-FKBP12 fusion polypeptide derivative vs. immobilized bi-FK506 showed no binding activity, indicating structure-functional loss of the FKBP12 derived part in the polypeptide as reported herein.

Upon these findings without being bound by theory the current SlyD-FKBP12-insertion structural model is that the polypeptide consists of a well folded SlyD moiety and a structurally handicapped FKBP12 fold, which is at least offering its single core Trp residue to the solvent. The polypeptide is monomeric, soluble, folds reversible and shows sufficient thermal stability for its application.

Therefore, the fusion polypeptides as reported herein are suitable scaffolds for mimicking a structural plurality of peptidic secondary structure motives, as long as the inserted peptidic secondary structure motive does not fold as a separated, autonomously folding structure.

A structural plurality of peptidic secondary structure motives is assumed e.g. to be presented in a paraffin-embedded, formalin-fixed tissue in immune histochemical experiments (Abe, et al., Anal. Biochem. 318 (2003) 118-123).

The amino acid sequence of $X_1$ or $X_0$, respectively, can be flanked by a G3S-linker sequence to ensure sufficient distance and flexibility to the amino acid sequence of the second polypeptide in order to avoid influence on the structural integrity of the amino acid sequence of $X_1$ or $X_0$, respectively.

The fusion polypeptides as reported herein have a molecular weight of at least 15 kDa. This eliminates the need to conjugate the polypeptide to carrier proteins (such as KLH or particles) or substances for immunization and reduces the occurrence of neo-epitopes by KLH coupling Nevertheless, should a conjugation be required this is possible by selectively activating the lysine residue in the sequence motif GSRKHHHHHHHH (SEQ ID NO: 16), which can be activated by the neighboring histidine and arginine residue with LC-SPDP (succinimidyl 6-(3-[2-pyridyldithio]-propionamido) hexanoate).

A structural or partial/total deformation or the generation of neo-epitopes under conditions of immunohistochemical analysis is normally not recognized during the preparation of proteinaceous immunogens. Especially during the formalin treatment the side chains of the amino acid residues Lys, Tyr, His, and Cys are cross-linked. Additionally the tertiary and quaternary structure of the polypeptides are distorted during the tissue preparation procedure using tissue fixation reagent, (heat-)incubation, paraffin embedding, and the tissue dehydration by alcoholic treatment (see e.g. Fowler, C. B., et al., Lab. Invest. 88 (2008) 785-791). It remains unclear whether antigen retrieval processes are able to completely remove formalin induced crosslinks in order to restore native conformational protein structures. Therefore, new secondary structures can be formed and neo-epitopes can be generated or remain even after a retrieval process.

These novel and non-native structures are not present during the immunization campaign. By using conventional antibody development techniques, no or if at all only a limited number of IHC-suited antibodies can be obtained.

Additionally, free polypeptides in solution have a large conformational entropy leading to a transient structure that makes an immune response against a defined enthalpic secondary structure epitope difficult (see e.g. Scott, K. A., et al., Proc. Natl. Acad. Sci. USA 104 (2007) 2661-2666; Gamacho, C. J., et al., PLoS Comput. Biol. 4 (2008) e1000231 1-8). Free peptides used as immunogens can result in developing only antibodies versus the termini of the respective peptide.

Besides the use in immunizing animals and the generation of an immune response the fusion polypeptides as reported herein can be used for the mapping of antibody epitopes, such as linear or conformational epitopes. Different structural motifs can be presented with the amino acid sequence of $X_1$ or $X_0$, respectively (=epitope, antigenic (immunogenic) amino acid sequence). These different structural motifs can also be used for the generation of immunohistochemistry (IHC) suited antibody with specificity for the amino acid sequence of $X_1$ or $X_0$, respectively. For this purpose the amino acid sequence of $X_1$ is selected in a way that only the formation of a limited number of neo-epitopes during formalin treatment can be expected. Especially the number of lysine, tyrosine, histidine, and cysteine residues can be minimized by selecting the appropriate sequence. It is also possible to substitute single residues, such as cysteine residues, by serine residues. As $X_1$ sequence e.g. small secondary structure motifs can be used, which show a high probability to refold into their conformational originating structure. By grafting $X_1$ into the FKBP domain the termini of the inserted polypeptide are no longer free and accessible and the structural enthalpy is increased.

One aspect as reported herein is a fusion polypeptide according to formula I $$NH_2—S_2—X_1—S_1—COOH \qquad \text{(formula I)}$$

wherein
$X_1$ comprises either a random amino acid sequence or an amino acid sequence derived from a first polypeptide,
$S_2$ and $S_1$ are non-overlapping amino acid sequences derived from a second polypeptide, and
— denotes a peptide bond,
wherein the second polypeptide is a polypeptide with peptidyl-prolyl cis/trans-isomerase activity (PPIase activity) or a member of the FKBP domain family.

In one embodiment the polypeptide with peptidyl-prolyl cis/trans-isomerase activity is SlyD.

In one embodiment the second polypeptide is a polypeptide from a thermophile.

In one embodiment the thermophile is a thermophile bacterium. In one embodiment the thermophile bacterium is from the family of Thermaceae. In one embodiment the thermophile is *Thermus thermophilus*.

In one embodiment the thermophile is a thermophile Archaea. In one embodiment the thermophile Archaea a hyperthermophilic Archaea. In one embodiment the thermophile is from the class of Thermococci. In one embodiment the thermophile is *Thermococcus gammatolerans*.

In one embodiment the thermophile has an optimal growth temperature of at least 60° C.

One aspect as reported herein is a fusion polypeptide according to formula II $$S_4—X_2—S_3—S_2—X_1—S_1—S_0 \qquad \text{(formula II)}$$

wherein
$X_1$ is either a random amino acid sequence or an amino acid sequence derived from a first polypeptide,
$S_{21}$ and $S_1$ are either non-overlapping amino acid sequences derived from a second polypeptide,
$S_3$ and $S_0$ are either absent or non-overlapping amino acid sequences derived from a third polypeptide,
$S_4$ is either absent or an amino acid sequence derived from a fourth polypeptide,
$X_2$ is either absent or a peptidic linker sequence, and
— denotes a peptide bond,
wherein the second polypeptide and the third polypeptide and the fourth polypeptide are different from each other and are polypeptides with peptidyl-prolyl cis/trans-isomerase activity (PPIase activity) or members of the FKBP domain family.

In one embodiment the fusion polypeptide as reported herein comprises an amino acid sequence tag.

In one embodiment the amino acid sequence tag is selected from the group of Poly-his-tag, Avitag, Poly-glu-tag, Poly-arg-tag, Strep-tag, Streptavidin Binding Peptide, Epitope-tags as well as combinations thereof.

In one embodiment the amino acid sequence tag is an octa-histidine-tag (SEQ ID NO: 137).

The term "amino acid sequence tag" denotes a sequence of amino acid residues connected to each other via peptide bonds that has specific binding properties. In one embodiment the amino acid sequence tag is an affinity or purification tag. In an embodiment the amino acid sequence tag is selected from Arg-tag, His-tag, Flag-tag, 3×Flag-tag, Strep-tag, Nano-tag, SBP-tag, c-myc-tag, S-tag, calmodulin-binding-peptide, cellulose-binding-domain, chitin-binding-domain, GST-tag, or MBP-tag. In a further embodiment the amino acid sequence tag is selected from SEQ ID NO: 16 (GSRKHHHHHHHH), or SEQ ID NO: 62 (RRRRR), or SEQ ID NO: 63 (RRRRRR), or SEQ ID NO: 64 (HHHHHH), or SEQ ID NO: 65 (KDHLIHNVHKEFHAHAHNK), or SEQ ID NO: 66 (DYKDDDDK), or SEQ ID NO: 67 (DYKDHDGDYKDHDIDYKDDDDK), or SEQ ID NO: 68 (AWRHPQFGG), or SEQ ID NO: 69 (WSHPQFEK), or SEQ ID NO: 70 (MDVEAWLGAR), or SEQ ID NO: 71 (MDVEAWLGARVPLVET), or SEQ ID NO: 72 (MDEKTTGWRGGHVVEGLAGELEQLRARLEHH-PQGQREP), or SEQ ID NO: 73 (EQKLISEEDL), or SEQ ID NO: 74 (KETAAAKFERQHMDS), or SEQ ID NO: 75 (KRRWKKNFIAVSAANRFKKISSSGAL), or SEQ ID NO: 76 (cellulose binding domain), or SEQ ID NO: 77 (cellulose binding domain), or SEQ ID NO: 78 (TNPGVSAWQVN-TAYTAGQLVTYNGKTYKCLQPHTSLAGWEPSNVPA LWQLQ), or SEQ ID NO: 79 (GST-tag), or SEQ ID NO: 80 (MBP-tag). In one embodiment of all aspect as reported before the amino acid sequence tag has the amino acid sequence selected from SEQ ID NO: 62 to SEQ ID NO: 80. In one embodiment the amino acid sequence tag has the amino acid sequence of SEQ ID NO: 16, or SEQ ID NO: 64, or SEQ ID NO: 68.

If a polypeptide is produced in an *E. coli* strain the amino-terminal methionine residue is usually not efficiently cleaved off by proteases, thus the amino-terminal methionine residue is partially present in the produced polypeptide. Therefore all sequences given herein are listed with the N-terminal methionine residue albeit this residue might be absent in the isolated polypeptide. Nevertheless the amino acid sequence comprising the N-terminal methionine shall also encompass an amino acid sequence wherein this methionine is missing.

If the $X_1$ or $X_0$ amino acid sequence, respectively, has a non-helical structure an additional GGGS linker (SEQ ID NO: 81) can be introduced N-terminal and C-terminal of the amino acid sequence of $X_0$ or $X_1$, respectively.

If the $X_1$ or $X_0$ amino acid sequence, respectively, has a helical structure a GGGSGGNP-linker (SEQ ID NO: 82) at the N-terminus and a GPTGGGS-linker (SEQ ID NO: 83) of the amino acid sequence of $X_0$ or $X_1$, respectively, can be inserted.

The SlyD/FKBP12-antigen, the Thermos *thermophilus* SlyD-antigen, and the *Thermococcus gammatolerans* SlyD-antigen fusion polypeptides can be used to present an antigen.

*Thermus Thermophilus* SlyD (Loew, C., et al., J. Mol. Biol. 398 (2010) 375-390) originates from the archaic bacterium *Thermus Thermophilus*. *Thermococcus gammatolerans* SlyD originates from the Archaea *Thermococcus gammatolerans*. Both proteins show elevated thermodynamic stability in contrast to human FKBP12, FKBP13, chimeric FKBP12/13, as well as *E. coli* SlyD. The N-terminal *E. coli* SlyD derived polypeptide (i.e. when the fourth polypeptide is *E. coli* SlyD) can be omitted when *Thermus Thermophilus* SlyD, or *Thermococcus gammatolerans* SlyD is contained in the fusion polypeptide as reported herein.

In general, the FKBP12-antigen fusion polypeptide comprising an amino acid sequence tag of SEQ ID NO: 16 has the following amino acid sequence:

(SEQ ID NO: 84)
MGVQVETISPGDGRTFPKRGQTAWHYTGMLEDGKKFDSSRDRNKPFKFM

LGKQEVIRGWEEGVAQMSVGQRAKLTISPDYAYGGGGS-X$_1$-

GGGSTLVFDVELLKLEGGGSRKHHHHHHHH, wherein $X_1$ is the amino acid sequence of a linker, or a peptide, or an antigen, or a secondary or tertiary structure to be presented by the FKBP12-antigen fusion polypeptide.

The human FKBP12 derived polypeptide can be N-terminally fused with an *E. coli* SlyD derived polypeptide.

The SlyD/FKBP12-antigen fusion polypeptide comprising an amino acid sequence tag of SEQ ID NO: 16 has the following amino acid sequence:

(SEQ ID NO: 85)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHDGGGSGGGSGGGSGGGSGGGSGGGGVQVETI

SPGDGRTFPKRGQTAVVHYTGMLEDGKKFDSSRDRNKPFKFMLGKQEVIR

GWEEGVAQMSVGQRAKLTISPDYAYGGGGS-X$_1$-

GGGSTLVFDVELLKLEGGGSRKHHHHHHHH, wherein $X_1$ is the amino acid sequence of a linker, or a peptide, or an antigen, or a secondary or tertiary structure to be presented by the SlyD/FKBP12-antigen fusion polypeptide.

The SlyD/FKBP12-control polypeptide (see FIG. 1 for SDS and Western Blot) comprising an amino acid sequence tag of SEQ ID NO: 16 as the following amino acid sequence:

(SEQ ID NO: 86)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHDGGGSGGGSGGGSGGGSGGGSGGGGVQVETI

SPGDGRTFPKRGQTAVVHYTGMLEDGKKFDSSRDRNKPFKFMLGKQEVIR

GWEEGVAQMSVGQRAKLTISPDYAYGGGGSGGNPGPTGGGSTLVFDVEL

LKLEGGGSRKHHHHHHHH.

The *Thermus Thermophilus*-SlyD-antigen fusion polypeptide comprising an amino acid sequence tag of SEQ ID NO: 16 has the following amino acid sequence:

(SEQ ID NO: 87)
MRGSKVGQDKVVTIRYTLQVEGEVLDQGELSYLHGHRNLIPGLEEALEGR

EEGEAFQAHVPAEKAYGPHG-X1-

GAGKDLDFQVEVVKVREATPEELLHGHAHGGGSRKHHHHHHHH, wherein $X_1$ is the amino acid sequence of a linker, or a peptide, or an antigen, or a secondary or tertiary structure to be presented by the *Thermus Thermophilus*-SlyD-antigen fusion polypeptide.

The *Thermococcus gammatolerans*-SlyD-antigen fusion polypeptide comprising an amino acid sequence tag of SEQ ID NO: 16 has the following amino acid sequence:

(SEQ ID NO: 114)
MKVERGDFVLFNYVGRYENGEVFDTSYESVAREQGIFVEEREYSPIGVTV

GAGEIIPGIEEALLGMELGEKKEVVVPPEKGYGMP-X₁-

AGKTAIFEIEVVEIKKAGEAGGGSRKHHHHHHHH, wherein X₁ is the amino acid sequence of a linker, or a peptide, or an antigen, or a secondary or tertiary structure to be presented by the *Thermococcus gammatolerans*-SlyD-antigen fusion polypeptide.

*Thermus thermophilus*-SlyD-antigen fusion polypeptide and *Thermococcus gammatolerans*-SlyD-antigen fusion polypeptide do not require an N-terminal *E. coli* SlyD chaperone domain. In these fusion polypeptides the immunogenic sequence (antigen sequence) insertion can be stabilized by a disulfide bond at the stem of the antigen loop, which is an embodiment as reported herein. In the *Thermus thermophilus*-SlyD-antigen fusion polypeptide two cysteine mutations can be set at amino acid position H66C and A70C and each a glycine residue can be introduced to optimize the junction between the scaffold and the insert.

The disulfide stabilized *Thermus Thermophilus*-SlyD-antigen fusion polypeptide comprising an amino acid sequence tag of SEQ ID NO: 16 has the following amino acid sequence:

(SEQ ID NO: 88)
MRGSKVGQDKVVTIRYTLQVEGEVLDQGELSYLHGHRNLIPGLEEALEGR

EEGEAFQAHVPAEKAYGPCG-X₁-

GCGKDLDFQVEVVKVREATPEELLHGHAHGGGSRKHHHHHHHH, wherein X₁ is the amino acid sequence of a linker, or a peptide, or an antigen, or a secondary or tertiary structure to be presented by the disulfide stabilized *Thermus Thermophilus*-SlyD-antigen fusion polypeptide.

The disulfide stabilized *Thermococcus gammatolerans*-SlyD-antigen fusion polypeptide comprising an amino acid sequence tag of SEQ ID NO: 16 can have the following amino acid sequence:

(SEQ ID NO: 115)
MKVERGDFVLFNYVGRYENGEVFDTSYESVAREQGIFVEEREYSPIGVTV

GAGEIIPGIEEALLGMELGEKKEVVVPPEKGYGMPCG-X₁-

GCAGKTAIFEIEVVEIKKAGEAGGGSRKHHHHHHHH, wherein X₁ is the amino acid sequence of a linker, or a peptide, or an antigen, or a secondary or tertiary structure to be presented by the *Thermococcus gammatolerans*-SlyD-antigen fusion polypeptide.

Anti-ERCC1 Antibodies Suitable for IHC Application:

A SlyD/FKBP12-ERCC1 fusion polypeptide was used as a screening reagent for the development of anti-ERCC1 antibodies suitable for IHC staining that are targeting the helix-loop-helix region within the C-terminal domain of ERCC1 (ERCC=Excision Repair Cross Complementing; Tripsianes, K., et al., Structure 13 (2005) 1849-1858).

The function of the ERCC1 polypeptide is predominantly in nucleotide excision repair of damaged DNA (Aggarwal, C., et al., J. Natl. Compr. Canc. Netw. 8 (2010) 822-832; Rahn, J. J., et al., Environment. Mol. Mutagen. 51 (2010) 567-581; Westerveld, A., et al., Nature 310 (1984) 425-429).

ERCC1 is of diagnostic relevance, as it is a predictive and prognostic marker tightly linked to various disease indications (Gandara, D. R., et al., J. Thorac Oncol. 5 (2010) 1933-1938; Hwang, LG., et al., Cancer 113 (2008) 1379-1386; Azuma, K., et al., Cancer Chemother. Pharmacol. 64 (2009) 565-573).

In general it is likely, that under IHC conditions neoepitopes are generated by formalin-induced crosslinking events (Lin, W., et al., J. Histochem. Cytochem. 45 (1997) 1157-1163, Webster, J. D., et al., J. Histochem. Cytochem. 57 (2009) 753-761). The genuine structure can be partly or completely denatured, or is at least structurally modified by the harsh conditions during the process of tissue preparation and subsequent antigen retrieval (Rait, V. K., et al., Lab. Invest. 84 (2004) 300-306). It is very likely, that the epitope region resembles a plurality of non-stable primary or secondary structures, which cannot be adequately represented by a linear, synthetically produced peptide. Therefore, an immunogen or a suitable antibody screening reagent, which is able to cope with all these tasks and which at the same time is stable and biochemically robust, has to be used.

The SlyD/FKBP12-ERCC1 scaffold can simulate the structural plurality of a linearized, completely denatured, in part denatured, in part refolded or intact secondary structure motif, like it is to be assumed in IHC application. At the same time the scaffold guarantees thermodynamic stability and robust handling.

A SlyD/FKBP12-ERCC1 fusion polypeptide was employed to screen anti-ERCC1 antibodies, which are suitable for IHC application, from a plurality of antibodies, which were obtained by a linear peptide immunization strategy.

The helix loop helix secondary structure motive was extracted from the ERCC1 (PDB 1Z00) structure (FIGS. 2A-B). The C-terminal ERCC1 domain can be structurally characterized as a primarily helical polypeptide. This makes it difficult to identify a continuous linear epitope, which is conventionally used for immunization approaches with linear peptides. A linear KHL-coupled peptide was used for the immunization of animals in order to obtain antibodies specifically recognizing the intended sequence motif.

The extracted human ERCC1 C274S sequence is the amino acid sequence IAASREDLALSPGLGPQKARRLFD (SEQ ID NO: 89). The sequence represents a helix-turn-helix motif. The cysteine residue originally present at position 11 (underlined in SEQ ID NO: 89) of the inserted sequence has been changed to a serine residue to avoid aggregation by oxidation.

As the inserted sequence has a helix conformation the additional amino acid sequence GGGSGGNP (SEQ ID NO: 82) was introduced at the N-terminus of the inserted amino acid sequence and the amino acid sequence GPTGGGS (SEQ ID NO: 83) has been introduced at the C-terminus of the inserted amino acid sequence. Thus, terminally flanking motifs GGGGSGGNP (SEQ ID NO: 138) and GPTGGGS (SEQ ID NO: 83) were obtained. Such motifs are, without being bound by theory, supposed to foster the helix propensity via the proline helix capping sequence motifs.

The FKBP12-ERCC1 fusion polypeptide comprising an amino acid sequence tag of SEQ ID NO: 16 has the following amino acid sequence:

(SEQ ID NO: 90)
MGVQVETISPGDGRTFPKRGQTAVVHYTGMLEDGKKFDSSRDRNKPFKF

MLGKQEVIRGWEEGVAQMSVGQRAKLTISPDYAYGGGGSGGNPIAASRE

DLALSPGLGPQKARRLFDGPTGGGSTLVFDVELLKLEGGGSRKHHHHHH

H.

The SlyD/FKBP12-ERCC1 fusion polypeptide comprising an amino acid sequence tag of SEQ ID NO: 16 has the following amino acid sequence:

(SEQ ID NO: 91)
MKVAKDLWSLAYVRTEDGVLVDESPVSAPLDYLHGHGSLISGLETALEGH

EVGDKFDVAVGANDAYGYDENLVRVPKDVFMGVDELVGMRFLAETDGP

VPVEITAVEDDHVWDGNHMLAGNLKFNVEWAIREATEEELAHGHVHGAH

DHHHDHDHDGGGSGGGSGGGSGGGSGGGSGGGGVVETISPGDGRTFPKR

GTAWHYTGMLEDGKKFDSSRDRNKPFKFMLGKEVIRGWEEGVAQMSVG

RAKLTISPDYAYGGGGSGGNPIAASREDLALSPGLGPQKARRLFDGPTGG

GSTLVFDVELLKLEGGGSRKHHHHHHHH.

The SlyD/FKBP12-ERCC1 fusion polypeptide and SlyD/FKBP12 control polypeptide were used in a screening approach to identify cell clones producing an anti-ERCC1 antibody.

The SlyD/FKBP12 control polypeptide has the amino acid sequence of SEQ ID NO: 86.

Generally, for the purification of the fusion polypeptides an affinity chromatography step was used under denaturing conditions in the presence of chaotropic agents. The fusion polypeptide was captured on the affinity matrix. The chaotropic buffer was transferred into native buffer conditions by washing the column with a physiological buffer solution. The E. coli SlyD moiety of the SlyD/FKBP12-ERCC1 fusion polypeptide was, thus, refolded. The refolded fusion polypeptide was recovered in a physiological buffer from the affinity chromatography column.

The affinity purified fusion polypeptide was dialyzed and filtrated (for SDS gel see FIG. 3). SlyD/FKBP12-ERCC1 was UV/Vis spectroscopically quantified. Protein fluorescence measurements were used to test the conformational nature of SlyD/FKBP12-ERCC1 (FIG. 4). The FKBP12 mutant C22A is especially useful as a carrier for polypeptide insertions, because the single FKBP12 Trp moiety can be used to determine the structural integrity of the FKBP12 moiety (Scholz, C., et al., J. Biol. Chem. 271 (1996) 12703-12707; Russo, A. T., et al., J. Mol. Biol. 330 (2003) 851-866). FKBP12 C22A in its native structure shows a single fluorescence emission peak at 320 nm (Zoldak, G., et al., J. Mol. Biol. 386 (2009) 1138-1152).

Without being bound by theory the intrinsic Trp solvatochromic fluorescence emission at 350 nm would be strongly quenched in a folded FKBP12 protein environment, whereas it increases with the unfolding of FKBP12. A temperature screen from 25° C. to 85° C. did not show any further fluorescence emission peaks, but a temperature-dependent fluorescence quenching of the 350 nm emission. The 320 nm emission, an indicator for structural integrity of FKBP12, could not be detected (see FIG. 4).

A BIAcore binding assay with the fusion polypeptide SlyD/FKBP12-ERCC1 as analyte in solution vs. the sensor surface presented ligand bi-FK506 (FIGS. 5 and 6) showed no FK506 binding activity, indicating a structure-function loss of the FKBP12 moiety in the fusion polypeptide. The control polypeptide FKBP12 (C22A) showed FK506 binding activity.

The non-binding of the SlyD/FKBP12-ERCC1 fusion polypeptide to the immobilized FK-506 provides evidence for a SlyD/FKBP12-ERCC1 structure, which deviates from that of the FKBP12 (C22A) conformation. This is accompanied by a loss of binding activity of the chimeric FKBP12 domain.

Fluorescence measurements and the FK506 binding assay provide evidence for a structure-function-loss of the SlyD/FKBP12-ERCC1 fusion polypeptide. The N-terminal E. coli SlyD domain keeps the fusion protein in its soluble and monomeric state. This was proven by HPLC analyses (see FIGS. 7 and 8) of the SlyD/FKBP12-ERCC1 and SlyD/FKBP12-ctrl fusion polypeptides.

Mice were subjected to intraperitoneal immunization with KHL-coupled peptide covering the amino acids 219-245 of human ERCC1 (Excision Repair Cross Complementing protein). The production of hybridoma primary cultures was done according to the procedure by Koehler and Milstein. The hybridomas were isolated and screened for antigen binding by ELISA methods as described. Primary hybridoma cell cultures, which showed a positive color formation in ELISA versus the peptide ERCC1[219-245] were transferred to kinetic screening (see FIGS. 9 to 12). In order to avoid the selection of IHC unsuitable antibodies, screening was performed using the fusion polypeptide as reported herein. The SlyD/FKBP12-ERCC1 fusion polypeptide and SlyD/FKBP12 control polypeptide were used in a kinetic screening approach to identify antibodies, binding with to the ERCC1 amino acid sequence motif. Suitable primary cultures were further expanded into clonal cultures. The properties of the selected cell clones are depicted in FIG. 12. FIG. 13 exemplary shows BIAcore measurements with the clone <ERCC1>-M-5.3.35. The SlyD/FKBP12-ERCC1 interaction is highly specific. No interaction with the SlyD/FKBP12 control sample was detected. No unspecific binding was detectable. The interaction refers to a Langmuir kinetic model.

For western blotting OVCAR-3 or HEK293 cell lysates were loaded per lane on an SDS gel. FIG. 14 shows a Western Blot result of clone <ERCC1>-M-5.1.35. An ERCC1 specific band at 37 kDa is detected.

For immunohistochemical detection of ERCC1 in FFPE embedded human cancer tissues sections of SCLC cancer samples were prepared. FIG. 15 shows the positive IHC staining pattern. White arrows indicate the specific staining loci of ERCC1. An analogous screening and selection process has been performed solely using a polypeptide with SEQ ID NO: 89, i.e. solely using a polypeptide without the integration into the fusion polypeptide as reported herein. From 14 identified candidate cell clones in this peptide-based screening nine would have been selected by both screening approaches. Five hits from the polypeptide based screening approach do not bind to the SlyD/FKBP12-ERCC1 fusion polypeptide despite identical capture level on the BIAcore chip.

It has been found that the E. coli SlyD-FKBP12-antigen fusion polypeptide and the Thermus Thermophilus SlyD-antigen fusion polypeptide (see e.g. Kang, C. B., et al., Neurosignals 16 (2008) 318-325) and the Thermococcus gammatolerans SlyD-antigen fusion polypeptide can be used as combined immunogen and screening tool for the development of epitope-specific monoclonal antibodies targeting the antigen that is contained in the polypeptide.

Furthermore, it has been found, that the E. coli SlyD-FKBP12/13-antigen fusion polypeptide and the Thermus Thermophilus SlyD-antigen fusion polypeptide and the Thermococcus gammatolerans SlyD-antigen fusion polypeptide all likewise can be posttranslationally modified and can then be used as combined immunogen and screening tool for the development of posttranslational site-specific monoclonal antibodies targeting the posttranslational modification that is contained in the polypeptide. In one embodiment one of the fusion polypeptides as reported herein is used for generating an antibody and a second different fusion polypeptide as reported herein is used to select an antibody obtained with the first fusion polypeptide, wherein both fusion polypeptides are different but comprise the same antigen amino acid sequence, i.e. either $X_1$ or $X_0$ is identical in both fusion polypeptides.

The fusion polypeptides as reported herein can be used for the generation of functional antibodies by a targeted epitope approach using a structural mimetic or a scaffold technology. Especially for the generation of antibodies against antigens that are not accessible in conventional immunization campaigns (so called hidden epitopes) the fusion polypeptides as reported herein are especially suited.

Anti-IGF-1 Antibody:

Human IGF-1 and IGF-2 show 67% amino acid sequence homology and high structural homology (see FIG. 16). In serum, IGF-2 is present with a 500-fold excess over IGF-1 (Jones, J. I. and Clemmons, D. R., Endocrin. Rev. 16 (1995) 3-34).

Thus, the generation of an IGF-1 specific antibody, i.e. an antibody without cross-reactivity to IGF-2, is challenging. There is a small sequential deviation between IGF-1 and IGF-2 in the turn-loop motif of IGF-1 at the IGF-1 amino acid position 74-90, starting the numbering with the signal and propeptide (UniProtKB entry P05019, IGF1 human). The corresponding amino acid sequence NKPTGYGSSSRRAPQTG (SEQ ID NO: 92) can be inserted in the SlyD/FKBP-12 fusion polypeptide, or the *Thermus thermophilus* SlyD fusion polypeptide, or the *Thermococcus gammatolerans* SlyD fusion polypeptide as reported herein as amino acid sequence $X_0$.

Fusion polypeptides comprising the amino acid sequence NKPTGYGSSSRRAPQTG (SEQ ID NO: 92) can be used for the immunization of animals in order to obtain antibodies specifically binding to this turn-loop motif.

In order to improve the presentation of the immunogenic polypeptide the IGF-1 turn-loop motif can be flanked either by an GGGS linker (SEQ ID NO: 81) N-terminal and C-terminal of the amino acid sequence or by an HG dipeptide N-terminal of the amino acid sequence and by an GA dipeptide C-terminal of the IGF-1 amino acid sequence.

A SlyD/FKBP12-IGF-1(74-90) fusion polypeptide was used as immunogen and also as screening reagent for the development of an anti-IGF-1 antibody that is specifically binding to the IGF-1 amino acid sequence of NKPTGYGSSSRRAPQTG (SEQ ID NO: 92).

The FKBP12-IGF-1(74-90) fusion polypeptide comprising an amino acid sequence tag of SEQ ID NO: 16 can have the following amino acid sequence:

(SEQ ID NO: 93)
MGVQVETISPGDGRTFPKRGQTAVVHYTGMLEDGKKFDSSRDRNKPFKF

MLGKQEVIRGWEEGVAQMSVGQRAKLTISPDYAYGGGGSNKPTGYGSSS

RRAPQTGGGSTLVFDVELLKLEGGGSRKHHHHHHHH.

The SlyD/FKBP12-IGF-1(74-90) fusion polypeptide comprising an amino acid sequence tag of SEQ ID NO: 16 can have the following amino acid sequence:

(SEQ ID NO: 94)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHDGGGSGGGSGGGSGGGSGGGSGGGGVQVETI

SPGDGRTFPKRGQTAVVHYTGMLEDGKKFDSSRDRNKPFKFMLGKQEVIR

GWEEGVAQMSVGQRAKLTISPDYAYGGGGSNKPTGYGSSSRRAPQTGGG

GSTLVFDVELLKLEGGGSRKHHHHHHHH.

The *Thermus Thermophilus*-SlyD wild-type polypeptide comprising a C-terminal amino acid sequence tag of SEQ ID NO: 16 has the following amino acid sequence:

(SEQ ID NO: 97)
MRGSKVGQDKVVTIRYTLQVEGEVLDQGELSYLHGHRNLIPGLEEALEGR

EEGEAFQAHVPAEKAYGPHDPEGVQVVPLSAFPEDAEVVPGAQFYAQDM

EGNPMPLTVVAVEGEEVTVDFNHPLAGKDLDFQVEVVKVREATPEELLHG

HAHGGGSRKHHHHHHHH.

A *Thermus Thermophilus*-SlyD-IGF-1(74-90) fusion polypeptide (see FIG. 17 for SDS Page and Western blot) was used as immunogen and also as screening reagent for the development of anti-IGF-1 antibodies that are targeting the IGF-1 amino acid sequence of NKPTGYGSSSRRAPQTG (SEQ ID NO: 92).

The *Thermus Thermophilus*-SlyD-IGF-1(74-90) fusion polypeptide comprising a C-terminal amino acid sequence tag of SEQ ID NO: 16 (see FIG. 3 for SDS and Western Blot) can have the amino acid sequence:

(SEQ ID NO: 95)
MRGSKVGQDKVVTIRYTLQVEGEVLDQGELSYLHGHRNLIPGLEEALEGR

EEGEAFQAHVPAEKAYGPHGNKPTGYGSSSRRAPQTGGAGKDLDFQVEV

VKVREATPEELLHGHAHGGGSRKHHHHHHHH, or the amino acid sequence:

(SEQ ID NO: 96)
MKVGQDKVVTIRYTLQVEGEVLDQGELSYLHGHRNLIPGLEEALEGREEG

EAFQAHVPAEKAYGPHGNKPTGYGSSSRRAPQTGGAGKDLDFQVEVVKV

REATPEELLHGHAHPSGHHHHHH.

For Screening and specificity testing a *Thermus thermophilus* SlyD-ΔIF fusion polypeptide was produced. The *Thermus thermophilus* SlyD-ΔIF fusion polypeptide lacks the IF domain, which was replaced by a short amino acid sequence motif.

The *Thermus thermophilus* SlyD-ΔIF fusion polypeptide comprising a C-terminal amino acid sequence tag of SEQ ID NO: 16 can have the amino acid sequence:

(SEQ ID NO: 116)
MRGSKVGQDKVVTIRYTLQVEGEVLDQGELSYLHGHRNLIPGLEEALEGR

EEGEAFQAHVPAEKAYGPHGAGSGSSGAGKDLDFQVEVVKVREATPEELL

HGHAHGGGSRKHHHHHHHH.

For Screening and specificity testing a *Thermococcus gammatolerans* SlyD fusion polypeptide was produced with the structurally homologous IGF-2(53-65) hairpin insertion.

The *Thermococcus gammatolerans* SlyD-IGF-2(53-65) fusion polypeptide comprising a C-terminal amino acid sequence tag of SEQ ID NO: 16 can have the amino acid sequence:

(SEQ ID NO: 117)
MKVERGDFVLFNYVGRYENGEVFDTSYESVAREQGIFVEEREYSPIGVTV

GAGEIIPGIEEALLGMELGEKKEVVVPPEKGYGMP-G-SRVSRRSRG-G-

AGKTAIFEIEVVEIKKAGEAGGGSRKHHHHHHHH.

All fusion polypeptides were produced in *E. coli*. All fusion polypeptides were purified and refolded by using virtually identical protocols as described herein. Mice were subjected to intraperitoneal immunization with the SlyD/FKBP12-IGF-1(74-90) fusion polypeptide and the *Thermus Thermophilus*-SlyD-IGF-1(74-90) fusion polypeptide. Ten weeks after immunization antibody titers were determined by means of ELISA (FIGS. 19 and 20). Mice immunized with the SlyD/FKBP12-IGF-1(74-90) fusion polypeptide showed low titers versus IGF-1, versus a constrained IGF-1(74-90) peptide loop, versus the SlyD/FKBP12-IGF-1(74-90) fusion polypeptide, and versus the SlyD/FKBP12 control polypeptide. Only one mouse provided for sufficiently high IGF-1 titer (K1576M1 in FIG. 19) and was used for the generation of hybridomas.

It has been found that mice immunized with the *Thermus Thermophilus*-SlyD-IGF-1(74-90) fusion polypeptide showed higher titers versus the *Thermus Thermophilus*-SlyD-IGF-1(74-90) fusion polypeptide than versus the SlyD/FKBP12-IGF-1(74-90) fusion polypeptide (see FIGS. 19 and 20).

The production of hybridoma primary cultures was done according to the procedure of Koehler and Milstein. The primary hybridomas were isolated by limiting dilution and screened for antigen binding by ELISA. Primary hybridoma cell cultures, which showed a positive color formation in ELISA versus the SlyD/FKBP12-IGF-1(74-90) fusion polypeptide, the *Thermus Thermophilus*-SlyD-IGF-1(74-90) fusion polypeptide, and IGF-1 as well as a lower signal versus the *Thermophilus*-SlyD-wild-type fusion polypeptide and the SlyD/FKBP12 control polypeptide were further evaluated using a kinetic screening method.

It has been found that only two primary cultures from the immunization campaign with the SlyD/FKBP12-IGF-1(74-90) fusion polypeptide had a positive ELISA signals versus IGF-1. After development into clonal cultures no kinetic binding signals were detectable in surface plasmon resonance (SPR) analyses. Several primary cultures, which showed suitable ELISA binding signals versus IGF-1 and the *Thermus Thermophilus*-SlyD-IGF-1(74-90) fusion polypeptide but reduced signal intensity versus the *Thermus Thermophilus*-SlyD wild-type polypeptide have been found (see FIG. 21).

The primary cultures were analyzed by a kinetic screening method versus native IGF-1, versus native IGF-2, versus the *Thermus Thermophilus*-SlyD-IGF-1(74-90) fusion polypeptide, and versus the *Thermus Thermophilus*-SlyD wild-type polypeptide (FIG. 22). IGF-1 specific antibody producing primary cultures were detected and expanded by limited dilution to obtain clonal cultures.

The clonal cultures were analyzed by means of ELISA for specific binding versus IGF-1 (see FIG. 23). In FIG. 24 exemplary BIAcore measurements of an anti-IGF-1 antibody, which was obtained from the *Thermus Thermophilus*-SlyD-IGF-1(74-90) fusion polypeptide immunization campaign, are shown. The antibodies specifically bind the *Thermus Thermophilus*-SlyD-IGF-1(74-90) fusion polypeptide and native IGF-1 with 10 pM binding affinity. Native IGF-2 and wild-type *Thermus Thermophilus* SlyD is not being bound (see FIG. 25).

It has been found that for the generation of IGF-1 specific antibodies, it is of importance, that the IGF-1 turn-loop motif is stabilized by a rigid, enthalpic scaffold to preserve its native fold. When being presented on a metastable polypeptide scaffold, like FKBP12, it is without being bound by this theory supposed, that the sequence NKPTGYGSSSRRAPQTG (SEQ ID NO: 92) has too many degrees of rotational freedom. Finally no native IGF-1 binding antibody was obtained.

It has been found by near-UV-CD spectroscopic measurements that the FKBP-12 portion in the SlyD/FKBP12-IGF-1(74-90) fusion polypeptide was unfolded. HPLC analyses showed that the SlyD/FKBP12-IGF-1(74-90) fusion polypeptide is monomeric. DSC measurements showed that the fusion polypeptide is able to reversibly fold and unfold. Without being bound by theory the reversibly foldable N-terminal *E. coli* SlyD domain keeps the fusion polypeptide stable and monomeric in solution even when the C-terminal FKBP domain is partly or completely unfolded (see FIG. 26).

Like already found for the SlyD/FKBP12-ERCC1 fusion polypeptide the SlyD/FKBP12-IGF-1(74-90) fusion polypeptide can present a structural plurality of a linearized, completely denatured, in part denatured, in part refolded or intact secondary structure motifs.

For the development of native IGF-1 binding antibodies it has been found that a scaffold has to be used, which presents the polypeptide insertion in its native conformation. The presenting fusion polypeptide therefore needs to be a stably folded polypeptide. It has been found that this can be achieved by using an FKPB domain from an extremophile (i.e. thermophile) organism, like *Thermus thermophilus* SlyD, or *Thermococcus gammatolerans* SlyD.

To examine whether the fusion polypeptides as reported herein adopt a folded conformation CD spectra in the near-UV region were determined. Near-UV-CD determines the asymmetric environment of aromatic residues in a polypeptide and is therefore a sensitive test for ordered tertiary structure. Native SlyD has a typical CD signature in the near-UV region. Thus, structural distortions or steric clashes due to an insertion in the IF domain should be visible in the near-UV CD spectrum. In FIG. 27 an overlay of the spectra of wild-type *Thermus thermophilus* SlyD, the FKBP domain of wild-type *Thermus thermophilus* SlyD lacking the IF domain (*Thermus thermophilus* SlyD-ΔIF fusion polypeptide) and *Thermus thermophilus* SlyD-antigen fusion polypeptide, wherein a 22 amino acid insertion from a human extracellular receptor fragment was inserted, is shown. It has been found that the replacement of the *Thermus thermophilus* IF domain does not result in a change of the overall structure of the remaining IF domain. It can be seen that the signature of the spectra is similar. Since unfolding would abolish any near-UV CD signal, this result provides evidence that a native-like fold is retained in the fusion polypeptide.

The *Thermus thermophilus* SlyD-antigen fusion polypeptide is a fusion polypeptide comprising a 22 amino acid beta hairpin secondary structure insertion from a human growth factor receptor extracellular domain (ECD). The CD signatures demonstrate that at 20° C. all polypeptides are well folded in their native structure.

FIG. 28 shows the temperature-dependent CD spectra of the *Thermus thermophilus* SlyD-ΔIF fusion polypeptide. After temperature-induced unfolding, the *Thermus thermophilus* SlyD FKBP domain can refold when being cooled down again. Due to this the fusion polypeptides can be affinity purified by on column refolding and, furthermore, in contrast to the findings with the SlyD-FKBP12-IGF-1 fusion polypeptide, the *Thermus thermophilus* SlyD-IGF-1(74-90) fusion polypeptide possesses structural stability to present the IGF-1 secondary structure motive on the FKBP domain in a stable conformation. The temperature-dependent near-UV CD spectra of the *Thermococcus gammatolerans* SlyD-antigen fusion polypeptide shows an even higher stability when compared to *Thermus thermophilus*-antigen fusion polypeptide (see FIG. 29). Both scaffolds carry the same 22 amino acids beta hairpin secondary structure insertion from a human growth factor receptor ECD. *Thermococcus gammatolerans* SlyD-antigen reversibly folds and unfolds. It has been found that under the given physical conditions no complete unfolding of the *Thermococcus gammatolerans* SlyD-antigen fusion polypeptide could be achieved even at a temperature of 100° C.

It has been found that the stability of archaic FKBP domains enables the grafting of immunogenic polypeptides by replacement of their IF domains whereby at the same time the overall stability of the newly generated chimeric scaffold protein is maintained.

The *Thermus thermophilus* SlyD-IGF-1(74-90) fusion polypeptide was purified as a stable and monomeric polypeptide (see FIG. 18).

The monomer fraction of the *Thermococcus gammatolerans* SlyD-antigen fusion polypeptide was rechromatographed after repeated freezing and thawing cycles and a temperature stress test (see FIG. 30).

Mice have been immunized with the polypeptide of SEQ ID NO: 96. The obtained B-cells were analyzed using an ELISA. *Thermus Thermophilus*-SlyD-IGF-1(74-90) fusion polypeptide, *Thermus Thermophilus*-SlyD-wild-type polypeptide, IGF-1 and IGF-2 were used as a control.

The *Thermus Thermophilus*-SlyD wild-type polypeptide comprising a C-terminal amino acid sequence tag of SEQ ID NO: 16 (see FIG. 31 for SDS and Western blot) has the following amino acid sequence:

(SEQ ID NO: 97)
MRGSKVGQDKVVTIRYTLQVEGEVLDQGELSYLHGHRNLIPGLEEALEGR

EEGEAFQAHVPAEKAYGPHDPEGVQVVPLSAFPEDAEVVPGAQFYAQDM

EGNPMPLTVVAVEGEEVTVDFNHPLAGKDLDFQVEVVKVREATPEELLHG

HAHGGGSRKHHHHHHHH.

All clone culture supernatants (CCS) form stable complexes with IGF-1 and the Thermo *Thermophilus* SlyD-IGF-1 fusion polypeptide at 37° C. No cross-reaction with the Thermo *Thermophilus* SlyD-wild-type polypeptide was detectable with any of the CCS. No cross-reactivity with IGF-2 was detectable, except for one clone (see FIGS. 32A-B). From FIG. 33 it can be seen that the first 8 clone culture supernatants have a t/2-diss of 2 minutes, whereas the analyte IGF-1 associates faster to the last 4 clone culture supernatants and dissociates slower. It stays in complex longer than 40 minutes. In FIG. 22 exemplary sensorgrams for one clone are shown. It can be seen that the antibody binds to IGF-1 and the *Thermus thermophilus*-IGF-1 fusion polypeptide whereas binding to IGF-1 and the *Thermus thermophilus*-wild-type polypeptide cannot be detected.

Thus, *Thermus Thermophilus* SlyD-antigen fusion polypeptides and *Thermococcus gammatolerans* SlyD-antigen fusion polypeptides can be used as combined immunogen and screening tools for the development of epitope-specific monoclonal antibodies targeting the immunogen that is contained in the polypeptide.

FIG. 25 shows, that the scaffold-derived monoclonal antibodies <IGF-1>M-11.11.17 and <IGF-1>M-10.7.9 have picomolar affinity versus IGF-1. Monoclonal antibody <IGF-1>M-11.11.17 shows an IGF-1 complex stability of t½ diss=560 min. No cross-reactivity versus IGF-2, wild-type *Thermus thermophilus* SlyD, wild-type *Thermococcus gammatolerans* SlyD, *Thermus thermophilus* SlyD-ΔIF, and *Thermococcus gammatolerans* SlyD-IGF-2(53-65) was detectable.

Monoclonal antibody M-2.28.44 has been obtained by conventional immunization of mice with recombinant human IGF-1. Although the antibody has a 30 pM binding affinity versus IGF-1, the antibody also has cross reactivity versus IGF-2 (binding affinity of 500 pM). Using the *Thermus thermophilus* SlyD-IGF-1(74-90) fusion polypeptide and the *Thermococcus gammatolerans* SlyD-IGF-2(53-65) fusion polypeptide as analyte it can be shown that the cross-reacting IGF-2 epitope is not in the IGF-½ hairpin region.

This was confirmed by a linear epitope mapping (see, e.g., Frank, R. and Overwin, H., Methods in Molecular Biology 66 (1996) 149-169. The linear IGF-1 binding contribution of clone 11.11.17 and 11.9.15 both recognize the epitope TGYGSSSR (SEQ ID NO: 124). The linear binding portion of clone 10.7.9 binds to the epitope PTGYGSSSR (SEQ ID NO: 125). The epitopes are located at the top of the IGF-1 hairpin-structure and are therefore not present in IGF-2.

In general, the fusion polypeptides as reported herein can be used for the generation of functional antibodies by a targeted epitope approach using a structural mimetic. Especially for the generation of antibodies against antigens that are not easily accessible by conventional immunization campaigns using recombinant immunogens the fusion polypeptides as reported herein are especially suited. It has been found that so called hidden epitopes, which are buried inside a native protein conformation, can be used as immunogen, when being well presented as insertion in the fusion polypeptides as reported herein. Especially neoepitopes, which are only targetable upon allosteric, ligand induced conformational changes, can be used as immunogen by grafting these structures into the fusion polypeptides as reported herein.

Chimeric FKBP12/13 Scaffolds:

Some fusion polypeptides as reported herein are based on a fusion polypeptide comprising parts of human FKBP12 and parts of *Arabidopsis thaliana* FKBP13. It has been found that a fusion polypeptide comprising at least a part of human FKBP12 and at least a part of *Arabidopsis thaliana* FKBP13 can be used as immunogen. In this fusion polypeptide the human FKBP12 derived part is thermodynamically stabilized as a scaffold. FKBP13 comprises a disulfide bond, which stabilizes the IF domain. This sequence was grafted into the human FKBP12 derive part to stabilize the fusion polypeptide.

The FKBP12/13 fusion polypeptide comprising a C-terminal amino acid sequence tag of SEQ ID NO: 16 has the amino acid sequence:

```
                                                (SEQ ID NO: 118)
MRSGVQVETISPGDGRTFPKRGQTAVVHYTGMLEDGKKFDSSRDRNKPFK

FMLGKQEVIRGWEEGVAQMSVGQRAKLTISPDYAYGDRGAGCGSGSSCLI

PPASVLVFDVELLKLEGGGSRKHHHHHHHH.
```

The FKBP12/13 fusion polypeptide was expressed in *E. coli* (see FIG. 34) as soluble protein. HPLC analyses (see FIG. 35) proved that the FKBP12/13 fusion polypeptide is monomeric. CD spectroscopic measurements were performed as described above. The CD spectra proved that the FKBP12/13 fusion polypeptide is folded at 20° C. *Thermus thermophilus* and *Thermococcus gammatolerans* based scaffolds show higher temperature-stability than the FKBP12/13 fusion polypeptide.

Anti-PLGF Antibody:

The inserted amino acid sequence in this case has a turn-loop motif and an IHC suited antibody shall be generated. The insert has the amino acid sequence DWSEYPSEVEHMFSPSS (SEQ ID NO: 98). The C-terminal cysteine residue in the immunogen has been changed to a serine residue.

The FKBP12-PLGF fusion polypeptide comprising a C-terminal amino acid sequence tag of SEQ ID NO: 16 has the following amino acid sequence:

```
                                                 (SEQ ID NO: 99)
MGVQVETISPGDGRTFPKRGQTAWHYTGMLEDGKKFDSSRDRNKPFKFM

LGKQEVIRGWEEGVAQMSVGQRAKLTISPDYAYGGGGSDWSEYPSEVEH

MFSPSSGGGSTLVFDVELLKLEGGGSRKHHHHHHHH.
```

The SlyD/FKBP12-PLGF fusion polypeptide comprising a C-terminal amino acid sequence tag has case the following amino acid sequence:

```
                                                (SEQ ID NO: 100)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHDGGGSGGGSGGGSGGGSGGGSGGGVQVETI

SPGDGRTFPKRGQTAVVHYTGMLEDGKKFDSSRDRNKPFKFMLGKQEVIR

GWEEGVAQMSVGQRAKLTISPDYAYGGGGSDVVSEYPSEVEHMFSPSSGG

GSTLVFDVELLKLEGGGSRKHHHHHHHH.
```

Mice were immunized with an immunogen containing the sequence of PLGF(60-76). Subsequently hybridomas were produced and ELISA as well as kinetic screening were performed.

In the kinetic screening process the SlyD/FKBP12-PLGF fusion polypeptide and a biotinylated PLGF(60-76) peptide, which was singly grafted on streptavidin, were used to identify primary culture supernatants with binding activity versus PLGF(60-76). Both analytes produced 1:1 Langmuir kinetics, but the fusion polypeptide showed a better dissociation fit with a lower chi2 value than the SA-probe grafted biotinylated PLGF peptide. Thus, a fusion polypeptide-based screening approach takes advantage of the monomeric state and the improved epitope accessibility of the immunogen in the fusion polypeptide when compared to a SA-probe.

Antibodies, developed by this approach, like clone 53.4.1, were able to specifically detect PLGF in Western blotting.

SlyD-FKBP12/13-CSF1R Fusion Polypeptide:

The term "SlyD-FKBP12/13-CSF1R fusion polypeptide" denotes a polypeptide that has the following amino acid sequence:

```
                                                (SEQ ID NO: 119)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHDGGGSGGGSGGGSGVQVETISPGDGRTFPKRG

QTAVVHYTGMLEDGKKFDSSRDRNKPFKFMLGKQEVIRGWEEGVAQMSV

GQRAKLTISPDYAYGDRGAGCGSGGVDYKNIHLEKKYVRRDSGFSSQGVD

TYVEMRPVSTSSNDSFSEQDLDKEDGGSSCLIPPASVLVFDVELLKLEGG

GSRPLLPPLPGGGSRKHHHHHHHH.
```

The polypeptide was expressed in *E. coli* as described herein and purified as described herein. After Ni-NTA affinity purification a size exclusion chromatography was performed. The fusion polypeptide was loaded on a HiLoad 26/60 Superdex™ 75 pg column. The elution fractions were analyzed using a native SDS gel (see FIG. 37).

The $X_1$ amino acid sequence used for the generation of antibodies corresponds to the CSF1R intracellular kinase insert domain. Src kinase, EGF1R and CSF1R itself can phosphorylate the tyrosine residues, especially the tyrosine residue in the kinase domain loop structure, which is flanked by threonine and valine (see the Y residue at position 297 in SEQ ID NO: 119, given also in italic and underlined).

After purification the fusion polypeptide can be phosphorylated using a suitable kinase. Thus, it is possible to provide an $X_1$ amino acid sequence having a post-translational modification and, thus, it is possible to generate antibodies against post-translationally modified polypeptides using a fusion polypeptide as reported herein. The fusion polypeptide can be used for different applications like screening, specificity testing or as an immunogen. In general, peptides which are substrates for enzymatic posttranslational or chemical modifications can be inserted into the scaffolds as $X_1$ amino acid sequence. Protein fluorescence measurements were used to test the conformational nature of the SlyD/FKBP12/13-CSF1R fusion polypeptide. At 20° C. and 25° C. the 300 nm to 425 nm scan peaks at 305 nm (see FIG. 38). The single tryptophane moiety in the FKBP12 domain shows the typical intrinsic tryptophane solvatochromic fluorescence emission as it is buried in the hydrophobic core of the FKBP12 domain. Therefore, it is assumed, that the FKBP12/13-CSF1R polypeptide portion is folded. At 50° C. the emission peak shifts to 344 nm, which is evidence, that the tryptophane moiety is now in an aqueous environment and the FKBP domain is in part or completely unfolded. At 30° C. and 40° C. intermediate states of folded and unfolded protein can be determined.

It has been found that it is possible to stabilize the FKBP12 domain in a fusion polypeptide by engineering FKBP12 into an FKBP12/13 fusion polypeptide, where the FLAP domain of FKBP12 was replaced by the disulfide containing FKBP13 structure and a loop structure motif from the CSF1R receptor.

Already at 40° C. the fusion polypeptide shows a significant unfolded protein portion, which mainly refers to the FKBP12/13-CSF1R domain as *E. coli* SlyD does not contain tryptophane.

In order to use a chimeric FKBP domain as a scaffold for the presentation of correctly folded, native secondary or tertiary structures as immunogens this finding underlines the need to further stabilize chimeric FKBP12 in order to generate non-metastable scaffolds. Furthermore, it is not possible to omit the *E. coli* SlyD domain in the fusion polypeptide, because then the expression yield dramatically decreases (no data shown).

Epitope Mapping:

SlyD-FKBP fusion polypeptides can also carry complex amino acid insertion motifs, like for example secondary structures containing disulfide bonds. As the fusion polypeptides are free of cysteines, on-column refolding under appropriate conditions facilitates the correct formation of disulfide bonds within the insertion, additionally assisted by the chaperone functionality of SlyD itself.

The fusion polypeptides SlyD-FKBP12-CD81 and SlyD-FKBP12-ctrl were used for the purpose of Epitope Mapping. Human CD81 is a receptor for the hepatitis C virus envelope E2 glycoprotein. CD81 is a transmembrane protein belonging to the tetraspanin family. CD81 is a 90 amino acid in length homodimeric protein, which displays a so called mushroom-like structure (PDB 1IV5). Residues known to be involved in virus binding can be mapped onto the so called 35 amino acid in length "head subdomain", providing a basis for the design of antiviral drugs and vaccines. As the head subdomain sequence of the virus binding site is just 35 amino acids in length it is difficult to map antibody epitopes on the 10 kDa CD81 protein using conventional cross-blocking experiments.

It is hard to discriminate antibodies, which bind directly on the mushroom-like head domain, from antibodies just binding nearby or elsewhere in the CD81LEL structure. All these antibodies would show an HCV E2 envelope protein competing effect, but without specifically binding to the target structure, the head domain. The grafting of the head domain structure into FKBP and a consecutive epitope mapping is therefore an advantageous method. First, some biochemical issues with the CD81LEL protein are circumvented, because the protein itself tends to oligomerize. Second, it is suitable to select antibody epitopes from a vast number of antibodies just binding to the full length CD81 protein.

SlyD-FKBP12-CD81 Fusion Polypeptide:

The term "SlyD-FKBP12-CD81 fusion polypeptide" denotes a polypeptide that has the following amino acid sequence:

(SEQ ID NO: 126)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHDGGGSGGGSGGGSGGGSGGGSGGGGVQVETI

SPGDGRTFPKRGQTAVVHYTGMLEDGKKFDSSRDRNKPFKFMLGKQEVIR

GWEEGVAQMSVGQRAKLTISPDYAYGGGGSCCGSSTLTALTTSVLKNNLC

PSGSNIISNLFKEDCGGGSTLVFDVELLKLEGGGSRKHHHHHHHH.

SlyD-FKBP12-Ctrl Fusion Polypeptide (See FIG. 1):

The term "SlyD-FKBP12-ctrl fusion polypeptide" denotes a polypeptide that has the following amino acid sequence:

(SEQ ID NO: 86)
MKVAKDLVVSLAYQVRTEDGVLVDESPVSAPLDYLHGHGSLISGLETALE

GHEVGDKFDVAVGANDAYGQYDENLVQRVPKDVFMGVDELQVGMRFL

AETDQGPVPVEITAVEDDHVVVDGNHMLAGQNLKFNVEVVAIREATEEEL

AHGHVHGAHDHHHDHDHDGGGSGGGSGGGSGGGSGGGSGGGGVQVETI

SPGDGRTFPKRGQTAVVHYTGMLEDGKKFDSSRDRNKPFKFMLGKQEVIR

GWEEGVAQMSVGQRAKLTISPDYAYGGGGSGGNPGPTGGGSTLVFDVEL

LKLEGGGSRKHHHHHHHH.

A BIAcore 2000 instrument (GE Healthcare) was used at 25° C. with a BIAcore CM5 sensor mounted into the system. Each protein ligand was immobilized by EDC/NHS chemistry into the flow cells 2, 3 and 4. Flow cell 1 was used as a reference. The following substances were immobilized on the sensor: Flow cell 2: SlyD-FKBP12ctrl, flow cell 3: SlyD-FKBP12-CD81, and flow cell 4: CD81LEL. 31 antibody analytes were injected. The sensorgrams were monitored as reference signals 2-1, 3-1 and 4-1 and were evaluated by using the BIAcore Evaluation software 4.1. At the end of the analyte injection a report point was set to quantify the maximum analyte binding signal. The highest analyte binding signal was set 100% to normalize the data. The normalized antibody binding responses showed that from 30 tested anti-CD81-LEL-antibodies only 6 show a binding to an epitope on the CD81 head domain. The negative control polypeptide SlyD-FKBP12ctrl was not bound. The positive control polypeptide CD81-LEL, which was the immunogen at the same time, was bound by all antibodies. Slyd-FKBP12-CD81 was only bound, when the antibody epitope was located in the mushroom domain.

Confirmation of the Epitope Mapping Results by X-Ray Crystallographic Analysis

Fab fragments of the antibodies K05 and K04 were co-crystallized by known methods with the CD81-LEL protein and were analyzed by x-ray diffraction analysis (Seth Harris, Palo Alto). The resolution obtained was 2.15 Å. K04 directly recognizes the target epitope sequence, whereas K05 binds off the target. Therefore, the x-ray analysis directly correlates with the scaffold-based epitope mapping approach.

The following examples, figures and sequences are provided to aid the understanding of the present invention, the true scope of which is set forth in the appended claims. It is understood that modifications can be made in the procedures set forth without departing from the spirit of the invention.

DESCRIPTION OF THE FIGURES

FIG. 6 300 nM SlyD/FKBP12-ERCC1 fusion polypeptide and 300 nM wild-type FKBP12 as analytes in solution vs. sensor surface presented biotinylated ligand bi-FK506.

FIG. 12 Table with kinetic properties of anti-ERCC1 antibodies determined by kinetic screening. BL: Binding Late, signal amplitude height in relative response units at the end of the SlyD/FKBP12-ERCC1 association phase. SL: Stability Late, signal amplitude height in relative response units at the end of the SlyD/FKBP12-ERCC1 dissociation phase. kd: dissociation rate constant (1/s) according to a Langmuir fit of the dissociation phase. t½diss: antibody-SlyD/FKBP12-ERCC1 complex half-life in minutes, calculated according to the formula t½ diss=ln(2)/(60*kd).

FIG. 19 Serum titers, determined by ELISA after 12 weeks immunization of NMRI mice with SlyD/FKBP12-IGF-1 (74-90). mE: milli Absorbance, IGF-1: native human IGF-1 (Peprotech).

FIG. 20 Serum titers, determined by ELISA after 12 weeks immunization of Balb/C and NMRI mice. mE: milli Absorbance, IGF-1: native human IGF-1 (Peprotech).

FIG. 21 ELISA screen of primary cultures with binding signals vs. IGF-1, *Thermus thermophilus* SlyD-IGF-1(74-90) fusion polypeptide and *Thermus thermophilus* SlyD wild-type polypeptide. mE: milli Absorbance, IGF-1: native human IGF-1 (Peprotech).

FIG. 23 ELISA screen of clone culture supernatants vs. IGF-1, *Thermus thermophilus* SlyD-IGF-1(74-90) fusion polypeptide and *Thermus thermophilus* SlyD wild-type polypeptide. Elevated binding absorption signals were detectable vs. IGF-1 and *Thermus thermophilus* SlyD-IGF-1(74-90) fusion polypeptide.

FIG. 25 Table with binding kinetics of fusion polypeptide-developed anti IGF-1 antibodies. mAb: monoclonal antibody; RU: Relative response unit of monoclonal antibody captured on the sensor; Antigen: antigen in solution; kDa: molecular weight of the antigens injected as analytes in solution; ka: association rate constant; kd: dissociation rate constant; t½ diss: antibody-antigen complex half-life calculated according to the formula t½ diss=ln(2)/60*kd; KD: dissociation constant; $R_{MAX}$: Binding signal at the end of the association phase of the 90 nM analyte injection; MR: Molar Ratio; Chi²: failure of the measurement; n.d.: not detectable.

FIGS. 32A-B Quantification of this kinetic screening approach for anti-IGF-1 antibodies (values for Ligands 10.0.15, 10.0.17, 10.0.01, 10.0.03, 10.0.04, 10.0.05, 10.0.07, and 10.0.08 is provided in FIG. 32A; values for Ligands 10.1.3, 10.2.3, 10.3.7, 10.4.7, 10.5.8, 10.6.8, 10.7.9, 10.8.9, 11.9.15, 11.10.15, 11.11.17, and 11.12.17 is provided in FIG. 32B). Empty cells denote that the respective value was not detectable/could not be determined.

FIG. 33 Kinetics of 12 clonal culture supernatants for the binding of IGF-1.

EXAMPLES

Example 1

Expression and Purification

Figure 1:
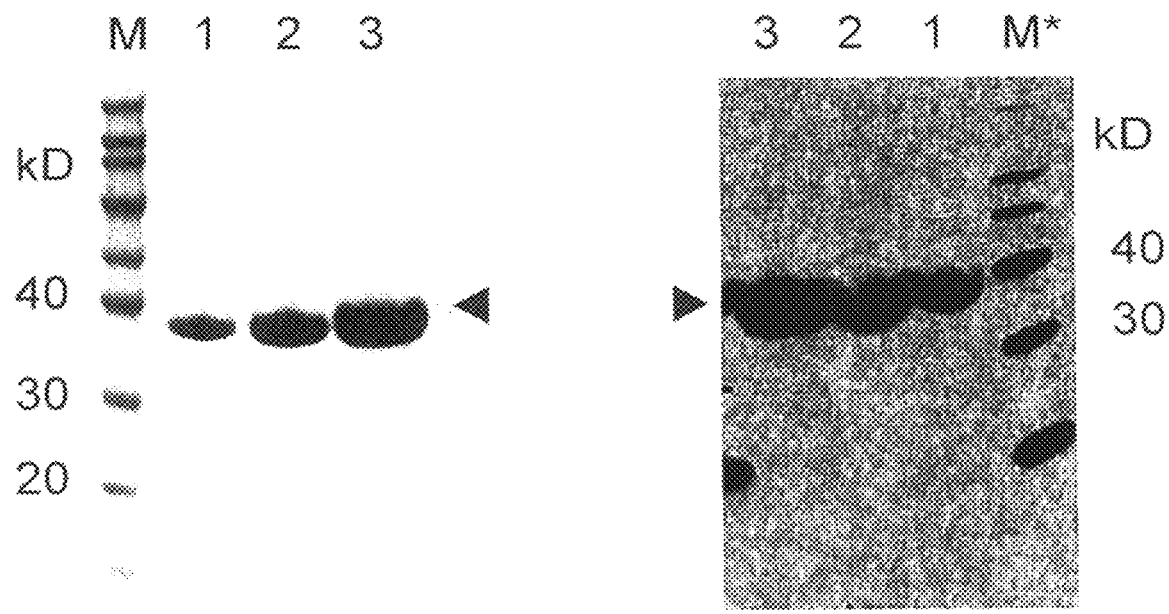
FIG. 1 SDS PAGE (Coomassie staining) and Western Blot (10 sec. incubation with anti-octa-his-tag antibody) ("octa-his" disclosed as SEQ ID NO: 137) of the SlyD/FKBP12-control polypeptide.

The polypeptides were produced in *E. coli* (pQE80L vector/*E. coli* BL21 CodonPlus-RP cell line) according to known methods.

For the purification of the crude polypeptides an affinity chromatography step was used either under native conditions or under denaturing conditions in the presence of chaotropic agents. For fusion polypeptide comprising the SlyD part purification in the presence of chaotropic agents is especially suited as the total amount of fusion polypeptide could be isolated from the *E. coli* cells. Additionally the entire fusion polypeptide is obtained in a random coil conformation. The fusion polypeptide still bound to the affinity chromatography material is transferred into native conditions by washing the column with a physiological salt solution. Due to the spontaneous folding of the SlyD and FKBP12 parts of the fusion polypeptide also the inserted amino acid sequence was transferred to its native conformation. The refolded fusion polypeptide was recovered with an imidazole gradient in a physiological buffer from the affinity chromatography column.

Example 2

Chemical Derivatization

The C-terminal lysine residue was activated under acidic conditions (pH 6) with LC-SPDP (Succinimidyl 6-(3-[2-pyridyldithio]-(propionamido) hexanoate)) ((Pierce, Cat.: 68181-17-9).

Arginine and lysine are bases that can take up the proton of lysine's alkyl ammonium group. The free amino can be derivatized with any hydroxyl succinimidyl-activated carbonic acid.

Example 3

Formalin Treatment

The derivatized fusion polypeptides can be treated with a formalin solution. Thereafter the fixated derivatized fusion polypeptides can be purified by size exclusion chromatography in order to obtain compositions with defined oligomerization status (monomeric, oligomeric, multimeric).

Example 4

BIAcore Characterization of Antibody Producing Clone Culture Supernatants

A BIAcore T100 instrument (GE Healthcare) was used with a BIAcore CM5 sensor mounted into the system. The sensor was preconditioned by a 1 min. injection at 100 µl/min of 0.1% SDS, 50 mM NaOH, 10 mM HCl and 100 mM $H_3PO_4$.

The system buffer was HBS-ET (10 mM HEPES (pH 7.4) supplemented with 150 mM NaCl, 1 mM EDTA, 0.05% (w/v) Tween® 20). The sample buffer was the system buffer.

The BIAcore T100 System was driven under the control software V1.1.1. Polyclonal rabbit IgG antibody <IgGFCγM>R (Jackson ImmunoResearch Laboratories Inc.) was immobilized at 30 µg/ml in 10 mM sodium acetate buffer (pH 4.5) at 6500 RU on the flow cells 1, 2, 3, and 4, respectively, via EDC/NHS chemistry according to the manufacturer's instructions. Finally, the sensor surface was blocked with a 1 M ethanolamine solution. The complete experiment was performed at 25° C.

The clone culture supernatants containing the respective antibodies at 35 nM to 190 nM were captured for 1 min. at a flow rate of 5 µl/min on the <IgGFCγM>R surface. As analytes in solution the recombinant antigen, the biotinylated disulfide-bridged recombinant antigen, SlyD/FKBP12-antigen, *Thermus thermophilus* SlyD-antigen, SlyD/FKBP12-control and/or *Thermus thermophilus* SlyD-wt fusion polypeptides were used. The respective analytes were injected at different concentration steps from 90 nM, 30 nM, 10 nM, 3.3 nM, 1.1 nM and 0 nM. The association phase was monitored for 3.5 min. at a flow rate of 100 µl/min. The dissociation was monitored for 15 min. at a flow rate of 100 µl/min. The system was regenerated using a 10 mM glycine buffer (pH 1.7). Kinetics were evaluated using the BIAcore Evaluation Software.

Example 5

IHC Sample Preparation

The matrix immobilized LC-SPDP fusion polypeptide was treated with organic solvent, heated and treated with an acidic buffer. Thereafter the matrix associated polypeptides are recovered and reducing conditions. To obtain a material with defined composition a size exclusion chromatography can be performed. The thereby obtained material has a defined oligomeric state (monomer, oligomer, and polymer) and can be used as immunogen for the immunization of experimental animals but it can also be used as test antigen for the selection and screening of antibodies.

Example 6

Immunization

The pre-formulated immunogenic fusion polypeptide is administered to an experimental animal, such as mouse, rat, rabbit, sheep, or hamster, intraperitoneally at different dosages. Prior to collection of the B-cells a boost immunization is performed. B-cell hybridomas can be obtained according to the method of Koehler and Millstein (Kohler, G. and Milstein, C., Nature 256 (1975) 495-497). The obtained hybridomas are deposited as single clones or cells in the wells of a multi well plate. Primary hybridoma cultures that were tested positive with respect to the binding of the antibody by the secreted antibody are further screened with a kinetic screening method.

Example 7

Anti-IGF-1 Antibodies

The cells obtained from four immunized NMRI-mice were analyzed using an ELISA. Nunc Maxisorb F multi well plates were coated with SlyD/FKBP12-IGF-1, SlyD/FKBP12-IGF-1(74-90), *Thermus thermophilus* SlyD-IGF-1, SlyD/FKBP12-control or *Thermus thermophilus* SlyD-wt by applying a solution comprising 0.41 μg polypeptide per ml. The isolated antigen IGF-1 was immobilized in the wells of StreptaWell High Bind SA multi well plates by applying a solution comprising 90 ng/ml biotinylated IGF-1 or 500 ng/ml biotinylated IGF-1-peptide loop.

Thereafter free binding sites were blocked by applying a solution comprising 1% RPLA in PBS for one hour at room temperature. The wells were washed three times with a solution comprising 0.9% (w/v) sodium chloride and 0.05% (w/v) Tween. As samples the mouse serum diluted 1:50 with PBS were used. Optional further dilution was performed in 1:4 steps until a final dilution of 1:819,200. The incubation time was one hour at room temperature. The wells were washed three times with a solution comprising 0.9% (w/v) sodium chloride and 0.05% (w/v) Tween. As detection antibody a polyclonal antibody against the constant domain of the target antibodies conjugated to a peroxidase was used (PAK<M-Fcγ>S-F(ab")$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) Tween. Afterwards the wells were incubated with an ABTS solution for 15 minutes at room temperature. The intensity of the developed color was determined photometrically. Exemplary results are presented in the following Table.

TABLE

| immobilized → mouse ↓ | IGF-1 | IGF-1-peptide loop | SlyD/FKBP12-IGF-1 SlyD/FKBP12-IGF-1(74-90) | SlyD/FKBP12-control |
|---|---|---|---|---|
| K1575M1 | 189 | 194 | 2911 | 8379 |
| K1575M2 | 395 | 678 | 1470 | 2546 |
| K1575M3 | 465 | 272 | 4126 | 10091 |
| K1575M4 | 564 | — | 2426 | 6337 |
| K1576M1 | 2143 | 2058 | 8302 | 9934 |
| K1576M2 | — | — | 2960 | 8816 |
| K1576M3 | — | — | 2978 | 7756 |
| K1576M4 | — | — | 6957 | 11095 |
| K1576M5 | — | — | 11221 | 16588 |

— : no binding detectable in ELISA

Example 8

Kinetic Screening of Hybridoma Culture Supernatants

For the selection of IHC suited antibodies a target complex half-live at 37° C. of 10 min. is set.

The kinetic screening was performed on a BIAcore A100 under control of the software version V1.1. A BIAcore CM5 chip is loaded to the machine and according to the manufacturers instruction addressed hydrodynamically and thereafter the chip is conditioned. As running buffer a HBS-EP buffer is used (10 mM HEPES (pH 7.4), 150 mM NaCl, 1 mM EDTA, 0.05% (w/v) P20). A polyclonal anti-IgG Fc capture antibody composition of a concentration of 30 pg/ml in 10 mM sodium acetate buffer (pH 4.5) is pre-concentrated to spots 1, 2, 4 and 5 in flow cells 1, 2, 3 and 4. The antibody is immobilized at 10,000 RU via NHS/EDC covalently. The sensor is deactivated thereafter by saturation with 1 M ethanolamine solution. Spots 1 and 2 were used for the determination and spots 2 and 4 were used as reference. Prior to application to the sensor chip the hybridoma culture supernatants were diluted 1:5 in HBS-EP buffer. The diluted solution was applied at a flow rate of 30 μl/min for 1 min. Immediately thereafter the antigen was injected at a flow rate of 30 μl/min for 2 min. Thereafter the signal is recorded for another 5 min. The sensor was regenerated by injecting a 10 mM glycine-HCl solution (pH 1.7) for 2 min. at a flow rate of 30 μl/min. The recorded signal shortly before the end of the injection of the antigen is denoted as binding late (BL). The recorded signal shortly before the end of the recording of the dissociation is denoted as stability late (SL). Therewith the apparent complex stability is calculated with the following formula:

(1−[BL (RU)−SL (RU)/BL (RU)].

The hybridoma cells selected in the kinetic screening were deposited as single cells by FACS (FACSAria (Becton Dickinson), Software V4.1.2). The monoclonal clones are cultivated in 24 well plates or in 100 ml spinner flasks in RPMI-1640 cultivation medium.

Example 9

Immunohistochemical Analysis

The IHC analysis was performed either manually or automated on a Ventana Benchmark XT or Discovery XT 8R machine. The antibodies were tested on suited positive or genitive, formalin fixed or cryo-conserved tissue or cells.

Alternatively cells are transfected with a nucleic acid encoding the target polypeptide. The transfected cells are lysed and tested for their suitability as positive or negative control by Western Blotting.

Example 10

SlyD/FKB12-Antigen Scaffold Assisted Production of Anti-ERCC1 Antibodies

Immunization 8-12 weeks old SJL mice, were subjected to intraperitoneal immunization with 100 μg of a KHL-coupled ERCC1 derived peptide covering the amino acids 219-245 of human ERCC1 (Excision Repair Cross Complementing). ERCC1 derivatives were produced synthetically by peptide synthesis.

The mice were immunized 3 times (initial and 6 weeks and 10 weeks after the initial boost). The first immunization was performed using complete Freud's adjuvant, the second and third immunization was done using incomplete Freud's adjuvant. The final boost was done i.v. using 100 μg of KLH-coupled peptide antigen three days before the hybridoma fusion took place. The production of hybridoma primary cultures was done according to Kohler and Milstein (Kohler, G. and Milstein, C., Nature 256 (1975) 495-497). The hybridomas were isolated into 96-well MTPs by limiting dilution and screened for antigen binding by means of ELISA. ELISA was driven by a Tecan Sunrise running under Firmware: V 3.15 19/03/01; XREAD PLUS Version: V 4.20. Primary hybridoma cell cultures, which showed a positive color formation upon binding versus a biotinylated ERCC1 derived peptide covering the amino acids 219-245 in ELISA, were transferred into the kinetic screening process as described herein.

In order to avoid the selection of IHC unsuitable, just linear peptide binding antibodies, further screening efforts were performed using a scaffold-based approach. The scaffold approach further deselected antibodies, which bound the immunogenic peptide at its termini.

Production of SlyD/FKBP12-ERCC1

A Synthetic gene encoding SlyD/FKBP12-ERCC1 and SlyD/FKBP12-ctrl was purchased from Sloning Biotechnology GmbH (Germany) and was cloned into a pQE80L expression vector. The polypeptides were produced as *E. coli* codon optimized gene constructs in *E. coli* BL21 CodonPlus-RP (see FIGS. 3 and 8)

Figure 3:
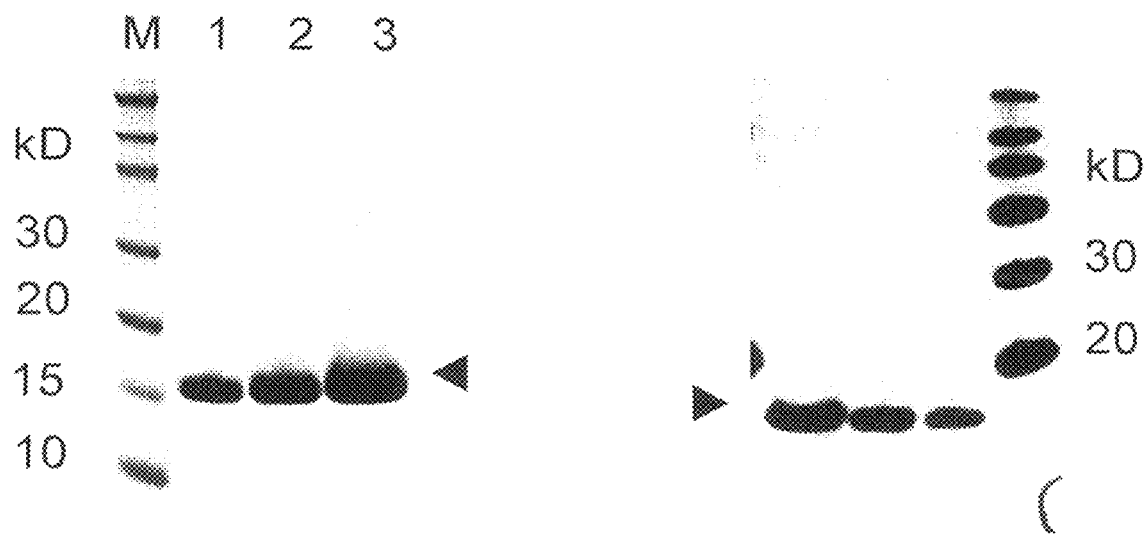
FIG. 3 SDS PAGE (Coomassie staining) and anti-his-tag Western Blot (10 sec exposition) of the SlyD/FKBP12-ERCC1 polypeptide. M—Novex Sharp Standard; 1—2.5 µg SlyD/FKBP12-ERCC1 fusion polypeptide; 2—5.0 µg SlyD/FKBP12-ERCC1 fusion polypeptide; 3—10 µg SlyD/FKBP12-ERCC1 fusion polypeptide; M*—Magic Mark.

For the purification of the crude fusion polypeptides an affinity chromatography step was used under denaturing conditions in the presence of chaotropic agents. For fusion polypeptide comprising the SlyD part purification in the presence of chaotropic agents is especially used as the total amount of fusion polypeptide could be isolated from the *E. coli* cells. Additionally the entire fusion polypeptide was obtained in a random coil conformation. The fusion polypeptide still bound to the affinity chromatography material was transferred into native conditions by washing the column with a physiological salt solution. Due to the spontaneous folding of the SlyD and FKBP1 2 parts of the fusion polypeptide also the inserted amino acid sequence can be transferred to its native conformation. The refolded fusion polypeptide was recovered with an imidazole gradient in a physiological buffer from the affinity chromatography column. An SDS gel and Western blot of the SlyD/FKBP12-ERCC1 fusion polypeptide is shown in FIG. 3. The <His6>-Western blot ("His6" disclosed as SEQ ID NO: 64) shows the C-terminal integrity of the fusion polypeptide. No other polypeptide bands are detectable.

Fluorescence Measurements

Figure 4:
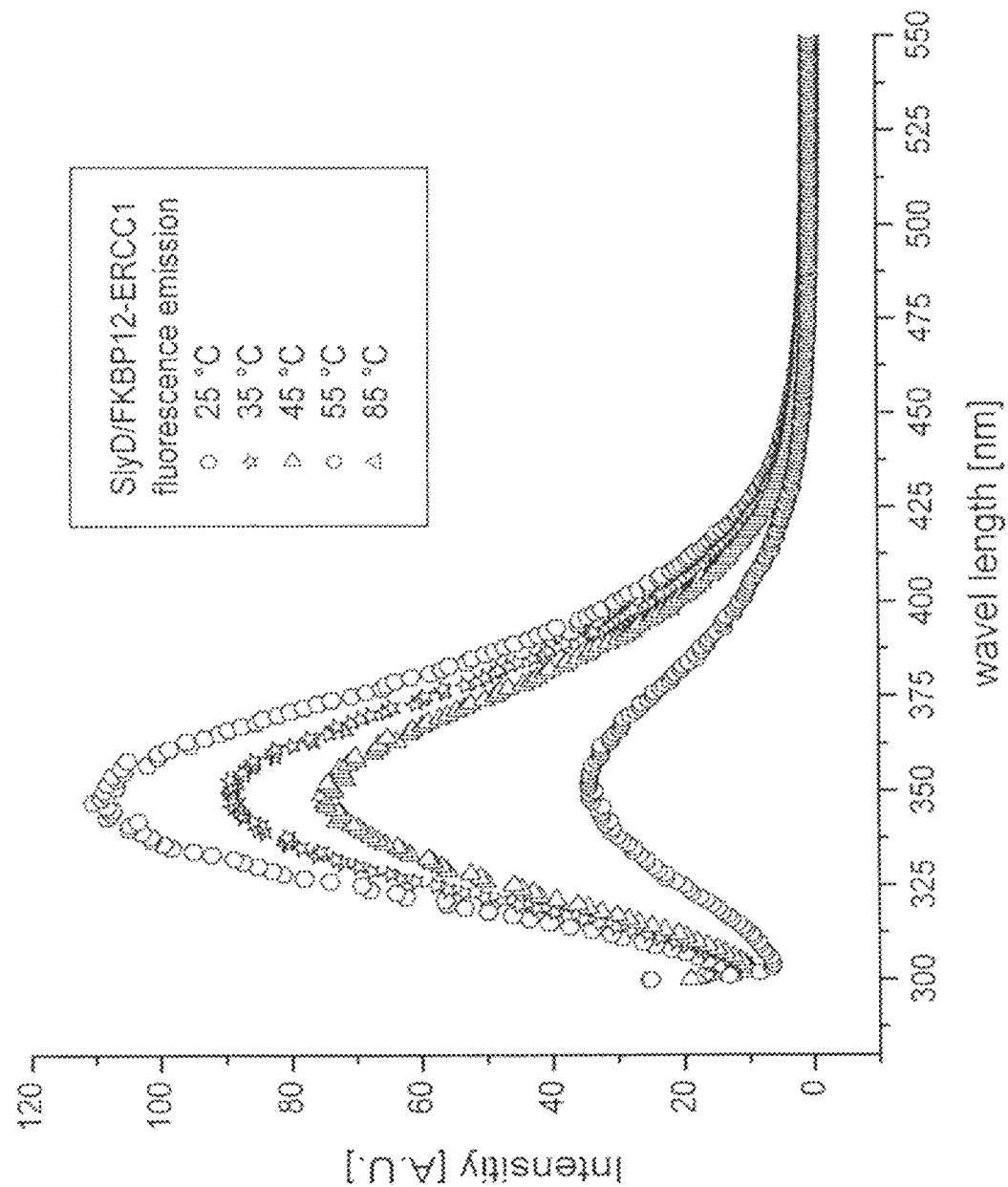
FIG. 4 Wavelength scan from 300 nm-600 nm was driven at 600 nm/min recoding fluorescence emission intensity of SlyD/FKBP12-ERCC1 fusion polypeptide at 25° C., 35° C., 45° C., 55° C., 85° C.

The affinity purified fusion polypeptide was dialyzed versus 75 mM HEPES buffer (pH 7.5, 150 mM NaCl, 6.5% (w/v) sucrose, 10 mM cysteine) and filtrated. SlyD/FKBP12-ERCC1 was UV/Vis spectroscopically quantified at 7.4 mg/ml using the calculated extinction coefficient for the 35380.301 Da polypeptide (FIG. 4). In the wavelength screen from 220 nm to 340 nm a 280 nm absorption peak deriving from the single FKBP12 Trp was obtained. No 340 nm absorption could be detected.

Protein fluorescence measurements were used to test the conformational nature of SlyD/FKBP12-ERCC1. FKBP12 C22A as a carrier for polypeptide insertions is especially useful, because the single FKBP12 Trp moiety can be used to diagnose the structural integrity of the FKBP12 moiety (Scholz, C., et al., J. Biol. Chem. 271 (1996) 12703-12707; Russo, A. T., et al., J. Mol. Biol. 330 (2003) 851-866). FKBP12 C22A in its native structure shows a single fluorescence emission peak at 320 nm (Zoldak, G., et al., J. Mol. Biol. 386 (2009) 1138-1152).

250 μl of 2.5 mg/ml SlyD/FKBP12-ERCC1 in HBS-E-buffer (pH 7.4) were analyzed at different temperatures. A Cary Eclipse instrument under the Scan Software Version: 1.1(132) was used at 5 nm band width for excitation and emission. A wavelength scan from 300 nm-600 nm was driven at 600 nm/min. The excitation of the intrinsic tryptophan fluorescence was set to 294 nm. A broad peak at 350 nm was obtained (FIG. 4). According to theory the intrinsic Trp solvatochromic fluorescence emission at 350 nm would be strongly quenched in a folded FKBP12 protein environment, whereas it increases with the unfolding of FKBP12. A temperature screen from 25° C. to 85° C. didn't show any further fluorescence emission peaks, but a temperature-dependent fluorescence quenching of the 350 nm emission. The 320 nm emission, an indicator for structural integrity of FKBP12, could not be detected.

Therefore, the single Trp residue in the SlyD/FKBP12-ERCC1 fusion polypeptide is exposed to the solvent already at 25° C., indicating that the chimeric FKBP12 in the SlyD-FKBP12 context is partially or completely unfolded.

Therefore, the scaffold is an ideal platform for mimicking and presenting a structural plurality of non-stable peptide conformations as they typically occur in paraffin-embedded, formalin-fixed tissue during immune histochemical experiments. (Abe, M., et al., Anal. Biochem. 318 (2003) 118-123).

FK506 BIAcore Binding Assay

A BIAcore 3000 instrument under control of the software version V4.1 was mounted with a sensor SAchip according to the manufacturer's instruction. As running buffer a HBS-EP buffer was used (10 mM HEPES, pH 7.4, 150 mM NaCl, 1 mM EDTA, 0.05% (w/v) P20 (10% aqueous solution of the non-ionic surfactant Polysorbate 20 (Tween 20)). 1213 RU of bi-linker-FK506 conjugate (Roche Diagnostics Mannheim, Germany) were captured on flow cell 4.

300 nM purified SlyD/FKBP12-ERCC1 fusion polypeptide and 300 nM SlyD/FKBP12 control polypeptide were injected into the system at 30 μl/min for 3 min. association time and 3 min. dissociation time The sensor was regenerated by injecting a 10 mM glycine-HCl solution (pH 1.7) for 2 min. at a flow rate of 30 μl/min.

Figure 5:
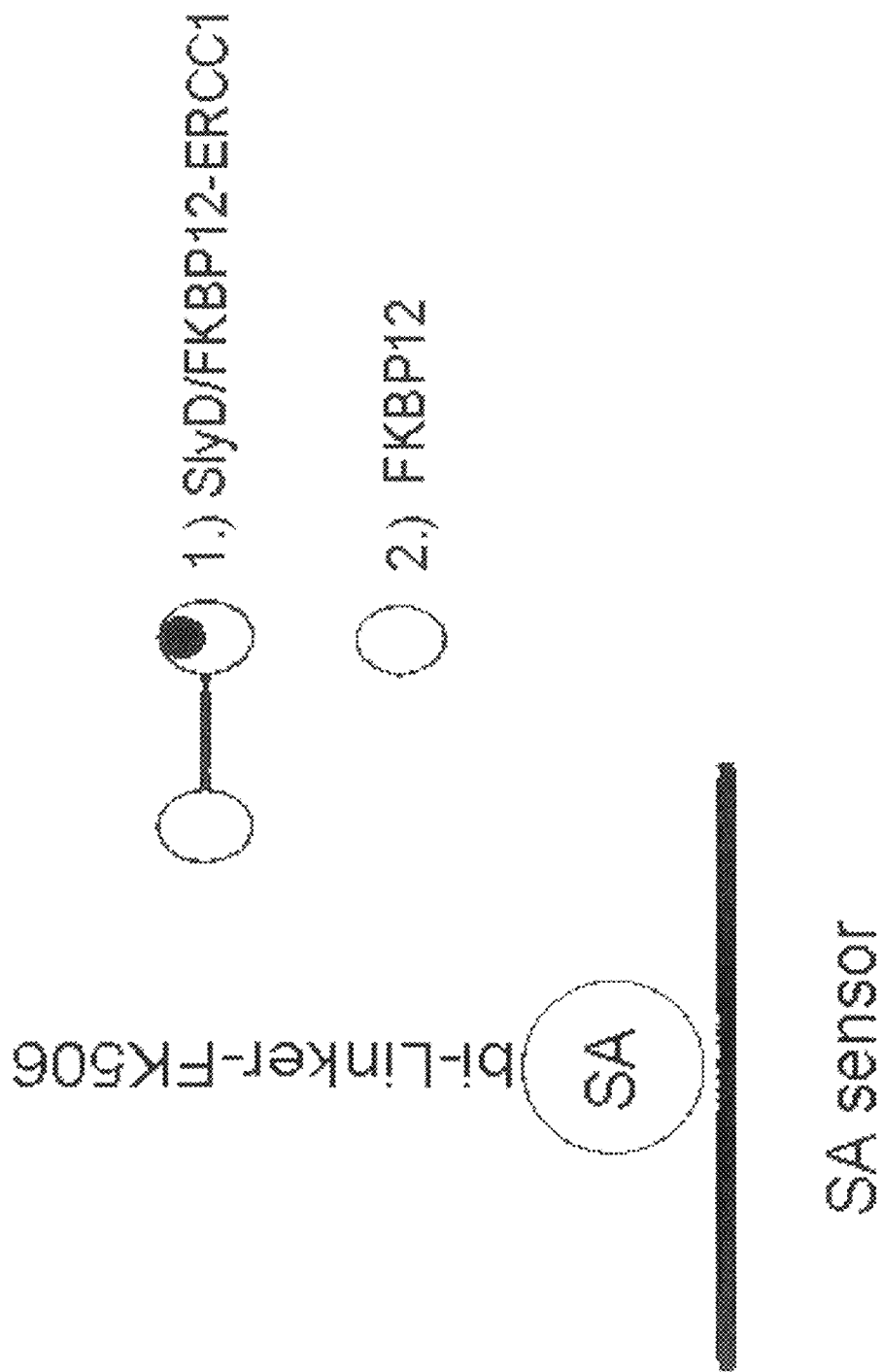
FIG. 5 Scheme of BIAcore assay for determining the binding of SlyD/FKBP12-ERCC1 fusion polypeptide to FK-506.
Figure 6:
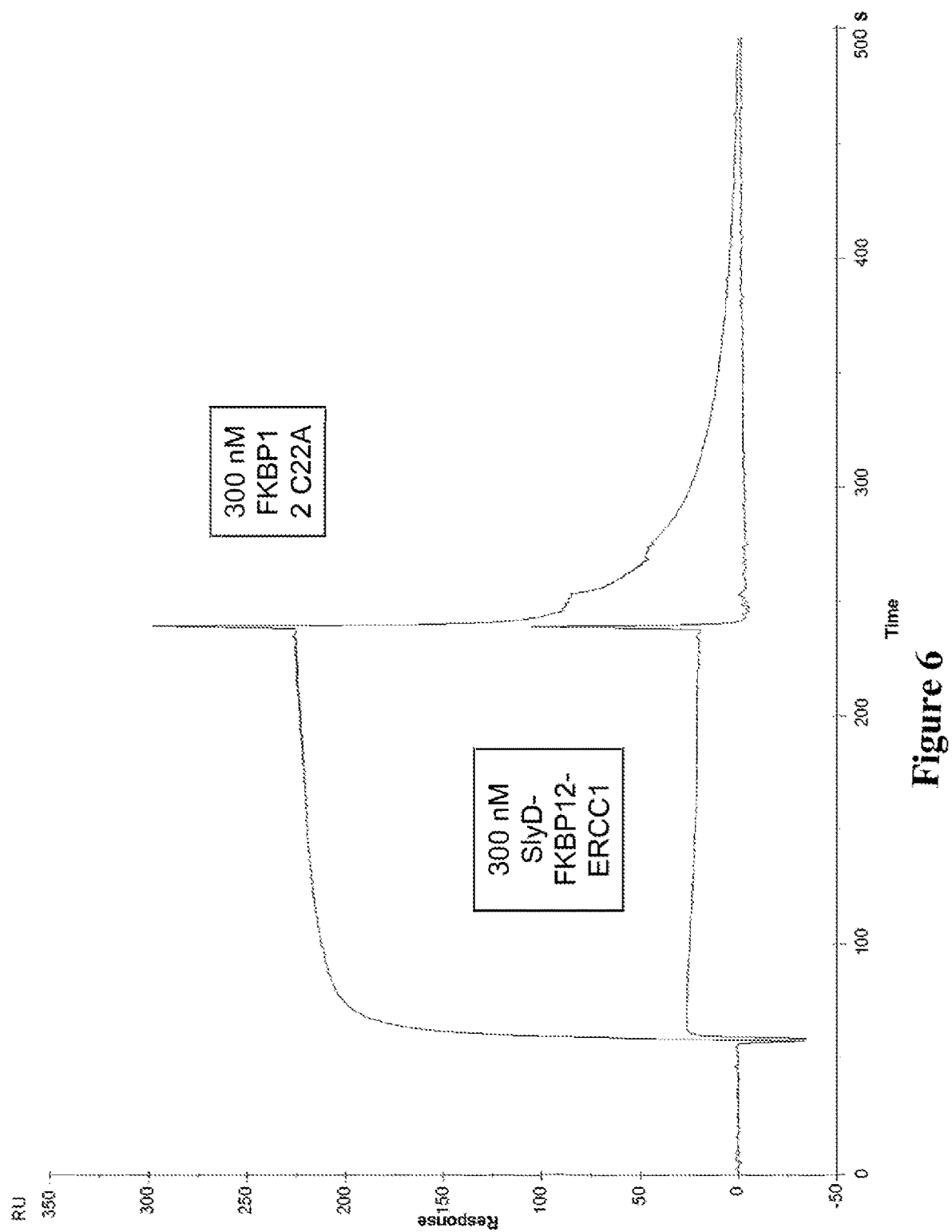

The BIAcore binding assay with 300 nM fusion polypeptide SlyD/FKBP12-ERCC1 as analyte in solution vs. the sensor surface presented ligand bi-FK506 (FIG. 5) showed no binding activity (FIG. 6), indicating a structure-functional loss of the FKBP12 moiety in the chimeric fusion polypeptide. The control polypeptide FKBP12 (C22A) showed binding activity.

The inability of the SlyD/FKBP12-ERCC1 fusion polypeptide to bind FK-506 provides another evidence for a SlyD/FKBP12-ERCC1 structure, which deviates from that of the FKBP12 (C22A) conformation. This is accompanied by a loss of binding activity of the chimeric FKBP12 domain.

Analytical HPLC Chromatographic Analyses

Figure 7:
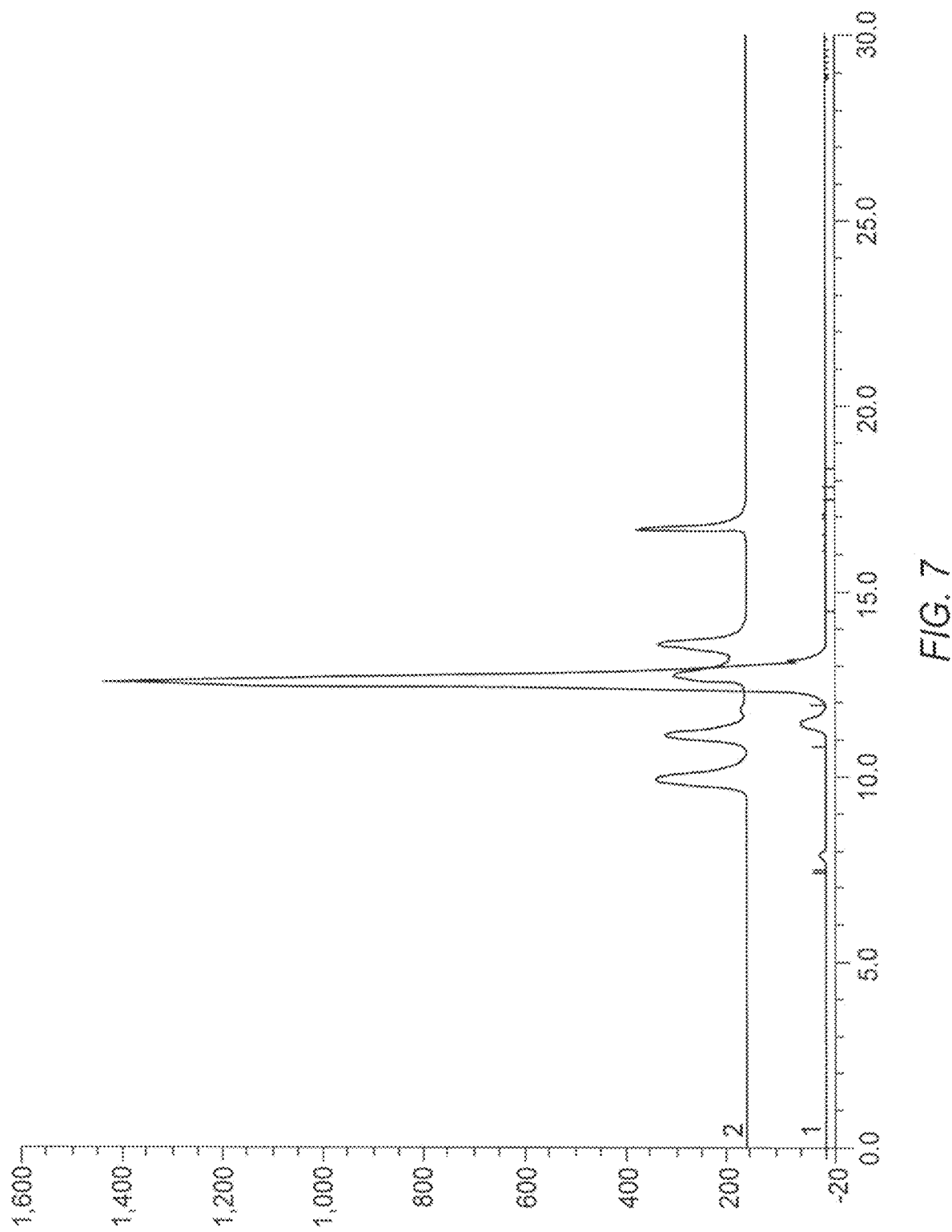
FIG. 7 Analytical HPLC chromatogram of the SlyD/FKBP12-ctrl fusion polypeptide. After Ni-NTA purification SlyD/FKBP12-ctrl elutes as a monomeric peak.
Figure 18:
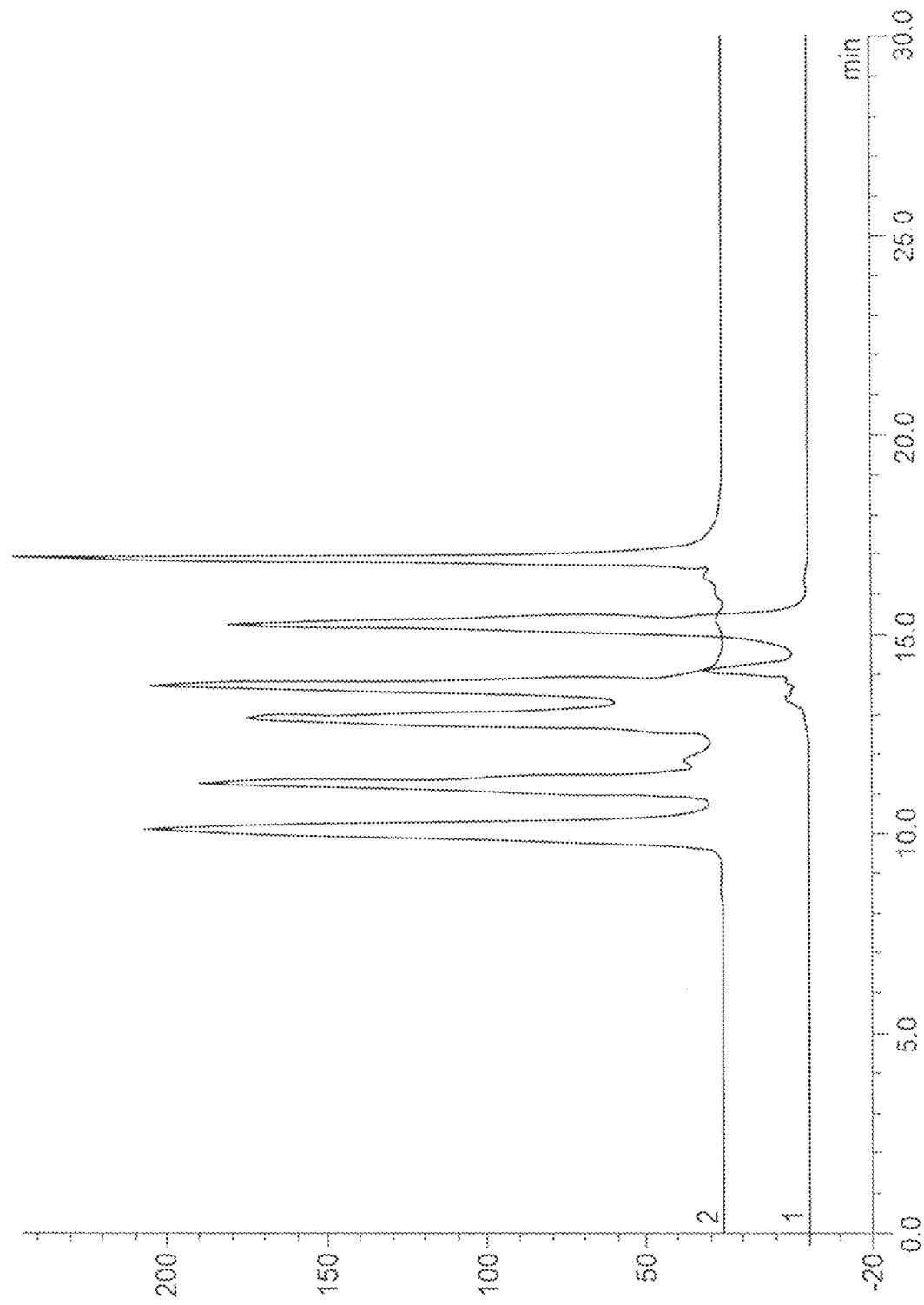
FIG. 18 Analytical HPLC chromatogram of *Thermus thermophilus* SlyD-IGF-1(74-90) fusion polypeptide.
Figure 22:
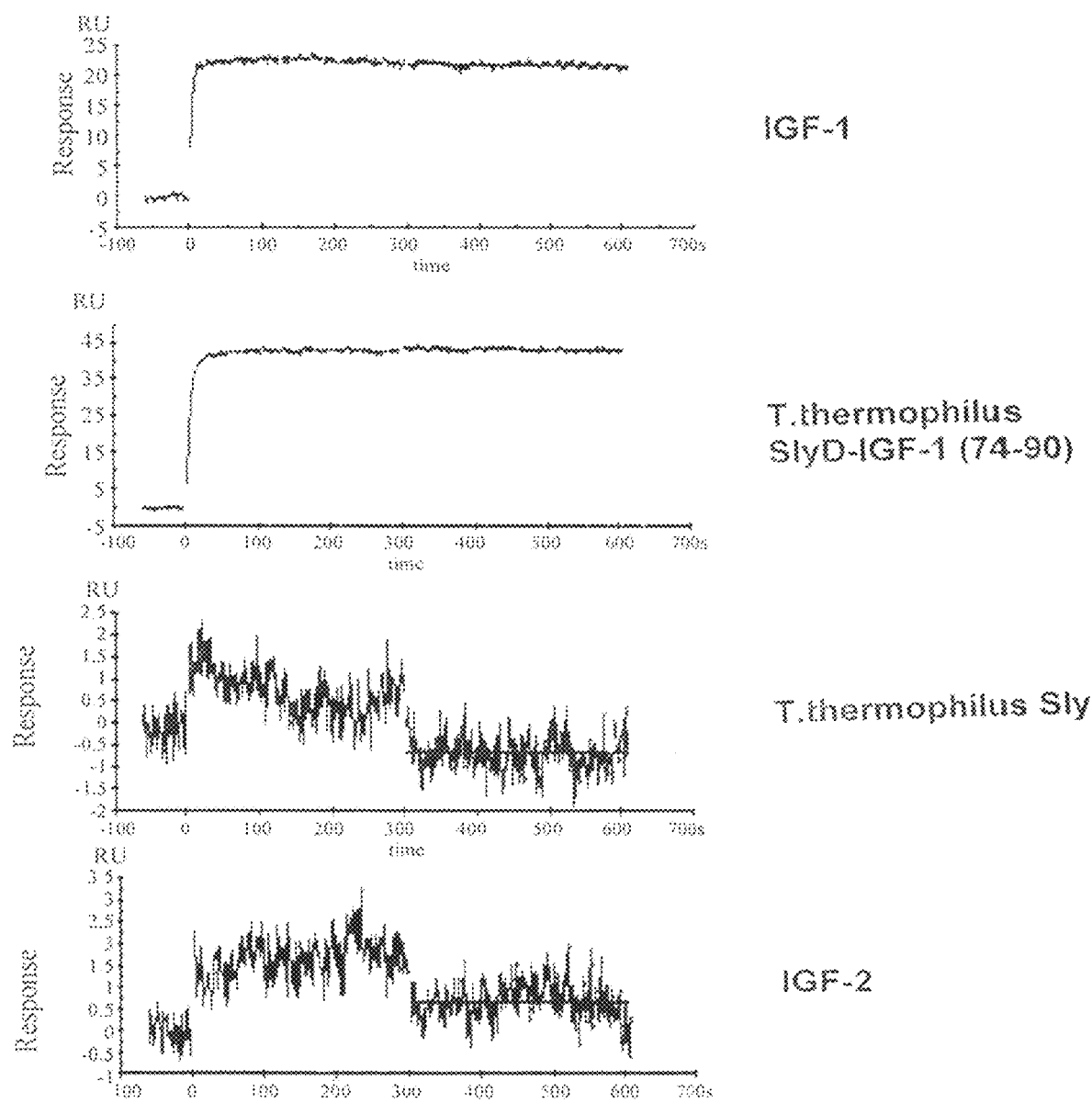
FIG. 22 Exemplary BIAcore kinetic screening of primary culture <IGF-1>M-11.0.15 vs. IGF-1, IGF-2, *Thermus thermophilus* SlyD-IGF-1(74-90) fusion polypeptide and *Thermus thermophilus* SlyD wild-type polypeptide.
Figure 24:
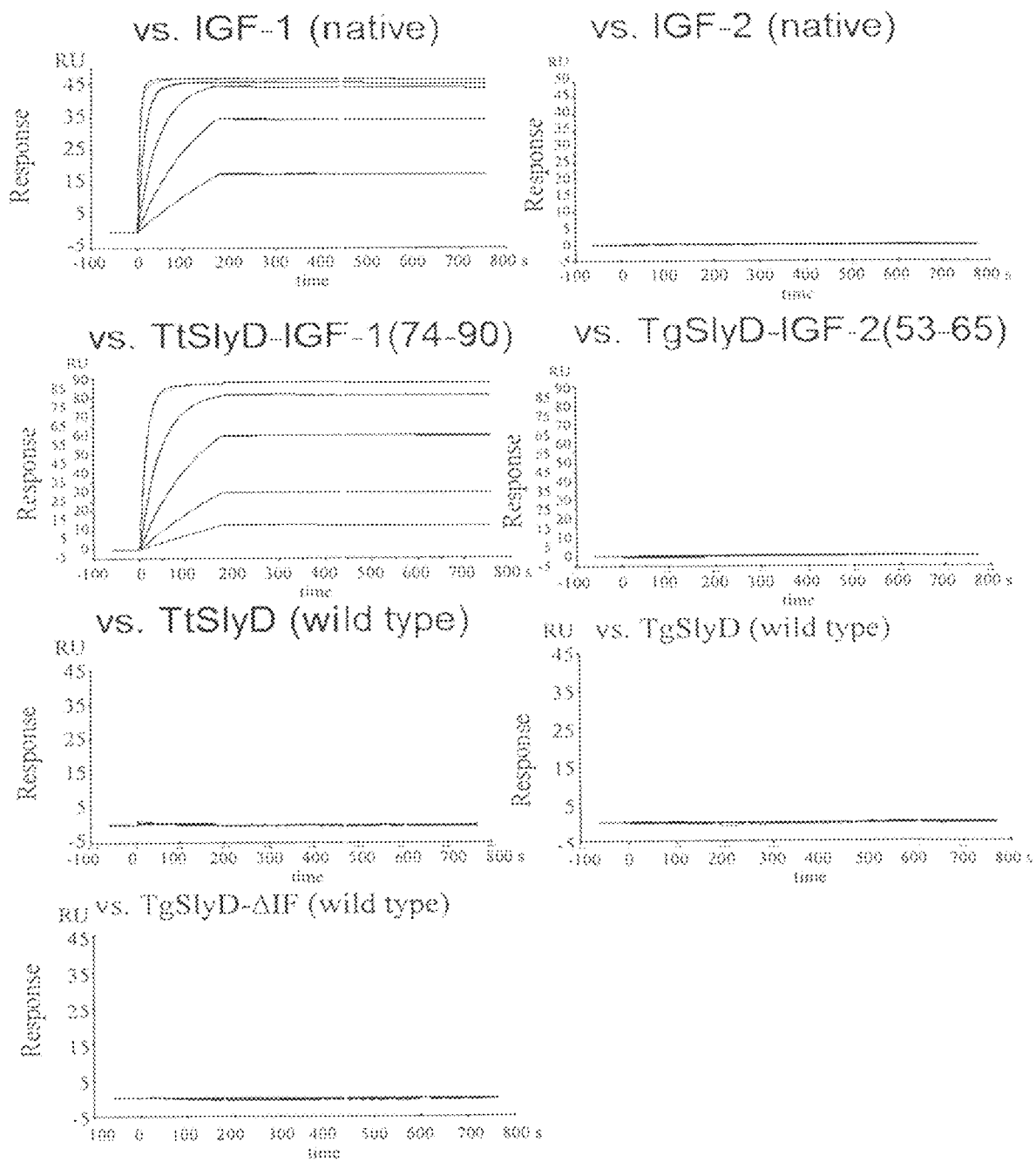
FIG. 24 BIAcore measurements of scaffold-developed <IGF-1>M-11.11.17-IgG vs. IGF-1, IGF-2, *Thermus thermophilus* SlyD-IGF-1(74-90) fusion polypeptide, *Thermus thermophilus* SlyD wild-type polypeptide, *Thermococcus gammatolerans* SlyD wild-type polypeptide, *Thermus thermophilus* SlyD-ΔIF fusion polypeptide, *Thermococcus gammatolerans* SlyD-IGF-2(53-65) fusion polypeptide.
Figure 26:
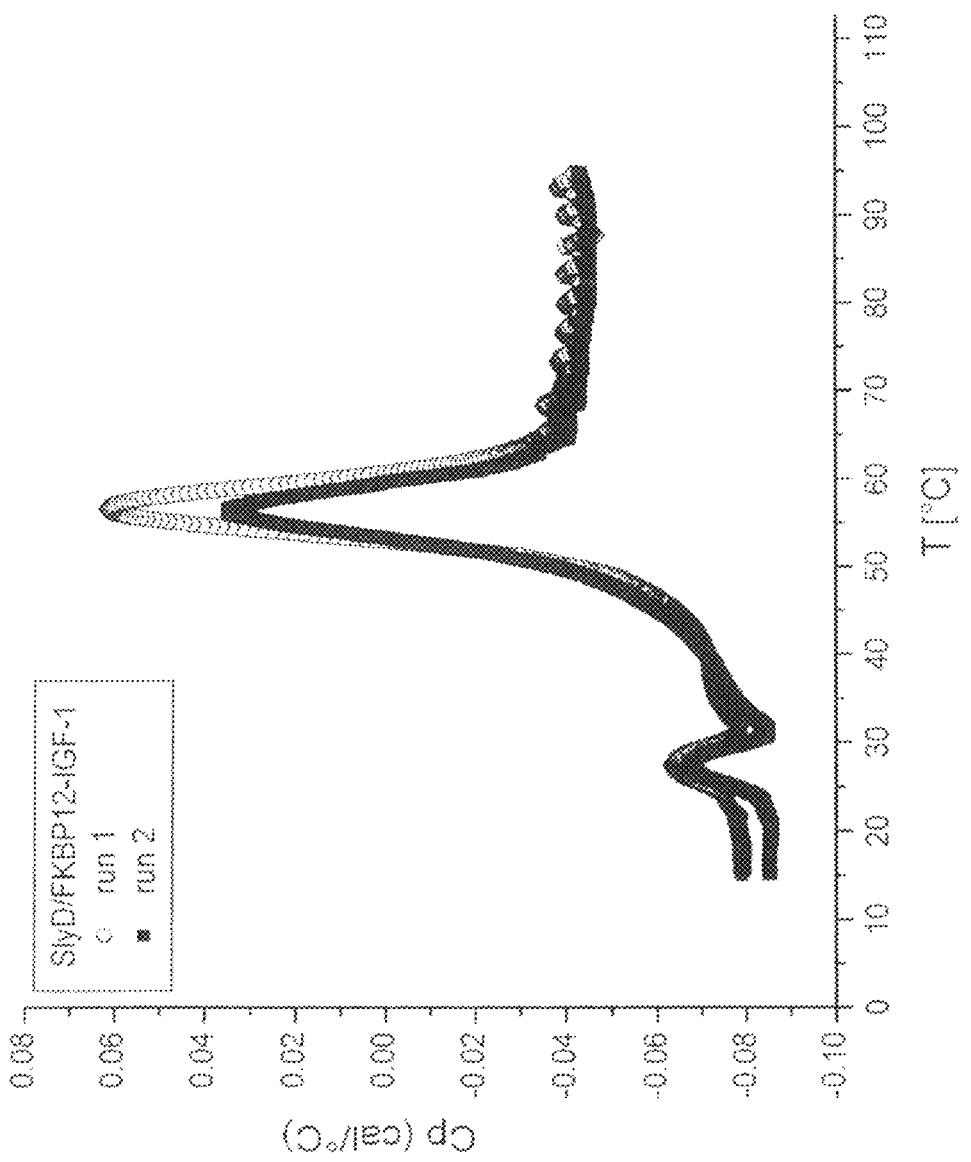
FIG. 26 DSC measurements, overlay plot of two runs melting SlyD/FKBP12-IGF-1(74-90) fusion polypeptide in the temperature gradient 10° C. to 95° C. SlyD/FKBP12-IGF-1(74-90) fusion polypeptide folds reversible.
Figure 36:
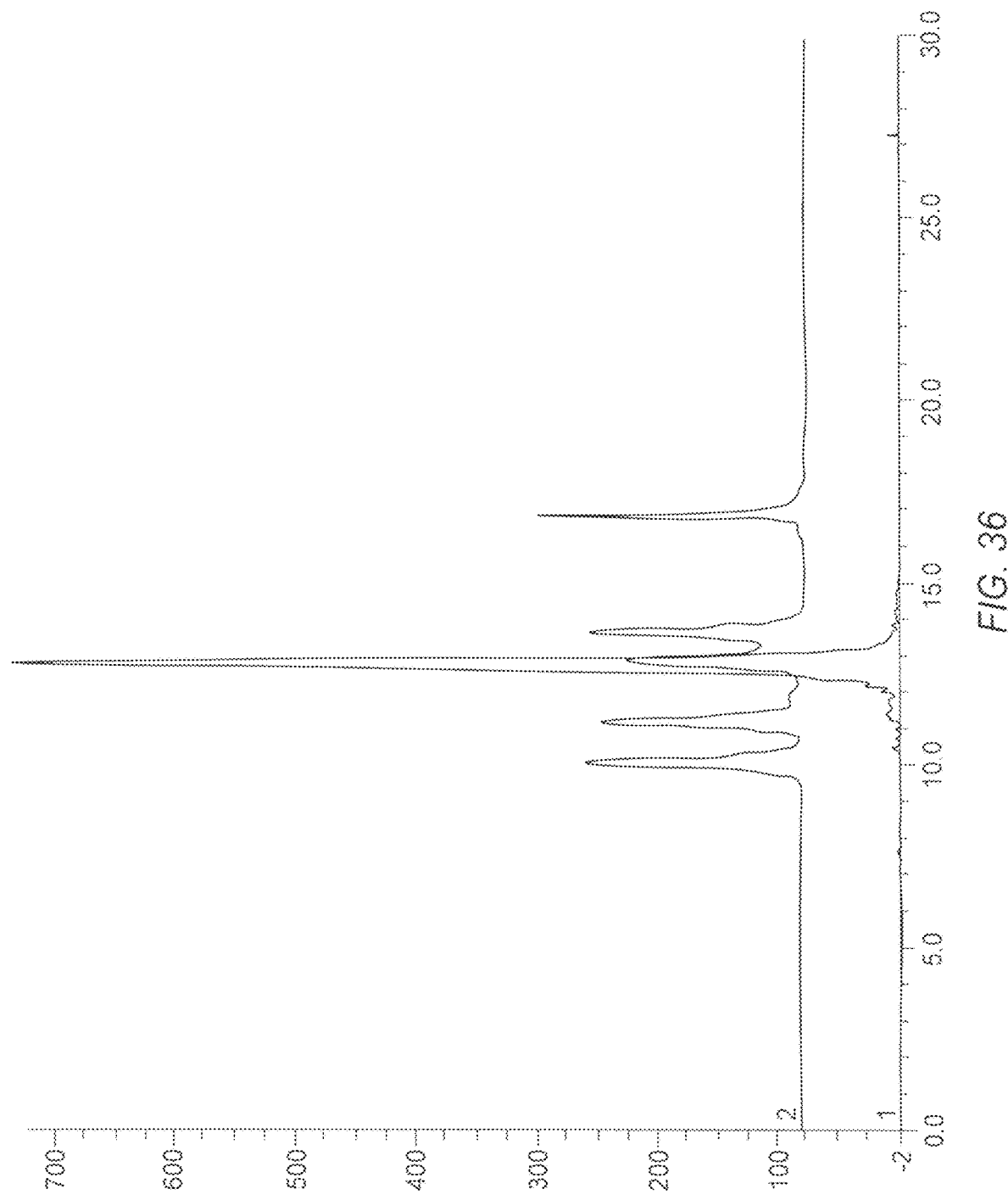
FIG. 36 Analytical HPLC chromatogram of the SlyD/FKBP12-IGF-1(74-90) fusion polypeptide.
Figure 37:
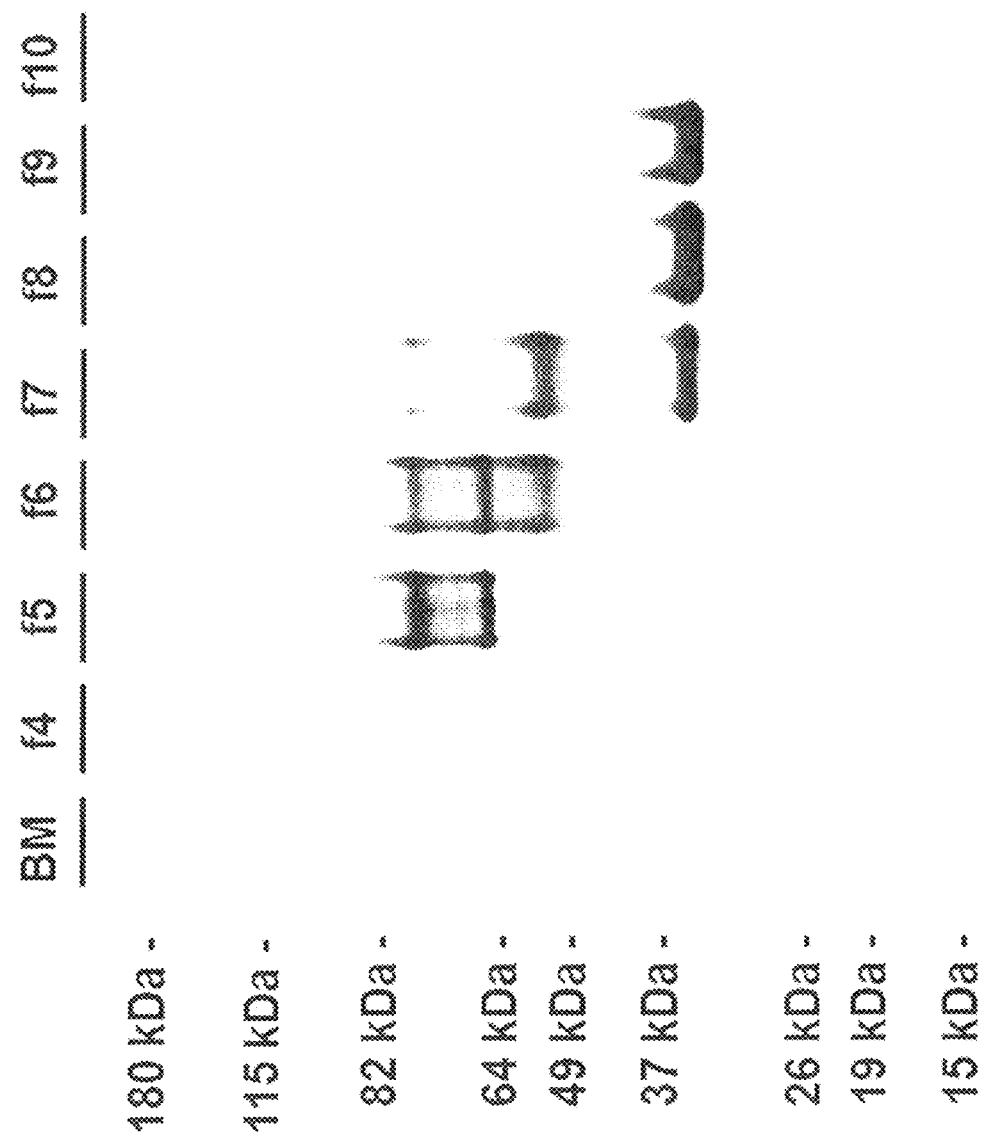
FIG. 37 Coomassie-stained native Novex® 8-16% Tris-Glycine Mini Gel (Invitrogen) BM: BenchMark™ Pre-Stained Protein Ladder (Invitrogen). F4 to f10: size exclusion chromatography elution fractions. Fraction 8 and fraction 9 show single distinct protein bands at 37 kDa.
Figure 38:
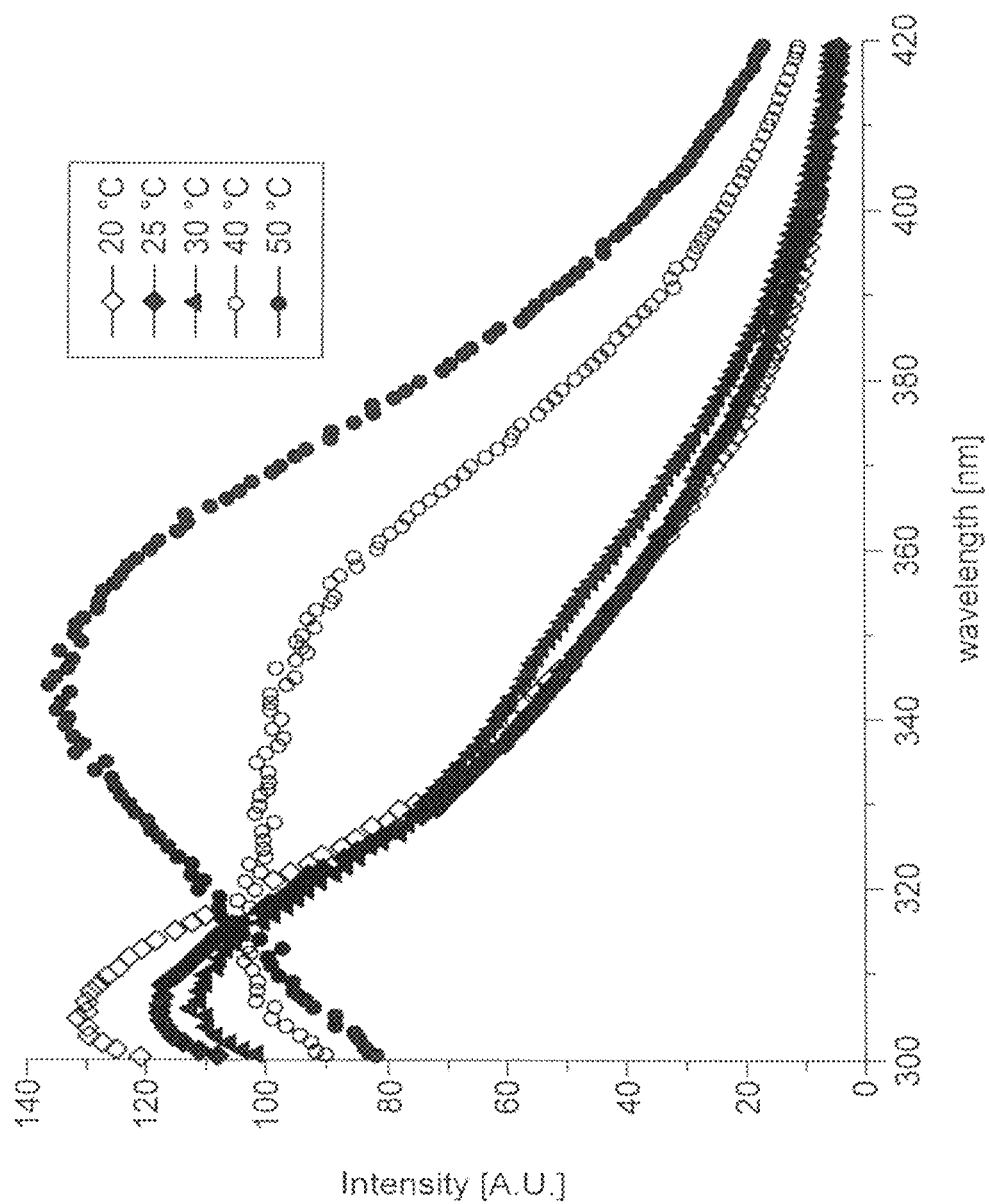
FIG. 38 Fluorescence emission of SlyD-FKBP12/13-CSF1R at different temperatures.
Figure 39:
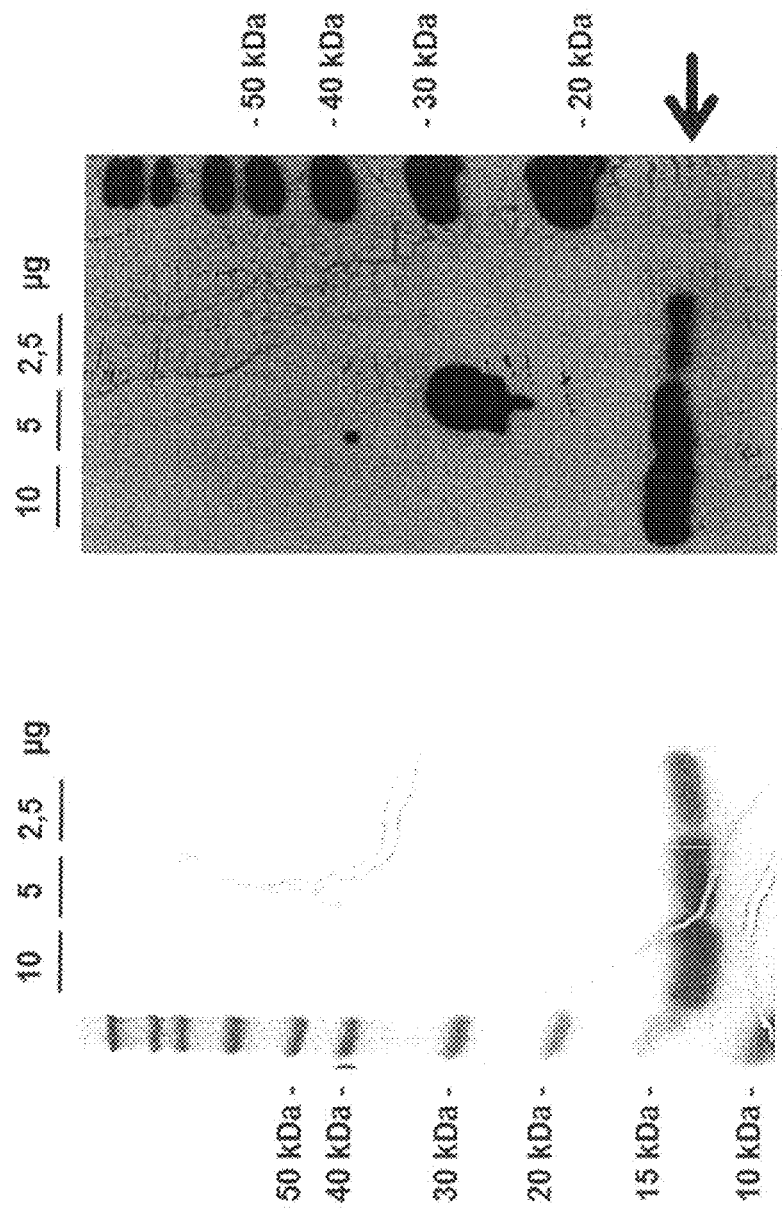
FIG. 39 SDS PAGE (Coomassie staining) and anti-his-tag Western Blot (10 sec exposition) of the *Thermus thermophilus* SlyD-ΔIF fusion polypeptide. Protein bands indicated by black arrow. M—Novex Sharp Standard; 1—2.5 µg *Thermus thermophilus* SlyD-ΔIF fusion polypeptide; 2—5.0 µg *Thermus thermophilus* SlyD-ΔIF fusion polypeptide; 3—10 µg *Thermus thermophilus* SlyD-ΔIF fusion polypeptide; M*—Magic Mark.

Analytical HPLC chromatographic analyses were performed with fusion polypeptides in order to analyze the oligomeric status of the fusion polypeptide A Chromeleon Dionex HPLC device was used as recommended by the manufacturer at 25° C. with a TSK3000SWXL column equilibrated in HBS-E-buffer (pH 7.4). The buffer flow was 0.7 ml/min. 100 μl of a SlyD/FKBP12-ERCC1 comprising solution (7.4 mg/ml) was injected into the system (see FIG. 8). In another workflow a SlyD/FKBP12 control containing solution (9.5 mg/ml) was injected into the system (see FIG. 7). In another workflow a *Thermus thermophilus* SlyD-IGF-1(74-90) containing solution (3 mg/ml) was injected into the system (see FIG. 18). In another workflow a SlyD/FKBP12-IGF-1(74-90) containing solution (5.4 mg/ml) was injected into the system (see FIG. 36). The UV/VIS Detector was set to 280 nm. The data was evaluated according to the manufacturer's instructions using the Dionex software version 6.80 SP2 Build 2284. The system was calibrated with the molecular standard Oriental Yeast, Cat 46804000.

Figure 8:
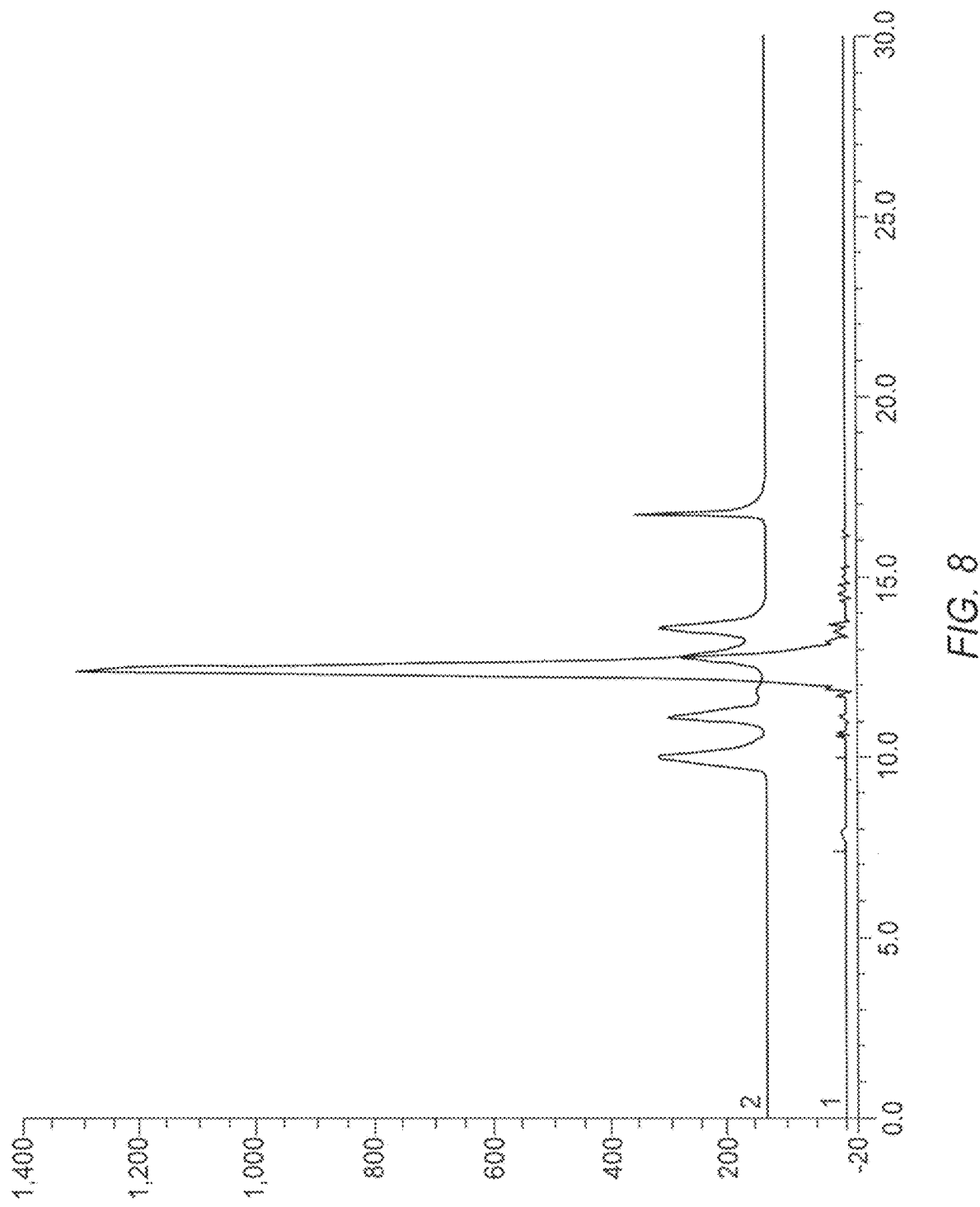
FIG. 8 Analytical HPLC chromatogram of the SlyD/FKBP12-ERCC1 fusion polypeptide. After Ni-NTA purification SlyD/FKBP12-ERCC1 elutes as a monomeric peak.

FIG. 8 shows the column elution profile of Ni-NTA affinity purified SlyD/FKBP12-ERCC1. 91.5% of the area integration of the complete elution profile can be found localized in peak No. 5 (1310.319 mAU) eluting at 12.37 min retention time. The profile indicates a monomeric SlyD/FKBP12-ERCC1 fusion polypeptide. Monomeric fusion polypeptide was already obtained after just an initial Ni-NTA purification step.

Kinetic Screening Using

The SlyD/FKBP12-ERCC1 fusion polypeptide was used in SPR binding analyses. It is helpful to use monomeric and monovalent analytes in solution to determine the antibody binding kinetics according to a Langmuir model. Furthermore, it is helpful for SPR measurements to use an analyte with increased, i.e. high, molecular weight to increase the mass sensitivity of the measurements. At the same time the epitope accessibility must be given.

Figure 9:
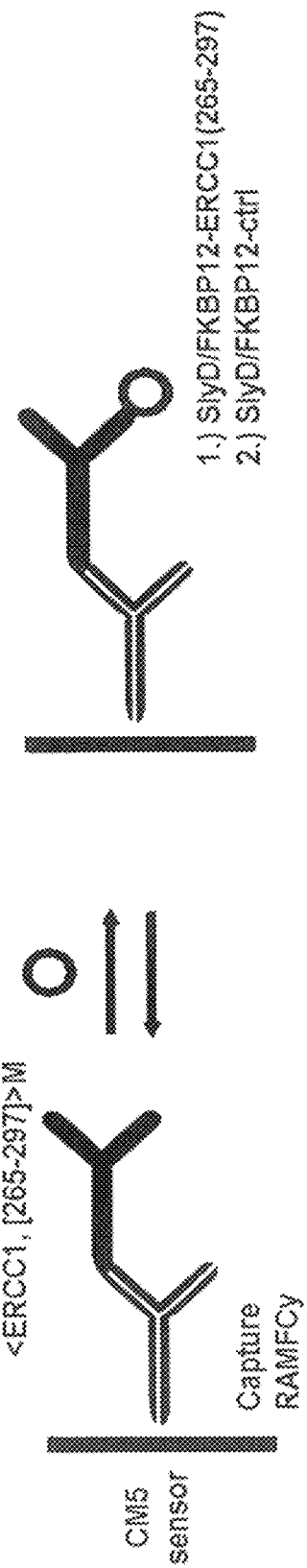
FIG. 9 Scheme of BIAcore binding assay kinetic screening with SlyD/FKBP12-ERCC1 fusion polypeptide and 300 nM SlyD/FKBP12-ctrl as analytes in solution. CM5 sensor, Capture RAMFCy: Rabbit anti mouse Fc gamma capturing antibody.

A scheme of the BIAcore screening assay is depicted in FIG. 9.

The kinetic screening was performed on a BIAcore A100 instrument under control of the software version V1.1. A BIAcore CMS chip was loaded to the machine and according to the manufacturer's instruction addressed hydrodynamically. Thereafter the chip was conditioned. As running buffer a HBS-EP buffer is used (10 mM HEPES, pH 7.4, 150 mM NaCl, 1 mM EDTA, 0.05% (w/v) P20). A polyclonal composition of anti-IgG Fc capture antibodies of a concentration of 30 μg/ml in 10 mM sodium acetate buffer (pH 4.5) is pre-concentrated to spots 1, 2, 4 and 5 in flow cells 1, 2, 3 and 4. The antibody was covalently immobilized at 10,000 RU via NHS/EDC chemistry. The sensor was deactivated thereafter with a 1 M ethanolamine solution. Spots 1 and 2 were used for the determination and spots 2 and 4 were used as reference. Prior to application to the sensor chip the hybridoma supernatants were diluted 1:5 in HBS-EP buffer. The diluted solution was applied at a flow rate of 30 μl/min for 1 min. Immediately thereafter the formulated antigen, such as the FKBP12 fusion polypeptide was injected at a flow rate of 30 μl/min for 2 min. Thereafter the signal is recorded for another 5 min. The sensor was regenerated by injecting a 10 mM glycine-HCl solution (pH 1.7) for 2 min. at a flow rate of 30 μl/min. The recorded signal shortly before the end of the injection of the antigen is denoted as binding late (BL). The recorded signal shortly before the end of the recording of the dissociation is denoted as stability late (SL). Both data points are plotted versus each other. Selected antibodies have a Binding Late value that is equal to the Stability Late value. These antibodies populate the area near the trend line indicating BL=SL in the plot.

Figure 10:
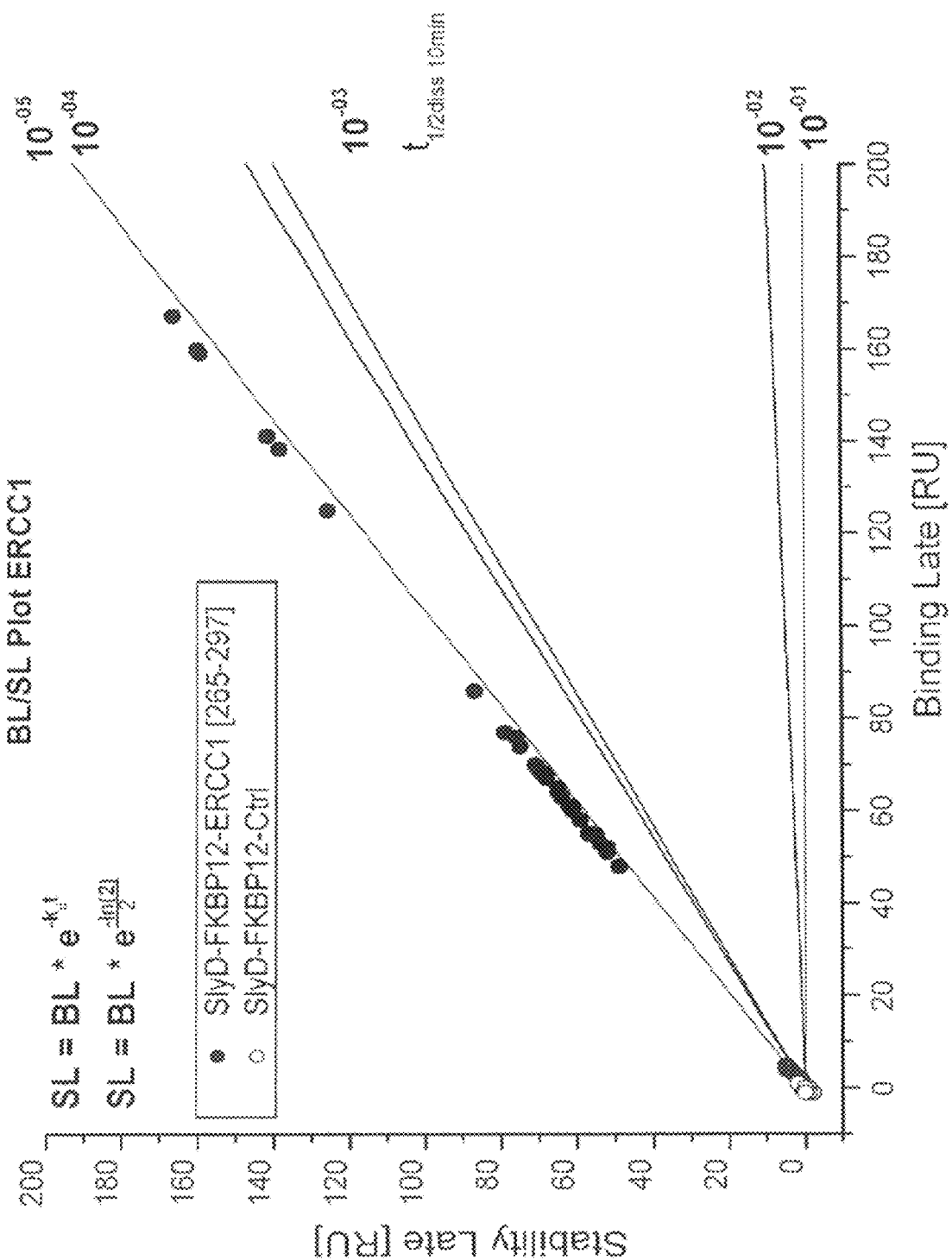
FIG. 10 Stability Late/Binding Late Plot showing kinetic properties of anti-ERCC1 antibodies determined by kinetic screening using SlyD/FKBP12-ERCC1 as analyte in solution. All clones populate the $10^{-5}$ 1/s trend line at Binding Late values >40 RU indicating extraordinary antigen complex stability. No binding versus SlyD/FKBP12-ctrl is detectable.

FIG. 10 shows the data for selected anti-ERCC1 antibodies. It can be seen that the SlyD/FKBP12-ERCC1 interaction is highly specific. No interaction with the SlyD/FKBP12 control sample can be detected. Overall no unspecific binding can be seen.

Figure 11:
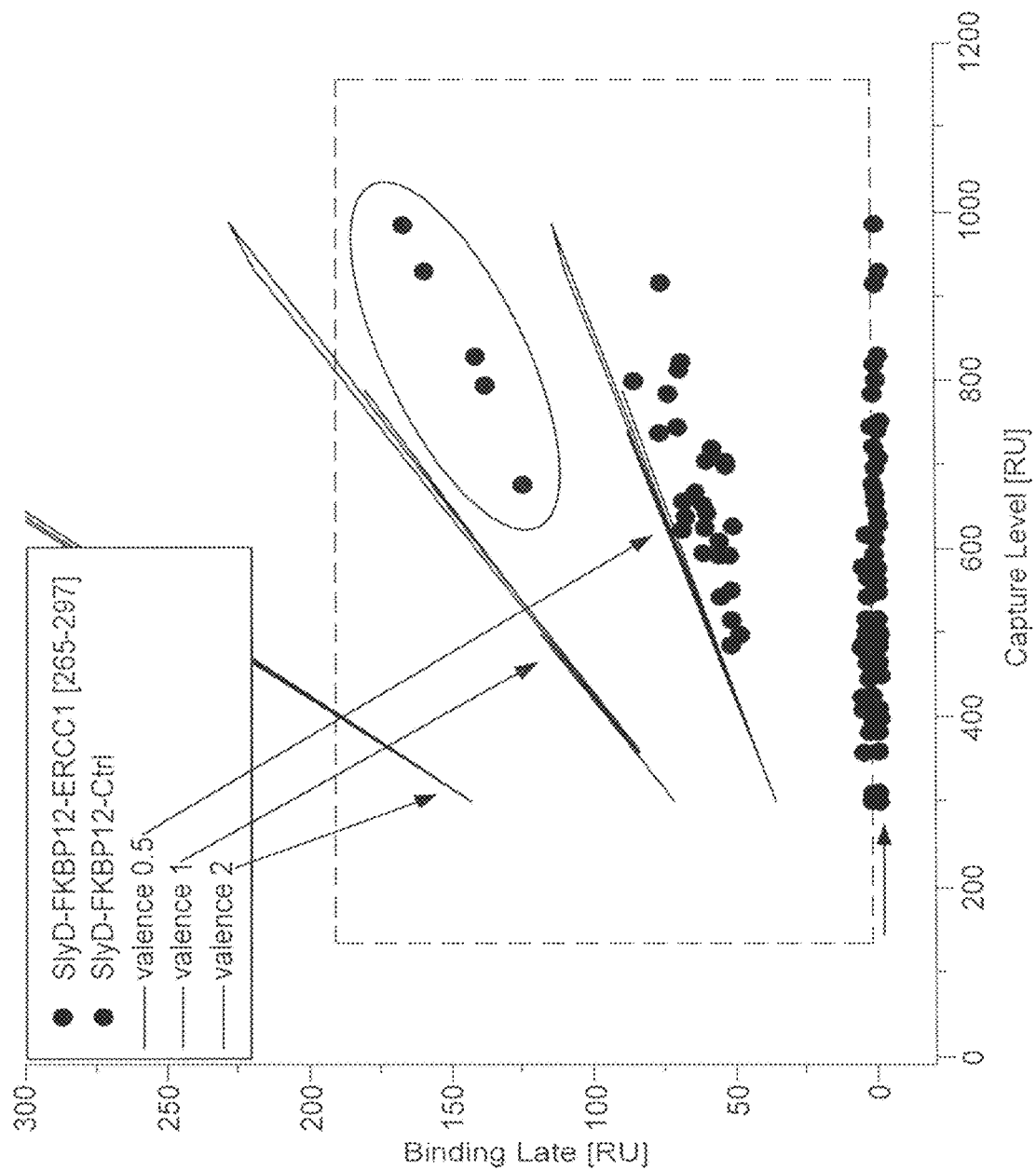
FIG. 11 Properties of anti-ERCC1 antibodies determined by kinetic screening. The Binding Late/Antibody Capture Level Plot indicates binding valence corridors by trend lines. All 5.00×0.35 sister clones (encircled) populate the valence corridor between a Molar Ratio=0.5 and Molar Ratio=1 and were selected for further processing.

FIG. 11 shows the valence analysis of the antibodies. The amount of antigen in response units (Binding Late, RU) saturating the surface presented antibody (Capture Level, RU) is shown. Trend lines and arrows in FIG. 11 indicate the valencies (Molar Ratio) of the surface presented antibodies. All sister clones (clone ID 5.00×0.35) populate the valence corridor MR 0.5-MR 1.0, whereas all the other clones populate the corridor below MR 0.5 indicating less functionality. No functional binding versus SlyD/FKBP12 control could be detected.

FIG. 12 shows the quantification of this kinetic screening approach. All six sister clones (5.001.35 to 5.006.35) show suitable Binding Late and Stability Late values. The dissociation rate kd (1/s) show high antigen complex stabilities fulfilling the requirements for an IHC suited antibody. The calculated $t_{1/2 diss}$ antigen complex stability halftimes are 204 min for all six sister clones.

Figure 13:
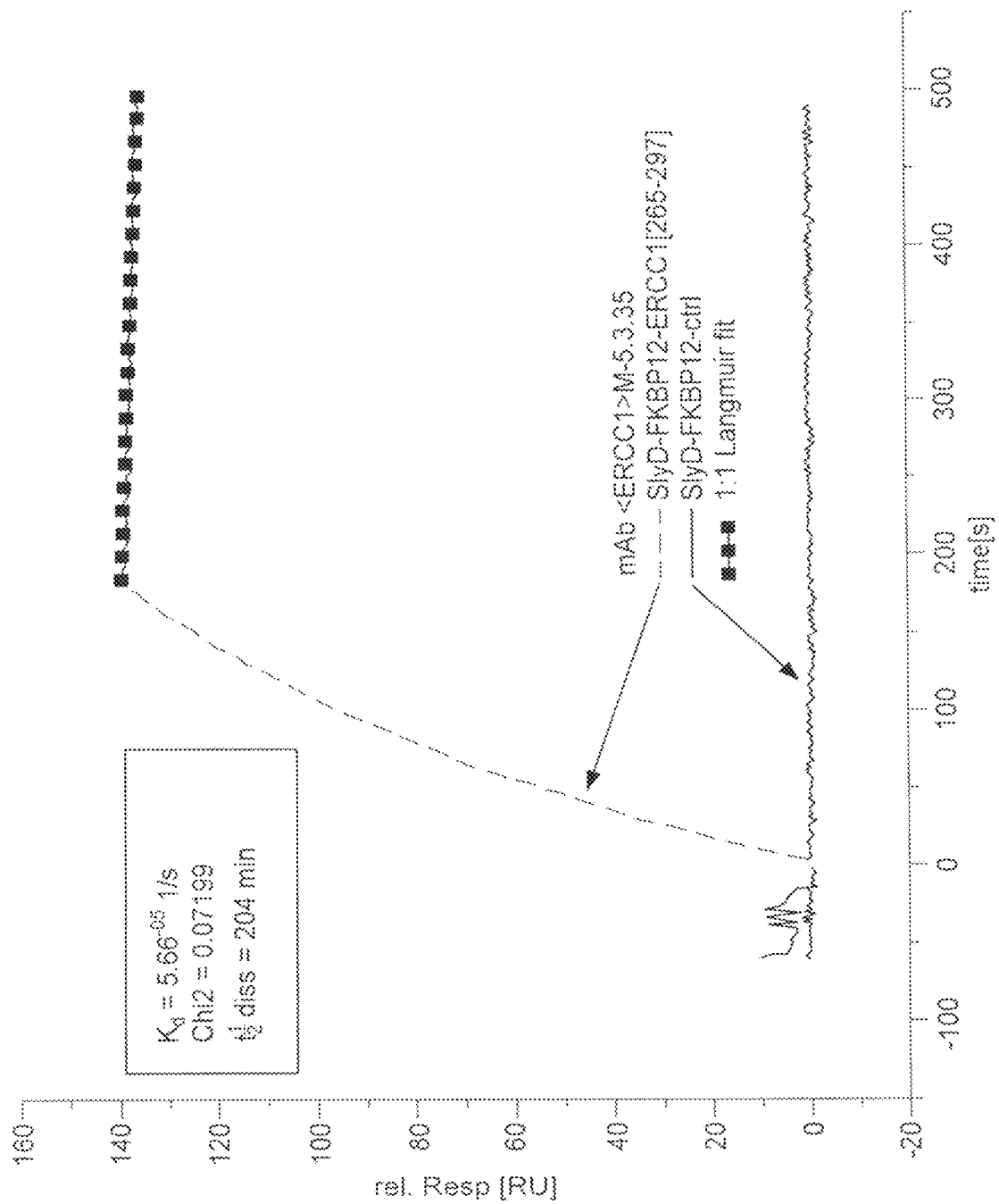
FIG. 13 Exemplary anti-ERCC1 antibody single concentration kinetic of clone <ERCC1>M-5.3.35 using SlyD/FKBP12-ERCC1 as analyte in solution.

FIG. 13 exemplarily shows the kinetic screening signature of clone 5.003.35 versus the analytes SlyD/FKBP12-ERCC1 and SlyD/FKBP12 control. Since SlyD/FKBP12-ERCC1 is a stable, soluble and monomeric analyte it perfectly fits to the 1:1 Langmuir dissociation model (black line on the dissociation raw data in red). No unspecific binding could be detected. No interaction versus SlyD/FKBP12 control was detected.

Western Blotting

Figure 14:
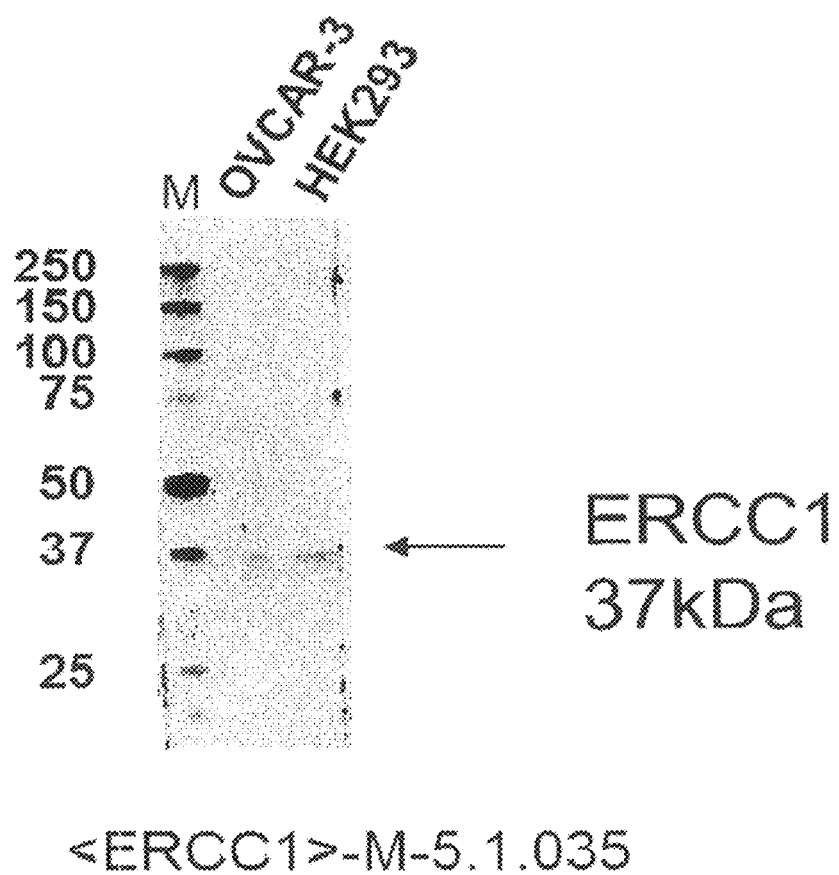
FIG. 14 Western blot using clone<ERCC1>M-5.1.35. 5 µg OVCAR-3 and HEK293 cell lysates were loaded per lane on a NuPAGE SDS gels (Invitrogen). A specific ERCC1 band at 37 kDa is detected.

FIG. 14 shows a Western blot experiment using clone 5.001.35. Western Blotting can be used as an indicator for the latter IHC suitability of the antibody.

For western blotting, 5 μg OVCAR-3 and 5 μg HEK-293 cell lysate were loaded into the gel lanes on 4-12% NuPAGE SDS gels (Invitrogen). Both cell lines were not pretreated e.g. by radiation or Cisplatin.

Western blotting was performed according to standard protocols with NuPAGE buffers and reagents (Invitrogen). The antibody 5.001.35 was used at a concentration of 50 ng/ml. Primary antibody incubation was performed for 30 min. at room temperature (RT). The membrane was developed using the LumiImager together with the LumiLight reagent according to the manufacturer's instructions (Roche Applied Science, Mannheim, Germany). The endogenous basal ERCC1 level was specifically detected as a single 37 kDa band in the Western blot.

IHC Experiments

Figure 15:
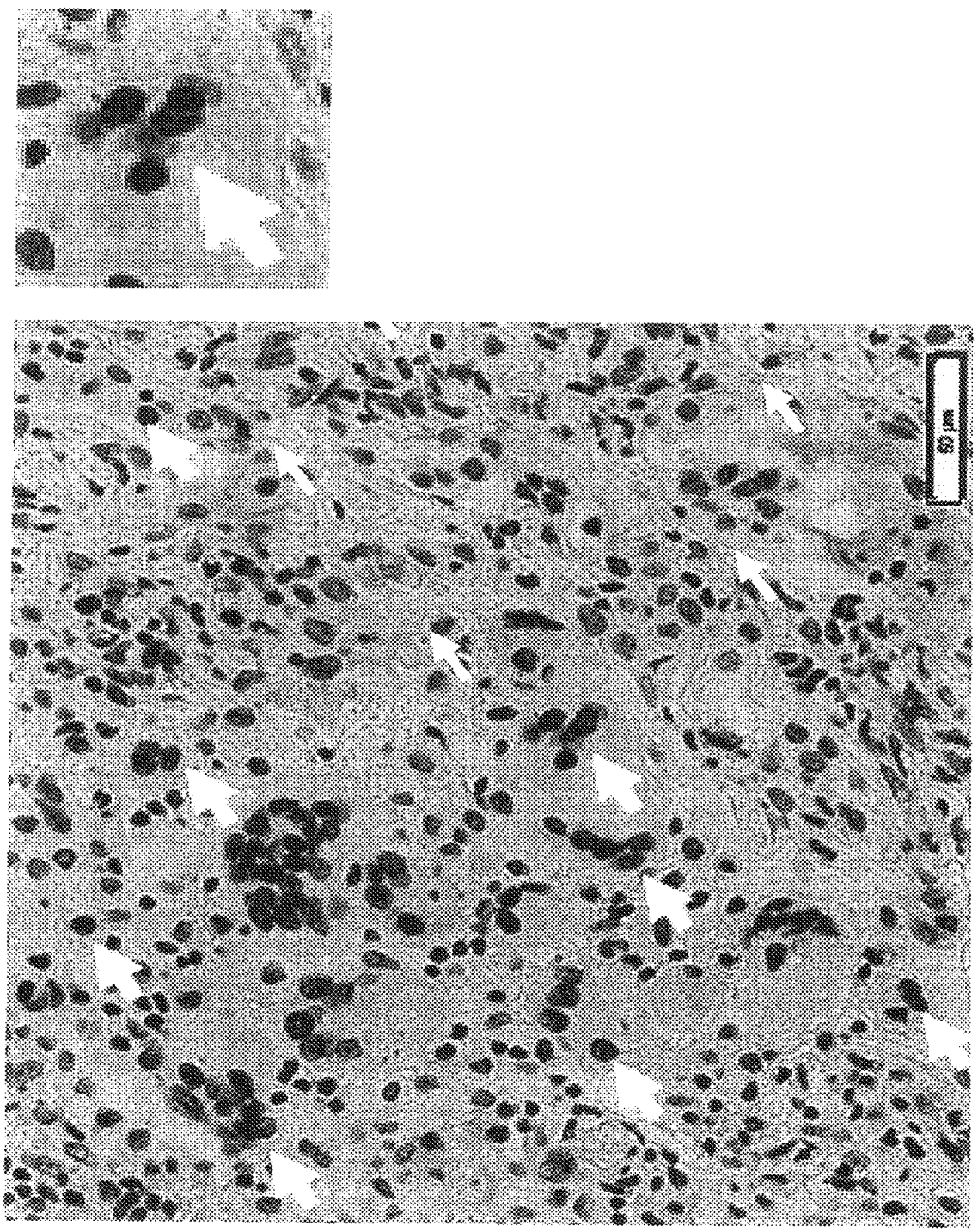
FIG. 15 Immunohistochemical detection of ERCC1 in FFPE embedded human cancer tissue of SCLC cancer sample. White arrows indicate cells with elevated ERCC1 level appearing in darker color.
Figure 16:
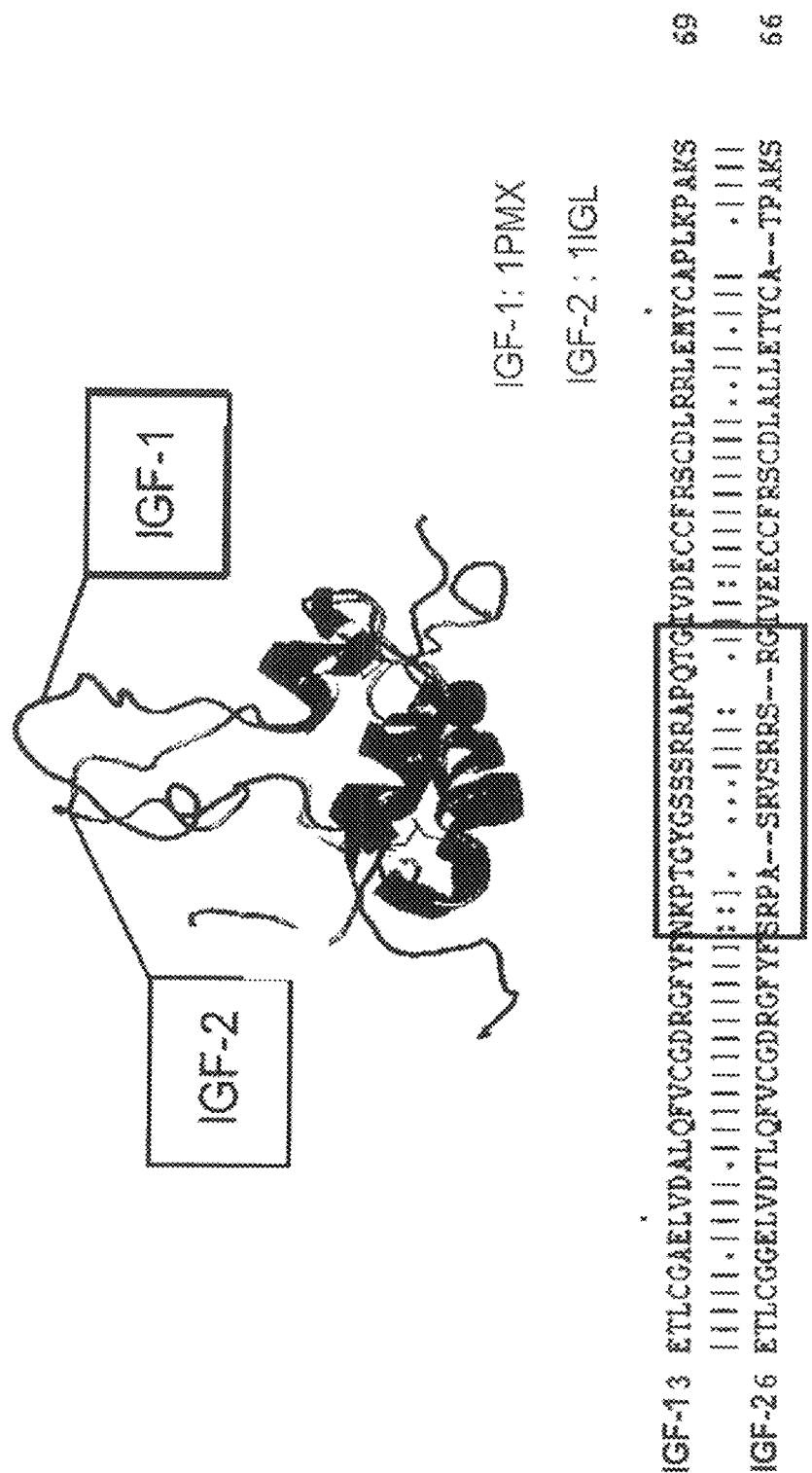
FIG. 16 Superimposition of IGF-1 (PDB:1PMX) and IGF-2 (PDB:1IGL) PyMOL 1.4. Sequence alignment (clustalW) of IGF-1 and IGF-2 (SEQ ID NOS 141 and 142, respectively). Black box denotes IGF-1(74-90) and IGF-2 (53-65) hairpin sequence.
Figure 17:
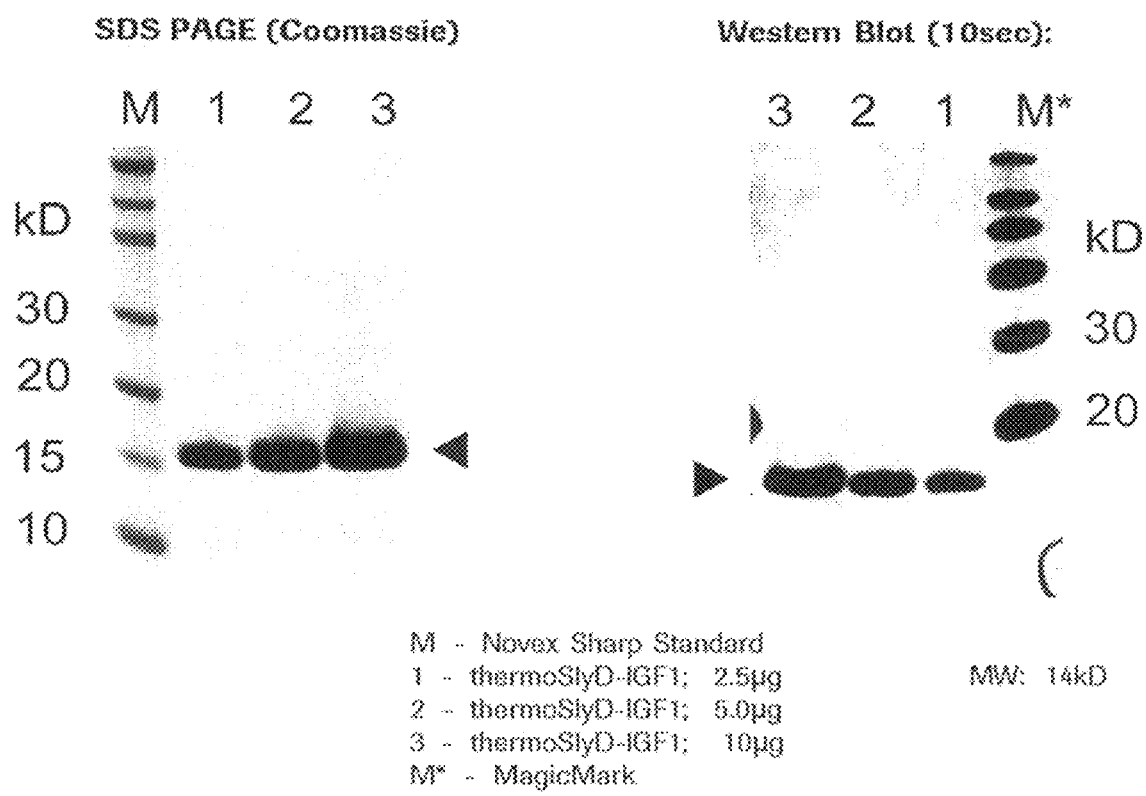
FIG. 17 SDS PAGE (Coomassie staining) and anti-his-tag Western Blot (10 sec exposition) of *Thermus thermophilus* SlyD-IGF-1(74-90) fusion polypeptide. M—Novex Sharp Standard; 1—2.5 µg *Thermus thermophilus* SlyD-IGF-1(74-90) fusion polypeptide; 2—5.0 µg *Thermus thermophilus* SlyD-IGF-1(74-90) fusion polypeptide; 3—10 µg *Thermus thermophilus* SlyD-IGF-1(74-90) fusion polypeptide; M*—Magic Mark.

FIG. 15 shows the IHC detection of ERCC1 in FFPE human cancer tissue. For immunohistochemical detection 2 μm sections of SCLC cancer samples were prepared. All staining procedures were performed on the Ventana Benchmark XT automated IHC stainer using Ventana buffers and reagents according to the manufacturers standard operating instructions. The primary antibody (clone <ERCC1>M-5.1.35) was used at a concentration of 5 pg/ml. The primary antibody was incubated on the sections for 32 min at 37° C. The primary antibody was detected using the Ventana iView™ detection kit as recommended by the manufacturer. The white arrows indicate cells with elevated ERCC1 level, appearing in darker color.

Summary

In contrast to the small molecular weight ERCC1 peptide (2 kDa) the scaffold as used herein is a high molecular weight analyte (36 kDa), which amplifies the signals in a SPR-based kinetic screening approach.

A peptide based screening reagent bears the risk of selecting antibodies recognizing the peptide's termini, which is completely avoided by using the scaffold approach as reported herein, in which the peptide is embedded in an N-terminal and C-terminal polypeptide context. Despite offering a plurality of meta-stable peptide insertions the scaffold fusion polypeptide as a whole is stable, soluble and monomeric. 1:1 Langmuir kinetics can be easily measured by means of biosensorics.

Using the fusion polypeptide in this set up, it is well suited to simulate the FFPE IHC situation and therefore is a well suited screening reagent for the development of IHC suited antibodies.

Without being bound by theory the fusion polypeptide comprises a folded SlyD derived part and an unfolded or partially unfolded human FKBP12 derived part, which offers at least its single core Trp residue for solvent contact, like it is shown for SlyD/FKBP12-ERCC1. SlyD folds reversible and shows thermal stability sufficient for technical applications.

The SlyD/FKBP-12 scaffold is a suitable platform for mimicking a plurality of peptidic secondary structure motives like those present in a paraffin-embedded, formalin-fixed tissue in immune histochemical experiments (see Abe, et al. (2003) supra).

The fusion polypeptide is especially suited as immunogen compared to the full length polypeptide from which the inserted (immunogenic) amino acid sequence is derived, e.g. with respect to solubility, reversible folding (naturation/denaturation), and the absence of disulfide bonds to be correctly formed. The fusion polypeptide as reported herein provides the scaffold into which the immunogenic amino acid sequence is inserted. It stabilizes the structure of the inserted immunogenic amino acid sequence (without being bound by theory by reducing the conformational entropy). Without being bound by theory it is assumed that the N-terminal SlyD fusion polypeptide keeps the complete chimeric fusion polypeptide in a soluble and thermodynamically stable but partly unfolded form.

Rebuzzini, G. (PhD work at the University of Milano-Bicocca (Italy) (2009)) reports a study of the hepatitis C virus NS3 helicase domain for application in a chemiluminescent immunoassay. In his work Rebuzzini reports that chimeric FKBP12 used as an immunogen for the presentation of the NS3 helicase domain with the insertion sequences according to Knappe, T. A., et al. (J. Mol. Biol. 368 (2007) 1458-1468) is thermodynamically instable. This correlates to our findings, that the chimeric FKBP12 moiety in the SlyD-FKBP12-antigen fusion polypeptide is partially or completely unfolded. In contrast to Rebuzzini's findings the SlyD/FKBP12-antigen fusion polypeptide has been found herein to be monomeric and stable.

Example 11

Production of IGF-1(74-90) Specific Antibodies

Antigen specific antibodies were obtained by immunization of mice with chimeric *Thermus Thermophilus*-SlyD-antigen fusion polypeptide. A plurality of epitopes can be targeted on the scaffold's surface, from which the antibodies binding to the target antigen can be identified by differential screening versus the wild-type *Thermus Thermophilus*-SlyD as a negative control, or versus the native recombinant antigen (IGF-1) as a positive control. In the following an example demonstrates the properties of archaic SlyD derivatives compared to the potentially metastable human FKBP12. *Thermus Thermophilus*-SlyD allows the presentation of enthalpic, rigid and stable structures and therefore is suitable for the development of monoclonal antibodies versus native protein structures.

Production of *Thermus thermophilus* SlyD Fusion Polypeptides

Guanidinium hydrochloride (GdmCl) (A-grade) was purchased from NIGU (Waldkraiburg, Germany). Complete® EDTA-free protease inhibitor tablets, imidazole and EDTA were from Roche Diagnostics GmbH (Mannheim, Germany), all other chemicals were analytical grade from Merck (Darmstadt, Germany). Ultrafiltration membranes (YM10, YM30) were purchased from Amicon (Danvers, Mass., USA), microdialysis membranes (VS/0.025 µm) and ultrafiltration units (Biomax ultrafree filter devices) were from Millipore (Bedford, Mass., USA). Cellulose nitrate and cellulose acetate membranes (1.2 µm, 0.45 µm and 0.2 µm pore size) for the filtration of crude lysates were from Sartorius (Goettingen, Germany).

Cloning of Expression Cassettes

The sequence of the SlyD polypeptide from *Thermus thermophilus* was retrieved from the SwissProt database (acc. no. Q72H58). The sequence of the SlyD polypeptide from *Thermococcus gammatolerans* was retrieved from the Prosite database (acc. no. C5A738). Synthetic genes encoding *Thermus thermophilus* SlyD, *Thermus thermophilus* SlyD-IGF-1(74-90), and *Thermus thermophilus* SlyD-ΔIF were purchased from Sloning Biotechnology GmbH (Germany) and were cloned into a pQE80L expression vector. The codon usage was optimized for expression in *E. coli* host cells. Synthetic genes encoding *Thermococcus gammatolerans* SlyD, *Thermococcus gammatolerans* SlyD-IGF-2 (53-65), *Thermus thermophilus* SlyD-antigen and *Thermococcus gammatolerans* SlyD-antigen were purchased from Geneart (Germany) and were cloned into pET24 expression vectors (Novagen, Madison, Wis., USA). The codon usage was optimized for expression in *E. coli* host cells.

Additionally, a GS-linker (GGGS, SEQ ID NO: 81) and a His-tag were fused to the carboxy terminal end in order to allow an affinity purification of the fusion polypeptides by an immobilized metal ion exchange chromatography.

In order to generate monoclonal antibodies specifically binding to the IGF-1-fragment 74-90 (amino acid sequence NKPTGYGSSSRRAPQTG, SEQ ID NO: 92) the respective peptide amino acid sequences was fused into the molecular chaperone SlyD derived from *Thermus thermophilus* by deleting amino acids 68-120 of the original protein. Due to an angle adaption of the IGF-1 insert, the Asp at position 70 and the Leu at position 88 were substituted by a Gly (D70G and L88G). Thus the fusion polypeptide has the amino acid sequence:

(SEQ ID NO: 101)
MRGSKVGQDKVVTIRYTLQVEGEVLDQGELSYLHGHRNLIPGLEEALEGR

EEGEAFQAHVPAEKAYGPHGNKPTGYGSSSRRAPQTGGAGKDLDFQVEV

VKVREATPEELLHGHAHGGGSRKHHHHHHHH.

As a control, the native wild-type SlyD from *Thermus thermophilus* was used:

(SEQ ID NO: 139)
MKVGQDKVVTIRYTLQVEGEVLDQGELSYLHGHRNLIPGLEEALEGREEG

EAFQAHVPAEKAYGPHDPEGVQVVPLSAFPEDAEVVPGAQFYAQDMEGN

PMPLTVVAVEGEEVTVDFNHPLAGKDLDFQVEVVKVREATPEELLHGHA

HGGGSRKHHHHHH.

For Screening and specificity testing a *Thermus thermophilus* SlyD-ΔIF fusion polypeptide was produced. *Thermus thermophilus* SlyD-ΔIF fusion polypeptide lacks the IF domain, which was replaced by the amino acid sequence motif AGSGSS (SEQ ID NO: 140), and comprises a C-terminal amino acid sequence tag of SEQ ID NO: 16:

(SEQ ID NO: 120)
MRGSKVGQDKVVTIRYTLQVEGEVLDQGELSYLHGHRNLIPGLEEALEGR

EEGEAFQAHVPAEKAYGPHGAGSGSSGAGKDLDFQVEVVKVREATPEELL

HGHAHGGGSRKHHHHHHHH.

As a control the native SlyD from *Thermococcus gammatolerans* comprising a C-terminal amino acid sequence tag of SEQ ID NO: 16 was used:

(SEQ ID NO: 121)
MKVERGDFVLFNYVGRYENGEVFDTSYESVAREQGIFVEEREYSPIGVT

VGAGEIIPGIEEALLGMELGEKKEVVVPPEKGYGMPREDLIVPVPIEQF

TSAGLEPVEGMYVMTDAGIAKILKVEEKTVRLDFNHPLAGKTAIFEIEV

VEIKKAGEAGGGSRKHHHHHH.

As a control for cross reactivity the structurally homologous hairpin sequence from human IGF-2(53-65) was inserted into *Thermococcus gammatolerans* SlyD, which was fused with a GS-linker and a hexahistidine-tag (SEQ ID NO: 64) at the C-terminus:

(SEQ ID NO: 122)
MKVERGDFVLFNYVGRYENGEVFDTSYESVAREQGIFVEEREYSPIGVT

VGAGEIIPGIEEALLGMELGEKKEVVVPPEKGYGMP-G-SRVSRRSRG-

G-AGKTAIFEIEVVEIKKAGEAGGGSRKHHHHHH.

Expression, Purification and Refolding of Fusion Polypeptides

All SlyD polypeptides can be purified and refolded by using almost identical protocols. *E. coli* BL21 (DE3) cells harboring the particular expression plasmid were grown at 37° C. in LB medium containing the respective antibiotic for selective growth (Kanamycin 30 µg/ml, or Ampicillin (100 µg/ml)) to an OD600 of 1.5, and cytosolic overexpression was induced by adding 1 mM isopropyl-ß-D-thiogalactoside (IPTG). Three hours after induction, cells were harvested by centrifugation (20 min at 5,000 g), frozen and stored at −20° C. For cell lysis, the frozen pellet was resuspended in chilled 50 mM sodium phosphate buffer (pH 8.0) supplemented with 7 M GdmCl and 5 mM imidazole. Thereafter the suspension was stirred for 2-10 hours on ice to complete cell lysis. After centrifugation (25,000 g, 1 h) and filtration (cellulose nitrate membrane, 8.0 µm, 1.2 µm, 0.2 µm), the lysate was applied onto a Ni-NTA column equilibrated with the lysis buffer. In the subsequent washing step the imidazole concentration was raised to 10 mM (in 50 mM sodium phosphate buffer (pH 8.0) comprising 7 M GdmCl, 5.0 mM TCEP) and 5 mM TCEP was added in order to keep the thiol moieties in a reduced form and to prevent premature disulfide bridging. At least 15 to 20 volumes of the reducing washing buffer were applied. Thereafter, the GdmCl solution was replaced by 50 mM sodium phosphate buffer (pH 8.0) comprising 100 mM NaCl, 10 mM imidazole, and 5 mM TCEP to induce conformational refolding of the matrix-bound SlyD fusion polypeptide. In order to avoid reactivation of co-purifying proteases, a protease inhibitor cocktail (Complete® EDTA-free, Roche) was added to the refolding buffer. A total of 15 to 20 column volumes of refolding buffer were applied in an overnight procedure. Thereafter, both TCEP and the Complete® EDTA-free inhibitor cocktail were removed by washing with 10 column volumes 50 mM sodium phosphate buffer (pH 8.0) comprising 100 mM NaCl and 10 mM imidazole. In the last washing step, the imidazole concentration was raised to 30 mM (10 column volumes) in order to remove tenacious contaminants. The native polypeptide was eluted by applying 250 mM imidazole in the same buffer. Protein-containing fractions were assessed for purity by Tricine-SDS-PAGE (Schaegger, H. and von Jagow, G., Anal. Biochem. 166 (1987) 368-379) and pooled. Subsequently, the protein was subjected to size-exclusion-chromatography (Superdex™ HiLoad, Amersham Pharmacia) using potassium phosphate as the buffer system (50 mM potassium phosphate buffer (pH 7.0), 100 mM KCl, 0.5 mM EDTA). Finally, the protein-containing fractions were pooled and concentrated in an Amicon cell (YM10) to a concentration of ~5 mg/ml.

UV Spectroscopic Measurements

Protein concentration measurements were performed with an UVIKON XL double-beam spectrophotometer. The molar extinction coefficients (ε280) for the SlyD variants were calculated according to Pace (Pace, C. N., et al., Protein Sci. 4 (1995) 2411-2423).

CD Spectroscopic Measurements

To examine whether the chimeric fusion proteins according to the invention adopt a folded conformation CD spectra in the near-UV region were measured. CD spectra were recorded and evaluated using A JASCO J-720 instrument and JASCO software according to the manufacturer's recommendations. A quartz cuvette with 0.2 cm pathlength was used. The instrument was set to 1° C. resolution, 1 nm band width, 5 mdeg sensitivity and accumulation mode 1. The sample buffer was 50 mM potassium phosphate pH 7.5, 100 mM NaCl, 1 mM EDTA. The protein analyte concentration for each analysis was 36 µM *Thermus thermophilus* SlyD wild-type, 23 µM *Thermus thermophilus* SlyD-ΔIF, 16 µM *Thermus thermophilus* SlyD-antigen, 19 µM *Thermococcus gammatolerans* SlyD wild-type, and 16 µM *Thermococcus gammatolerans* SlyD-antigen. CD signals between 250 nm and 330 nm with 0.5 nm resolution and 20 nm scan per minute were recorded at 20° C. In a subsequent experimental embodiment the CD signals were determined in temperature gradients (20° C.-100° C.) and (100° C.-20° C.) for *Thermococcus gammatolerans* SlyD derivatives, respectively (20° C.-85° C.) and (85° C.-20° C.) for *Thermus thermophilus* SlyD derivatives at 277 nm constant wavelength. The temperature gradient was driven at 1° C. per minute.

Figure 27:
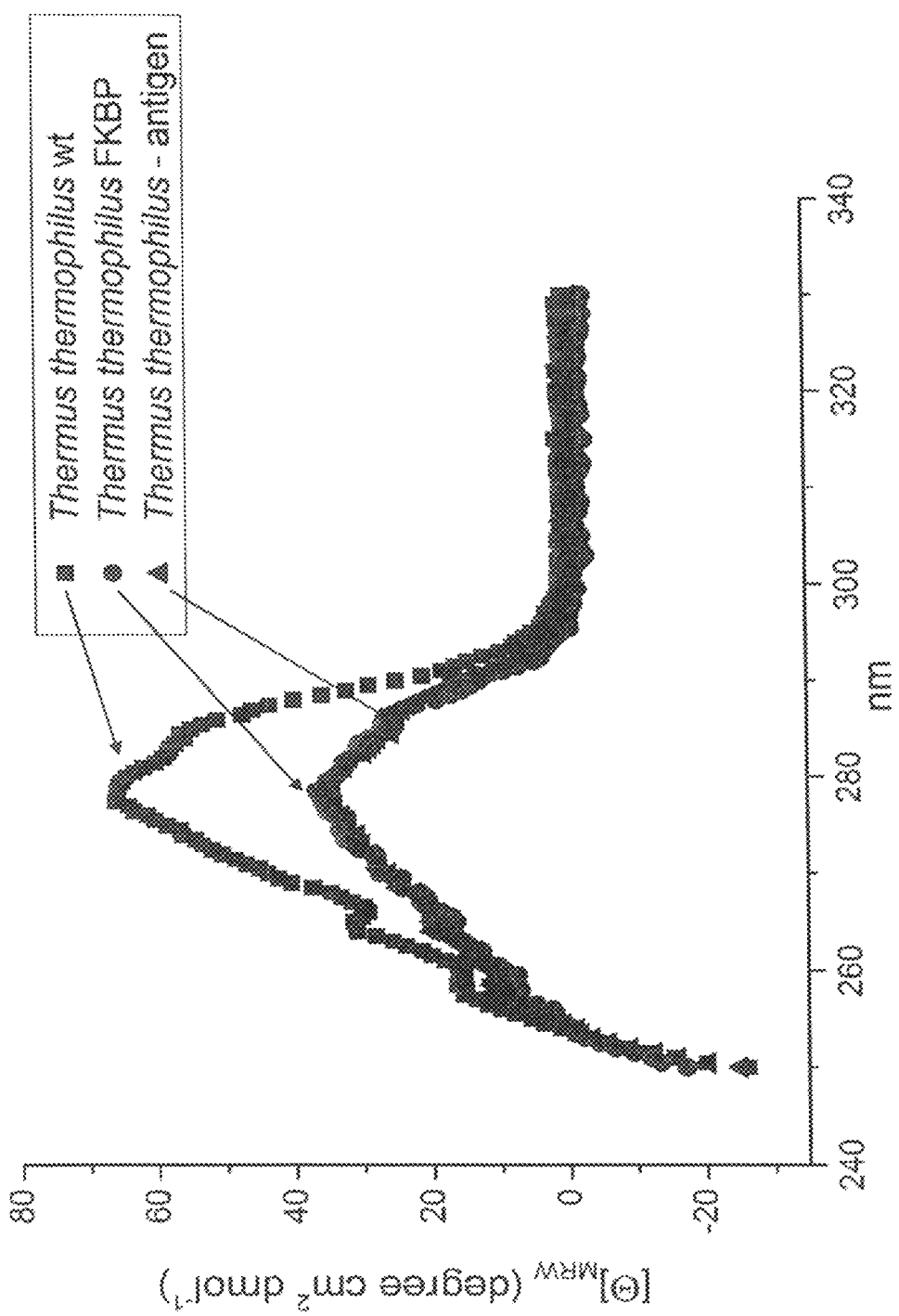
FIG. 27 Near UV CD spectra of *Thermus thermophilus* SlyD wild-type polypeptide, *Thermus thermophilus* SlyD-ΔIF fusion polypeptide (FKBP) and *Thermus thermophilus* SlyD-antigen fusion polypeptide. At 20° C. all polypeptides are folded in their native structure.

FIG. 27 shows an overlay plot of three CD spectra of the fusion polypeptides *Thermus thermophilus* SlyD wild-type, *Thermus thermophilus* SlyD-ΔIF and *Thermus thermophilus* SlyD-antigen. The CD signatures show that at 20° C. all fusion polypeptides are folded in their native structure, even when the IF Domain is missing or is being replaced by an amino acid graft.

Figure 28:
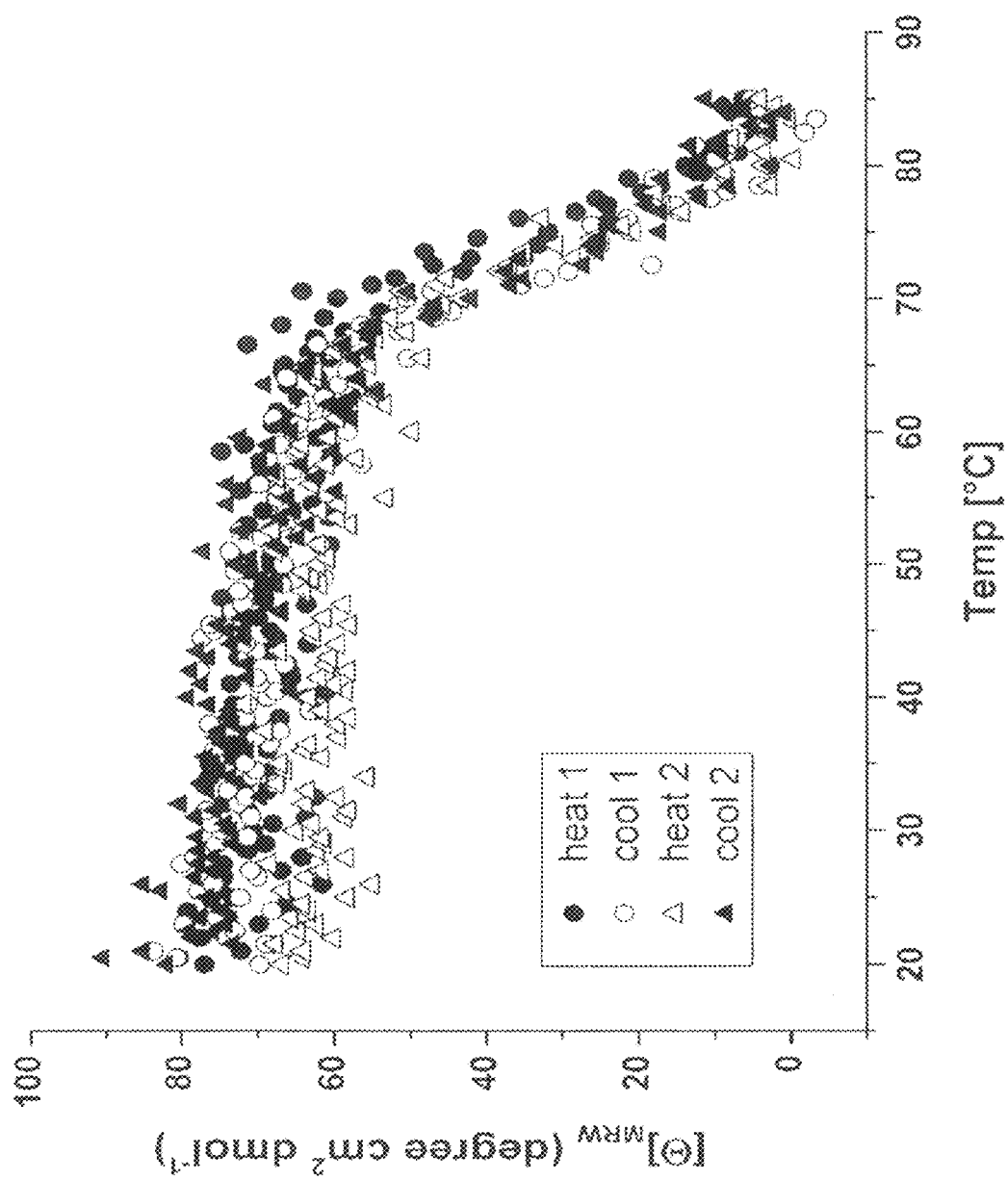
FIG. 28 Temperature-dependent CD spectra of the *Thermus thermophilus* SlyD-ΔIF fusion polypeptide. Repeated heating and cooling shows that the FKBP domain of *Thermus thermophilus* SlyD reversibly folds. *Thermus thermophilus* SlyD-ΔIF fusion polypeptide is stable up to 65° C. and unfolded at 85° C.

FIG. 28 shows a temperature-dependent near UV CD spectra of the fusion polypeptide *Thermus thermophilus* SlyD-antigen in the temperature gradient 20° C. to 85° C. *Thermus thermophilus* SlyD-antigen reversibly unfolds and refolds.

Figure 29:
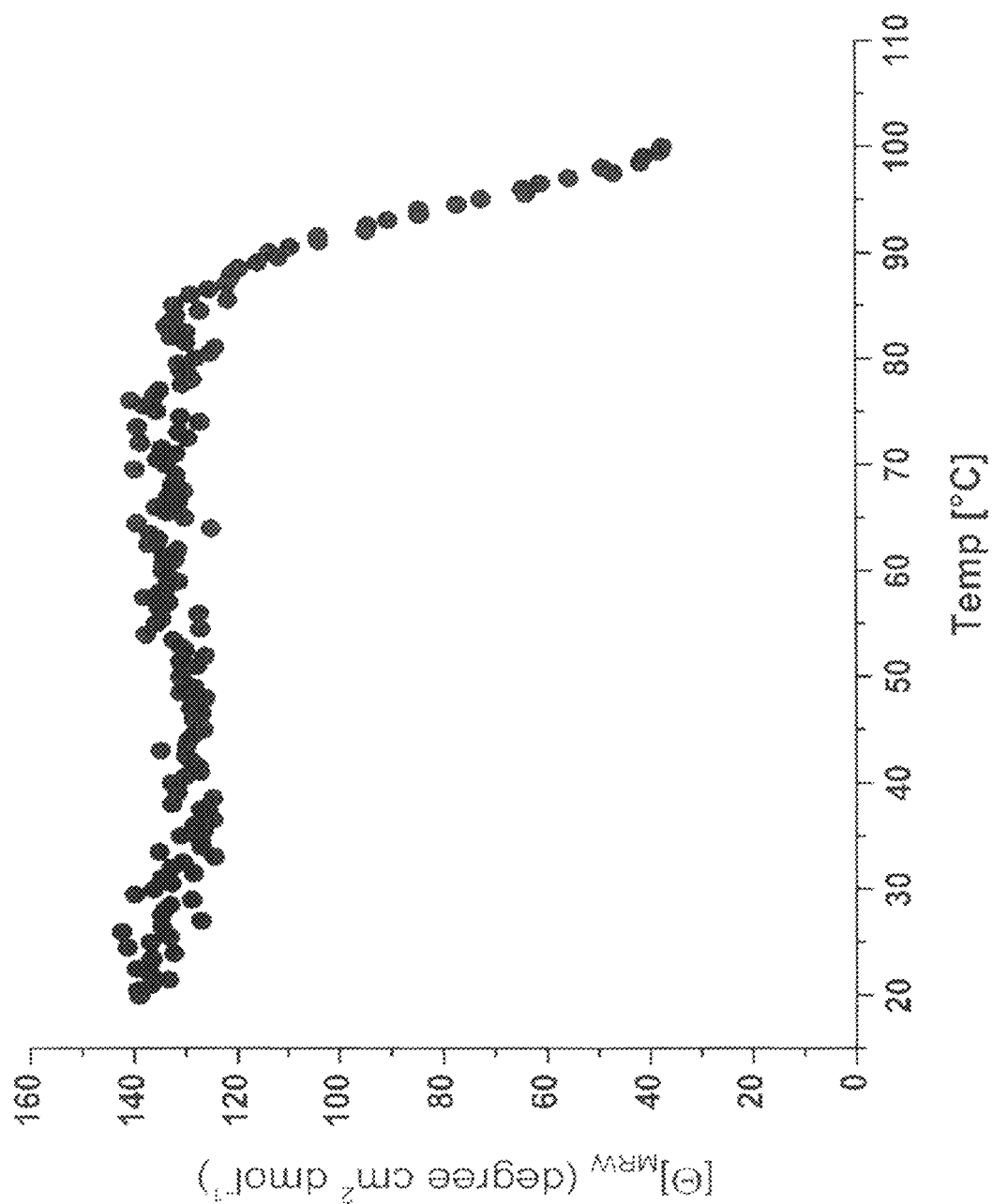
FIG. 29 Temperature-dependent CD spectra of the *Thermococcus gammatolerans* SlyD-antigen fusion polypeptide. At 100° C. no lower signal plateau was reached, indicating that the fusion polypeptide is not yet completely unfolded. Up to 80° C. the fusion polypeptide is stable and folded.
Figure 30:
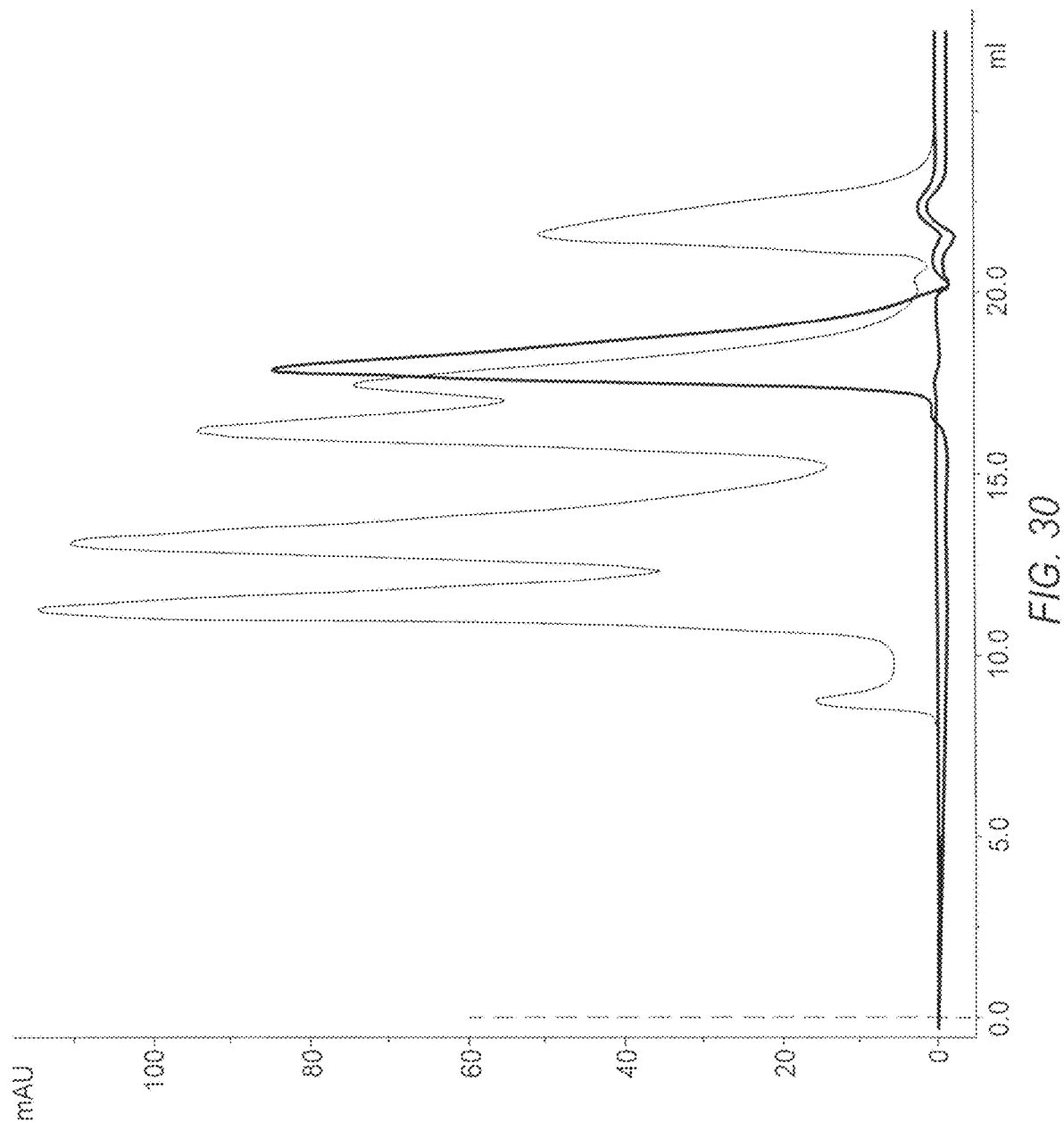
FIG. 30 The monomeric *Thermococcus gammatolerans* SlyD-antigen fusion polypeptide comprising fraction was rechromatographed after repeated freezing and thawing cycles and a temperature stress test. 280 nm SUX 200 profile of 300 µg Ni-NTA elution fraction of *Thermococcus gammatolerans* SlyD-antigen fusion polypeptide in 100 µl 50 mM $K_2HPO_4/KH_2PO_4$, pH 7.0, 100 mM KCl, 0.5 mM EDTA at 0.75 ml/min.
Figure 31:
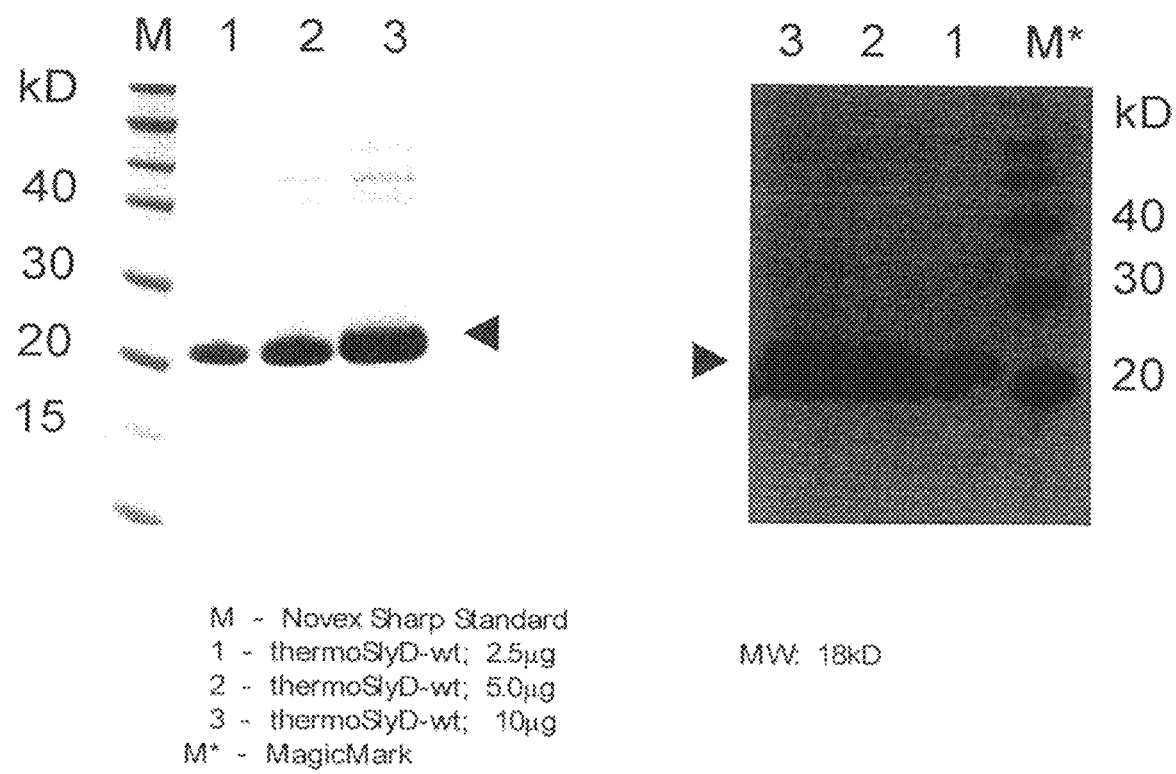
FIG. 31 SDS PAGE (Coomassie staining) and Western Blot (10 sec incubation with anti-octa-his-tag antibody) ("octa-his" disclosed as SEQ ID NO: 137) of the *Thermus thermophilus* SlyD-wild-type polypeptide.
Figure 34:
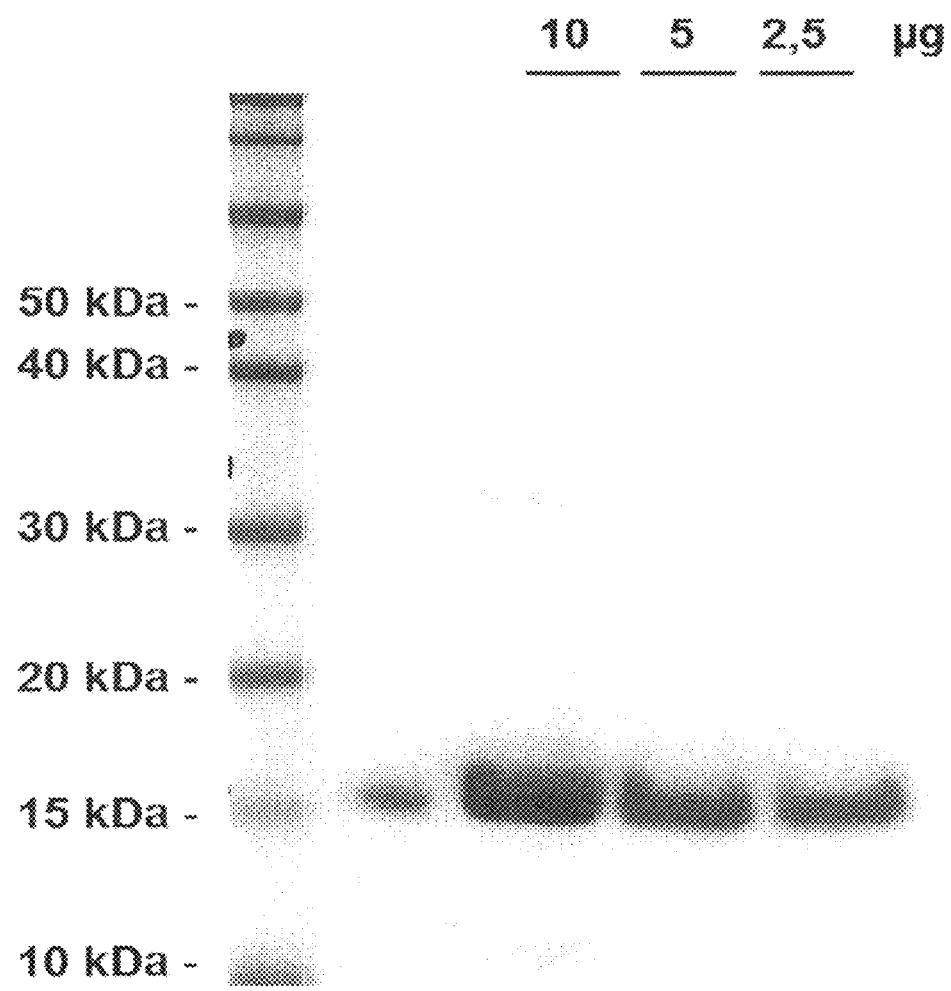
FIG. 34 SDS PAGE (Coomassie staining) of the FKBP12/13 fusion polypeptide expressed in *E. coli*.
Figure 35:
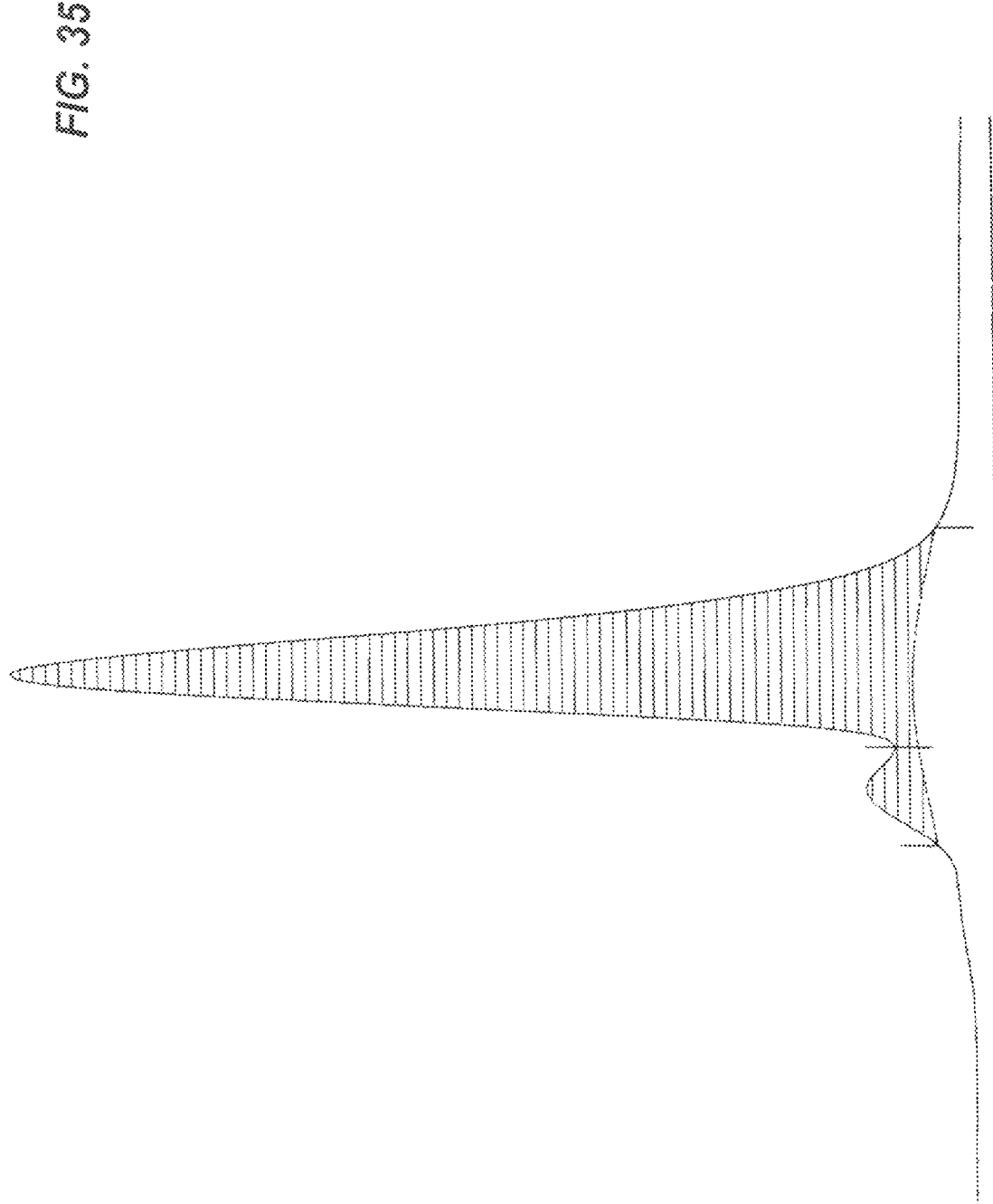
FIG. 35 FKBP12/13 fusion polypeptide: HPLC SEC-elution profile of Ni-NTA purified material. FKBP12/13 fusion polypeptide is mostly monomeric.

Under the given physical conditions no complete unfolding of *Thermococcus gammatolerans* SlyD-antigen could be achieved even at 100° C. (see FIG. 29). The extraordinary stability of archaic FKBP domains enables the grafting of polypeptides by replacement of their IF domains where at the same time the overall stability of the newly generated chimeric scaffold protein is kept up.

Immunization of Mice with *Thermus thermophilus* SlyD-IGF-1(74-90) and Development of Monoclonal Antibodies Versus IGF-1

8-12 weeks old Balb/c and NMRI mice were subjected to repeated intraperitoneal immunizations with 100 µg of *Thermus Thermophilus* SlyD-IGF-1(74-90). The mice were immunized three times, at the time points of 6 weeks and 10 weeks after the initial immunization. The first immunization can be performed using complete Freud's adjuvant, the second and third immunizations were done using incomplete Freud's adjuvant. The mice serum titers versus native recombinant IGF-1 and *Thermus Thermophilus* SlyD-IGF-1(74-90) were tested after 12 weeks by ELISA methods as described in the following. After 12 weeks serum titers were analyzed using ELISA. The ELISA was driven by a Tecan Sunrise running under Firmware: V 3.15 19/03/01; XREAD PLUS Version: V 4.20. Nunc Maxisorb F multi well plates were coated with *Thermus Thermophilus* SlyD-IGF-1(74-90) by applying a solution comprising 0.5 µg polypeptide per ml. The isolated antigen IGF-1 was immobilized in the wells of StreptaWell High Bind SA multi well plates by applying a solution comprising 90 ng/ml biotinylated IGF-1. Thereafter free binding sites were blocked by applying a solution comprising 1% RPLA in PBS for one hour at room temperature. The wells were washed three times with a solution comprising 0.9% (w/v) sodium chloride and 0.05% (w/v) Tween. As samples the mouse serum diluted 1:50 with PBS was used. Optional further dilution was performed in 1:4 steps until a final dilution of 1:819,200. The incubation time was one hour at room temperature. The wells were washed three times with a solution comprising 0.9% (w/v) sodium chloride and 0.05% (w/v) Tween. As detection antibody a polyclonal antibody against the constant domain of the target antibodies conjugated to a peroxidase was used (PAK<M-Fcγ>S-F(ab')$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) Tween. Afterwards the wells were incubated with an ABTS solution for 15 minutes at room temperature. The intensity of the developed color was determined photometrically. FIG. 20 shows mice serum titers obtained.

Three days before preparation of spleen cells and fusion with a myeloma cell line, the final booster immunization was performed by i.v. injection of 100 µg of *Thermus Thermophilus* SlyD-IGF-1(74-90) fusion polypeptide. The production of hybridoma primary cultures can be done according to the procedure of Koehler and Milstein (Koehler, G. and Milstein, C., Nature. 256 (1975) 495-497).

ELISA Screening

Primary culture supernatants were tested by ELISA for reactivity against the immunogen *Thermus Thermophilus* SlyD-IGF-1(74-90), biotinylated native IGF-1 and wild-type *Thermus Thermophilus* SlyD respective a blank plate. Elisa was driven with a Tecan SUNRISE, Firmware: V 3.15 19/03/01; XREAD PLUS Version: V 4.20. Nunc Maxisorb F multi well ELISA plates were coated with 5 µg/ml SlyD-fusion polypeptides. StreptaWell High Bind SA multi well plates were coated with 125 ng/ml recombinant biotinylated IGF-1 antigen. Thereafter free binding sites were blocked by 1% RPLA in PBS for one hour at room temperature. The wells were washed three times with a solution comprising 0.9% (w/v) sodium chloride and 0.05% (w/v) Tween. Undiluted hybridoma supernatants in RPMI 1640 medium were used as samples. The incubation time was one hour at room temperature. The wells were washed three times with a solution comprising 0.9% (w/v) sodium chloride and 0.05% (w/v) Tween. As detection antibody a polyclonal antibody against the constant domain of the target antibodies conjugated to a peroxidase was used (PAK<M-Fcγ>S-F(ab')$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) Tween. Afterwards the wells were incubated with an ABTS solution for 15 minutes at room temperature. The intensity of the developed color was determined photometrically at t 405 nm. The reference wavelength was 492 nm. Primary hybridoma supernatants, showing fast and strong color formation in ELISA upon binding to recombinant IGF-1, *Thermus Thermophilus* SlyD-IGF-1(74-90) and less binding to *Thermus Thermophilus* SlyD were transferred into the kinetic screening process as described in the following.

SPR-Based Kinetic Screening

*Thermus Thermophilus* SlyD-IGF-1(74-90), native recombinant IGF-1, native recombinant IGF-2, wild-type *Thermus Thermophilus* SlyD, and *Thermus Thermophilus*-SlyD-IGF-1(74-90) were used in an SPR-based kinetic screening analysis. For SPR analyses it is generally accepted to use monomeric and monovalent analytes in solution to determine the antibody binding kinetics according to a Langmuir model. Furthermore, it is rather advantageous for SPR measurements to use an analyte with higher molecular weight to increase the sensitivity of the measurements, since SPR is a mass sensitive analysis.

The kinetic screening was performed on a BIAcore A100 instrument under control of the software version V1.1. A BIAcore CMS chip was mounted into the instrument and was hydrodynamically addressed conditioned according to the manufacturer's instructions. As a running buffer an HBS-EP buffer was used (10 mM HEPES (pH 7.4), 150 mM NaCl, 1 mM EDTA, 0.05% (w/v) P20). A polyclonal rabbit anti-mouse IgG Fc capture antibody is immobilized at 30 µg/ml in 10 mM sodium acetate buffer (pH 4.5) to spots 1, 2, 4 and 5 in flow cells 1, 2, 3 and 4 at 10,000 RU (FIG. 23). The antibody is covalently immobilized via NHS/EDC chemistry. The sensor was deactivated thereafter with a 1 M ethanolamine solution. Spots 1 and 5 were used for the determination and spots 2 and 4 were used as reference. Prior to application to the sensor chip the hybridoma supernatants were diluted 1:2 in HBS-EP buffer. The diluted solution was applied at a flow rate of 30 µl/min for 1 min. Immediately thereafter the analyte, such as the *Thermus Thermophilus* SlyD-IGF-1(74-90), fusion polypeptide, is injected at a flow rate of 30 µl/min for 2 min. Thereafter the signal is recorded for 5 min. dissociation time. The sensor is regenerated by injecting a 10 mM glycine-HCl solution (pH 1.7) for 2 min. at a flow rate of 30 µl/min. Two report points, the recorded signal shortly before the end of the analyte injection, denoted as binding late (BL) and the recorded signal shortly before the end of the dissociation time, stability late (SL), were used to characterize the Kinetic Screening performance.

Furthermore, the dissociation rate constant kd (1/s) was calculated according to a Langmuir model and the antibody/antigen complex half-life can be calculated in minutes according to the formula ln(2)/(60*kd).

Antibodies were obtained by immunization with the antigen *Thermus Thermophilus* SlyD-IGF-1(74-90), and screening with *Thermus Thermophilus* SlyD-IGF-1(74-90), *Thermus Thermophilus* SlyD wild-type, native IGF-1 and native IGF-2. The scaffold-based screening approach allows to specifically develop antibodies binding to the predefined IGF-1 hairpin epitope.

The primary culture supernatants were further developed by limited dilution into clone culture supernatants by methods known. The clone culture supernatants were tested in a functional assay for affinity and specificity.

BIAcore Characterization of Antibody Producing Clone Culture Supernatants

A BIAcore T200 instrument (GE Healthcare) was used with a BIAcore CM5 sensor mounted into the system. The sensor was preconditioned by a 1 min. injection at 100 µl/min of 0.1% SDS, 50 mM NaOH, 10 mM HCl and 100 mM $H_3PO_4$.

The system buffer was PBS-DT (10 mM $Na_2HPO_4$, 0.1 mM $KH_2PO_4$, 2.7 mM KCl, 137 mM NaCl, 0.05% Tween® 20, 5% DMSO). The sample buffer was the system buffer.

The BIAcore T200 System was driven under the control software V1.1.1. Polyclonal rabbit IgG antibody <IgGFCγM>R (Jackson ImmunoResearch Laboratories Inc.) was immobilized at 30 µg/ml in 10 mM sodium acetate buffer (pH 4.5) at 6500 RU on the flow cells 1, 2, 3, and 4, respectively, via EDC/NHS chemistry according to the manufacturer's instructions. Finally, the sensor surface was blocked with a 1 M ethanolamine solution. The complete experiment was performed at 25° C.

The clone culture supernatants containing the respective antibodies at approx. 40 nM were captured for 2 min. at a flow rate of 5 µl/min on the <IgGFCγM>R surface. As analytes in solution the recombinant native IGF-1, recombinant native IGF-2, *Thermus thermophilus* SlyD-IGF-1(74-90), recombinant wild-type *Thermus thermophilus* SlyD, recombinant *Thermus thermophilus* SlyD-ΔIF, recombinant wild-type *Thermococcus gammatolerans* SlyD, recombinant *Thermococcus gammatolerans* SlyD-IGF-2 (53-65) fusion polypeptides were used. *Thermus thermophilus* SlyD-ΔIF is solely the FKBP domain of *Thermus thermophilus* SlyD lacking the IF domain. *Thermococcus gammatolerans* SlyD-IGF-2(53-65) was used to counterscreen and investigate the specificity for the IGF-1 hairpin in contrast to the IGF-2 hairpin insertion. The respective analytes were injected at different concentration steps from 90 nM, 30 nM, 10 nM, 3.3 nM, 1.1 nM and 0 nM. The association phase was monitored for 3 min. at a flow rate of 100 µl/min. The dissociation was monitored for 10 min. at a flow rate of 100 µl/min. The system was regenerated using a 10 mM glycine buffer (pH 1.7). Kinetics were evaluated using the BIAcore Evaluation Software.

The following terms are used herein: mAb: monoclonal antibody; RU: Relative response unit of monoclonal antibody captured on the sensor; Antigen: antigen in solution; kDa: molecular weight of the antigens injected as analytes in solution; ka: association rate constant; kd: dissociation rate constant; t½ diss: antibody-antigen complex half-life calculated according to the formula t½ diss=ln(2)/60*kd; KD: dissociation constant; $R_{MAX}$: Binding signal at the end of the association phase of the 90 nM analyte injection; MR: Molar Ratio; Chi²: failure of the measurement; n.d.: not detectable.

FIG. 25 shows, that the scaffold-derived monoclonal antibodies M-11.11.17 and M-10.7.9 have been developed with picomolar affinity versus IGF-1. No cross-reactivity versus IGF-2, nor versus wild-type *Thermus thermophilus* SlyD, nor versus wild-type *Thermococcus gammatolerans* SlyD, nor versus *Thermus thermophilus* SlyD-ΔIF fusion polypeptide, nor versus *Thermococcus gammatolerans* SlyD-IGF-2(53-65) fusion polypeptide was detectable.

M-2.28.44 is a monoclonal antibody obtained by conventional immunization of mice with recombinant human IGF-1. Despite the fact that the antibody shows a 30 pM affinity versus IGF-1, a 500 pM cross reactivity can be detected versus IGF-2. Using *Thermus thermophilus* SlyD-IGF-1(74-90) and *Thermococcus gammatolerans* SlyD-IGF-2 (53-65) as analyte it can be seen that the cross-reacting IGF-2 epitope is not the IGF hairpin region.

Example 12

Generation of Anti-PLGF Antibodies

Mice were immunized with an immunogen containing the sequence of PLGF(60-76). Subsequently hybridomas were produced and ELISA and Kinetic Screening were performed (for detailed general procedure see Examples 10 and 11).

In the Kinetic Screening process, SlyD/FKBP12-PLGF and a biotinylated peptide PLGF(60-76)-bi, which was singly grafted on streptavidin were used to identify primary culture supernatants with binding activity versus PLGF(60-76). Both analytes produced 1:1 Langmuir kinetics, but the scaffold showed a better dissociation fit with a lower chi2 value, than the SA-probe grafted bi-peptide. Without being bound by theory, a scaffold-based screening approach takes advantage of the monomeric state and the improved epitope accessibility of the scaffold, when compared to the carefully prepared SA-probe.

Antibodies, developed by this approach, like clone 53.4.1 were able to specifically detect PLGF in Western blotting.

Example 13

Anti-IGF-1 Antibodies Produced with SlyD-FKBP12-IGF-1(74-90)

Figure 2A:
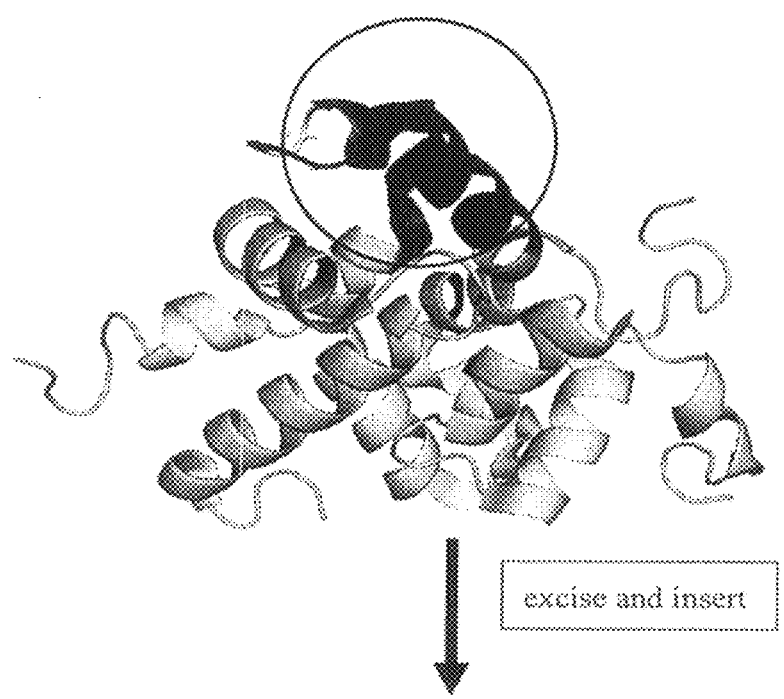
FIGS. 2A-B ERCC1 (PDB 1Z00): encircled helix turn helix motif (IAASREDLALSPGLGPQKARRLFD (SEQ ID NO: 89), C274S) (FIG. 2A); FKBP12 C22A; encircled sequence replaced; FKBP12 chimera C-terminally was fused to *E. coli* SlyD (FIG. 2B).
Figure 2B:
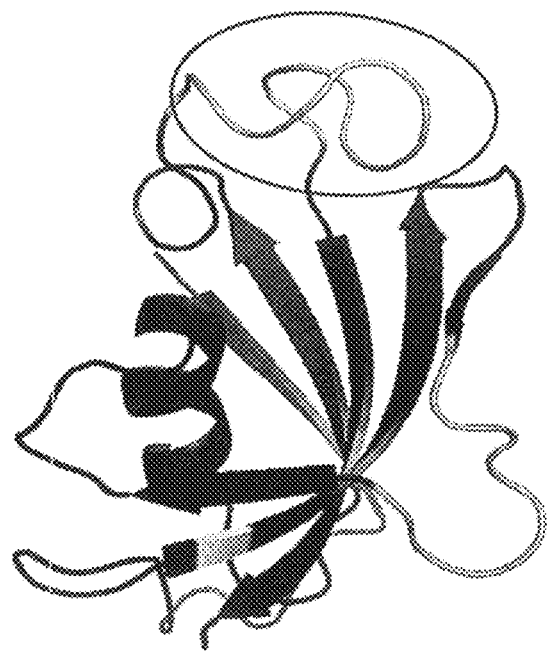

SlyD/FKBP12-IGF-1(74-90) (see FIGS. 2A-B and 8) and SlyD/FKBP12-ctrl (see FIG. 7) fusion polypeptides were produced in *E. coli* (pQE80L vector/*E. coli* BL21 Codon-Plus-RP cell line) according to known methods. 8-12 weeks old Balb/c and NMRI mice were subjected to repeated intraperitoneal immunizations with 100 µg of SlyD/FKBP12-IGF-1(74-90).

After 10 weeks the serum titers were analyzed using ELISA. Nunc Maxisorb F multi well plates were coated with SlyD/FKBP12-IGF-1(74-90) by applying a solution comprising 0.41 µg polypeptide per ml. The isolated antigen IGF-1 was immobilized in the wells of StreptaWell High Bind SA multi well plates by applying a solution comprising 90 ng/ml biotinylated IGF-1. Thereafter free binding sites were blocked by applying a solution comprising 1% RPLA in PBS for one hour at room temperature. The wells were washed three times with a solution comprising 0.9% (w/v) sodium chloride and 0.05% (w/v) Tween. As samples the mouse serum diluted 1:50 with PBS were used. Optional further dilution was performed in 1:4 steps until a final dilution of 1:819,200. The incubation time was one hour at room temperature. The wells were washed three times with a solution comprising 0.9% (w/v) sodium chloride and 0.05% (w/v) Tween. As detection antibody a polyclonal antibody against the constant domain of the target antibodies conjugated to a peroxidase was used (PAK<M-Fcγ>S-F(ab')$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) Tween. Afterwards the wells were incubated with an ABTS solution for 15 minutes at room temperature. The intensity of the developed color was determined photometrically. FIG. 19 shows mice serum titers obtained. Lower titers where obtained with SlyD/FKBP12-IGF-1(74-90), when compared to the immunization with *Thermus thermophilus* SlyD-IGF-1(74-90) (FIG. 20). Further antibody development was done like described under example 12. Finally no antibodies with binding versus IGF-1 could be selected in a BIAcore kinetic screening approach as already described.

Example 14

Antibodies Produced with FKBP12/13 Fusion Polypeptide

The fusion polypeptide as reported herein and used in this examples comprises a part derived from human FKBP12 and a part derived from *Arabidopsis thaliana* FKBP13. A fusion polypeptide consisting of at least one amino acid sequence from human FKBP12 and at least one amino acid sequences from *Arabidopsis thaliana* FKBP13 can thermodynamically stabilize human FKBP12 as a scaffold and circumvents the N-terminal fusion of FKBP12 with *E. coli* SlyD. In nature, FKBP13 contains a disulfide bond. This FKBP13 sequence was grafted into FKBP12 in order to stabilize the chimeric polypeptide for further sequence grafting approaches.

The chimeric FKBP12/13 fusion polypeptide comprising a C-terminal amino acid sequence tag of SEQ ID NO: 16 has the sequence:

(SEQ ID NO: 123)
MRSGVQVETISPGDGRTFPKRGQTAVVHYTGMLEDGKKFDSSRDRNKPFK

FMLGKQEVIRGWEEGVAQMSVGQRAKLTISPDYAYGDRGAGCGSGSSCLI

PPASVLVFDVELLKLEGGGSRKHHHHHHH.

The FKBP12/13 fusion polypeptide was expressed in *E. coli* as described as a soluble and monomeric protein. CD spectroscopic measurements were performed like described in example 12. The CD spectra showed that the FKBP12/13 fusion polypeptide is folded at 20° C.

Example 15

Generation of SlyD-FKBP12/13-CSF1R Fusion Polypeptide

The polypeptide was expressed in *E. coli* like as described above and purified as described above. After Ni-NTA affinity purification a size exclusion chromatography was performed. 50 mg of protein were loaded in a HiLoad 26/60 Superdex™ 75 pg (GE Healthcare). The elution fractions were loaded into a native gel and resolved according to known methods.

The affinity purified fusion polypeptide was dialyzed versus 50 mM KH$_2$PO$_4$ buffer, pH 7.0, comprising 100 mM KCl and 0.5 mM EDTA and filtrated trough a 0.22 μm filter. SlyD/FKBP12/13-CSF1R was UV/Vis spectroscopically quantified at 1.19 mg/ml using the calculated extinction coefficient e=20525 L·mol-1·cm-1 for the 39744.9 Da polypeptide.

Protein fluorescence measurements were used to test the conformational nature of SlyD/FKBP12/13-CSF1R. FKBP12 C22A as a carrier for polypeptide insertions can be used as a reference, because the single FKBP12 Trp moiety can be used to diagnose the structural integrity of the FKBP12 moiety (Scholz, C., et al., J. Biol. Chem. 271 (1996) 12703-12707; Russo, A. T., et al., J. Mol. Biol. 330 (2003) 851-866). FKBP12 C22A in its native structure shows a single fluorescence emission peak at 320 nm (Zoldak, G., et al., J. Mol. Biol. 386 (2009) 1138-1152).

250 μl of 1.19 mg/ml SlyD-FKBP12/13-CSF1R in KH$_2$PO$_4$ buffer pH 7.0 were analyzed at different temperatures. KH$_2$PO$_4$ buffer pH 7.0 was used as a reference. A Cary Eclipse instrument under the Scan Software Version 1.1 (132) was used at 5 nm band width for excitation and emission. A wavelength scan from 300 nm-425 nm was driven at 120 nm/min. The excitation wavelength of the intrinsic tryptophane fluorescence was set to 280 nm.

Example 16

Scaffold-Based Counter-Screening Approach for the Selection of Antigen Binding Antibodies Six week old NMRI mice were subjected 3-times to intraperitoneal immunization with 100 μg recombinant chimeric fusion polypeptide comprising the element *Thermococcus gammadurans* SlyD-antigen (TgSlyD-antigen). After 10 weeks the mice were boosted two times with 25 μg TgSlyD-antigen. Hybridoma cells were produced according to known methods. The primary hybridomas were isolated by limiting dilution and screened for antigen binding by ELISA.

50 ng/ml of TgSlyD-antigen fusion polypeptide, 50 ng/ml of TgSlyDΔIF and 1 μg/ml isolated antigen were each coated in 30×384 well (Nunc) plates overnight at 4° C. Coating buffer was freshly prepared with 1 carbonate-bicarbonate tablet (Sigma, C3041-100CAP99) resolved in 100 ml doubly distilled H$_2$O (ddH$_2$O). 100 μl Washing buffer (150 mM NaCl, 10 ml Tween 20 (Sigma), 40 ml Bromidox L (Roche) in 1 l dH$_2$O). The wells were washed three times with 100 μl washing buffer (150 mM NaCl, 10 ml Tween20 (Sigma), 40 ml Bromidox L (Roche) in 1 l dH$_2$O) using a BioTek washer. The wells were blocked with 30 μl blocking buffer (10 g BSA, 10×PBS pellets (Gibco) in 1 L ddH$_2$O) for one hour at RT, followed by 3 times washing with 100 μl washing buffer. 30 μl of 1:1000 diluted hybridoma supernatants were transferred into the wells using a Liquidator and were incubated for one hour at RT. As a positive control an antigen-positive serum was used. The wells were washed three times with 100 μl washing buffer. Peroxidase conjugated F(ab')2 fragment Goat anti-Mouse IgG antibody (Dianova) was diluted 1:30000 in blocking buffer and 30 μl were transferred into each well. Incubation for one hour at RT was followed by three times washing with 100 μl washing buffer. 30 μl ready to use ABTS substrate was incubated for 30 min at RT in each well. The absorption signals were monitored as reference signals at 405 nm/492 nm using a PowerWave XS Reader (BioTek). 15 hybridoma cultures, which showed positive ELISA signals versus the TgSlyD-antigen comprising fusion polypeptide and the isolated antigen and no signal versus the TgSlyDΔIF comprising fusion polypeptide were selected and further cultivated.

The primary hybridoma supernatants were isolated and screened for antigen binding by a second ELISA counter-screening, performed in the same way as described above. In the second screening additional screening reagents were used to precise the specificity of the antibody containing culture supernatants.

50 ng/ml of TgSlyD-antigen fusion polypeptide, 50 ng/ml TgSlyDΔIF, 500 ng of ttSlyD-antigen fusion polypeptide and 1 µg/ml isolated antigen were coated in 384 well (Nunc) plates for one hour at room temperature (RT). The ELISA was performed as described above. Due to their different species origin T.th.SlyD and T.g.SlyD show little sequence homology. Only 36% of the amino acids are identical and according to a blossom 62 calculation there is only 48% sequence similarity. TgSlyDΔIF is lacking the insertion anyway. Therefore, the polypeptides are very well suited to be used in an ELISA counter-screening.

Therefore, by immunization with the scaffold surrogate polypeptide a specific epitope in the native antigen domain could be pre-targeted.

Example 17

Epitope Mapping

SlyD-FKBP fusion polypeptides can also carry complex amino acid insertion motifs, like for example secondary structures containing disulfide bonds. Since the fusion polypeptides are free of cysteines, on-column refolding under appropriate conditions facilitates the correct formation of disulfides within the insertion, additionally assisted by the chaperone functionality of SlyD itself. The SlyD-FKBP fusion polypeptides were expressed in E. coli and on-column refolded as described above. SlyD-FKBP12ctrl was dialyzed in 75 mM HEPES buffer (pH 7.5) comprising 150 mM NaCl, 6.5% (w/v) Saccharose, 10 mM cysteine at a concentration of 9.5 mg/ml. A 1 mg/ml portion of the SlyD-FKBP12-CD81 fusion polypeptide was dialyzed in 50 mM potassium phosphate buffer pH 7.0, comprising 100 mM NaCl, 1 mM EDTA in order to avoid disulfide shuffling in the CD81 insertion, which contains 4 cysteines forming two disulfide bonds with structure functional relevance. The fusion polypeptides SlyD-FKBP12-CD81 and SlyD-FKBP12ctrl were used for the purpose of epitope mapping.

Human CD81 is a receptor for the hepatitis C virus envelope E2 glycoprotein. CD81 is a transmembrane protein belonging to the tetraspanin family. CD81 is a 90 amino acid in length homodimeric protein, which displays a so called mushroom-like structure (PDB 1IV5). Residues known to be involved in virus binding can be mapped onto the so called 35 amino acid in length "head subdomain", providing a basis for the design of antiviral drugs and vaccines. Since the head subdomain sequence of the virus binding site is just 35 amino acids in length it is difficult to map antibody epitopes on the 10 kDa CD81 protein using conventional cross-blocking experiments. It is difficult to discriminate antibodies, which specifically bind directly on the relevant mushroom-like head domain, from antibodies binding nearby or elsewhere in the CD81LEL structure. All antibodies would show independently of their binding site an HCV E2 envelope protein competing effect, but without specifically binding to the target structure, i.e. the head domain. The grafting of the relevant head domain structure into FKBP and a consecutive epitope mapping is therefore a useful method for various reasons. First, some biochemical issues with the CD81LEL protein are circumvented, because the protein itself tends to oligomerize. Second, it is rather suitable to identify antibody epitopes from a vast number of antibodies all binding to the full length CD81 protein.

Figure 40:
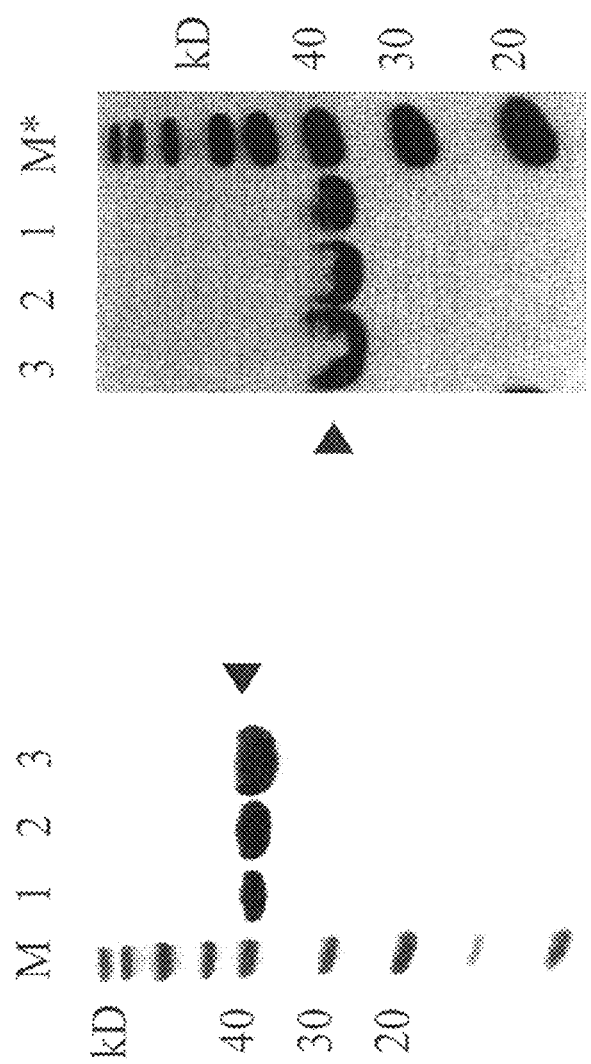
FIG. 40 SDS page (left) and Western Blot (right) of Ni-NTA chromatographically purified SlyD-FKBP12-CD81. M: Novex Sharp Standard, 1: SlyD/FKBP12-CD81; 2.5 µg MW: 36 kD, 2: SlyD/FKBP12-CD81; 5.0 µg, 3: SlyD/FKBP12-CD81; 10 µg M*: Magic Mark.

In FIG. 40 an SDS page (left) and Western Blot (right) of Ni-NTA chromatographically purified SlyD-FKBP12-CD81 is shown.

A BIAcore 2000 instrument (GE Healthcare) was used at 25° C. with a BIAcore CM5 sensor mounted into the system. The sensor was preconditioned by a 1 min. injection at 100 µl/min of 0.1% SDS, 50 mM NaOH, 10 mM HCl and 100 mM $H_3PO_4$. As a running buffer an HBS-EP buffer was used (10 mM HEPES (pH 7.4), 150 mM NaCl, 1 mM EDTA, 0.05% (w/v) P20). The sample buffer was the system buffer. Each protein ligand was immobilized by EDC/NHS chemistry at 30 µg/ml in 10 mM sodium acetate buffer (pH 4.0) into the flow cells 2, 3 and 4. Flow cell 1 was used as reference. The sensor was deactivated with a 1 M ethanolamine pH 8.0 solution. The following masses in response units (RU) were immobilized on the sensor: flow cell 2: 1800 RU SlyD-FKBP12ctrl (32.8 kDa), flow cell 3: SlyD-FKBP12-CD81 (35.8 kDa), flow cell 4: 900 RU CD81LEL (10 kDa). 31 antibody analytes were injected at 30 µl/min at 50 nM each for 3 min. association and 3 min. dissociation phase. 30 antibodies were derived from an immunization campaign with the 10 kDa CD81LEL protein. The sensor surface was regenerated using 100 mM HCl at 20 µl/min for 3 consecutive 30 sec. injections at 20 µl/min. The sensorgrams were monitored as reference signals 2-1 (flow cell 2 minus flow cell 1), 3-1 and 4-1 and were evaluated by using the BIAcore Evaluation software 4.1. At the end of the analyte injection a report point was set to quantify the maximum analyte binding signal. The highest analyte binding signal was set 100% to normalize the data.

In the following table the normalized antibody binding responses are shown. From 30 tested <CD81-LEL>M-antibodies only 6 (bold) show a precise epitope on the CD81 head domain. The negative control polypeptide SlyD-FKBP12ctrl was not bound. The positive control polypeptide CD81-LEL, which was the immunogen at the same time, was recognized by all antibodies. Slyd-FKBP12-CD81 was only bound, when the antibody epitope precisely locates in the mushroom domain.

TABLE

| Ligands Analytes | Slyd-FKBP12-ctrl | Slyd-FKBP12-CD81 | CD81-LEL |
|---|---|---|---|
| | normalized ref. binding signal (%) | | |
| HBS-ET | 0 | 0 | 0 |
| K01 | 0 | 0 | 63 |
| K02_1 | 0 | 0 | 62 |
| K02_2 | 0 | 0 | 61 |
| K03 | 0 | 47 | 93 |
| K04 | 0 | 0 | 80 |
| K05 | 0 | 26 | 100 |
| K06 | 0 | 32 | 74 |
| K07 | 0 | 0 | 62 |
| K08 | 0 | 0 | 56 |
| K10 | 0 | 0 | 46 |
| K21 | 0 | 0 | 77 |
| K22 | 0 | 29 | 80 |
| K23 | 0 | 0 | 37 |
| K24 | 0 | 17 | 86 |
| K25 | 0 | 0 | 38 |
| K27 | 0 | 29 | 81 |
| K28 | 0 | 0 | 41 |
| K30 | 0 | 0 | 52 |
| K31 | 0 | 0 | 66 |
| K32 | 0 | 0 | 53 |
| K34 | 0 | 0 | 66 |
| K35 | 0 | 0 | 44 |

TABLE-continued

| Ligands Analytes | Slyd-FKBP12-ctrl | Slyd-FKBP12-CD81 | CD81-LEL |
|---|---|---|---|
| | normalized ref. binding signal (%) | | |
| K36 | 0 | 0 | 54 |
| K37 | 0 | 0 | 52 |
| K38 | 0 | 0 | 65 |
| K39 | 0 | 0 | 66 |
| K40 | 0 | 0 | 51 |
| K41 | 0 | 0 | 67 |
| K42 | 0 | 0 | 60 |
| K43 | 0 | 0 | 58 |

Confirmation of the Epitope Mapping Results by X-Ray Crystallographic Analysis

Fab fragments of the antibodies K05 and K04 were co-crystallized with the CD81-LEL protein and were analyzed by x-ray diffraction analysis (Seth Harris, Palo Alto). The resolution obtained was 2.15 Å. Whereas antibody K05 binds in the mushroom domain, antibody K04 binds to an epitope off site of the mushroom sequence.

The invention claimed is:

1. A method for producing an antibody specifically binding to a target antigen comprising the following steps:
   a) recovering from an experimental animal after the administration of a fusion polypeptide comprising a polypeptide according to formula I

    (formula I)

wherein
   $X_1$ comprises a random amino acid sequence or an amino acid sequence derived from a first polypeptide,
   $S_2$ and $S_1$ are non-overlapping amino acid sequences derived from a second polypeptide, and
   — denotes a peptide bond,
   wherein the second polypeptide is selected from the group consisting of human FKBP12, *Arabidopsis thaliana* FKBP13, *Thermus thermophilus* SlyD, *Escherichia coli* SlyD and *Thermococcus gammatolerans* SlyD, and
   wherein $X_1$ is inserted in place of the insert-in-flap-domain (IF-domain) of the second polypeptide; and
   wherein $X_1$ is the amino acid sequence of the polypeptide B-cells that produce the antibody specifically binding to the amino acid sequence of $X_1$, and
   b) cultivating a cell comprising a nucleic acid enc